US012599429B2

(12) United States Patent
Sano et al.

(10) Patent No.: US 12,599,429 B2
(45) Date of Patent: Apr. 14, 2026

(54) METHODS FOR CONTROLLING TREATMENT VOLUMES, THERMAL GRADIENTS, MUSCLE STIMULATION, AND IMMUNE RESPONSES IN PULSED ELECTRIC FIELD TREATMENTS

(71) Applicant: North Carolina State University, Raleigh, NC (US)

(72) Inventors: Michael Benjamin Sano, Cary, NC (US); Christopher Fesmire, Raleigh, NC (US); Ross A. Petrella, Richmond, VA (US)

(73) Assignee: NORTH CAROLINA STATE UNIVERSITY, Raleigh, NC (US)

( * ) Notice: Subject to any disclaimer, the term of this patent is extended or adjusted under 35 U.S.C. 154(b) by 874 days.

(21) Appl. No.: 17/779,306

(22) PCT Filed: Nov. 23, 2020

(86) PCT No.: PCT/US2020/061756
§ 371 (c)(1),
(2) Date: May 24, 2022

(87) PCT Pub. No.: WO2021/108292
PCT Pub. Date: Jun. 3, 2021

(65) Prior Publication Data
US 2023/0000543 A1    Jan. 5, 2023

Related U.S. Application Data

(60) Provisional application No. 62/941,069, filed on Nov. 27, 2019.

(51) Int. Cl.
A61B 18/14 (2006.01)
A61B 17/00 (2006.01)
A61B 18/00 (2006.01)

(52) U.S. Cl.
CPC A61B 18/1477 (2013.01); A61B 2017/00194 (2013.01); A61B 2018/00005 (2013.01);
(Continued)

(58) Field of Classification Search
CPC ...... A61B 18/1477; A61B 2017/00194; A61B 2018/00005; A61B 2018/00023;
(Continued)

(56) References Cited

U.S. PATENT DOCUMENTS 6,506,189 B1 *    1/2003    Rittman, III ....... A61B 18/1482
                                                              606/49
7,226,447 B2 *    6/2007    Uchida .............. A61B 18/1206
                                                              606/34
(Continued)

FOREIGN PATENT DOCUMENTS

WO       2019232358 A1    12/2019

OTHER PUBLICATIONS

Sano et al. "Burst and continuous high frequency irreversible electroporation protocols evaluated in a 3D tumor model" Phys Med Biol 63(13):135022 (Jul. 6, 2018).
(Continued)

*Primary Examiner* — Michael F Peffley
(74) *Attorney, Agent, or Firm* — Myers Bigel, P.A.

(57) ABSTRACT

Pursuant to embodiments of the present invention, a method of performing electronically controlled electrotherapy may include modifying or killing target cells and simultaneously modifying a secondary outcome by delivering electrical pulses and dynamically adjusting an energy delivery profile of the electrical pulses in response to a measurement. The secondary outcome may be a physical outcome, a biological outcome, and/or a systemic outcome.

20 Claims, 74 Drawing Sheets

(52) U.S. Cl.
CPC ............... *A61B 2018/00023* (2013.01); *A61B 2018/00577* (2013.01); *A61B 2018/00672* (2013.01); *A61B 2018/00678* (2013.01); *A61B 2018/00702* (2013.01); *A61B 2018/00744* (2013.01); *A61B 2018/00761* (2013.01); *A61B 2018/00767* (2013.01); *A61B 2018/00791* (2013.01)

(58) Field of Classification Search
CPC ........... A61B 2018/00577; A61B 2018/00613; A61B 2018/00642; A61B 2018/00648; A61B 2018/00672; A61B 2018/00678; A61B 2018/00702; A61B 2018/0072; A61B 2018/00726; A61B 2018/00744; A61B 2018/00761; A61B 2018/00767; A61B 2018/00791; A61B 2018/00839; A61B 2018/00875; A61B 2018/00892; A61B 2034/104; A61B 2090/374; A61B 2090/3762; A61B 2090/378; A61N 1/0502; A61N 1/06; A61N 1/1327; A61N 1/36002
See application file for complete search history.

(56) References Cited

U.S. PATENT DOCUMENTS

| | | | | |
|---|---|---|---|---|
| 8,992,517 | B2 * | 3/2015 | Davalos ............. | A61B 18/1477 |
| | | | | 606/41 |
| 9,414,881 | B2 * | 8/2016 | Callas ................... | A61B 18/14 |
| 10,136,943 | B1 * | 11/2018 | Cosman, Jr. ....... | A61B 18/1482 |
| 2007/0078454 | A1 | 4/2007 | McPherson | |
| 2007/0239059 | A1 | 10/2007 | McIver | |
| 2008/0147131 | A1 | 6/2008 | Mathiesen et al. | |
| 2008/0287944 | A1 | 11/2008 | Pearson et al. | |
| 2012/0022612 | A1 | 1/2012 | Littlewood et al. | |
| 2016/0022985 | A1 | 1/2016 | Desimone et al. | |
| 2017/0042617 | A1 | 2/2017 | Prakash et al. | |
| 2017/0065343 | A1 | 3/2017 | Mickelsen | |
| 2017/0266438 | A1 * | 9/2017 | Sano ..................... | A61N 1/327 |

OTHER PUBLICATIONS

Sano et al. "Reduction of Muscle Contractions during Irreversible Electroporation Therapy Using High Frequency Bursts of Alternating Polarity Pulses: a Laboratory Investigation in an Ex Vivo Swine Model" J. Vasc. Interv. Radiol. (2017).

Hondroulis et al. "Immune Nanoparticles Integrated Electrical Control of Targeted Cancer Cell Development Using Whole Cell Bioelectronic Device" Theranostics 4(9):919-930 (Jul. 13, 2014).

International Search Report and Written Opinion corresponding to International Patent Application No. PCT/US2020/061756 (Feb. 16, 2021).

"European Search Report in Corresponding Application No. 20892520. 6, mailed Nov. 24, 23, 9 pages".

* cited by examiner

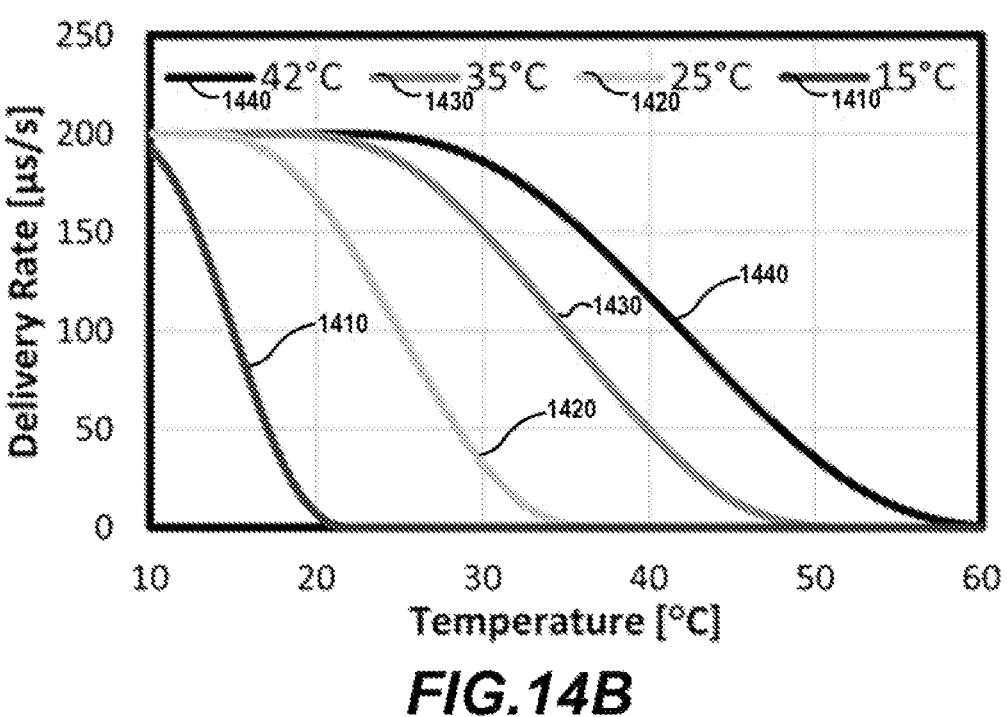
FIG.14B
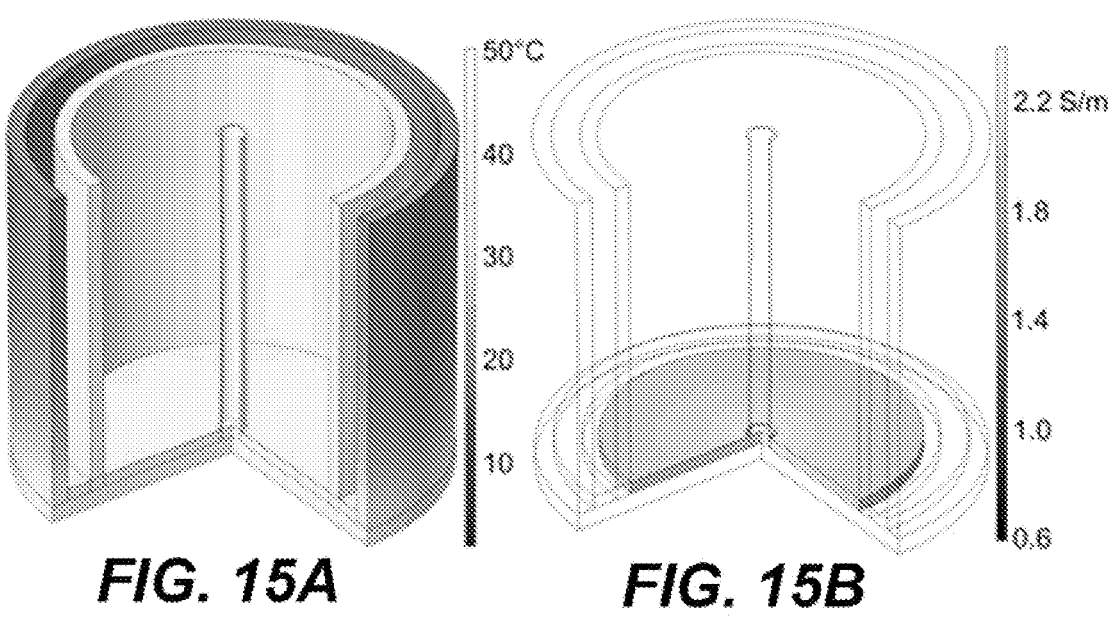
FIG. 15A          FIG. 15B

TEMPERATURE
SENSOR

ELECTRODE

SOURCE ELECTRODE WIRE    APPLICATOR HANDLE    RING ELECTRODE (SINK)    TEMPERATURE SENSOR

SINK ELECTRODE WIRE    NEEDLE ELECTRODE (SOURCE)

RING ELECTRODE (SINK)

OPTIONAL SECONDARY TEMPERATURE SENSOR

NEEDLE ELECTRODE (SOURCE)

APPLICATOR DELIVERING ENERGY

TISSUE POST-TREATMENT

METHODS FOR CONTROLLING TREATMENT VOLUMES, THERMAL GRADIENTS, MUSCLE STIMULATION, AND IMMUNE RESPONSES IN PULSED ELECTRIC FIELD TREATMENTS

CLAIM OF PRIORITY

This application is a 35 U.S.C. § 371 national stage application of PCT Application No. PCT/US2020/061756, filed on Nov. 23, 2020, which claims priority to U.S. Provisional Application Ser. No. 62/941,069, filed Nov. 27, 2019, the entire contents of which are hereby incorporated by reference. The above-referenced PCT Application was published in the English language as International Publication No. WO 2021/108292 A1 on Jun. 3, 2021.

FIELD OF THE INVENTION

The present invention relates generally to methods and devices for destruction of unwanted tissues (tumors, vasculature, endothelium, etc.) and, more specifically, to pulsed electric field therapies.

BACKGROUND OF THE INVENTION

The ablation of unwanted soft tissue can be achieved by many means, including surgical excision, application of excessive amount of ionizing radiation or other forms of energy (excessive heating and cooling), exposure to cytotoxic chemicals, or by a combination of these means. It is common to use these means to destroy neoplasms. Treatments known in the art involve surgical intervention to physically remove the aberrant cell mass, radiation to kill the cells of the aberrant cell mass, exposure of aberrant cells to toxic chemicals (i.e., chemotherapy), or a combination of such techniques. While each treatment modality has shown significant effectiveness in treatment of various cell proliferative diseases, no one technique has been shown to be highly effective at treating all types of cell proliferative diseases and disorders.

While surgical intervention is effective at removal of solid tumors on tissues and organs that are physically accessible and capable of sustaining physical damage or capable of regeneration, surgical intervention can be difficult to perform on tumors that are not readily accessible or on organs that do not regenerate. In these cases, surgical intervention can often involve substantial physical damage to the patient, requiring extensive recuperation times and follow-on treatments. At other times, the extensive growth of the neoplasm prevents removal, since attempts at removal would likely kill the patient. Likewise, treatment with radiation can result in collateral damage to tissue surrounding the tumor, and can cause long-lasting side-effects, which can lower the quality of life of the patient. Chemotherapeutic treatments can cause systemic damage to the patient, and can result in significant side effects that might require a long recuperation period or cause permanent damage to tissues and organs.

Recent work by the inventors has focused on the ablation of unwanted soft tissue (malignant tumors) by application of excessive electrical energy, using a technique termed Irreversible Electroporation (IRE). Successful control and/or ablation of soft tissue sarcoma and malignant glioma have been achieved. Irreversible electroporation (IRE) involves placing electrodes within or near the targeted region to deliver a series of low energy, microsecond electric pulses.

These pulses permanently destabilize the cell membranes of the targeted tissue (e.g., tumor), thereby killing the cells.

SUMMARY OF THE INVENTION

The foregoing and other objects and aspects of the present invention are explained in greater detail in the drawings herein and the specification set forth below. The disclosures of all United States patent references cited herein are to be incorporated herein by reference.

Pursuant to embodiments of the present invention, a method of performing electronically controlled electrotherapy may include modifying or killing target cells and simultaneously modifying a secondary outcome by delivering electrical pulses and dynamically adjusting an energy delivery profile of the electrical pulses in response to a measurement. The secondary outcome may be a physical outcome, a biological outcome, and/or a systemic outcome.

In some embodiments, the target cells may be cancerous cells inside or outside of a tumor.

In some embodiments, the target cells may be healthy cells of or in the liver, kidney, brain, blood, lungs, spleen, gastrointestinal tract, skin, lymphatic system, or other organs.

In some embodiments, modifying the target cells may include introducing new DNA or genetic material, introducing a drug or chemotherapy, stimulating protein expression, stimulating antigen production, preventing or inhibiting mitosis, and/or preventing or inhibiting cell replication.

In some embodiments, killing target cells may include inducing necrosis, apoptosis, thermal necrosis, non-thermal necrosis, a loss of homeostasis, senescence, cell membrane rupture, membrane permeabilization, pore formation, delayed cell death, instantaneous cell death, coagulative necrosis, liquefactive necrosis, fat necrosis, fibrinoid necrosis, necroptosis, cell membrane rupture, activation-induced cell death, autophagy, anoikis, ferroptosis, an accumulation of lipid peroxides leading to cell death, ischemic cell death, mitotic catastrophe, immunogenic cell death, pyroptosis, or caspase-independent programmed cell-death.

In some embodiments, the physical outcome may include a change in temperature, impedance, pH, mechanical properties, light absorbance, light reflectance, ultrasound reflectance, ultrasound absorbance, and/or medical imaging contrast (e.g., ultrasound MM or CT).

In some embodiments, the measurement may include a measurement of the secondary outcome or a measurement of an independent change in temperature, impedance, pH, density, water content, stiffness, strength, viscoelasticity, other mechanical properties, light absorbance, light reflectance, ultrasound reflectance, ultrasound absorbance, medical imaging contrast (e.g., ultrasound MM or CT), acceleration due to muscle contractions, and/or a user controlled input device.

In some embodiments, the biological outcome may include muscle contractions, nerve stimulation, cardiac rhythm, protein expression, insulin production, hormone production, edema, and/or swelling.

In some embodiments, the systemic outcome may include the induction of an immune response, induction of an abscopal response, induction of a vaccine-like response, and/or reduction of pain.

In some embodiments, delivering electrical pulses may include delivering a plurality of electrical pulse waveforms that comprise only positive polarity pulses, only negative polarity pulses, or a combination of positive and negative polarity pulses.

In some embodiments, adjusting the energy delivery profile may include modulating a delay between successive waveforms of the electrical pulses, increasing or decreasing a width of a positive and/or negative pulses of the electrical pulses that are delivered, and/or modifying a delay between polarity changes of the electrical pulses.

In some embodiments, adjusting the energy delivery profile may include changing a volume of coolant flowing through electrodes used to deliver the electrical pulses.

Pursuant to embodiments of the present invention, a method of performing electronically controlled electrotherapy may include delivering a waveform comprising a plurality of electrical pulses to a patient; and modifying or killing target cells and simultaneously reducing or eliminating muscle contractions by adjusting an energy delivery profile of the waveform in response to a measurement of an accelerometer, imaging, or a user controlled input.

In some embodiments, a width of at least one of the electrical pulses may be decreased to reduce muscle stimulation.

In some embodiments, a symmetry of the waveform may be modulated to reduce muscle stimulation.

In some embodiments, a rate of energy delivery of the electrical pulses may be increased to reduce muscle stimulation.

In some embodiments, a width of the electrical pulses may be decreased, and a rate of energy delivery of the electrical pulses is increased, to maintain a constant energy delivery rate between 1 and 10,000 microseconds per second, preferably between 10 and 500 microseconds per second.

In some embodiments, a width of the electrical pulses may be modified, and a target treatment dose may be modified, to achieve a target dose associated with the modified electrical pulse width.

In some embodiments, a width of the electrical pulses may be increased, and the target treatment dose may be decreased, to achieve a target dose associated with the modified electrical pulse width.

In some embodiments, a width of the electrical pulses may be decreased, and the target treatment dose may be increased, to achieve a target dose associated with the modified electrical pulse width.

Pursuant to embodiments of the present invention, a method of performing electronically controlled electrotherapy may include: delivering a waveform comprising a plurality of electrical pulses to a patient; and modifying or killing target cells and simultaneously reducing or eliminating thermal injury, tissue burning, tissue charring, nerve, and/or blood vessel damage by adjusting an energy delivery profile of the waveform in response to a measurement and/or a user controlled input.

In some embodiments, the method may further include selecting a target ablation size and maximum temperature; automatically selecting a treatment voltage, a treatment waveform, and/or a target dose to be delivered responsive to the selection of the target ablation size and the maximum temperature.

In some embodiments, the measurement may include a signal from a temperature sensor placed inside an electrode, adjacent to the electrode, or at a location remote from the electrode.

In some embodiments, the measurement may include a temperature of coolant exiting an internally perfused electrode.

In some embodiments, the measurement may include a difference in temperature between coolant entering and exiting an internally perfused electrode.

In some embodiments, the measurement may include Mill, ultrasound, or CT imaging.

In some embodiments, the energy delivery profile may be modified by reducing the repetition rate of the electrical pulses to prevent the measured temperature from exceeding a specific value.

In some embodiments, the energy delivery profile may be modified by increasing a repetition rate of the electrical pulses to enable a measured temperature to reach a threshold.

In some embodiments, the energy delivery profile may be modified by reducing a width of the electrical pulses delivered to prevent a measured temperature from exceeding a threshold, and a target dose to be delivered is increased to a value associated with the reduced pulse width.

In some embodiments, the energy delivery profile may be modified by increasing a width of the electrical pulses delivered to enable a measured temperature to reach a threshold, and a target dose to be delivered is decreased to a value associated with the increased pulse width.

In some embodiments, the energy delivery profile may be modified by reducing a voltage of the electrical pulses delivered to prevent a measured temperature from exceeding a threshold, and a target dose to be delivered is increased to a value associated with the reduced voltage.

In some embodiments, the energy delivery profile may be modified by increasing a voltage of the electrical pulses delivered to enable a measured temperature to reach a threshold, and a target dose to be delivered is decreased to a value associated with the increased voltage.

Pursuant to embodiments of the present invention, a method of performing electronically controlled electrotherapy method may include modifying or killing target cells and simultaneously inducing a secondary immune response by delivering electrical pulses and dynamically adjusting an energy delivery profile of the electrical pulses in response to a measurement to induce cell modification or death via one or more desired pathways.

In some embodiments, the secondary immune response may include a systemic response to a local or metastatic disease.

In some embodiments, the secondary immune response may include an antigen specific response of the adaptive immune system triggered by a release of tumor antigens.

In some embodiments, the secondary immune response may include a recruitment of T-cells, B-cells, neutrophils, macrophages, dendritic cells, leukocytes, hematopoietic stem cells, Gamma delta T cells, Helper T cells, granulocytes (e.g., neutrophils, mast cells, basophils, or eosinophils), innate lymphoid cells (e.g., natural killer cells, Group 1, Group 2, or Group 3 ILCs), natural helper cells, nuocytes, innate helper cells, and/or other immunological cells to the treatment site.

In some embodiments, the secondary immune response may include a stimulation of the complement system, induction of a biochemical cascade, or activation of the innate immune system.

In some embodiments, the secondary immune response may be induced via a release of antigens, proteins, neoantigens, pathogen-associated molecular patterns (PAMPs) (e.g., peptidoglycan, nucleic acid, RNA, dsRNA, CpG oligodeoxynucleotides), damage-associated molecular patterns (DAMPs) (e.g., chromatin-associated leaderless secreted proteins, DNA, RNA. calcium modulated proteins, S100 proteins, nucleotides such as ATP, nucleosides such as adenosine, monosaccharides, polysaccharides), transmembrane proteins, toll-like receptor (TLR) binding molecules, inflammasomes, inflammatory cytokines, tumor markers (e.g., Alphafetoprotein, Carcinoembryonic antigen, CA-125, MUC-1, Epithelial tumor antigen, Tyrosinase, Melanoma-associated antigen, RAS, p53, Alpha fetoprotein, CA15-3, CA27-29, CA19-19, CA-125, Calcitonin, Calretinin, CD34, CD99, CD117, Chromogranin, Cytokeratin, Glial fibrillary acidic protein, HMB-45, HER-2, MART-1, Melanin-A, prostate specific antigen), and/or other molecules that are released from a cell, cell membrane, organelles, organelle membranes, nucleus, and/or nuclear envelope to induce an immune response.

In some embodiments, antigens, proteins, and/or molecules released by treatment may be protected from thermal damage by adjusting the energy delivery profile to prevent temperatures from exceeding a value that would result in the denaturing of molecules or reduction of a utility of the molecules to the immune system.

In some embodiments, cell death may be induced via thermal necrosis, non-thermal necrosis, coagulative necrosis, liquefactive necrosis, fat necrosis, fibrinoid necrosis, necroptosis, cell membrane rupture, activation-induced cell death, apoptosis, autophagy, anoikis, ferroptosis, an accumulation of lipid peroxides, ischemic cell death, mitotic catastrophe, immunogenic cell death, pyroptosis, and/or caspase-independent programmed cell-death.

In some embodiments, the method may further include: selecting an immune-stimulatory or non-immuno-stimulatory cell death pathway; and automatically adjusting treatment parameters to favor one treatment outcome over another by controlling a target temperature, pulse waveform, dose, and/or voltage.

In some embodiments, the method may further include adjusting the energy delivery profile based on a temperature measurement as the measurement to produce a first zone of thermal necrosis surrounded by a second zone of non-thermal necrosis or apoptosis.

In some embodiments, a first zone of thermal necrosis may be surrounded by a second zone of cells that have been modified by introducing new DNA or genetic material, introducing a drug or chemotherapy or nano-particle, and/or stimulated to enhance protein or antigen expression.

In some embodiments, a first zone of cell death via non-thermal necrosis or apoptosis may be surrounded by a second zone of cells which have been modified by introducing new DNA or genetic material, introducing a drug or chemotherapy, and/or stimulated to enhance protein or antigen expression.

In some embodiments, the new DNA or genetic material may be designed to produce or release molecules which stimulate an immune response.

In some embodiments, the method may further include injecting adjunctive drugs or particles into a tumor prior to, during, or after the electrical pulses are delivered.

In some embodiments, the method may further include delivering adjunctive drugs or particles prior to, during, or after electrical energy is delivered.

In some embodiments, the adjunctive drug may be an immunostimulant, steroid, check point inhibitor, interleukin (IL-12) or immunotherapy including Anti-PD-1 (e.g., Nivolumab, Pembrolizumab, Cemiplimab), Ant-CTLA-4 (Ipilimumab), Anti-PD-L1 (e.g., Atezolizumab, Avelumab, Durvalumab), Anti-CD20 (e.g., Rituximab, Retuxan, Truxima).

In some embodiments, the adjunctive particle may be a protein, live bacteria, dead bacteria, live virus, dead virus, inactivated virus, DNA, RNA, a nanoparticle, and/or a nanotube configured to enhance an immune response or to traffic molecules and/or antigens to the lymphatic system.

In some embodiments, the energy delivery profile may include a waveform with a positive polarity pulse, followed by a delay, followed by a negative polarity pulse that is repeated until a target dose is reached.

In some embodiments, the positive and negative polarity pulses may be of a same duration between 1 nanosecond and 1 millisecond, preferably between 0.1 and 10 microseconds.

In some embodiments, the positive and negative polarity pulses may be of different durations, with each pulse preferably having a duration between 0.1 and 10 microseconds.

In some embodiments, only positive polarity pulses may be delivered or negative polarity pulses are delivered.

In some embodiments, a width of the positive and/or negative polarity pulses in the waveform may be modified response to the measurement.

In some embodiments, the delay between positive and negative polarity pulses may be between 1 nanosecond and 1 millisecond, preferably between 0.1 and 10 microseconds.

In some embodiments, the delay between positive and negative polarity pulses in the waveform may be modified in response to the measurement.

In some embodiments, a delay between successive waveforms comprising one positive polarity pulse and one negative polarity pulse may be between 1 nanosecond and 10 seconds, preferably between 1 and 10,000 microseconds.

In some embodiments, the delay between successive waveforms may be modified responsive to the measurement.

Pursuant to embodiments of the present invention, an apparatus for electronically controlled electrotherapy may include one or more electrodes for insertion into a target tissue, one or more sensors, and a computer controller configured to perform operations include: selecting a pulse waveform comprising a plurality of electrical pulses; acquiring a measurement from the one or more sensors and/or determining a parameter from acquired imaging; generating the plurality of electrical pulses having the selected pulse waveform, wherein the pulse waveform has a delay between ones of the electrical pulses; controlling the delay between the ones of the plurality of electrical pulses, widths of ones of the plurality of electrical pulses, and/or amplitudes of ones of the plurality of electrical pulses based on the measurement from the one or more sensors and/or the parameter from the acquired imaging; and delivering the plurality of electrical pulses through the one or more electrodes.

In some embodiments, the measurement may include a thermal measurement, an acceleration measurement, an impedance measurement, a voltage measurement, a current measurement, an ultrasound measurement, a cardiac measurement, an electrocardiogram measurement, an electroencephalogram measurement, a blood pressure measurement, a pulse-oxygen measurement, an electrocardiogram measurement, a respiration measurement, an acoustic measurement, a photo-acoustic measurement, an infrared thermometry, video, magnetic resonance imaging, x-ray imaging, and/or a computed tomography measurement.

In some embodiments, the computer controller may be further configured to obtain thermal, acceleration, impedance, voltage, current, ultrasound, cardiac, electrocardiogram, electroencephalogram, blood pressure, pulse-oxygen, electrocardiogram, respiration, acoustic, photo-acoustic, infrared thermometry, video, magnetic resonance imaging, x-ray imaging, and/or computed tomography measurements.

In some embodiments, the computer controller may be further configured to determine whether the measurement is above, below, or at a target value, or within a tolerance window.

In some embodiments, the computer controller may be further configured to reduce or increase a duration of the electrical pulses.

In some embodiments, the computer controller may be further configured to increase or decrease a delay between sequential electrical pulses of the plurality of electrical pulses.

In some embodiments, the computer controller may be further configured to increase or decrease the amplitude of a voltage or a current delivered by the plurality of electrical pulses.

In some embodiments, the computer controller may be further configured to increase or decrease an average energy delivery rate of the plurality of electrical pulses.

In some embodiments, the apparatus may further include a high voltage switching circuit comprising a plurality of switches to create an H-Bridge configuration that are configured to deliver the plurality of electrical pulses comprising positive and negative polarity from a high voltage power supply In some embodiments, the apparatus may further include: a plurality of switches in an H-Bridge or totem pole configuration that are configured to deliver the plurality of electrical pulses comprising positive and negative polarity from a positive and a negative power supply.

In some embodiments, the apparatus may further include: a transformer coupled to a plurality of switches in an H-Bridge or totem pole configuration to step up a lower voltage to a higher voltage.

In some embodiments, the apparatus may further include a voltage source connected to a capacitor or a plurality of capacitors.

In some embodiments, the delay between the ones of the plurality of electrical pulses may be between 0.1 and 10 microseconds.

In some embodiments, a delay between positive and negative pulses in the waveform may be modified in response to a measurement.

In some embodiments, a delay between successive waveforms comprising one positive pulse and one negative pulse may be between 1 microsecond and 10 seconds.

In some embodiments, the delay between successive waveforms may be modified response to a measurement.

In some embodiments, the width of positive or negative pulses may be modified response to a measurement.

In some embodiments, a voltage of positive or negative pulses may be modified response to a measurement.

In some embodiments, the electrodes may be actively cooled.

In some embodiments, the apparatus may be further configured to acquire temperature measurements from an inlet or an outlet of the actively cooled electrodes and the temperature measurements are used to modify an energy delivery profile of the plurality of electrical pulses.

In some embodiments, the apparatus may further include an applicator comprising a first electrode that makes contact with a surface of the target tissue and a second electrode that is inserted into the target tissue.

In some embodiments, an electric field magnitude of the first electrode may point completely or predominantly in one direction.

In some embodiments, an electric field magnitude of the second electrode points predominantly in the radial direction between the first electrode and the second electrode.

In some embodiments, the first electrode includes a ring-shaped electrode in contact with the surface of the target tissue.

In some embodiments, the apparatus may further include a pad, mesh and/or conductive material in contact with the surface of the target tissue.

In some embodiments, the second electrode includes a needle that is inserted into the target tissue, wherein the needle is partially or fully insulated.

In some embodiments, the second electrode includes an internally cooled electrode.

In some embodiments, the second electrode includes one or more inner lumens for perfusing the second electrode with coolant.

In some embodiments, the apparatus may further include a temperature sensor that is configured to measure a coolant temperature as it enters and/or exits the second electrode.

In some embodiments, the apparatus may further include a temperature sensor inside of the second electrode.

In some embodiments, the apparatus may further include a temperature sensor in contact with the tissue, within the tissue, or adjacent to the tissue.

In some embodiments, a depth of the insertion of the second electrode is configured to be adjusted.

In some embodiments, an amount of insulation or exposed electrode of the second electrode is configured to be adjusted.

In some embodiments, the first electrode may have a diameter between 0.1 mm and 8 mm.

In some embodiments, the first electrode may have a length of 0.1 to 250 mm.

In some embodiments, the first electrode may be insulated along its entire length except for a distal region measuring between 0.1 and 40 mm.

Pursuant to embodiments of the present invention, a computer program product may include a tangible non-transitory computer readable storage medium comprising computer readable program code embodied in the computer readable storage medium that when executed by at least one processor causes the at least one processor to perform operations comprising: measuring a value from a sensor or image during a pulsed electric field therapy comprising a plurality of electrical pulses; and dynamically modifying a delivery profile of the electrical pulses responsive to the value from the sensor

BRIEF DESCRIPTION OF THE DRAWINGS

FIG. 14B is a graph illustrating a discretized Heaviside step function according to some embodiments of the present disclosure.

FIGS. 15A to 15E illustrate simulation results according to some embodiments of the present disclosure.

DETAILED DESCRIPTION

Figure 1A:
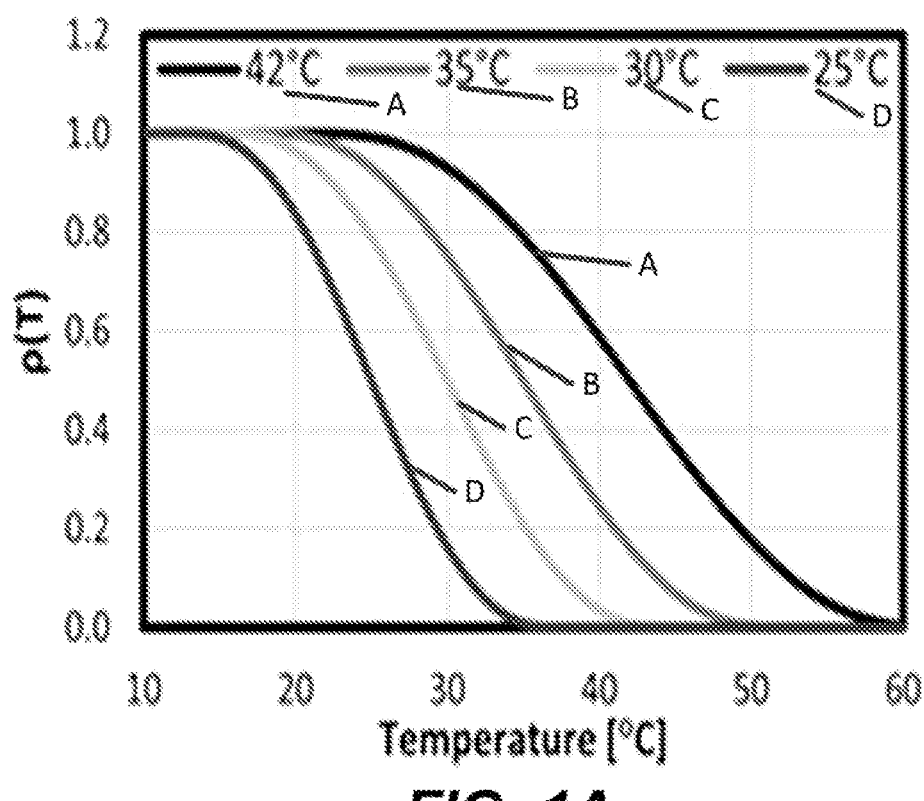
FIG. 1A is a graph illustrating a discretized Heaviside step function according to some embodiments of the present disclosure.

Irreversible electroporation is a tumor ablation technique which utilizes high voltage pulsed electric fields to destroy tumors. While these procedures are generally considered non-thermal, the non-thermal designation only refers to the mechanism of cell death, being the cell membrane phospholipid bilayer reorientation in response to the electric field and the formation of cytotoxic aqueous pores which traverse the cell membrane. In practice, some of the electrical energy which is applied to the cells or tissue is lost in the form of heat described by Joule heating.

Joule heating adds confounding variables to any irreversible electroporation treatment as heat is known to change the biophysical response of cells. For example, when hyperthermia is maintained for extended periods of time proteins begin to denature. Electrically, there are temperature dependent spatio-temporal changes in cell media and tissue conductivity leading to a dynamic reduction in resistance which may need to be accounted for in pulsed electric field treatment planning. For in vitro experiments, elevated temperatures will cause collagen to denature at temperatures above approximately 42° C. This limitation can make investigating the combinatorial effects of pulsed fields and hyperthermic temperatures challenging in 3D tumor models where the melt point of the matrix is less than the applied Joule heating.

While the heating effects in irreversible electroporation could be minimized by reducing the pulse repetition rate or decreasing the width of the pulses, this has not been the standard practice. Previous irreversible electroporation protocols have been prescribed in terms of pulse number, amplitude, and repetition rate in order to achieve a targeted treatment energy dose. Temperature is allowed to increase unregulated throughout the duration of the treatment. Although, side effects are rare for irreversible electroporation treatments, uncontrolled elevated temperatures may be a contributing factor to adverse side effects such as coagulative necrosis, thrombosis, and fistulas.

Uncontrolled tissue ablation protocols could be characterized as open loop, being devoid of a feedback mechanism dependent on a process output. The closed loop, dynamically controlled, pulsed electric field ablation technique presented here, algorithmically controlled electrotherapy (ACE), uses real time feedback in order to dynamically adjust the energy delivery profile to control multiple physiological, biological, and systemic responses to the treatment. ACE uses a set of process inputs (e.g. voltage, temperature, imaging, and pulse delivery rate) to find an improved pulse delivery rate which establishes a steady state value for a physical response, biological response, or systemic response based on a measurement acquired from a remote sensor or imaging. In the case of temperature measurements, the location of temperature sensing could be anywhere throughout the intended ablation volume or at a remote location of interest. In vivo, temperature data could be acquired either at the electrode, distal to the electrode, or from imaging data in order to protect critical structures such as nerves, blood vessels, bile ducts, or other critical structures from thermal injury. Selection of appropriate pulse widths, voltages, doses and energy delivery rates provide the ability to selectively control the predominant form of cell death occurring following ACE therapy enables the delivery of treatments which are more likely to induce a favorable immune response. In conjunction with adjunctive therapeutics this treatment enables local gene-therapy to further enhance anti-tumor effects.

Experiments were conducted to validate both the operation of the temperature control software and investigate the cytotoxic effects of pulsed electric fields delivered with respect to a temperature control algorithm. The basis of this temperature control paradigm was a proportionate control algorithm which adjusts the rate of pulse delivery depending on the difference between a measured temperature and a target temperature value. Pulses are delivered algorithmically until a target total pulse on time or integrated energized time (IET) is achieved. When combined with a pulsed power supply, an ACE system was demonstrated for 500V, 750V and 1000V treatments. Without thermal control, temperature increases of 5.3±0.3° C., 11.4±0.7° C., and 22.0±4.7° C. were observed from a baseline of 20° C. respectively. With temperature control enabled and a target temperature of 25° C., 24.5±0.5° C. was achieved for 1000V treatments with similar results observed for lower voltage treatments. Biological experiments have indicated that ACE is capable of achieving treatment zones similar to those created with non-temperature controlled irreversible electroporation. The results highlight the thermal dependence of cell death for pulses with durations on the order of 2 μs which has not been observed in non-thermal irreversible electroporation clinical protocols utilizing longer pulse lengths (50-100 μs). The findings from this study set the foundation for in vivo experiments utilizing a temperature-controlled pulse delivery rate, as described herein.

Methods

Experimental Temperature Control Algorithm

The ACE algorithm has been designed to dynamically adjust the rate of pulse delivery to achieve and maintain a target temperature. The aim is for the temperature to rapidly increase according to a user defined maximum delivery rate ($R_{max}$) and then decrement to a steady state delivery rate where the targeted temperature is maintained. The rate specifies the amount of pulse on time compared to the total treatment time of an individual pulse sequence. For a biphasic pulse sequence, the $R_{max}$ pulse delivery rate is given by:

$$R_{max} = \frac{\tau_p + \tau_n}{\delta} \left[ \frac{\mu s}{s} \right] \qquad (1)$$

where $\tau_p$ is the pulse width of the positive phase of the delivered pulse, $\tau_n$ is pulse width of the negative phase of the delivered pulse, and $\delta$ is the temporal delay between pulse sequences. This rate calculation assumes an ideal square wave pulse.

Figure 1B:
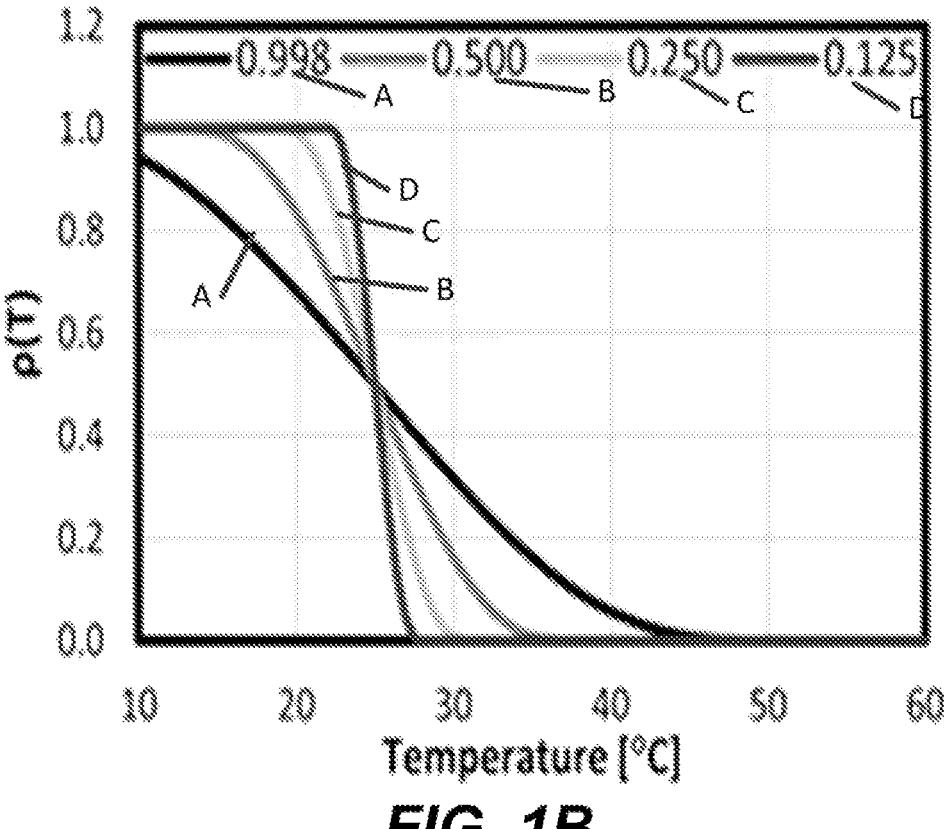
FIG. 1B is a graph illustrating the effect of co on the Heaviside step function.

After sampling the temperature, T, the instantaneous rate of pulse delivery as a function of temperature, R(T), is calculated as a fraction of $R_{max}$ by an adjustment equation, $\rho$(T), according to a discretized Heaviside step function. The delivery rate R(t) was controlled via the Heaviside function $\rho$(T) which was dependent on the instantaneous temperature (T) measured inside the center pin electrode. FIG. 1A is a graph illustrating a discretized Heaviside step function according to some embodiments of the present disclosure. In FIG. 1A, the experimental values for $\rho$(T) are shown for target temperatures (Ttarget) of 25° C. (reference designator 'D'), 30° C. (reference designator 'C'), 35° C. (reference designator 'B'), and 42° C. (reference designator 'A') as a function of instantaneous temperatures (T) between 10 and 60° C. The implementation of this was performed according the following governing equations:

$$R(T) = \rho(T) \cdot R_{max} \left[ \frac{\mu s}{s} \right] \qquad (2)$$

$$\rho(T) = 0.5 - 0.9375 \cdot \Gamma(T) + 0.625\Gamma \cdot (T)^3 - 0.1875 \cdot \Gamma(T)^5 \qquad (3)$$

$$\Gamma(T) = \frac{(T - T_{target})}{\beta} \qquad (4)$$

$$\beta = T_{target} \cdot \omega \qquad (5)$$

where T is the measured temperature, $T_{target}$ is the user defined temperature set point, and $\beta$ is the gain adjustment expression where $\omega$ is the coefficient affecting the slope between maximum and minimum pulse delivery rate. FIG. 1B is a graph illustrating the effect of $\omega$ on the Heaviside step function. The choice of value for the parameter $\omega$ affects the behavior of $\rho$(T) by modulating how aggressively the algorithm approaches the target temperature. Values in FIG. 1B are shown for a target temperature (Ttarget) of 25° C. and w values of 0.125 (reference designator 'D'), 0.25 (reference designator 'C'), 0.5 (reference designator 'B'), and 0.998 (reference designator 'B'). A value of $\omega$=0.5 was implemented in some experiments described herein. Though the value of $\omega$ may be held constant at 0.5 for certain experiments, the value can be adjusted in some embodiments to modulate the rate at which the target temperature is achieved.

Figure 1C:
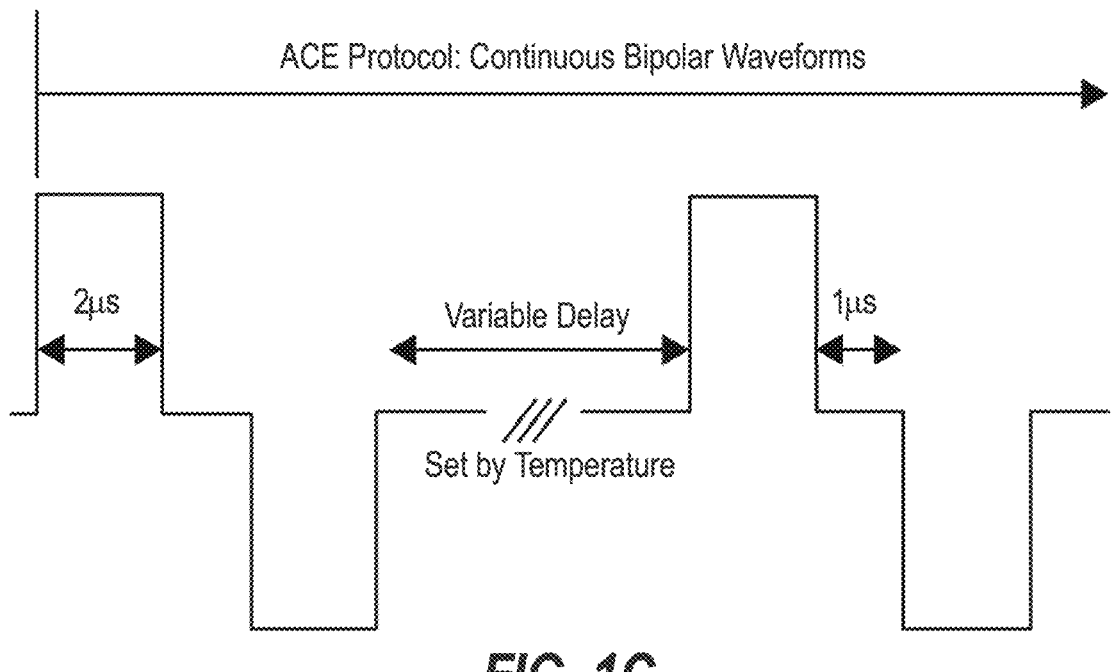
FIG. 1C illustrates treatment waveforms consistent with the treatments according to some embodiments of the present disclosure.

FIG. 1C illustrates treatment waveforms consistent with the treatments according to some embodiments of the present disclosure. The ACE protocol used in some embodiments described herein delivered bipolar 2 µs pulses with a 1 µs delay between polarity changes. The algorithm adjusts the inter-waveform delay as a function of temperature. Waveforms consisting of 2 µs bipolar pulses were delivered according to this algorithm until a user specified dose was achieved. The dose was defined by the integrated energized time (IET) which is calculated by summing the pulse widths of all applied pulses and was calculated as:

$$IET = \sum_0^N \tau_p + \tau_n [s] \qquad (6)$$

where N is the number of applied biphasic waveforms. Prior experiments have utilized IET as a metric for dosing as a simplified approach for comparing treatments across a wide spectrum of pulse widths. On this basis, 0.01 s IET was used for all in vitro experiments to approximate doses utilized in typical clinical pulsed electric field procedures and in vitro experiments which delivered 90-100× monopolar pulses or bipolar bursts with durations of 100 µs (100×100 µs=0.01 s).

Figure 2:
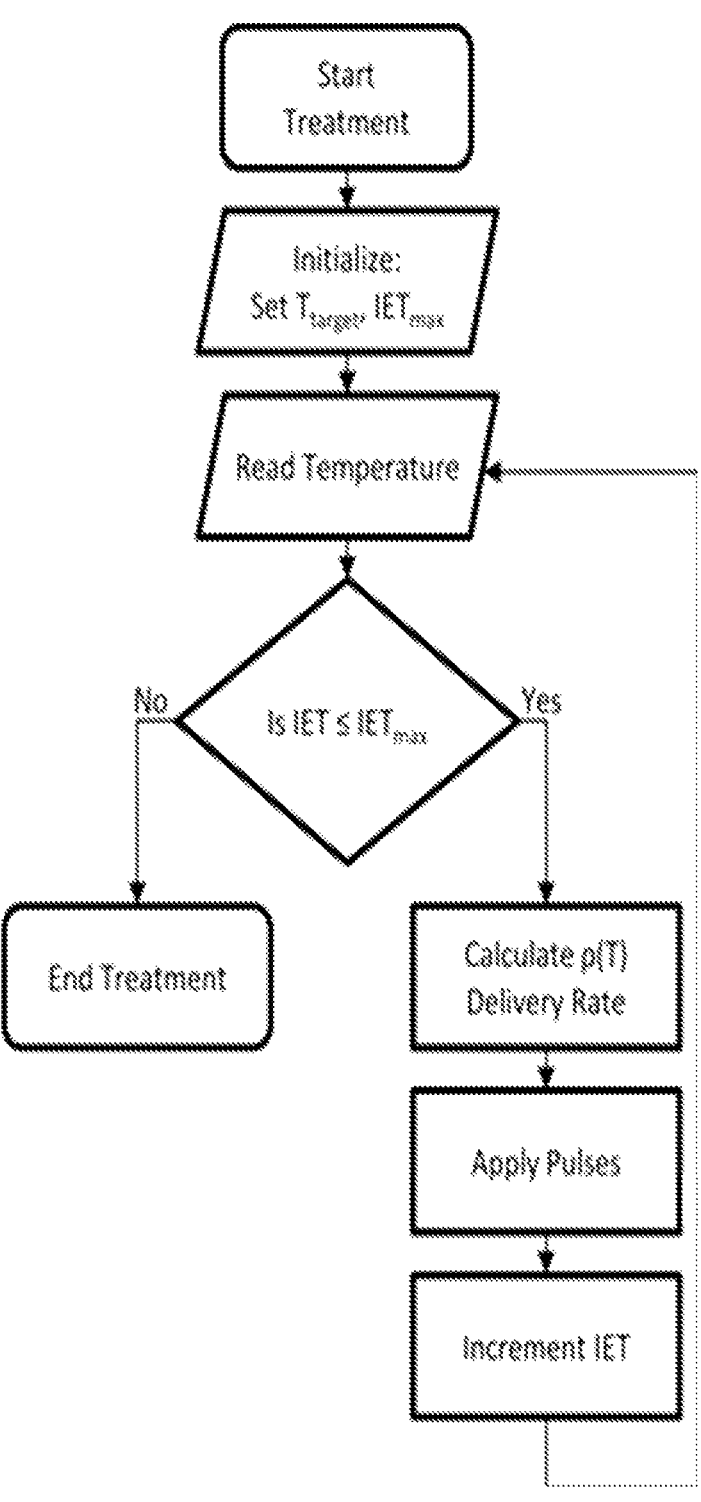
FIG. 2 is an algorithm flow chart depicting the method of temperature control by adjustment of the pulse delivery rate according to some embodiments described herein.

The previous equations were implemented in software, via a custom Python application which was used to control the pulse generator. A process flow chart describing the implementation can be seen in FIG. 2. FIG. 2 is an algorithm flow chart depicting the method of temperature control by adjustment of the pulse delivery rate according to some embodiments described herein. When the temperature is less than the target temperature, the maximum delivery rate is set by the user. In the event that the temperature is higher than the Ttarget, the rate of pulse delivery is decreased. A steady state temperature is established when the delivery rate is constant.

In operation, the user specifies the max temperature ($T_{max}$) and treatment IET ($IET_{max}$). Using a temperature sensor, the instantaneous temperature at the center of the treatment zone is read. The IET of the administered dose is then determined by summing the durations of all previously administered pulses (e.g. Equation 6). If the IET is greater than or equal to $IET_{max}$ the treatment is completed. Otherwise, the instantaneous temperature is used to calculate the energy delivery rate (2-5). Pulses are then applied according to the calculated rate. Upon completion of the pulse delivery, the IET is incremented and the temperature is rechecked restarting the feedback loop.

Algorithmically Controlled Electroporation System

Figure 3A:
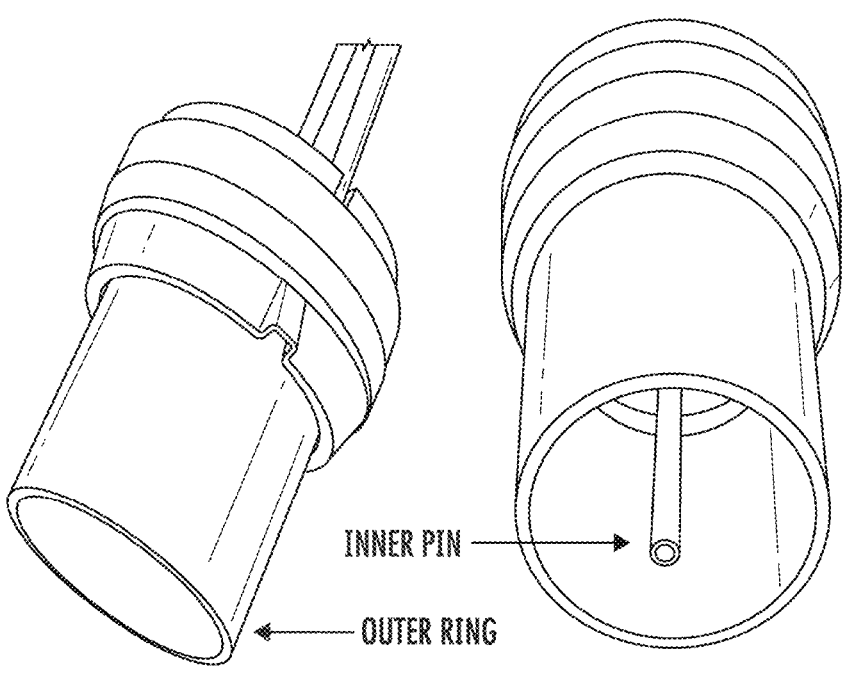
FIGS. 3A and 3B illustrates an electroporation system according to some embodiments of the present disclosure.
Figure 3B:
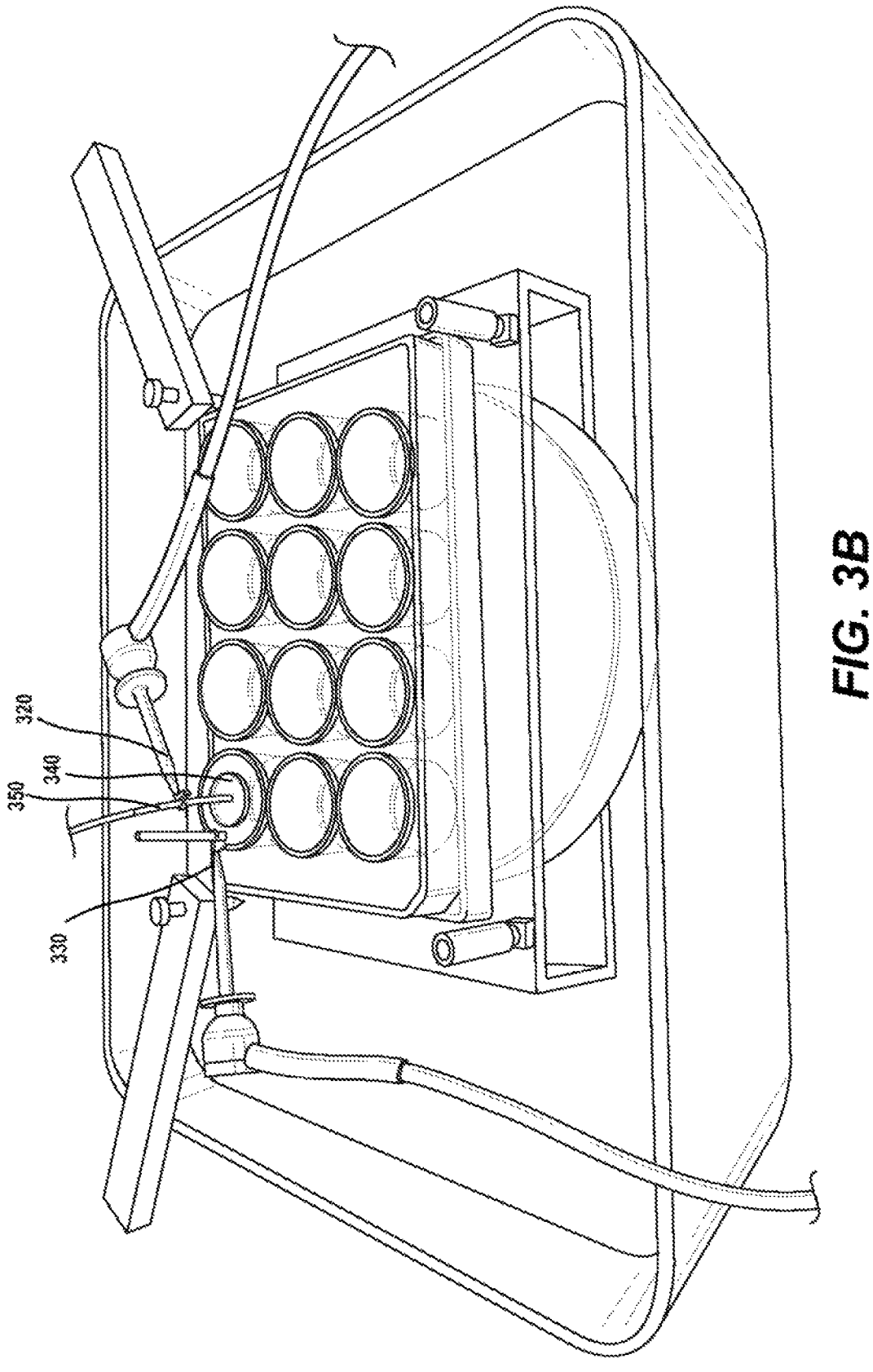

The temperature control algorithm was integrated with a pulse power supply and temperature sensor to create an algorithmically controlled electroporation (ACE) system. FIGS. 3A and 3B illustrate an electroporation system according to some embodiments of the present disclosure. The supply's voltage and current transients have previously been verified both in vitro and in ex vivo tissue. Briefly, the electronics system used in the experiments was a solid state switched square wave generator with a 20 µF capacitor bank. Biphasic pulses were created using an H-bridge topology. Examples of similar systems are described, for example, in publication M. B. Sano et al., "Burst and continuous high frequency irreversible electroporation protocols evaluated in a 3D tumor model," Phys Med Biol, vol. 63, no. 13, p. 135022, Jul. 6, 2018, publication M. B. Sano et al., "Reduction of Muscle Contractions during Irreversible Electroporation Therapy Using High Frequency Bursts of Alternating Polarity Pulses: A Laboratory Investigation in an Ex Vivo Swine Model," J. Vasc. Interv. Radiol., 2017, and International Patent Application Publication WO2019/232358 to Michael Sano, et al., published on Dec. 5, 2019. The load was a coaxial or ring-and-pin electrode as shown in FIG. 3A which has been modeled using a finite element model and validated in vitro. The coaxial electrode consists of a stainless-steel outer conductor, hollow inner conductor, and a laser cut acrylic securing ring. The outer ring was fabricated from 19 mm outer diameter 0.89 mm thick 316 stainless steel tubing (89785K259, McMaster-Carr, Douglasville, GA). The inner pin was fabricated from a 1.64 mm outer diameter blunt 304 stainless steel dispensing needle (75165 A552, McMaster-Carr, Douglasville, GA). The ring and pin assembly was held in place using a friction fit to a custom laser cut acrylic holder and an electrical connection to the outer ring was made via a friction fit to a 1.64 mm outer diameter blunt 304 stainless steel dispensing needle. The experimental setup is shown in FIG. 3B. The assembly was designed to hold the electrodes 340 flush against the bottom at the center of a 12-well culture dish. The coaxial electrode 340 is inserted into a single well of the 12-well culture dish and the fiber optic temperature sensor 350 is inserted into the center electrode. Test leads 320, 330 make the electrical connection to the pulse generator.

Temperature was monitored using an electro-optic temperature probe with an accuracy of ±0.2° C. (TS5, Micronor Inc., Camarillo, CA) placed inside the center conductor of the electrode's inner pin. Temperatures were acquired by a signal conditioner (Fotemp, Micronor Inc., Camarillo, CA) and recorded at 3 Hz. Occasional artifacts from communications errors between the signal conditioner and the pulse generator were removed in post-processing. Refinements to the system to improve EMI management ultimately rendered error correction obsolete.

Validation of ACE Temperature Control

To validate the operation of the combined temperature control algorithm and pulsed power supply, a probing of the spatial temperature distribution was conducted. To perform this, the temperature sensor was placed inside the hollow center conductor of the coaxial electrode. To the electrode one of three pulse sequences were applied. The basis of all three pulsed power treatments was a biphasic waveform with a transient consisting of a 2 µs positive phase, 1 µs delay, and a 2 µs negative phase, referred to here as a 2-1-2 waveform.

Figure 4A:
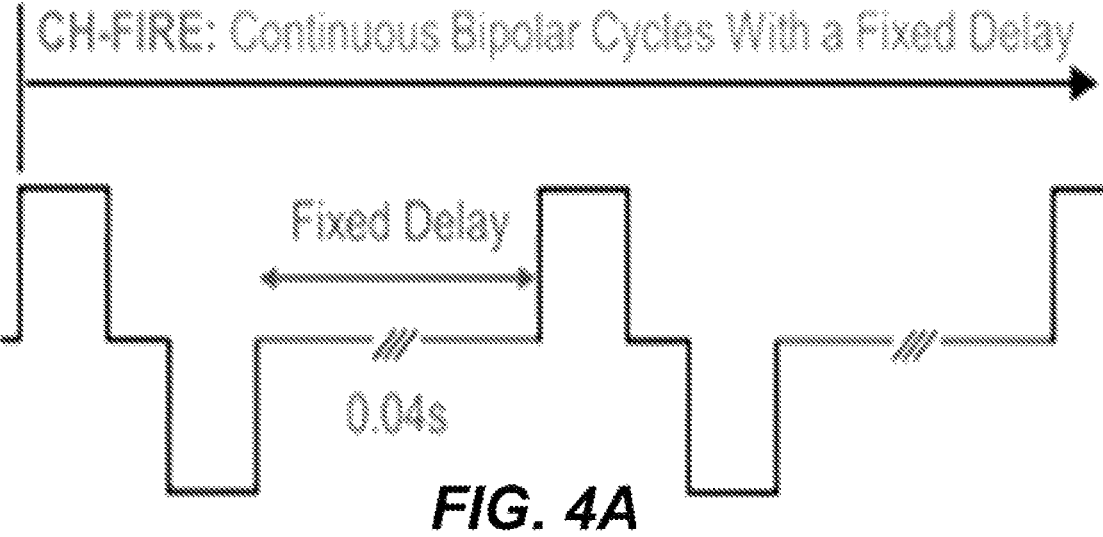
FIGS. 4A and 4B illustrate waveforms of treatment options, according to some embodiments of the present disclosure.
Figure 4B:
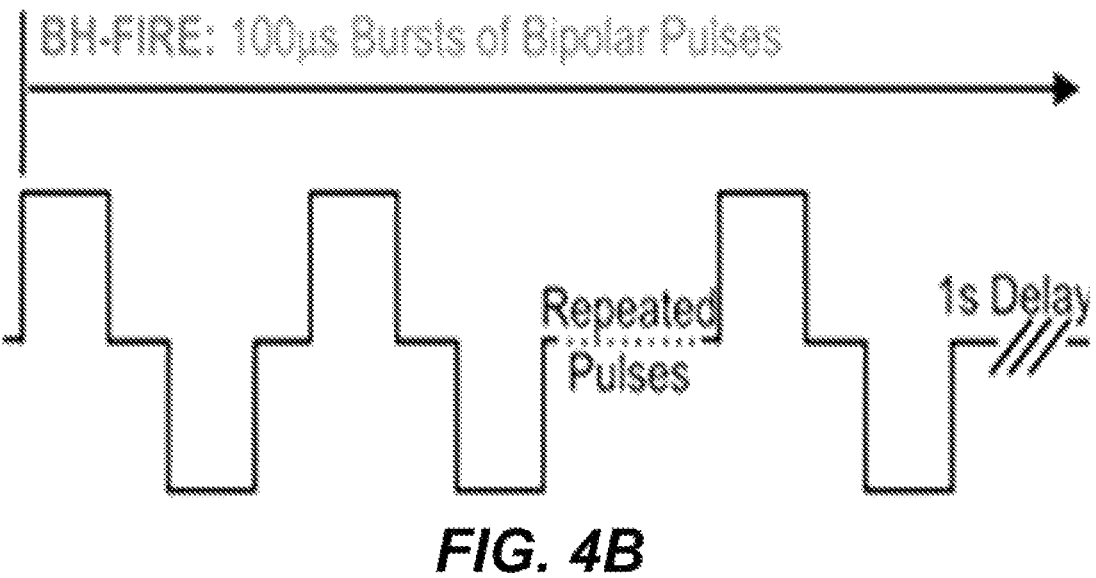

FIGS. 4A and 4B illustrate waveforms of treatment options, according to some embodiments of the present disclosure. FIG. 4A illustrates CH-FIRE treatments delivered at a 2-1-2 waveform (2 µs positive phase, 1 µs delay, 2 µs negative phase) continuously with a 0.04 s delay between waveforms (25 Hz) until an 0.01 s IET dose was delivered (100 s). FIG. 4B illustrates BH-FIRE treatments that repeat the 2-1-2 waveform 25 times in a rapid burst followed by a 1 second delay. These bursts are repeated 100× at 1 Hz to achieve a 0.01 s IET dose. FIG. 1C illustrates that ACE treatments deliver a 2-1-2 waveform followed by a variable delay determined by the temperature control algorithm. These waveforms are delivered 2500× to achieve a 0.01 s IET dose. First, a continuous high frequency irreversible electroporation (see FIG. 4A) treatment, which has previously been used in vitro without temperature control, was conducted. The treatment protocol for this was 2-1-2 waveforms delivered 2500× with a repetition rate of 25 Hz (e.g. R(T)=100 µs/s). This treatment had an integrated energized time of 0.01 s (e.g. 2500×4 µs=0.01 s). Next, a burst high frequency electroporation (see FIG. 4B) treatment, which has been demonstrated in vitro and in vivo, was conducted. This consisted of rapidly delivered 2-1-2 waveforms repeated 25× to create a 100 µs burst which was repeated 100× with a repetition rate of 1 Hz (e.g. R(T)=100 µs/s, IET=100×100 µs=0.01 s). Finally, for the ACE treatment a total of 2500× 2-1-2 waveforms were applied with the delivery rate being adjusted by the algorithm (see FIG. 1C). For the algorithm inputs, $R_{max}$ was 200 µs/s and the target temperature ($T_{target}$) was 25° C. To investigate the effects of applied voltage on the control algorithm's behavior and biological outcomes, each of these three treatment regimens were investigated with applied voltages of 500V, 750V, and 1000V with an initial baseline temperature of 20° C.

To investigate the effects of target temperature ($T_{target}$) on biological outcomes a series of ACE experiments were conducted (0.01 s IET, 1000V, 2-1-2 waveforms) with an initial baseline temperature of 20° C. and target temperatures ($T_{target}$) of 25° C., 30° C., 35° C., and 42° C. This maximum temperature was chosen to prevent melting of the collagen hydrogels, which occurs at approximately 43-45° C., from confounding the results.

Figure 5A:
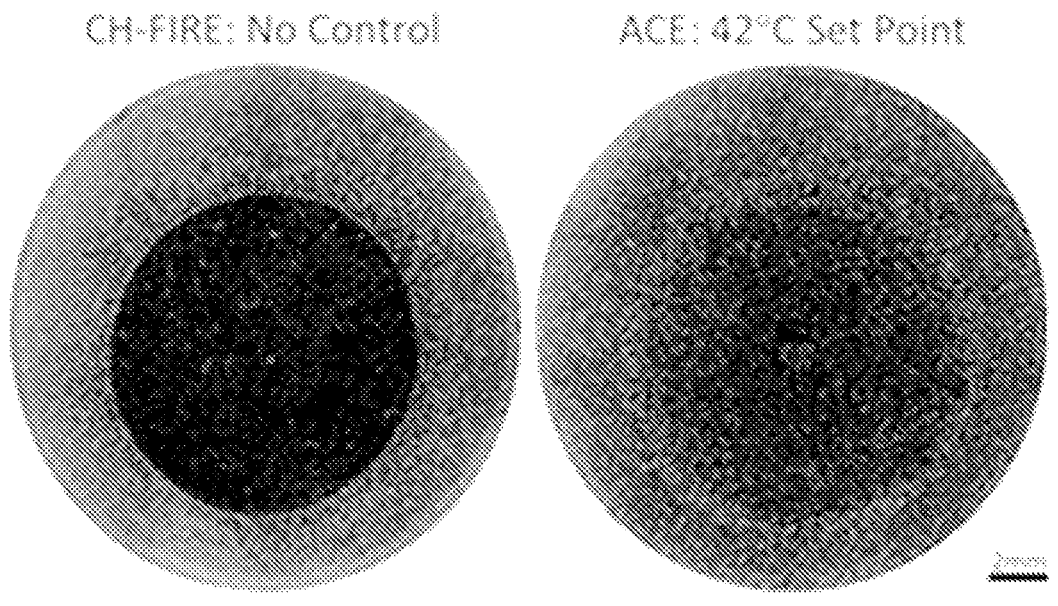
FIGS. 5A and 5B illustrate outcome comparisons according to some embodiments of the present disclosure.
Figure 5B:
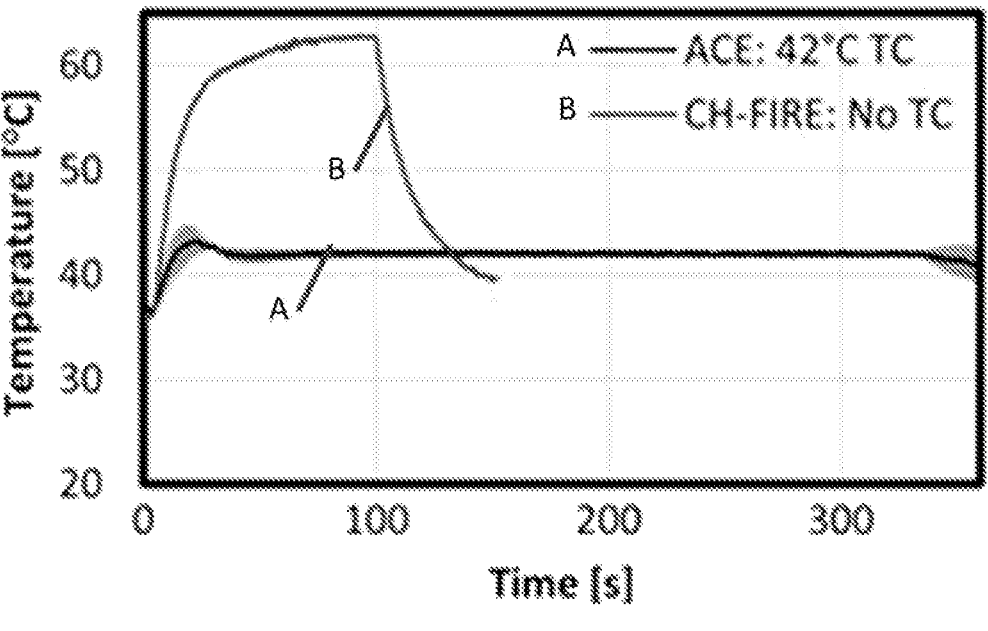

To investigate the effects of baseline temperature on biological outcomes ACE experiments were conducted (0.01 s IET, 1000V, 2-1-2 waveforms) with an initial temperature of 37° C. and a target temperature ($T_{target}$) of 42° C. Matched uncontrolled, open loop CH-FIRE treatments (0.01 s IET, 1000V, 2-1-2 waveform, 100 µs/s) resulted in abrupt melting of the collagen hydrogels. FIGS. 5A and 5B illustrate outcome comparisons according to some embodiments of the present disclosure. FIGS. 5A and 5B illustrate comparison of outcomes for 1 kV 0.01 s IET treatments starting at 37° C. with CH-FIRE (left image in FIG. 5A) delivered at a rate of 100 µs/s without temperature control and ACE (right image in FIG. 5A) using a 42° C. set point. The CH-FIRE treatments resulted in the rapid melting and distortion of the collagen tumor mimics inhibiting the ability to accurately measure the treatment diameter. FIG. 5B illustrates temperature profiles from the CH-FIRE (n=1) and ACE treatments (n=4). The shaded areas represent on standard deviation from the mean where applicable.

Figure 6A:
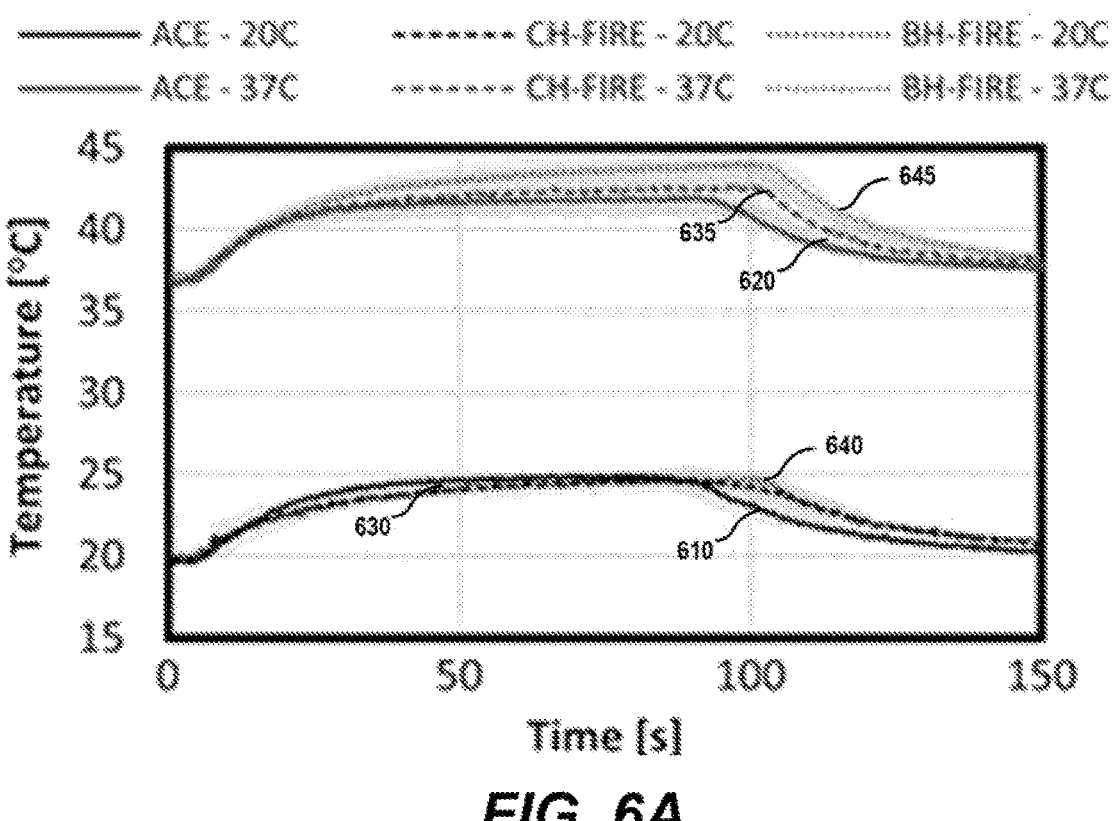
FIGS. 6A to 6D illustrate outcome comparisons according to some embodiments of the present disclosure.
Figure 6B:
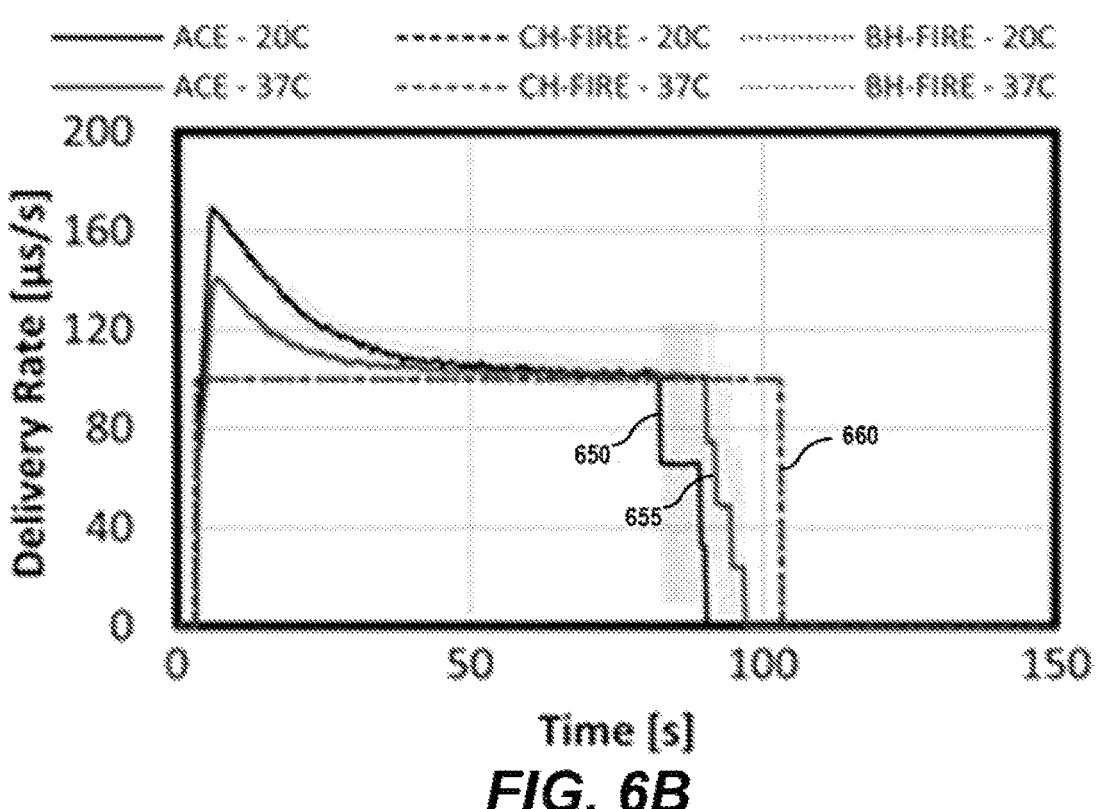
Figure 6C:
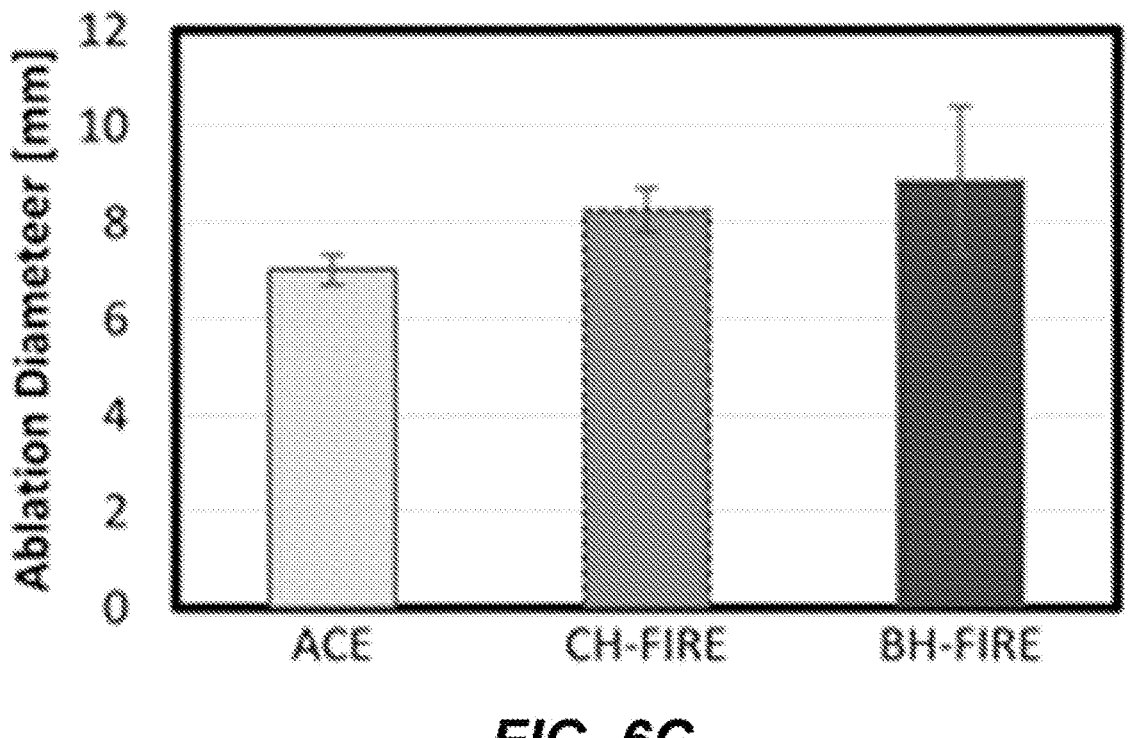
Figure 6D:
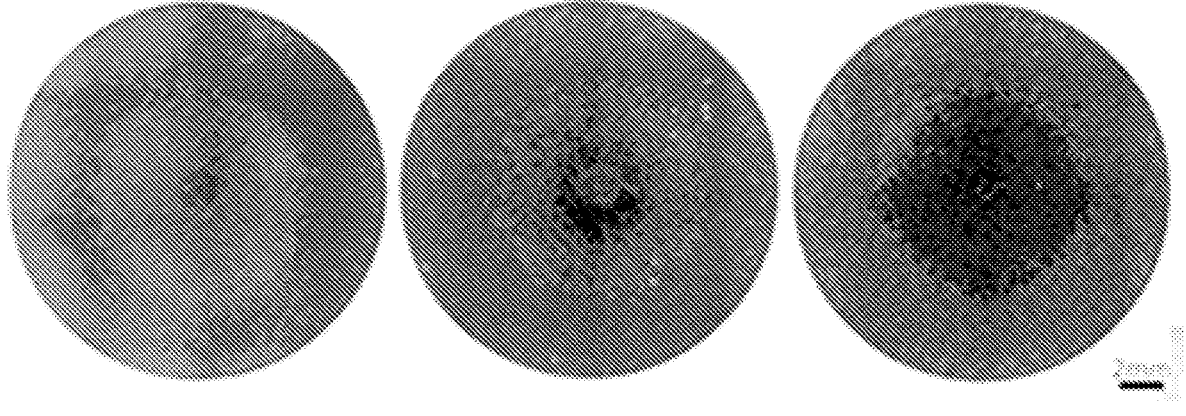

This experimental setup had previously been tuned to achieve an approximate 5° C. temperature rise when 500V treatments were administered at a rate of 100 µs/s which was additionally re-validated here for CH-FIRE, BH-FIRE, and ACE treatments starting at 20° C. and 37° C. FIGS. 6A to 6D illustrate outcome comparisons according to some embodiments of the present disclosure. FIG. 6A illustrates temperature transients representative of 0.01 s IET treatments with initial temperatures of 20° C. (solid line 610) and 37° C. (solid line 620). Compared to CH-FIRE (dashed lines 630 for 20° C., 635 for 37° C.) and BH-FIRE (dotted lines 640 for 20° C., 645 for 37° C.), ACE treatments (solid lines 610, 620) have a lower peak temperature but shorter treatment times. FIG. 6B illustrates dynamic energy delivery rates throughout the treatments. It should be noted that the CH-FIRE and BH-FIRE energy delivery rate (100 µs/s) was tuned to minimize heating above 42° C. to prevent thermal damage to the collagen hydrogel matrix prior to implementation of the temperature control algorithms. In FIG. 6B, line 650 illustrates ACE at 20° C., line 655 illustrates ACE at 27° C., and line 660 illustrates the CH-FIRE and BH-FIRE energy delivery. FIG. 6C illustrates mean ablation diameters for the 37° C. treatments. FIG. 6D illustrates representative ablations for the 37° C. treatments, where the left image is a result of ACE treatments, the middle image is a result of CH-FIRE treatments, and the right image is a result of BH-FIRE treatments.

Figure 7A:
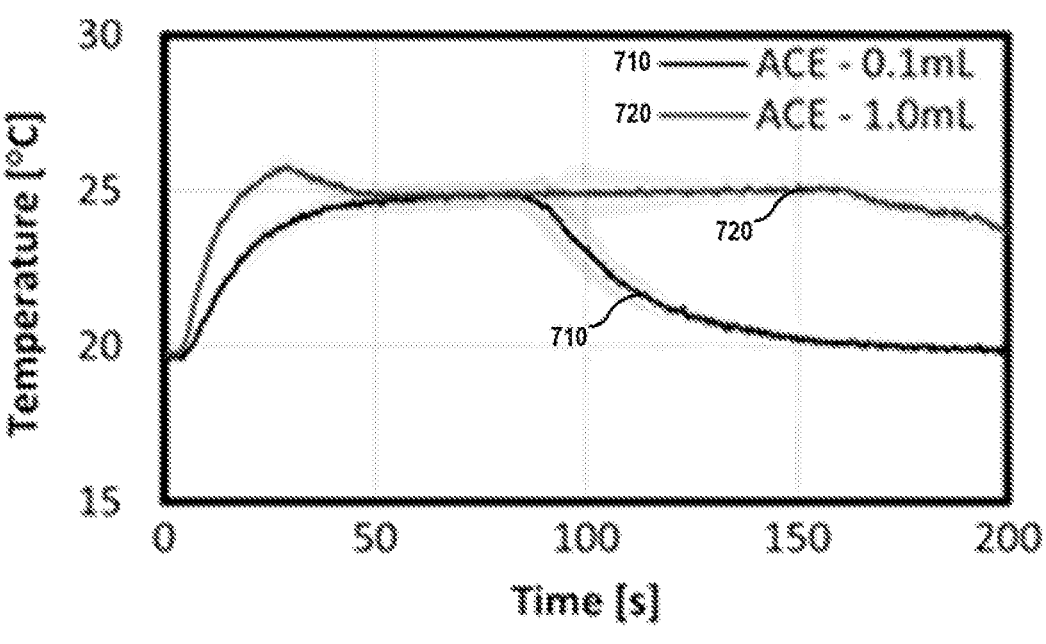
FIGS. 7A to 7D illustrate outcome comparisons according to some embodiments of the present disclosure.
Figure 7B:
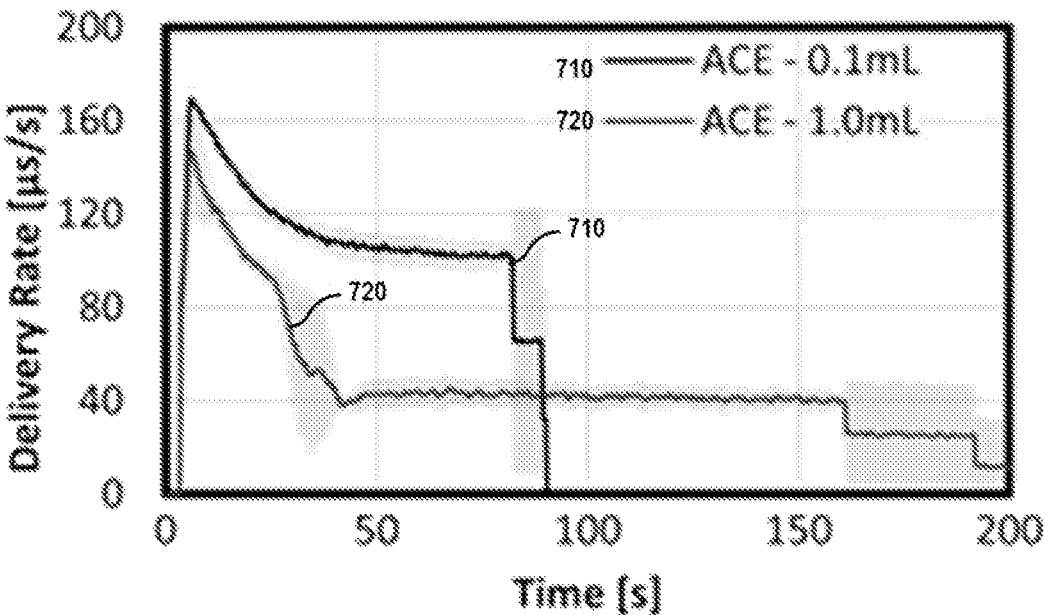
Figure 7C:
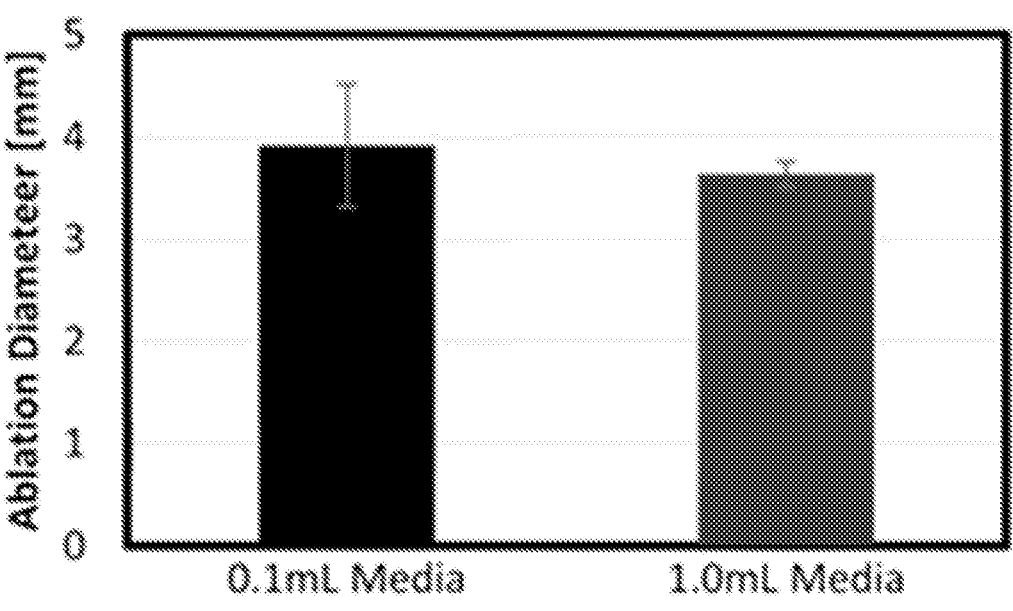
Figure 7D:
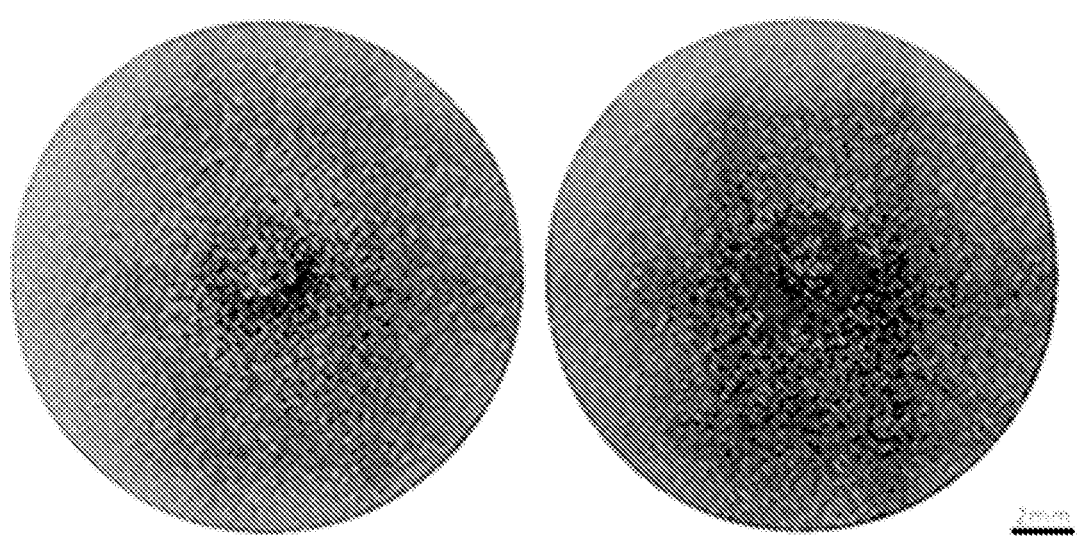

As a matter of experimental consistency, the volume of the collagen hydrogel and supplemental media were fixed to 500 µL and 100 µL, respectively, in the experiments as described below. However, an additional experimental group was conducted with 1000 µL of supplemental cell culture media to investigate how elevated treatment currents and resulting increased rate of Joule heating affected the ability of the algorithm to maintain adequate temperature stability. All experiments were conducted a minimum of three (N=3) times and data is presented as mean±standard deviation. FIGS. 7A to 7D illustrate outcome comparisons according to some embodiments of the present disclosure. FIGS. 7A to 7D illustrate that temperature control rapidly adjusts to variability in experimental conditions. FIG. 7A is a graph of temperature plots and FIG. 7B is a graph of delivery rates for 500V ACE treatments when individual 12-wells had 0.1 mL (line 710) and 1.0 mL (line 720) of cell culture media above the 3D tumor models. The temperature control algorithm rapidly accounts for the increased conductivity and resulting Joule heating associated with a 10× increase in media within the wells. FIG. 7C is a bar graph illustrating ablation diameters the 0.1 mL and 1.0 mL treatment groups and FIG. 7D are example ablations for the 0.1 mL (left image) and 1.0 mL (right image) treatment groups.

Figure 8A:
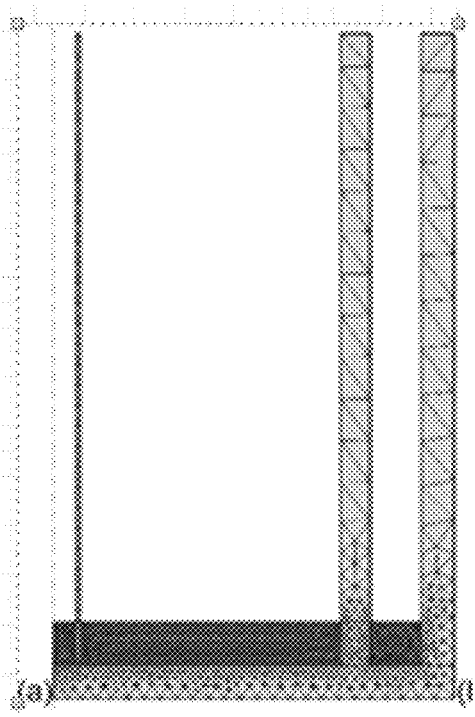
FIGS. 8A to 8C illustrate models used in numerical simulations according to some embodiments of the present disclosure.
Figure 8B:
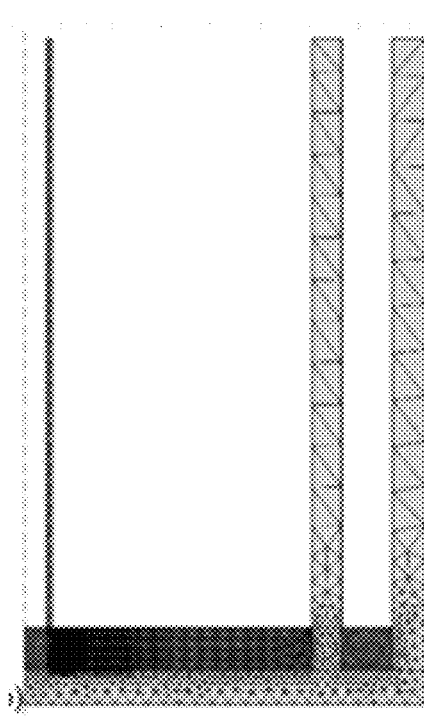
Figure 8C:
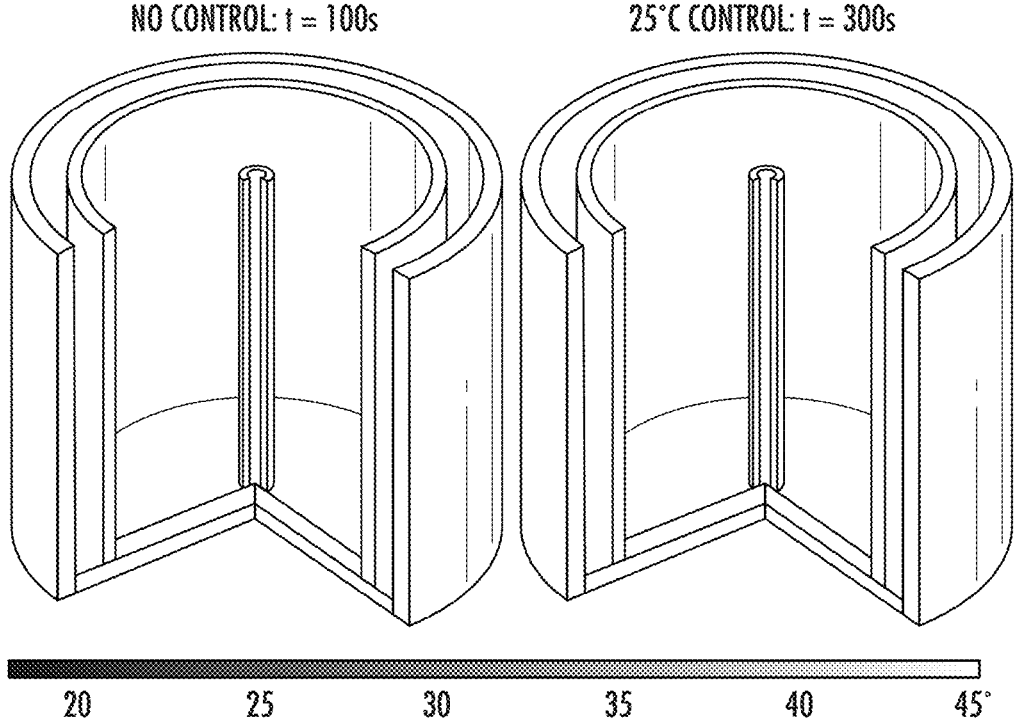

Finally, it was of interest to determine how the temperature varied spatially within the region around the electrode to supplement data generated in numerical simulations. FIGS. 8A to 8C illustrate models used in numerical simulations according to some embodiments of the present disclosure. FIGS. 8A to 8C illustrate numerical simulations to predict the temperature distribution within the 3D tumor during H-FIRE and ACE treatments. FIG. 8A illustrates the initial axisymmetric mesh and FIG. 8B illustrates a refined mesh having a dense mesh in regions where temperature and electric field were of interest. FIG. 8C illustrates the resulting temperature distributions following 1 kV 0.01 s IET treatments without temperature control (left image) and continuous delivery at a rate of 100 µs/s and with dynamic temperature control with a 25° C. temperature set point (right image). It should be noted that these treatments required 100 s and 300 s to complete, respectively.

In a subset of experiments, with the center pin acting as the temperature control sensor, three additional temperature sensors were used to simultaneously record data at locations approximately corresponding to the radius of observed treatment zones (2.5 mm, 4.0 mm, 5.5 mm). The use of these additional sensors slowed the hardware data sampling rate to 2 Hz resulting in less granular data and was therefore not used for the majority of experiments.

Cell Culture

Treatment of brain tumors with irreversible electroporation is of interest and is representative of an irreversible electroporation application where precise control over thermal conditions is desirable. Grade IV human glioblastoma cells (U118, HTB-15, ATCC Inc., Manassas, VA) were cultured in a complete media consisting of Dulbecco's Modified Eagle Medium (DMEM)(11965118, Gibco, Gaithersburg, MD), supplemented with 10% V/V Fetal Bovine Serum (A3160601, Gibco, Gaithersburg, MD) and 2% V/V Penicillin-Streptomycin solution (15070063, Gibco, Gaithersburg, MD) until reaching approximately 80% confluence. The cells were then harvested via trypsinization (25200056, Gibco, Gaithersburg, MD), centrifuged, and suspended in media at a concentration of $1\times10^6$ cells/mL. The cells were suspended at a 1:1 ratio in complete cell culture media and PureCol EZ gel (5074-35 ML, Advanced Biomatrix, San Diego, CA) with a final cell density of $5\times10^5$ cells/mL. 500 µL of the mixture was transferred into each well of a 12-well plates (see FIG. 3B) to create a 3D culture model approximately 2 mm in height. The mixture was then incubated for 24 hours at 37° C. to allow the collagen to solidify and for the cells to stretch out, resulting in a more physiological morphology of the cells. The collagen scaffolds were incubated with 500 µL of additional media before and after treatments. However, immediately before treatments the volume was reduced to 100 µL to ensure a consistent electrical resistance between experiments.

In Vitro Evaluation of ACE Ablation Geometry

Finally, it was of interest to determine whether closed loop temperature-controlled treatments with a dynamic pulse delivery rate produces different sized ablations than a standard open loop treatment. To test this, the 3D cell culture model was used with the ring-and-pin electrode. The three pulse protocols which were described in the temperature control verification section were then applied to the well plate. For all cell experiments, the starting temperature was 20° C. In ACE treatments the target temperature was 25° C.

Following treatment, the cells were incubated for 24 hours. Each well was then stained with 2 µL of 4 µM Calcein AM (C3100MP, Invitrogen, Carlsbad, CA) to identify viable cells (green) and 50 µL of 100 mg/mL propidium iodide (0219545825, MP Biomedicals, Santa Ana, CA) to identify dead cells (red). A Leica DMi8 microscope with a 4.2-megapixel digital camera (DFC9000GT, Leica Inc., Wetzlar, Germany) was used to capture images at 1.25× and 2.5× which were stitched together using the microscope's software (LASX, Leica Inc. Wetzlar, Germany). The electrode geometry used produced a circular region of cell death. The diameter was measured horizontally, vertically, and twice diagonally using the microscope's software. This is a technique which is representative of how tumor ablations would be described in vivo. Values from these measurements and calculations are presented as mean±standard deviation. Measurements comparing ACE to both CH-FIRE and BH-FIRE were statistically compared using a two sample t-test assuming equal variance at a significance level of α=0.05.

Computational Modeling of ACE Temperature Profiles In Vitro

To determine the electric field distribution within the 12-well a 2D axisymmetric model was used in conjunction with the Electric Currents module in COMSOL Multiphysics (V5.3, COMSOL Inc., Los Altos, CA) which solve the equations:

$$\nabla \cdot J = 0 \tag{7}$$

$$J = \sigma E \tag{8}$$

$$E = -\nabla V \tag{9}$$

where J is the local current density, s is the electrical conductivity, E is the electric field, and V is the local voltage. This system was considered electroquasistatic as the geometry can be considered electrically small compared to the skin depth and wavelength calculated for the pulses used in this study. Similarly, dielectric charging of the media was considered to be instantaneous due to the high conductivity and small relative permittivity of cell culture media.

Geometries representing a single well within a 12 well (see FIG. 3B) plate were created based on manufactures' schematics and caliper measurements with separate domains representing the plastic well, cell culture media, and the experimental electrodes.

Experimental voltages were applied to the topmost surface of the center pin electrode. The top surface of the outer ring electrode was set to ground:

$$V = 0 \, [V] \tag{10}$$

All external domain boundaries which did not contact another domain (e.g. the interface between plastic and air) were set as electrical insulation:

$$n \cdot J = 0 \tag{11}$$

The electrical conductivity ($\sigma$) was set to $4\times10^6$ S/m for the electrodes and $1\times10^{-6}$ S/m for the plastic well plate components. Media conductivity (am) was calculated using a dynamic temperature dependent conductivity function[2]:

$$\sigma_m(T)=0.0284\cdot T+\sigma_i \qquad [12]$$

where $\sigma_i$ was a baseline conductivity parameter determined via a parametric analysis (0.25 S/m) to match the temperature profiles observed in preliminary experiments. Heat transfer and Joule heating calculations were completed using the Heat Transfer in Solids and Electromagnetic Heating modules in COMSOL which combined solve the equations:

$$\nabla\cdot(-k\nabla T)=Q_h \qquad [13]$$

$$Q_h=R(T)J\cdot E \qquad [14]$$

where k is the thermal conductivity, T is the local temperature, and $Q_h$ is the electromagnetic Joule heating associated with energy delivery. $Q_h$ was scaled by a factor R(T) which was equivalent to energy deliver rate to account for the dynamic duty cycle associated with active temperature control. Simulations of with dynamically controlled energy delivery rates were algorithmically controlled to set the Joule heating condition to zero once a specified integrated energized time (IET) was achieved. This enabled the investigation of heat dissipation after treatment delivery.

A free tetrahedral mesh was generated in the media domain with minimum and maximum element sizes of 1.21 $\mu$m and 200 $\mu$m, respectively. All other domains had initial maximum and minimum element sizes of 0.02 cm maximum and $1.21\times10^{-4}$ cm, respectively. For each simulation four rounds of adaptive mesh refinement were conducted using a functional error indicator with the equation root.comp1.efield where efield was a variable defined as the magnitude of the electric field (ec.normE) only in the media domain. The initial mesh consisted of approximately 1863 triangular elements which increased to approximately 8961 elements after four rounds of adaptive meshing. The simulations required approximately 2.8 minutes to solve for each experimental parameter on a ten core Intel i7-6950X processor with 64 GB of RAM.

ACE Validation Results

Validation of the Algorithm

Figure 9A:
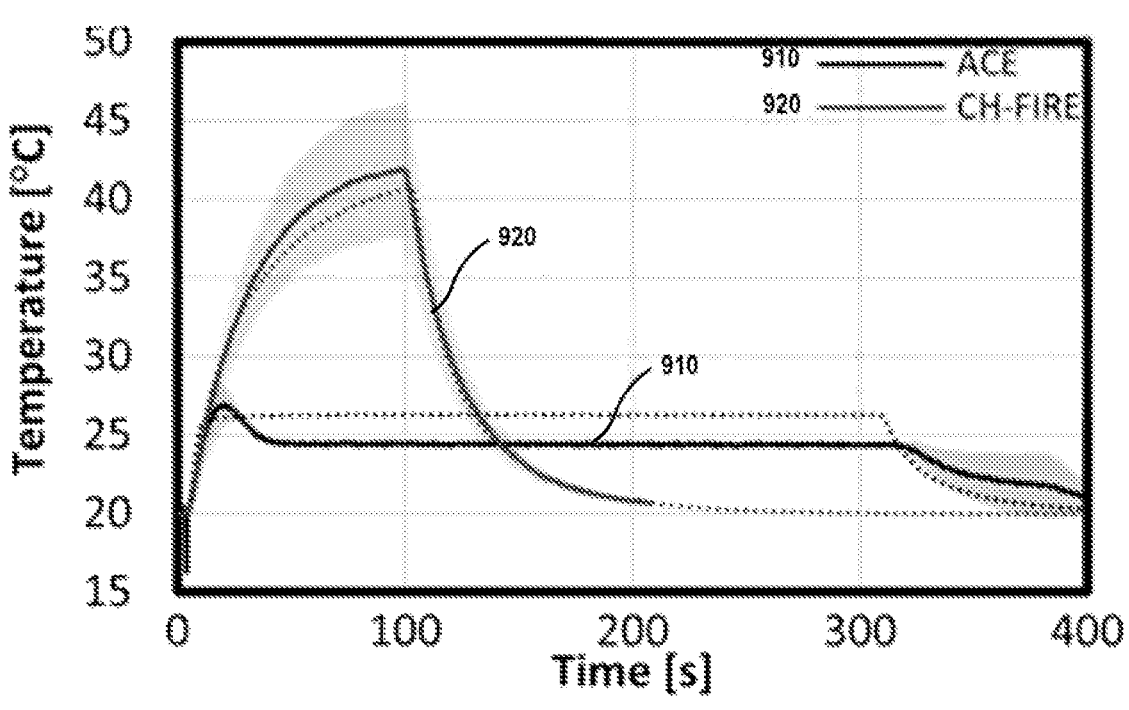
FIGS. 9A and 9B are graphs illustrating temperature transients and delivery rates for 1000V 0.01 s IET treatments with initial temperatures of 20° C. according to some embodiments of the present invention.
Figure 9B:
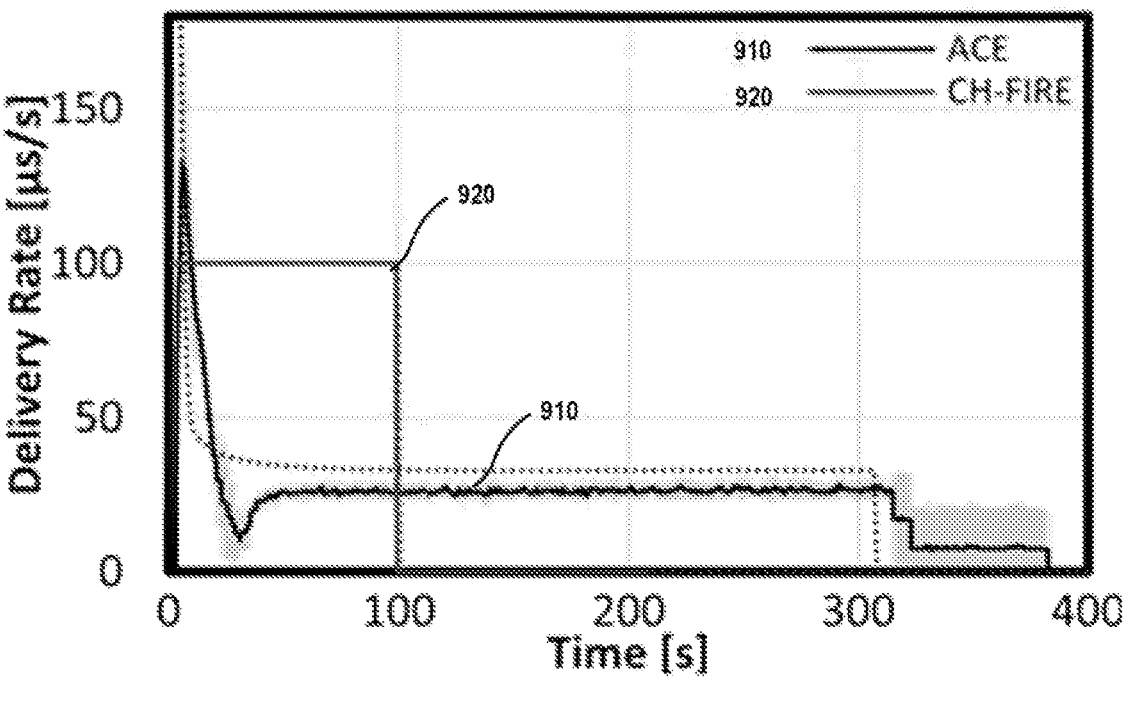

To validate the operation of the ACE algorithm and system, two initial starting temperatures with two $T_{target}$ levels were evaluated. These outcomes were then compared to a non-temperature-controlled CH-FIRE and BH-FIRE treatment. For ACE, the results show that the treatment was successful at elevating the temperature to a set $T_{target}$ and maintaining the temperature for the duration of the treatment. FIGS. 9A and 9B are graphs illustrating temperature transients and delivery rates for 1000V 0.01 s IET treatments with initial temperatures of 20° C. according to some embodiments of the present invention. Referring to FIG. 9A, ACE treatments (line 910) have a lower peak temperature but longer treatment times than uncontrolled CH-FIRE treatments (line 920). Referring to FIG. 9B, in ACE the dynamic energy delivery rates are automatically adjusted (line 910) to maintain the desired treatment temperature throughout the treatments. In contrast, CH-FIRE treatments (line 920) have a single energy delivery rate (100 $\mu$s/s) throughout the treatment. Solid lines represent mean experimentally measured temperatures, dotted lines represent simulated temperatures, and shaded areas represent one standard deviation from the mean. The temperature transient (see FIG. 9A) shows that for a programmed 5° C. increase, the temperature reaches the intended $T_{target}$ after approximately 11 s of energy delivery.

For both ACE and CH-FIRE the profile of the temperature increase was approximately exponential. After the initial temperature increase in ACE, the temperature waveform had a flat top with an average temperature of 24.4±0.3° C. for the $T_{target}$=25° C. treatment. In contrast, the matching CH-FIRE treatment reached a peak temperature of 42.0±4.2° C. These treatments were completed after 340.1±36.9 s and 100.0±0.0 s respectively.

These temperature results are mirrored in the temporal development of the pulse delivery rate (see FIG. 9B). Initially in ACE, the pulse delivery rate was set to 200 $\mu$s/s. Due to the rapid increase in temperature, there was a reduction in the pulse delivery rate governed by Eq. 2-5. For the 25° C. treatment the steady state pulse delivery rate was 26.7±7.8 $\mu$s/s; whereas, the pulse delivery rate was 100 $\mu$s/s for the matched CH-FIRE and BH-FIRE treatments.

An overshoot of approximately 2° C. was observed for 1 kV ACE treatments with a 25° C. temperature set point which was mirrored in the numerical simulations (see FIG. 9A). This was accounted for experimentally by incrementally decreasing the energy delivery rate when sustained temperatures above the set point were detected. Overshoot was not observed for 500V ACE treatments where 0.1 mL of supplemental media was added to the wells (the standard, protocol, see FIGS. 6A to 7D), but was observed in experiments where 1.0 mL of media were present in the wells (see FIGS. 7A to 7D) indicating that treatment current, rate of heating, treatment load impedance, and temperature set points affect algorithmic performance.

In contrast to ACE treatment, both the CH-FIRE and BH-FIRE treatments had a significant increase in temperature beyond the $T_{target}$ used for ACE with no steady state temperature being reached across the voltage range tested. Temperature increases only stopped when the full IET was delivered and treatment was stopped. Both CH-FIRE and BH-FIRE had a constant pulse delivery rates of 100 $\mu$s/s (see FIG. 9B).

Figure 10A:
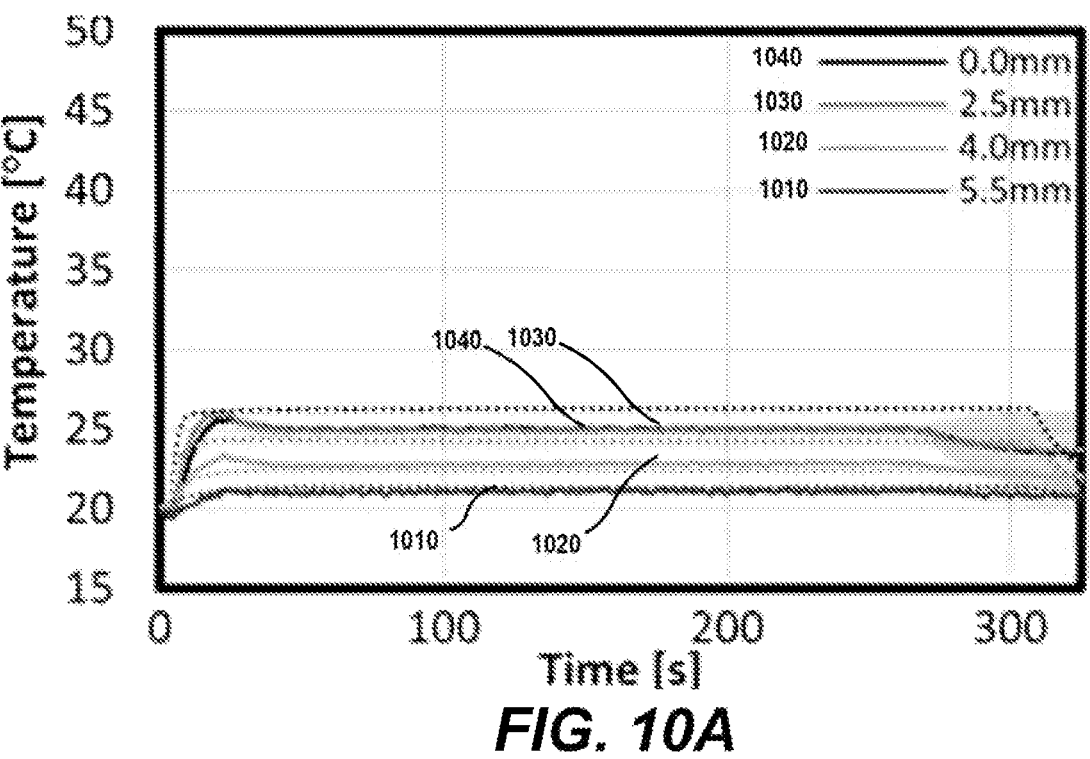
FIGS. 10A and 10B are graphs of temperature near the treatment electrode, according to some embodiments of the present invention.
Figure 10B:
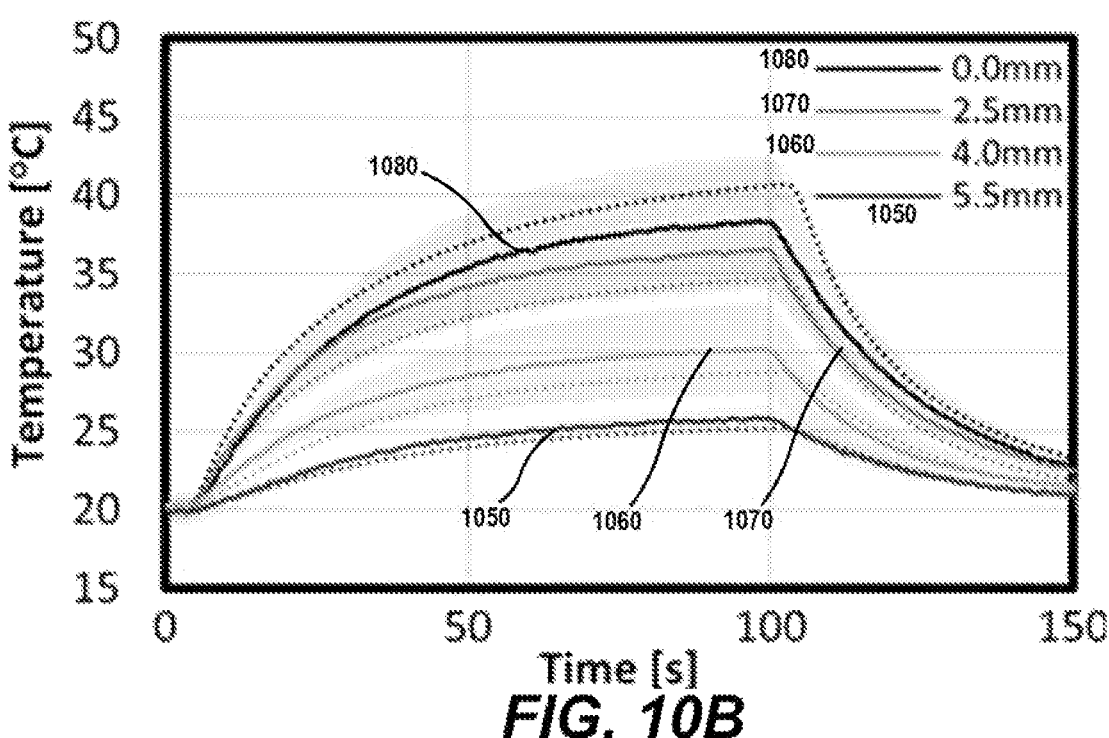

FIGS. 10A and 10B are graphs of temperature near the treatment electrode by distance, according to some embodiments of the present invention. FIGS. 10A and 10B illustrate that the temperature around the center electrode decreases radially. Referring to FIG. 10A, in 1 kV ACE treatments there is a rapid increase in temperature to the set point of 25° C. at the center of the coaxial electrode (line 1040). The temperature increases throughout the gel in a transient manner which mirrors the center electrode. At a radius of 5.5 mm (line 1010) the ACE treatment has a peak temperature of 21.2° C. Referring to FIG. 10B, in CH-FIRE treatments the temperature increases throughout the 100 s of treatment time. At the center electrode (line 1080) the temperature reached a mean peak of 38.3° C. The temperature gradient extended outward reaching a temperature of 25.2° C. at a radius of 5.5 mm (line 1050). In FIGS. 10A and 10B, solid lines represent mean experimentally measured temperatures, dotted lines represent simulated temperatures, and shaded areas represent one standard deviation from the mean.

Outside of the central electrode, which was the feedback location used in ACE treatments, the temperature was found to vary spatially (see FIG. 10A). Points distal to the center electrode were found to have similar temperature transients to the center electrode in that there was a rapid increase in temperature which then reached a steady state value. For the points measured this was 25.0±0.3° C. at 2.5 mm, 22.8±0.2° C. at 4 mm, and 21.1±0.2° C. at 5.5 mm from the treatment center.

The temperature around the center electrode in the 1000V CH-FIRE treatments were also found to vary spatially reaching mean peak temperatures of 36.6±1.4° C. at 2.5 mm, 30.2±1.3° C. at 4.0 mm, and 25.9±1.1° C. at 5.5 mm from the treatment center.

Biological Effects are Conditionally Temperature Dependent

Figures 11A, 11B, 11C:
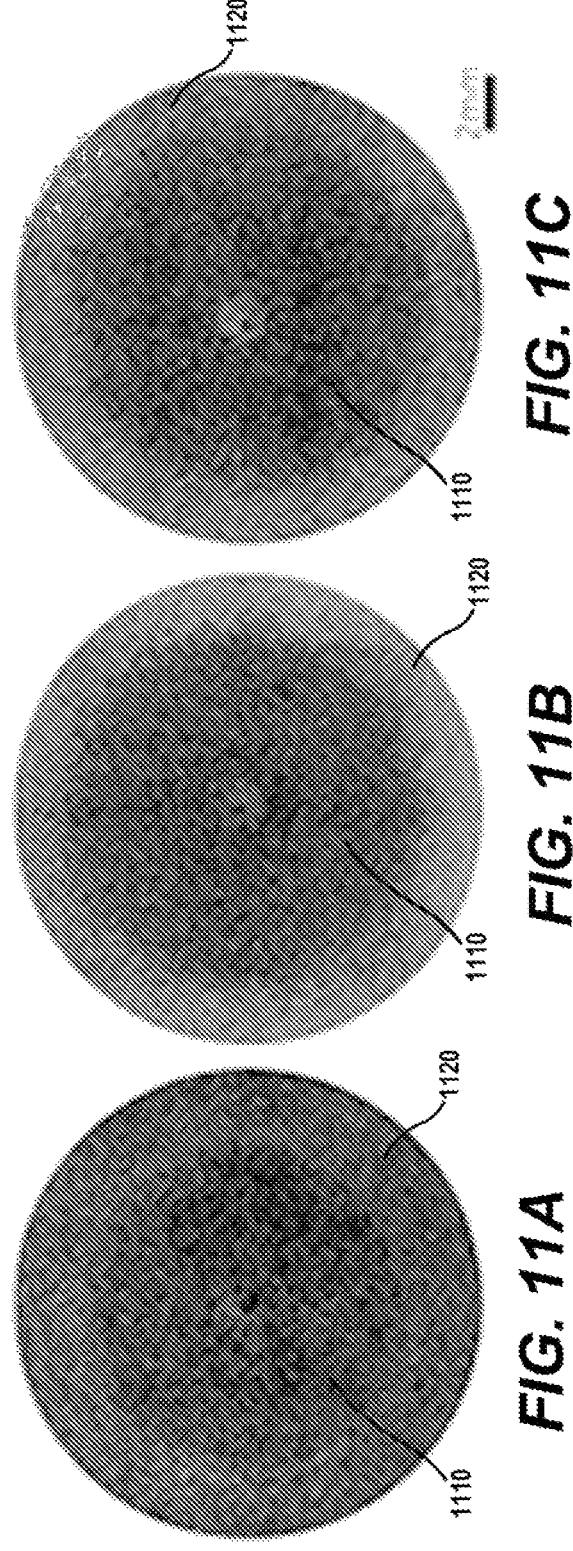
FIGS. 11A to 11C are microscope images comparing treatment ablations, according to some embodiments of the present invention.

Having established the effectiveness of the combined ACE algorithm and pulse power supply, it was of interest to determine whether ACE would produce different ablations than that of either CH-FIRE or BH-FIRE. Representative fluorescence microscopy images showing ablations of 1 kV, 0.01 s IET treatments with a baseline temperature of 20° C. can be seen in FIGS. 11A to 11C. FIGS. 11A to 11C compare ACE (FIG. 11A), CH-FIRE (FIG. 11B), and BH-FIRE (FIG. 11C) ablations following treatment with 1 kV waveforms and an IET of 0.01 s for treatments with a baseline temperature of 20° C. Cell death is indicated by the red propidium iodide staining (designator 1110) and live cells are green due to activated Calcein AM. The presence of live (green, designator 1120) cells in the center of the treatment zones indicate that cells were unaffected by temperature transients and were not exposed to lethal electric fields inside of the hollow pin electrode. Generally, the shape of the ablation was circular around the center electrode which is characteristic of the electrode geometry. The margin or transition between live and dead cells was sharp in all three tests and similar to previous ablations using this electrode geometry.

Figure 12:
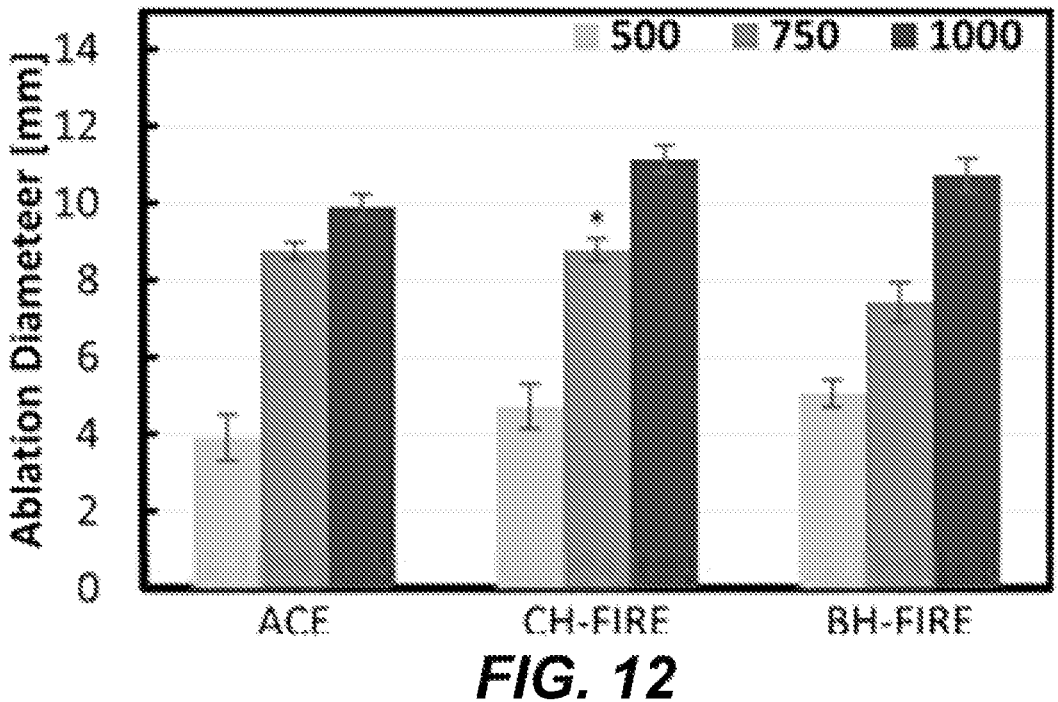
FIG. 12 is a graph illustrating a comparison of ablation sizes across pulsed electric field schemes at different voltages, according to some embodiment of the present disclosure.

Measurements of the ablation diameters were used to indicate the effectiveness of the treatment. For all treatment profiles the ablation diameter was dependent on the applied voltage. FIG. 12 is a graph illustrating a comparison of ablation sizes across pulsed electric field schemes at different voltages, according to some embodiment of the present disclosure. As illustrated in FIG. 12, the size of the ablation increases with applied voltage. At 500 V, ACE ablation diameter was different than H-FIRE and BH-FIRE with ACE producing smaller ablations. At 750 V, ACE was equivalent to H-FIRE and different than BH-FIRE with BH-FIRE being smaller. At 1000 V, ACE was different than both H-FIRE and BH-FIRE with ACE having the smaller ablation diameter. The ACE treatments had a 25° C. temperature set point. The '*' symbol in FIG. 12 indicates treatments which were found to be statistically equivalent to voltage matched ACE treatments (p=0.9).

An increase in voltage resulted in a larger ablation. The increase in ablation diameter was non-linear. For example, in ACE treatments there was a rapid increase in ablation diameter from 3.9 mm to 8.8 mm when the voltage was increased from 500 V to 750 V (125% increase). On the other hand, there was only a moderate increase in ablation size from 8.8 mm to 9.9 mm (12.5% increase) when ACE voltage was increased from 750 V to 1000 V. CH-FIRE exhibited a similar dependence on voltage. Between 500 V and 750 V there was 87% increase in ablation diameter. Whereas, between 750 V and 1000 V there was a 26% increase in the ablation diameter. In the tested voltage range BH-FIRE was approximately linear. When comparing 500 V and 1000 V, a doubling in voltage resulted in an approximate doubling of ablation diameter.

Of the protocols comparing ACE, CH-FIRE, and BH-FIRE only two pairs had ablation measurements that were found to be statistically indistinguishable, 500V BH-FIRE with 500V CH-FIRE (p=0.08) and 750V ACE with 750V CH-FIRE (p=0.9). All other treatment protocol combinations were found to have ablation measurements which were statistically different (p=0.0001-0.03). In summary, five of the six comparisons yielded ACE ablation diameters which statistically different than CH-FIRE and BH-FIRE (p<0.0001). In each of these cases, the ACE treatment zone was smaller than the equivalent CH-FIRE or BH-FIRE treatment.

Figure 13A:
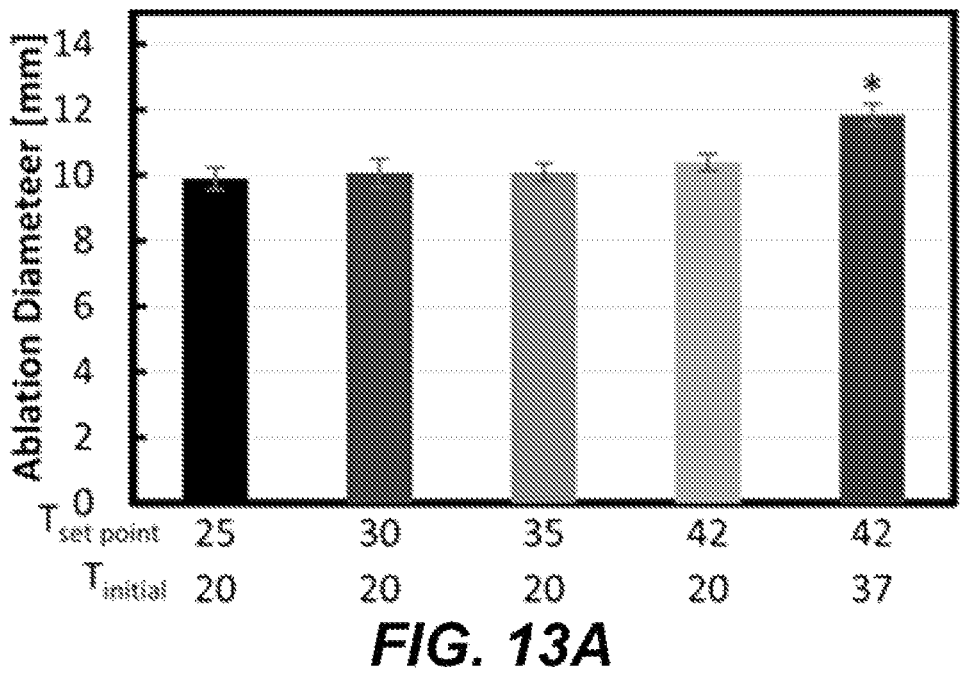
FIGS. 13A and 13B are graphs illustrating ablation diameters and temperature profiles, according to some embodiments of the present disclosure.
Figure 13B:
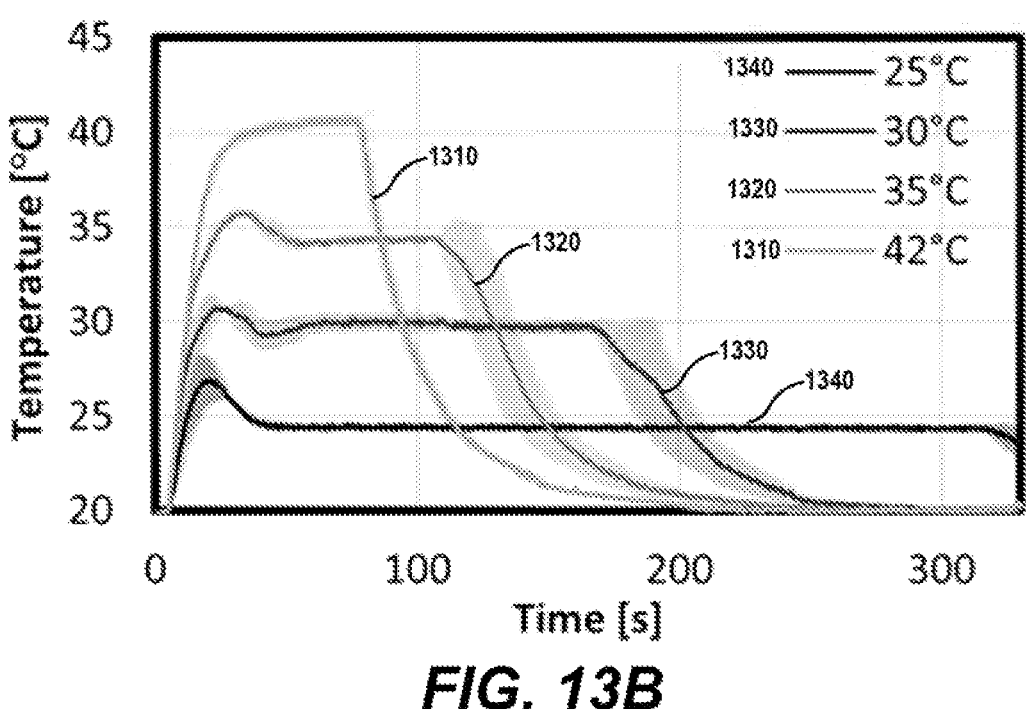

FIGS. 13A and 13B are graphs illustrating ablation diameters and temperature profiles, according to some embodiments of the present disclosure. FIG. 13A is a graph illustrating ablation diameters as a function of initial temperature ($T_{initial}$) and temperature set point ($T_{set\ point}$). FIG. 13B illustrates mean temperature profiles from these treatments where the shaded regions represent one standard deviation. In FIG. 13A, an asterisk indicates significantly significant difference from all 20° C. baseline treatments (p<0.0001). For 1 kV ACE treatments with an initial temperature of 20° C. (see FIG. 13A) the smallest ablations, measuring 9.9±0.3 mm, were created for treatments with a temperature set point of 25° C. Larger ablations were created for treatments with set points of 30° C. (10.1±0.4), 35° C. (10.1±0.3), and 42° C. (10.4±0.3). A statistically significant difference (p=0.0003) was found between the 25° C. and 42° C. temperature set point groups. Analysis of the temperature profiles (see FIG. 13B) for these treatments indicated that the 25° C. set point temperature (line 1340) was achieved in 13.2±4.0 s and the algorithm maintained a steady state temperature of 24.4±0.3° C. throughout the remainder of the treatment. The 30° C. set point (line 1330) was reached in 22.44±4.5 s and the steady state temperature was 29.8±0.3° C. The 35° C. set point (line 1320) was reached in 25.0±2.13 s the steady state temperature was 34.6±0.5° C. The 42° C. set point (line 1310) was approached, but not achieved prior to the treatment delivering the prescribed 0.01 s IET dose. In these experiments, the temperature reached 40° C. in an average of 36±5.5 s and had a mean temperature of 40.3±0.2° C. from this time (36 s) until the end of treatment.

ACE treatments with a starting temperature of 37° C. (see FIG. 5A, right image) were found to be statistically (p<0.0001) larger than any of the ACE treatments conducted with a baseline temperature of 20° C. (see FIG. 13A). These 37° C. baseline ACE treatments were also statistically larger than the 1 kV CH-FIRE and BH-FIRE treatments conducted with a baseline temperature of 20° C. (see FIG. 12, p<0.0001). Matching 1 kV BH-FIRE and CH-FIRE treatments were attempted at a baseline temperature of 37° C., however, rapid uncontrolled heating resulted in denaturing and melting of the collagen hydrogels (see FIG. 5A, left image) preventing direct comparison for these protocols.

When 500V ACE treatments were conducted with a baseline temperature of 37° C. (see FIGS. 6A to 6D) the treatment yielded peak temperatures of 42.1±0.5° C. and resulted in ablations measuring 7.0±0.3 mm. Matching CH-FIRE and BH-FIRE treatments yielded peak temperatures of 42.8±0.2 and 43.6±1.1° C. and ablations which were sequentially larger than the matching ACE treatment, measuring 8.3±0.5 mm and 8.9±1.6 mm, respectively.

Temperature Dependence of ACE Protocols

The impact of local temperatures on ablation size was investigated for pulsed electric field treatments with constitutive pulses between 1 and 100 μs. An active temperature feedback process (algorithmically controlled electrotherapy, ACE) was integrated into the pulse delivery protocol to regulate Joule heating and mitigate temperature changes as confounding variables. Experiments were conducted on cells grown in a 3D tumor platform with baseline temperatures of 10° C., 20° C., 30° C. and 37° C. The 3D tumors were exposed to treatments at 500V with integrated energized times (IET), a measure of dose independent of pulse width, between 0.01 and 0.1 s.

It was found that treatments containing constitutive pulse durations of 1, 2, 4, and 8 μs are significantly more sensitive to both local temperature and total dose than treatments with 100 μs pulse durations. At physiological temperatures, increasing the treatment dose from 0.01 to 0.1 s resulted in 39% and 7% increases in ablation diameter for treatments consisting of 1 μs and 100 μs pulses, respectively. When treatment dose was fixed to 0.1 s, increasing the baseline temperature from 20° C. to 37° C. resulted in ablation diameter increases of 66% and 4% for treatments consisting of 1 μs and 100 μs pulses, respectively. Combined, elevated temperature (20-37° C.) and dose (0.01-0.1 s) resulted in ablation diameter increases of 165%, 128%, 48%, 46%, and 34% for treatments consisting for 1 μs, 2 μs, 4 μs, 8 μs, and 100 μs waveforms, respectively. These results indicate that irreversible electroporation is a thermally mediated dose dependent ablation modality for treatments with pulses on the order of 1 μs. Using these results, it is conceivable that in vivo treatment protocols employing microsecond electrical pulses could achieve larger ablation volumes given the proper combination of dose, voltage, and treatment temperature.

Methods

Cell Culture and Treatment Imaging

Human glioblastoma cells (U118, ATCC, Manassas, VA) were used due to interest in the use of electroporation in the treatment of brain tumors. Cells were cultured in DMEM (11965118, Gibco, Gaithersburg, MD), supplemented with 10% V/V Fetal Bovine Serum (A3160601, Gibco, Gaithersburg, MD) and 2% V/V Penicillin-Streptomycin solution (15070063, Gibco, Gaithersburg, MD) until reaching approximately 80% confluence. The cells were then harvested via trypsinization (25200056, Gibco, Gaithersburg, MD), centrifuged, and suspended in fresh media at a concentration of $1 \times 10^6$ cells/mL. Three-dimensional (3D) tumor constructs were created by mixing the concentrated cell suspension with PureCol EZ gel (5074-35 ML, Advanced Biomatrix, San Diego, CA) in a 1:1 ratio to achieve a 2.5 mg/mL concentration of type 1 collagen and $5 \times 10^5$ cells/mL. 500 μL of the cell-collagen mixture was then transferred into each well of 12-well plates. The mixture was allowed to solidify overnight at 37° C. in an incubator then an additional 500 μL of media was added to keep the gels hydrated until treatment. Immediately prior to treatment, 400 μL of media was removed to limit treatment currents and was replaced with an equivalent volume of fresh media following treatment completion. The tumor models were then incubated at 37° C. for 24 hours before imaging.

Stock solutions of 1 mg/mL propidium iodide (MP Biomedicals, Santa Ana, CA) were prepared by adding 25 mL of sterile PBS (MP Biomedicals, Santa Ana, CA) to 25 mg of powdered dye and stored at 4° C. Stock solutions of 4 μM Calcein AM (Invitrogen, Carlsbad, CA) were prepared by adding 125 μL of sterile DMSO (MP Biomedicals, Santa Ana, CA) to 50 of powdered dye and stored at −20° C. A mixture containing 2 μL Calcein AM (live stain, green), 100 μL of PI (dead stain, red) stock solutions, and 100 μL of Phosphate Buffered Saline (PBS, MP Biomedicals, Santa Ana, CA) was added to each well 24 hours after treatments. The tumor models were incubated for 30 minutes followed by removal of media, and two rinse cycles with 500 μL of PBS to reduce background fluorescence. The treatment zones were imaged using a Leica DMi8 microscope with a 4.2-megapixel digital camera (DFC9000GT, Leica Inc., Wetzlar, Germany). Images of the entire well were captured at 2.5× and stitched together using the microscope's software (LASX, Leica Inc. Wetzlar, Germany).

After imaging, the cross-sectional diameters of the ablations were measured. The margin of measurement was defined as the transition from viable (green) to dead cells (red) in the images. Each ablation was measured 4 times, once in the horizontal and vertical directions, and two diagonal sections. Each parameter was evaluated a minimum of three times (N=3) yielding at least 12 measurements for each parameter which were averaged and are presented as mean±standard deviation.

Treatment Protocols

Figure 14A:
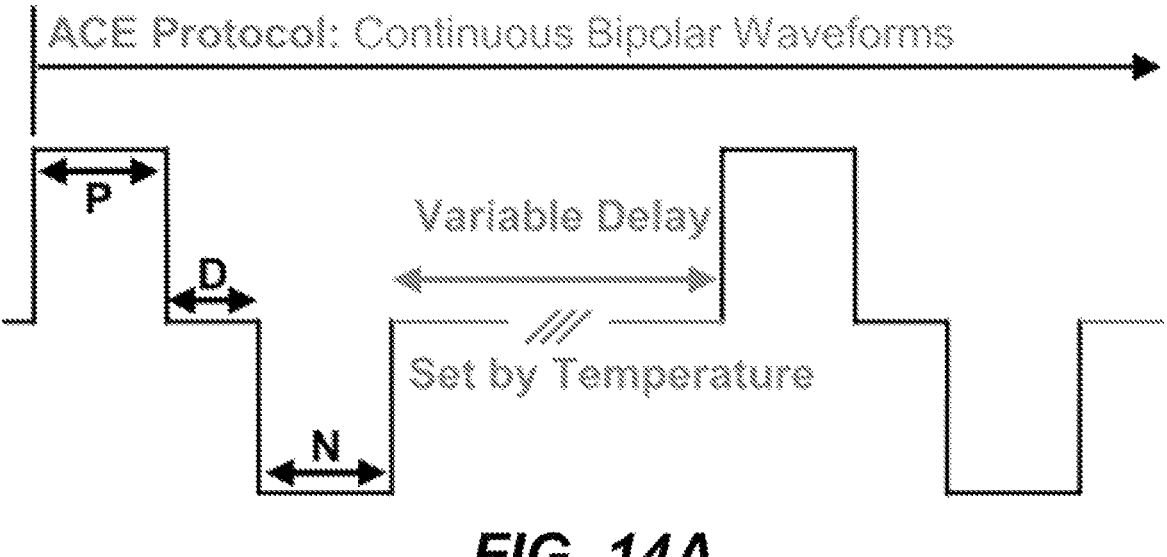
FIG. 14A illustrates treatment waveforms consistent with the treatments according to some embodiments of the present disclosure

With the goal of the selecting pulse parameters which span current clinical treatment modalities and considering the safe operating parameters of the pulse generation system utilized a series of waveforms consisting of pulses with durations between 1 μs and 100 μs were evaluated. FIG. 14A is a schematic waveform representing the ACE protocol consisting of bipolar electrical pulses with a variable delay between successive waveforms modified by a temperature control algorithm. Given their clinical utility in alleviating muscle stimulation an alternating polarity waveform consisting of a positive polarity pulse duration (P), a delay (D), and a negative polarity pulse duration (N) was investigated (see FIG. 14A) and is presented using the notation P-D-N where durations have units of microseconds [μs]. Symmetric waveforms with pulse durations of 2 μs, 4 μs, 8 μs and a 1 μs delay between polarity changes (e.g. 8-1-8) were investigated to span the pulse duration space in proximity to the charging time of the cell membrane. Additional experiments were conducted with monopolar 100 μs pulses (100-0-0) to replicate the pulses used in clinical reversible and irreversible electroporation treatments. All treatments were administered with pulse amplitudes of 500V via a custom pulse generator based on an H-Bridge topology with an integrated 100 MSPS data acquisition system which recorded and displayed the pulse waveforms in real time.

Treatments were administered through a custom coaxial ring and pin electrode configuration (see FIG. 3A). The outer ring was fabricated from 19 mm outer diameter 0.89 mm thick 316 stainless steel tubing (89785K259, McMaster-Carr, Douglasville, GA). The inner pin was fabricated from a 1.64 mm outer diameter blunt 304 stainless steel dispensing needle (75165 A552, McMaster-Carr, Douglasville, GA). An electrical connection to the outer ring was made via a friction fit to a 1.64 mm outer diameter blunt 304 stainless steel dispensing needle.

In order to remove temperature changes as an experimental variable a temperature control algorithm was implemented to achieve a 5° C. temperature change from the initial temperature. A fiber optic temperature sensor (TS5, Micronor Inc., Camarillo, CA) was placed inside the center pin electrode (see FIG. 3B). Temperatures were acquired by a signal conditioner (Fotemp, Micronor Inc., Camarillo, CA), transmitted over a Serial connection, and recorded at 3 Hz using a custom application which controlled the pulse generator output. This temperature value was used to determine the rate (R) at which energy was delivered:

$$R(T) = R_{max} \cdot \rho(T)[\mu s/s] \qquad (15)$$

$$\rho(T) = 0.5 - 0.9375 \cdot \Gamma(T) + 0.625 \cdot \Gamma(T)^3 - 0.1875 \cdot \Gamma(T)^5 \qquad (16)$$

$$\Gamma(T) = \frac{T - T_t}{\beta} \qquad (17)$$

$$\beta = T_t * \omega \qquad (18)$$

where $R_{max}$ is the maximum energy delivery rate [μs/s] prescribed, T is the instantaneous temperature [° C.], $T_t$ is the target temperature [° C.], and ω is a coefficient affecting the slope between maximum and minimum energy delivery rates which was held constant at 0.5 for all experiments presented here (see FIG. 14B). Referring to FIG. 14B, the energy delivery rate was dynamically adjusted based on real time temperature readings to achieve a 5° C. increase in temperature to either 25° C. or 42° C. independent of the treatment dose or constitutive pulse width. Temperature undershoot and overshoot were accounted for by programmatically decreasing $T_t$ to accelerate or decelerate the pulse delivery rate.

Integrated Energized Time

Treatment waveforms were repeated to deliver a specified electrical dose with an integrated energized time (IET) calculated as:

$$IET = \sum_0^N \tau_p + \tau_n [s] \tag{19}$$

where N is the total number of waveforms delivered and $\tau_p$ and $\tau_n$ are the positive and negative pulse durations, respectively. The delay (δ) between sequential waveforms was dynamically adjusted using the temperature control algorithm to achieve the algorithm's specified energy delivery rate (R) calculated as:

$$\delta = \frac{\tau_p + \tau_n}{R} [s] \tag{20}$$

Integrated times of 0.01 s and 0.1 s were investigated based on similarity to clinical protocols (0.01 s) and in vitro results which indicate diminishing returns for longer treatments (0.1 s)

Experiments were conducted with initial temperatures of 10° C., 20° C. (room temperature), 30° C., and 37° C. (physiological temperature). Prior to treatment, the 12 well plates were placed on a benchtop Peltier heating/cooling system (AHP-301CPV, Thermoelectric Cooling America Corporation, Chicago, IL) using a custom machined aluminum plate to aid in thermal transfer through direct mechanical contact (see FIG. 3B). A thin layer of ethanol was administered between the aluminum and well plate to eliminate any air pockets and ensure efficient thermal transfer. The sample temperature was then allowed to settle to the specified treatment temperature before initiating treatment.

Finite Element Analysis

The electric field within the coaxial electrode is known to be spatially non-uniform. As such, the lethal electric field threshold ($E_{Lethal}$) or the minimum electric field necessary to cause cell death can be numerically determined using a finite element analysis simulation of the electric field within the electrode. A 2D axisymmetric model was used in conjunction with the Electric Currents module in COMSOL Multiphysics (V5.3, COMSOL Inc., Palo Alto, CA) which solve the equations:

$$\nabla \cdot J = 0 \tag{21}$$

$$J = \sigma E \tag{22}$$

$$E = -\nabla V \tag{23}$$

where V is the local voltage, E is the electric field, σ is the electrical conductivity, and J is the local current density.

Dielectric charging of the media was considered to be instantaneous due to the high conductivity and relative permittivity of cell culture media.

Figure 15C:
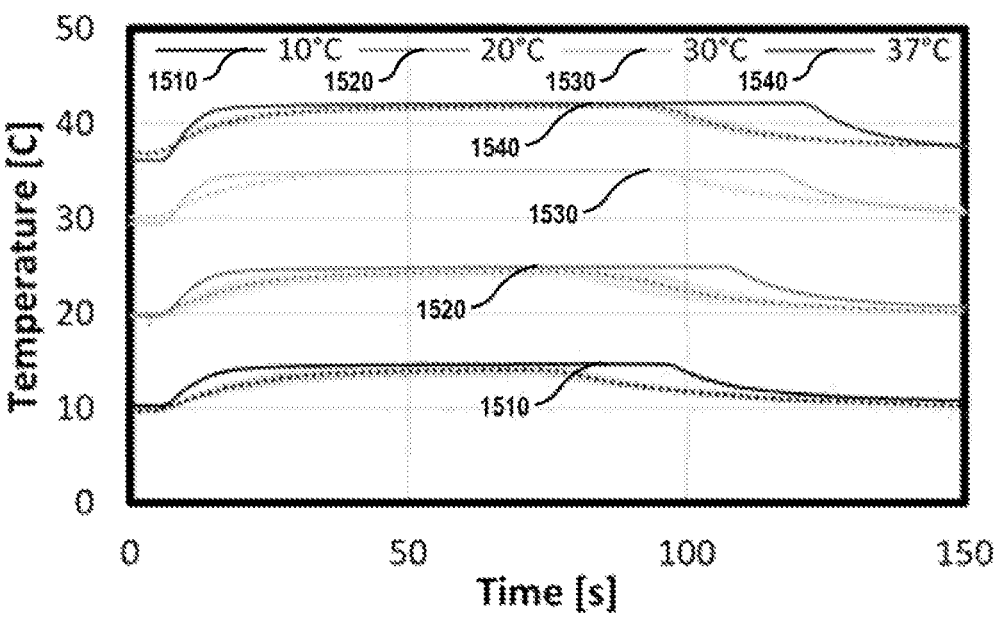
Figure 15D:
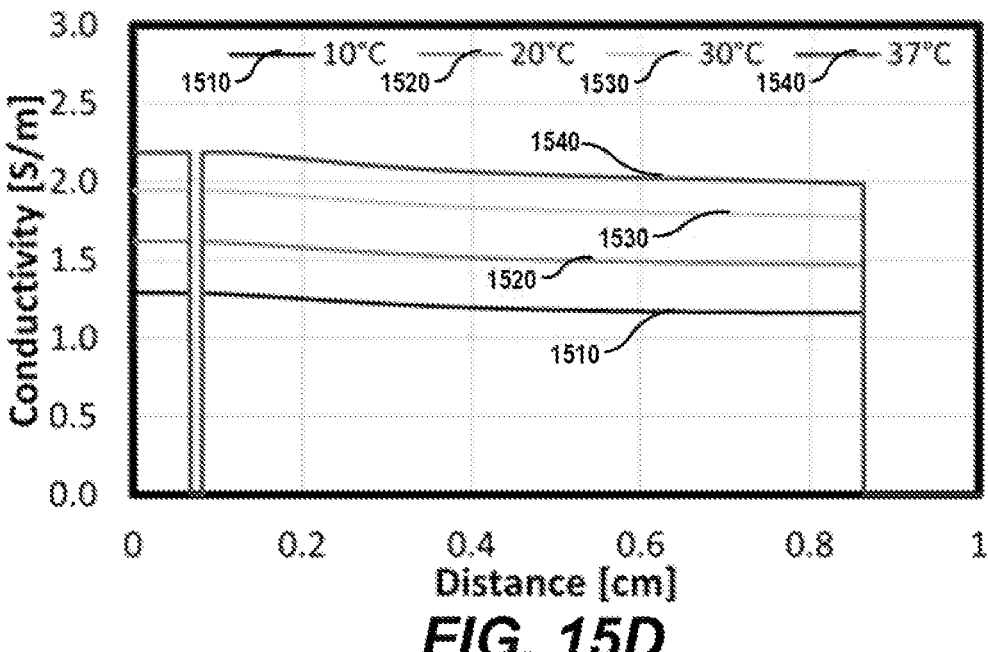
Figure 15E:
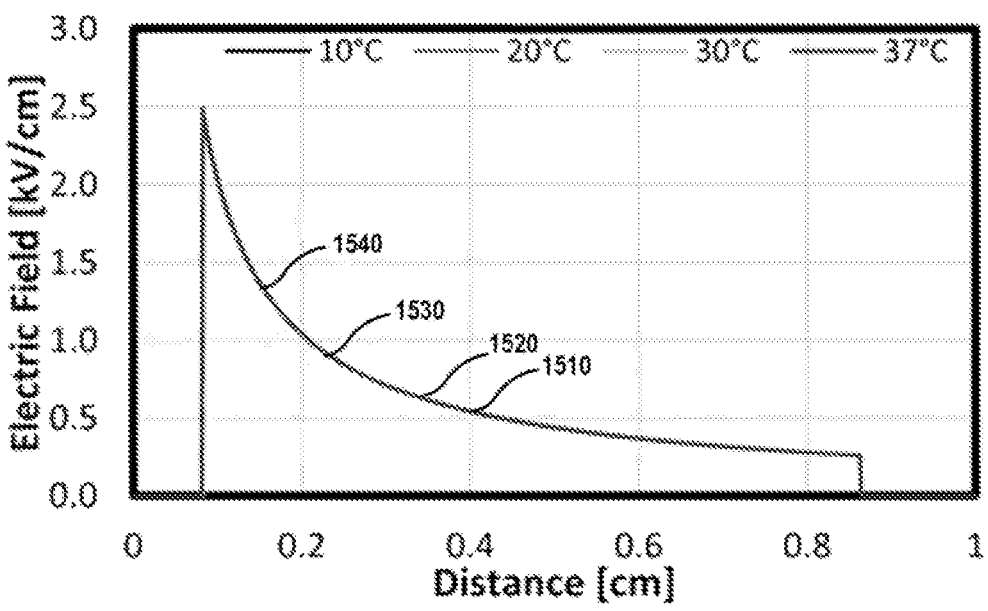

FIGS. 15A to 15E illustrate simulation results according to some embodiments of the present disclosure. FIGS. 15A to 15E illustrate results of finite element simulations. FIG. 15A illustrates the temperature distribution and FIG. 15B illustrates the electrical conductivity distribution for 500V 0.01 s simulations with a 37° C. initial temperature and a 42° C. temperature set point at the end of the treatment (t=150 s). FIG. 15C is a graph illustrating temperature profiles for treatments with 10° C. (line 1510), 20° C. (line 1520), 30° C. (line 1530), and 37° C. (line 1540) starting temperatures at the center of the pin electrode. Solid lines represent simulated temperature profiles while dotted lines represent experimentally measured values. The shaded regions represent one standard deviation from the mean experimentally measured values. FIG. 15D illustrates the conductivity profiles at the end of each treatment (10° C. (line 1510): 115 s, 20° C. (line 1520): 130 s, 30° C. (line 1530): 140 s, 37° C. (line 1540), 150 s) and FIG. 15E illustrates the electric field distribution. Data for each conductivity and electric field plot was derived from the bottom, center, and top of the 3D tumor geometry and is presented as the mean value. Shaded regions, representing one standard deviation from the mean, were plotted for the measured conductivity values and simulated electric field values but were not sufficiently large enough to be visible.

Geometries representing a single well within a 12 well plate were created based on manufacturers' schematics and caliper measurements with separate domains representing the plastic well, cell culture media, and the experimental electrodes. Experimental voltages were applied to the topmost surface of the center pin electrode model. The top surface of the outer ring electrode was set to ground:

$$V = 0 [V] \tag{24}$$

All external domain boundaries which did not contact another domain were set as electrical insulation:

$$n \cdot J = 0 \tag{25}$$

The electrical conductivity (σ) was set to $4.032 \times 10^6$ S/m for the stainless-steel electrodes, and $1 \times 10^{-11}$ S/m for the plastic well plate components. To account for potential changes in the electric field distribution due to temperature changes the conductivity of the 3D tumors ($\sigma_m$) was modeled as:

$$\sigma_m(T_L) = \alpha + \beta \cdot T_L \left[ \frac{s}{m} \right] \tag{26}$$

where α was 0.6506 S/m and β was 0.0284 S/(m ° C.) and $T_L$ was the local temperature in degrees Celsius. Heat transfer and Joule heating calculations were completed using the Heat Transfer in Solids and Electromagnetic Heating modules in COMSOL which combined solve the equations:

$$\nabla \cdot (-k \nabla T) = Q_h \tag{27}$$

$$Q_h = R(T) J \cdot E \tag{28}$$

where k was the thermal conductivity, T was the local temperature, J was the local current density, and E was the local electric field. $Q_h$ was the electromagnetic Joule heating associated with energy delivery which was scaled by a factor R(T), a value equivalent to the energy delivery rate to account for the dynamic duty cycle associated with active temperature control. Simulations of with dynamically controlled energy delivery rates were algorithmically controlled to set the Joule heating condition to zero once a specified integrated energized time (JET) was achieved. Boundaries which were experimentally in contact with air were modeled as blackbody radiators:

$$n \cdot k \nabla T = \varepsilon(G - e_b(T)) \tag{29}$$

$$e_b = n^2 \sigma T^4 \tag{30}$$

where G is a contribution due to irradiation, $e_b$ is the contribution due to blackbody hemispherical total emissive power, and ε is surface emissivity defined as 0.9, 0.075, and 0.97 for media, stainless steel, and plastic components, respectively. Here, the effects of external irradiance were considered negligible (0 W/m²).

A free tetrahedral mesh was generated in all domains using mesh elements with $1.18 \times 10^{-2}$ cm maximum and $2.36 \times 10^{-5}$ cm minimum mesh element sizes. Two rounds of adaptive meshing were completed using the electric field in the 3D tumors as the error indicator to ensure convergence. The final mesh consisted of 173,090 triangular elements. The simulations required approximately 15.3 minutes to solve a 200 s simulation for each parameter set on a ten core Intel i7-6950x processor with 64 GB of RAM.

For each experimental value, three 2D cut lines from the center of the inner pin electrode to the edge of the outer ring electrode was created. The z-axis of these cut lines corresponded to the top, middle, and bottom of the 3D tumor geometry to account for slight variations in temperature in the z-direction. The magnitude of the local electric fields (V/cm), temperature (° C.), and electrical conductivity (S/m) along the 2D cut lines were captured at 0.001 cm intervals and exported to a spreadsheet where the values were averaged and are presented in figures as mean±standard deviation. A lookup table was then used to correlate the radius of each experimental ablation, calculated as one half of each measured diameter, to a corresponding electric field value. The electric field values were then averaged for each parameter set and are presented as mean±standard deviation. Experimental results were statistically compared using a two-sample t-test assuming equal variance at a significance level of α=0.01.

Results

Simulated Changes in Local Conductivity

The effect of temperature change (see FIG. 15A) and temperature dependent electrical conductivity (see FIG. 15B) on the electric field distribution within the 3D tumor models was investigated numerically to determine if these factors were responsible for changes in biological response observed experimentally. These simulations also served to validate the temperature dependent ACE algorithm (Equations 15-20). Simulated temperature profiles (see FIG. 15C), measured at the center of the pin electrode, rapidly approached the temperature set point (5° C. greater than baseline) followed by steady state temperatures of 14.98±0.11, 25.21±0.09, 35.37±0.09, and 42.46±0.08° C. (see FIG. 15C). There was spatially varying electrical conductivity distribution (see FIG. 15D) at the end of energy delivery for all treatments with the highest simulated conductivity occurring at the interface between the pin electrode and the surrounding material. The profile of the conductivity distribution was similar between treatments simulated at 10, 20, 30, and 37° C. with the magnitude being dependent on the initial temperature. However, the simulated electric field distribution within the 3D tumors (see FIG. 15E) was found to be independent of the initial temperature.

Ablation Size as a Function of Pulse Width

Figure 16A:
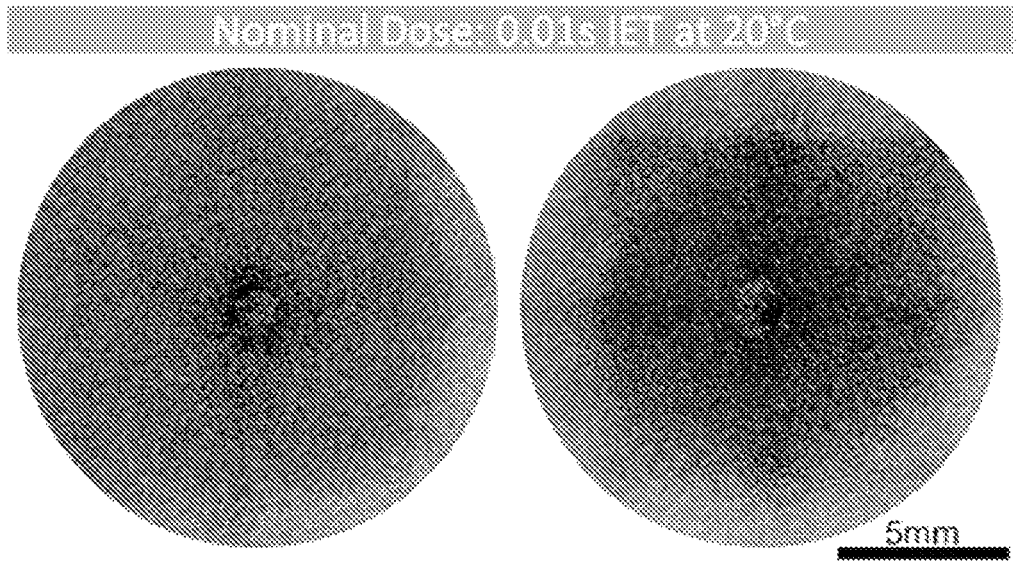
FIGS. 16A to 16C illustrate models used in numerical simulations according to some embodiments of the present disclosure.
Figure 16B:
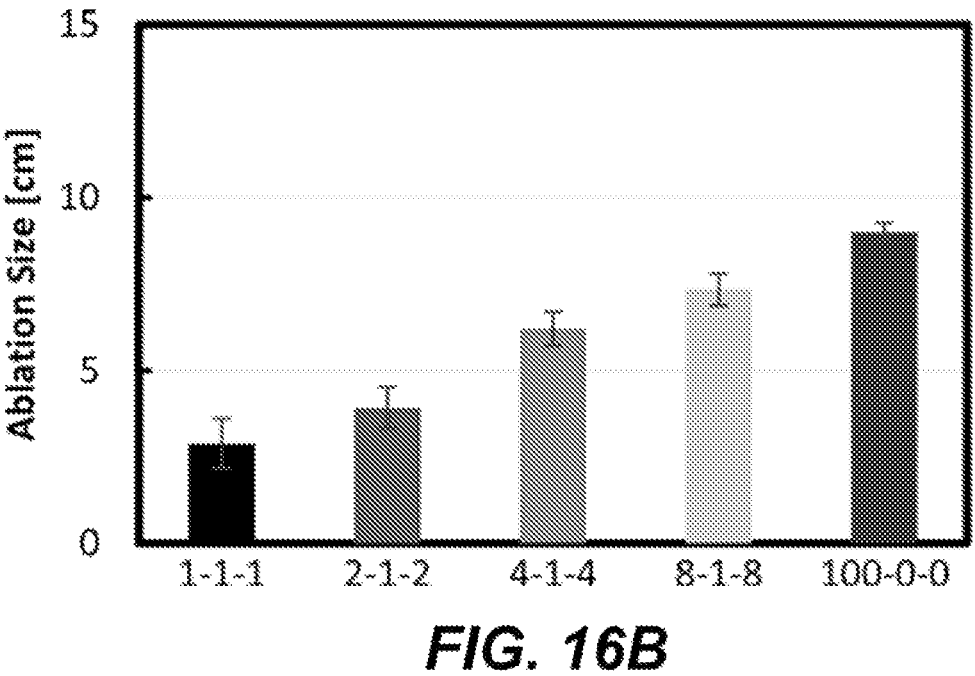
Figure 16C:
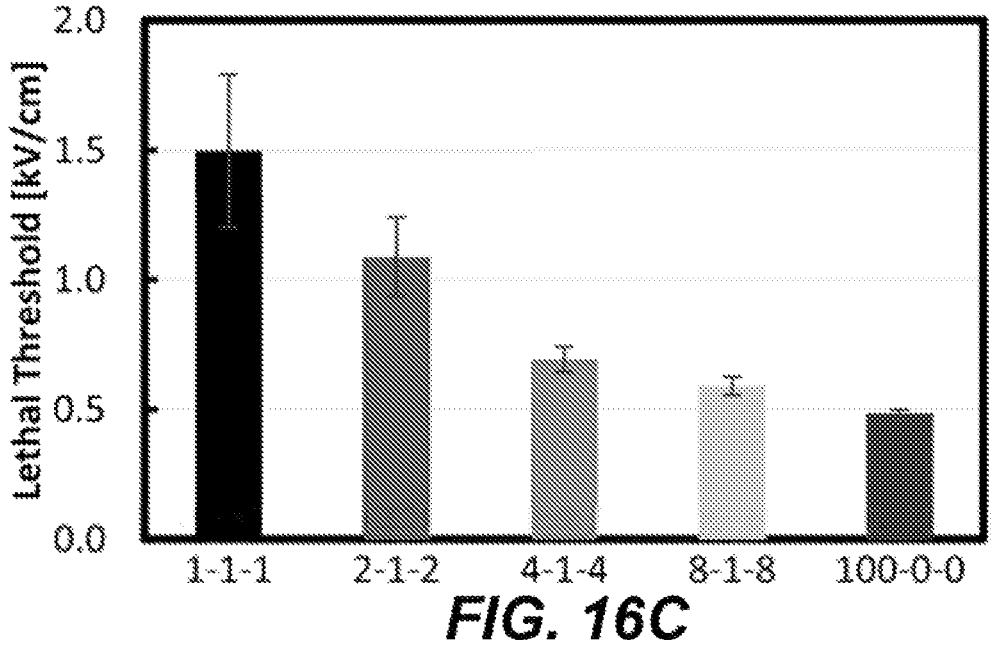

Experiments conducted at 20° C. were used as a baseline representing experiments which are traditionally conducted at room temperature. FIGS. 16A to 16C illustrate models used in numerical simulations according to some embodiments of the present disclosure. As illustrated in FIGS. 16A to 16C, ablation size is a function of pulse duration. FIG. 16A includes images of representative ablations created by the 1-1-1 (left image) and 100-0-0 (right image) 500V 0.01 s IET Treatments administered at 20° C. (room temperature) showing live (green) and dead (red) cells.

The treatments resulted in circular zones of dead cells which were stained red by propidium iodide (see FIG. 16A) surrounded by live cells which were enzymatically metabolizing Calcein AM into its green fluorescent components. A smaller circular region of live cells was observed in the center of the ablations corresponding the region inside of the center pin electrode where there is no electric field, and where temperature increases due to Joule heating were at a theoretical maximum. For treatments with IET of 0.01 s it was found that ablation size increased as a function of pulse width. The smallest ablations, measuring 2.9±0.7 mm were found for treatments with 1 μs pulse durations (see FIG. 16A, left image) while the largest ablations, measuring 9.0±0.3 mm, were found for treatments with 100 μs pulse durations (see FIG. 16A, right image). FIG. 16B is a graph of ablation size based on pulse length, according to some embodiments of the present disclosure. Between these pulse lengths, ablation size was found to sequentially increase with pulse length (see FIG. 16B) with ablations measuring 3.9±0.6, 6.2±0.5, and 7.3±0.5 mm, for treatments with 2, 4, and 8 μs constitutive pulse durations.

The lethal electric field thresholds for these treatments (500V, 0.01 s IET, 20° C.) were similarly found to be a function of constitutive pulse width (see FIG. 16C). Lethal thresholds of 1544±311, 1110±162, 689±52, 581±37, and 472±14V/cm were found for 1, 2, 4, 8, and 100 μs pulse width treatments.

Ablation Size as a Function of Temperature

Figure 17A:
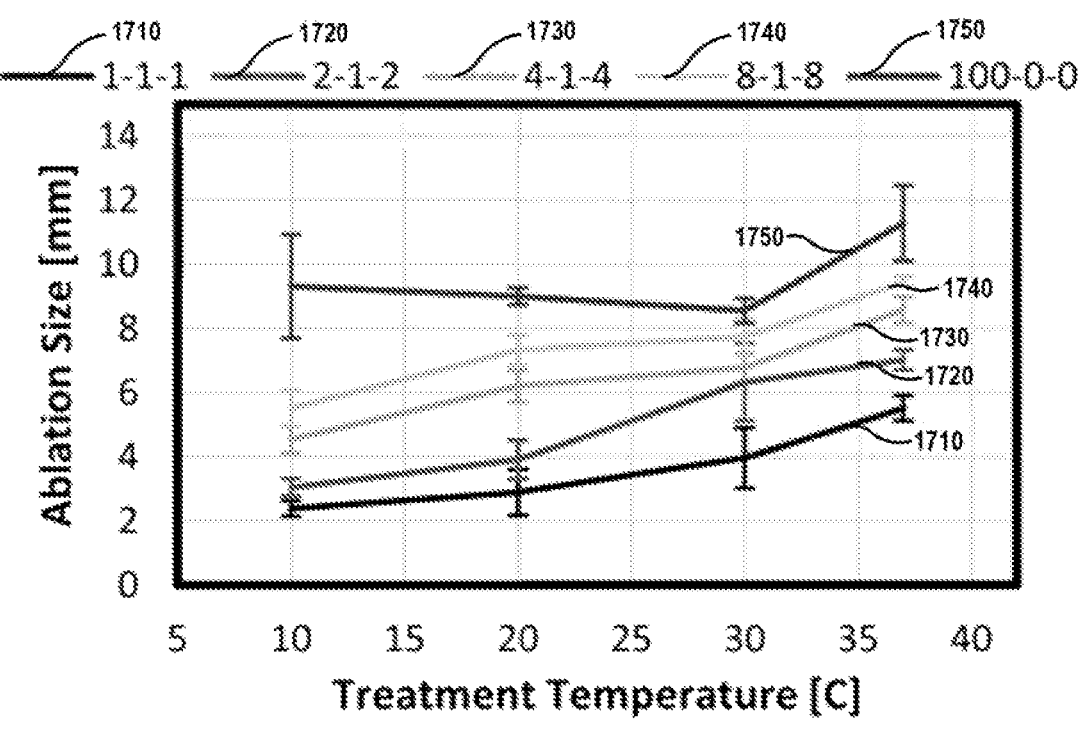
FIGS. 17A and 17B are graphs illustrating ablation sizes as a function of initial treatment temperature, according to some embodiments of the present disclosure.
Figure 17B:
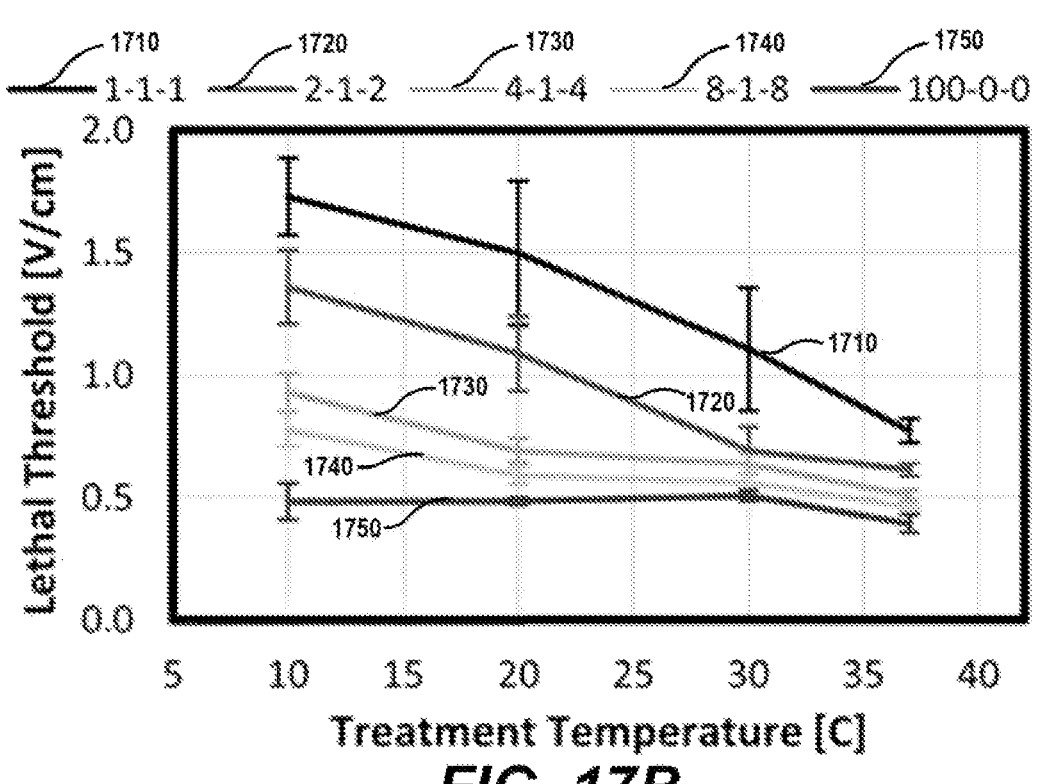

FIGS. 17A and 17B are graphs illustrating ablation sizes as a function of initial treatment temperature, according to some embodiments of the present disclosure. FIG. 17A illustrates ablation sizes and FIG. 17B illustrates lethal thresholds for 500V, 0.01 s IET as a function of starting temperature for 1-1-1, 2-1-2, 4-1-4, 8-1-8, and 100-0-0 waveforms. For the 1-1-1 treatments at 10° C. ablations measuring 2.4±0.2 mm were observed. The size of the ablation zone sequentially increased for treatments administered at 20° C. (2.9±0.7 mm), 30° C. (4.0±1.0 mm), and 37° C. (5.5±0.3 mm). A similar trend was found for the 2-1-2, 4-1-4, and 8-1-8 treatment waveforms with the smallest ablations occurring at 10° C. and sequentially larger ablations found for treatments at 20° C., 30° C., and 37° C. (see FIG. 17A). The smallest variation in ablation size was found for the 100-0-0 waveform treatments. For this waveform, the 10, 20, and 30° C. treatments were not found to be statistically significantly different (p>0.072). However, the 37° C. 100-0-0 ablation was found to be significantly larger than found for each of the three lower temperatures (p<0.001).

The smallest lethal electric field thresholds were found for the treatments with baseline temperatures of 37° C. and were calculated as 774±52, 605±26, 496±23, 449±8, and 380±37 V/cm for the 1-1-1, 2-1-2, 4-1-4, 8-1-8, and 100-0-0 waveforms, respectively. A full accounting of ablation sizes and lethal electric field thresholds can be found in Table 1.

TABLE 1

| | 10° C. | 20° C. | 30° C. | 37° C. |
|---|---|---|---|---|
| Ablation Diameter [mm] | | | | |
| 1-1-1 | 2.4 ± 0.2 | 2.9 ± 0.7 | 4.0 ± 1.0 | 5.5 ± 0.4 |
| 2-1-2 | 3.1 ± 0.3 | 3.9 ± 0.6 | 6.3 ± 1.2 | 7.0 ± 0.3 |
| 4-1-4 | 4.5 ± 0.4 | 6.2 ± 0.5 | 6.8 ± 0.5 | 8.6 ± 0.4 |
| 8-1-8 | 5.5 ± 0.6 | 7.3 ± 0.5 | 7.7 ± 0.6 | 9.5 ± 0.2 |
| 100-0-0 | 9.3 ± 1.6 | 9.0 ± 0.3 | 8.6 ± 0.4 | 11.3 ± 1.2 |
| Lethal Threshold [V/cm] | | | | |
| 1-1-1 | 1729 ± 158 | 1497 ± 294 | 1107 ± 251 | 773 ± 49 |
| 2-1-2 | 1359 ± 150 | 1088 ± 153 | 692 ± 96 | 614 ± 25 |
| 4-1-4 | 929 ± 78 | 693 ± 49 | 636 ± 41 | 507 ± 23 |
| 8-1-8 | 777 ± 69 | 591 ± 35 | 561 ± 40 | 462 ± 8 |
| 100-0-0 | 483 ± 74 | 485 ± 14 | 509 ± 22 | 394 ± 37 |

Table 1 includes ablation diameters and calculated lethal electric field thresholds for 500V treatments with 0.01 s doses when treatments were administered at 10° C., 20° C., 30° C., and 37° C.

Ablation Size as a Function of Integrated Energized Time

Figure 18A:
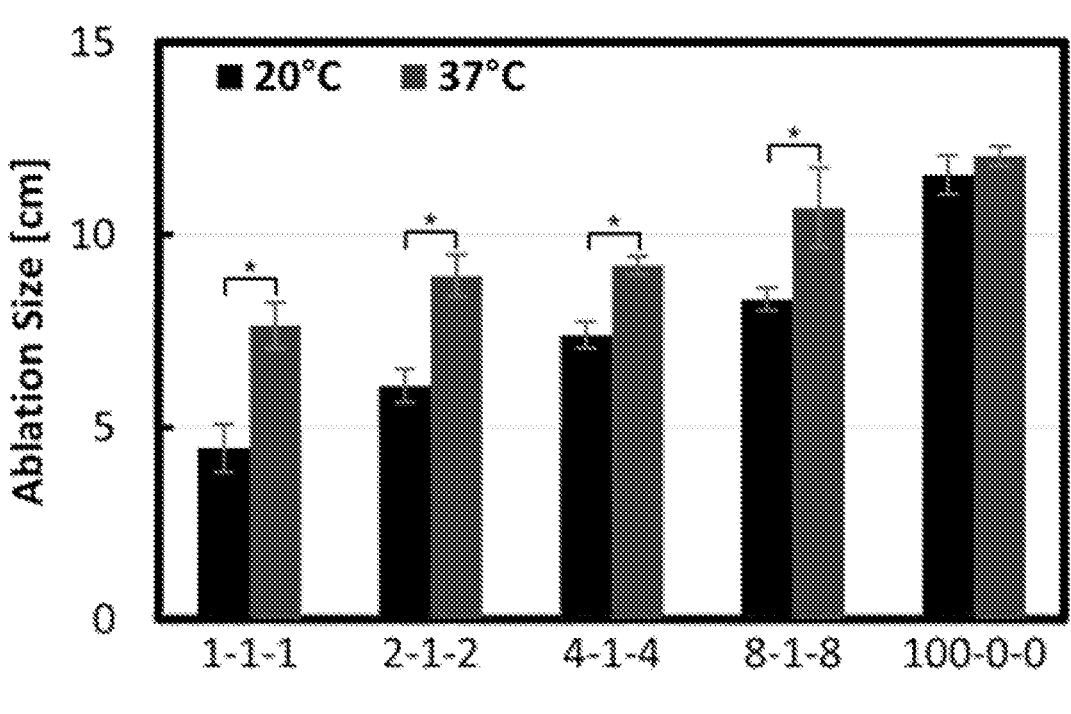
FIGS. 18A and 18B are graphs illustrating ablation sizes as a function of integrated energized time, according to some embodiments of the present disclosure.
Figure 18B:
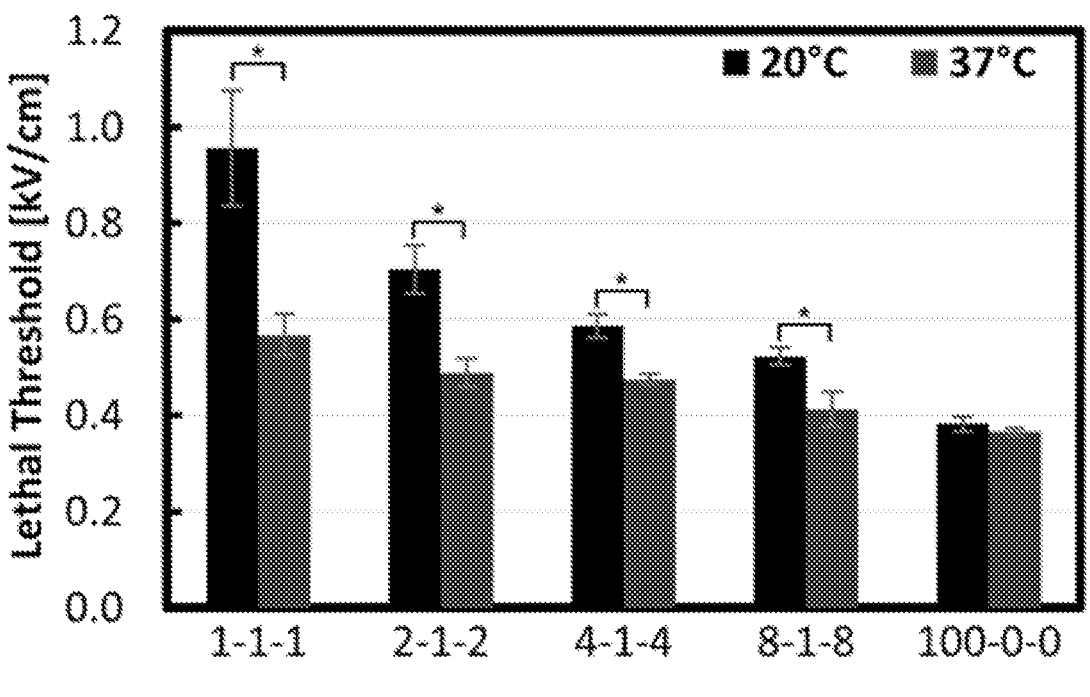

A similar temperature dependent response was observed for treatments where the delivered dose was increased by a factor of 10 (from 0.01 to 0.1 s IET). FIGS. 18A and 18B are graphs illustrating ablation sizes as a function of integrated energized time, according to some embodiments of the present disclosure. FIGS. 18A and 18B illustrate that outcomes from treatments with large 0.1 s IET doses are temperature dependent. FIG. 18A illustrates ablation sizes and FIG. 18B illustrates lethal thresholds for 500V, 0.1 s IET treatments as a function of starting temperature for 1-1-1, 2-1-2, 4-1-4, 8-1-8, and 100-0-0 waveforms. In FIGS. 18A and 18B, an '*' represents values which were found to be statistically significantly different (p<0.001). The smallest ablations in this treatment group (500V, 0.1 s IET) were found for protocols utilizing the 1-1-1 waveform with an initial temperature of 20° C. (4.5±0.6 mm). Increasing the initial temperature to 37° C. resulted in a significant (p<0.0001) increase in ablation size to 7.6±0.6 mm. This yielded a significant (p<0.0001) decrease in lethal threshold from 955±138 V/cm to 558±45 V/cm. Similar statistically significant (p<0.0001) increases in ablation diameter (see FIG. 18A) and decreases in lethal threshold (see FIG. 18A) were found for the 2-1-2, 4-1-4, and 8-1-8 waveform 0.1 s IET treatments when the initial temperature was increased from 20° C. to 37° C. However, significant differences in ablation size (p=0.03) and lethal thresholds (p=0.44) were not found for the 100-0-0 waveforms between the 20° C. and 37° C. treatments. A full accounting of the ablation diameters and lethal thresholds for treatments with IETs of 0.1 s can be found in Table 2.

TABLE 2

| | 20° C. | 37° C. |
|---|---|---|
| Ablation Diameter [mm] | | |
| 1-1-1 | 4.5 ± 0.6 | 7.7 ± 0.6 |
| 2-1-2 | 6.1 ± 0.4 | 8.9 ± 0.6 |
| 4-1-4 | 7.4 ± 0.4 | 9.2 ± 0.2 |
| 8-1-8 | 8.3 ± 0.3 | 10.7 ± 1.0 |
| 100-0-0 | 11.6 ± 0.5 | 12.0 ± 0.3 |
| Lethal Threshold [V/cm] | | |
| 1-1-1 | 957 ± 120 | 568 ± 44 |
| 2-1-2 | 705 ± 50 | 489 ± 29 |
| 4-1-4 | 586 ± 25 | 475 ± 12 |

TABLE 2-continued

| | 20° C. | 37° C. |
|---|---|---|
| 8-1-8 | 523 ± 18 | 414 ± 36 |
| 100-0-0 | 383 ± 16 | 366 ± 7 |

Table 2 provides ablation diameters and calculated lethal electric field thresholds for 500V treatments with 0.1 s doses when treatments were administered at 20° C. and 37° C.

Relative Impact of Dose and Temperature

Figure 19:
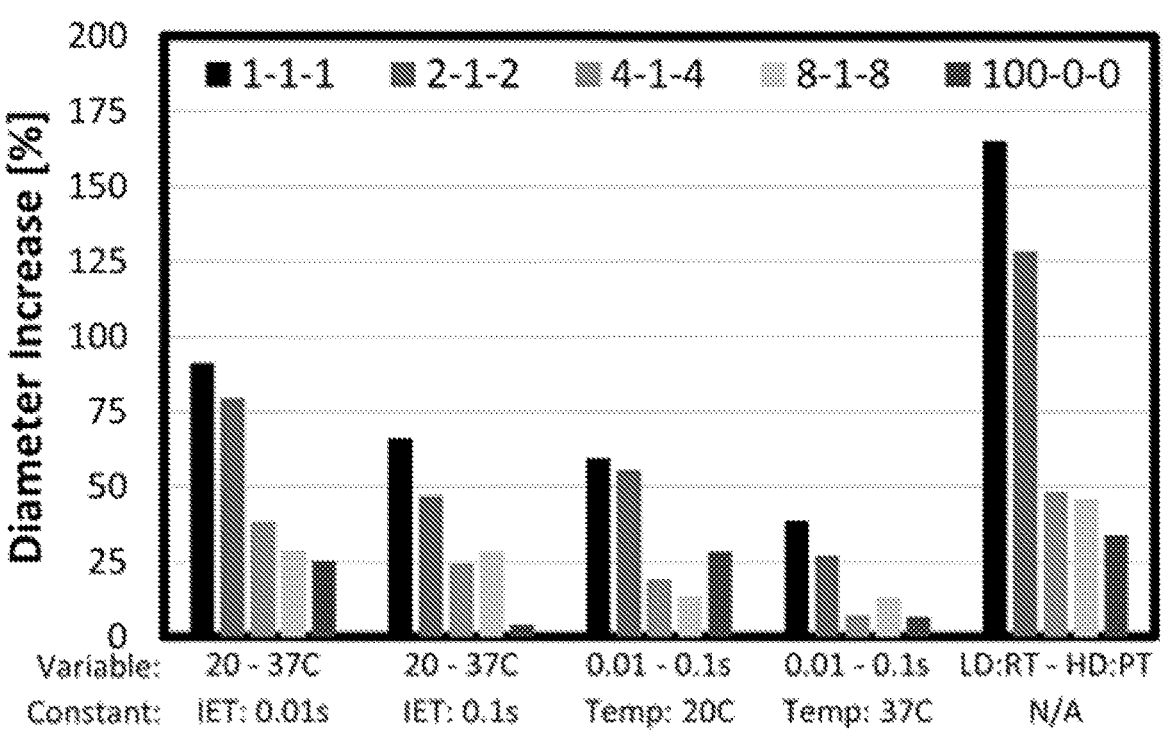
FIG. 19 is a graph of the relative impact of temperature and IET on ablation diameters, according to some embodiments of the present disclosure.

Ablations created with the 1-1-1 waveform exhibited the greatest sensitivity to changes in IET and starting temperature. FIG. 19 is a graph of the relative impact of temperature and IET on ablation diameters, according to some embodiments of the present disclosure. In FIG. 19, the arrangement of the bars in each of the variable categories match the order in the arrangement at the top of FIG. 19. Variables represent the conditions which were changed for a given constant parameter (IET or initial temperature). LD:RT represents the low dose (0.01 s) room temperature (20° C.) treatment groups. HD:PT represents the high dose (0.1 s) physiological temperature (37° C.) treatment groups With IET fixed to 0.01 s, these ablations increased in diameter by 91% when starting temperature was increased from room temperature (20° C.) to physiological temperature (37° C.). With the same waveform, an increase in diameter of 66% was observed for 10× greater dose (0.1 s IET) treatments over this temperature range (20-37° C.). In contrast, ablations created by the 100-0-0 waveform increased in diameter by 25% and 4% over this temperature range (20-37° C.) for IET of 0.01 and 0.1 s, respectively. The 2-1-2, 4-1-4, and 8-1-8 waveform treatments were also sensitive to changes in either IET or starting temperature with a general trend of decreasing effect size as pulse width increased. Comparisons of low dose (0.01 s IET) room temperature (20° C., LD:RT) to high dose (0.1 s IET) physiological temperature (37° C., HD:PT) treatments yielded increases in ablation diameters of 165%, 128%, 48%, and 46%, for 1-1-1, 2-1-2, 4-1-4, and 8-1-8 waveforms, respectively.

At physiological temperatures (37° C.) the 100-0-0 waveform displayed relatively little dependence on IET and a 10× increase from 0.01 s to 0.1 s resulted in only a 6.8% increase in ablation diameter. This waveform was similarly unaffected by treatment temperature (20° C. vs 37° C.) for treatments with IET of 0.1 s, yielding a 4.2% increase in ablation diameter. In combination the transition from the LD:RT to HD:PT protocol resulted in an increase in ablation diameter of 34% which was smaller than any of the other waveforms investigated.

ACE for Liver Ablation

ACE is a potential solution as the first controlled method for automated adjustments of pulse delivery rate for temperature regulation of an ablation region. This enables ACE to be both truly non-thermal and controllably thermal. For non-thermal treatments, ACE allows for the shortest treatment times while mitigating thermal damage to the patient. In a controllably thermal configuration, ACE could allow for clinicians to determine the extent of thermal damage that a tumor receives. Alternatively, a temperature control point can be placed near to tissue that ought to be preserved after treatment. This allows for safer operation near critical structures with potential for reduced side effects.

In this study we demonstrate ACE as a control schema to maximize pulse delivery rates, minimize treatment times, and provide a mechanism for clinicians to control thermally and electrically induced ablative outcomes. An ex vivo perfused liver model was used to demonstrate the use of dynamic temperature control algorithms to produce 4 cm ablation zones in under 27 minutes with a three-applicator array. In separate experiments, these algorithms were able to rapidly achieve and maintain temperatures of 45, 60, or 80° C. at the tissue-electrode interface. A single applicator approach was used to correlate the measured ablation zones to electric field isocontours in order to determine lethal electric field thresholds for ACE treatments of 708 V/cm and 867 V/cm for 45° C. and 60° C. ACE treatments, respectively. These results establish ACE as a viable method for hepatic tumor treatment with ablation profiles equivalent to other energy-based ablation techniques.

Methods

Tissue Preparation and Processing

All experiments were conducted on ex vivo porcine livers following a previously established technique for organ preservation and evaluation. Livers obtained from a local slaughterhouse were flushed with 200 mL of 1× Phosphate Buffered Saline (PBS)(IS25049, Aldon Corp. Avon NY) to remove large blood clots then transported on ice to the laboratory. A peristaltic pump (EW-77921-65, Cole-Palmer, Vernon Hills, IL) was attached to the liver hepatofugally via the vena cava and perfusion with PBS was initiated using a flow rate between 18-25 mL/hour. To simulate venous pressure and increase the volume of fluid within the organ the flow of perfusate exiting the portal vein was restricted via a plastic luer lock (4551100, Cole-Palmer, Vernon Hills, IL) coupled to 1 mm inner diameter tubing. To facilitate the removal of any potential blood clots the liver was gently massaged and continuously perfused until tissue blanching occurred indicating that the organ had been flushed and all lobes were receiving PBS. Finally, the existing perfusate was discarded and replaced with fresh PBS which was occasionally refreshed during the experiments.

Post-treatment the organs were moved to a standard laboratory refrigerator at 4° C. and perfused for 10-15 hours to allow for delayed cell death processes associated with the treatment to occur. For the three-applicator array (3 AA) protocol, treatment sites were identified and sectioned by hand perpendicular to applicator insertion in 0.5 to 1.0 cm thick slices. This yielded between six and ten measurable ablation zones per treatment site. For single applicator and grounding pad (A+GP) protocols a single section was made parallel to and along the applicator insertion path yielding two measurable ablation zones per treatment site. The tissue sections were placed in a bath containing 10 g/L triphenyl tetrazolium chloride (TTC, A1087009, Alfa Aesar, Tewksbury, MA) in PBS overnight in a dark environment to enhance visibility of the ablation zones (FIG. 29). TTC enzymatically reduces into red 1,3,5-triphenylformazan in living cells and excluded from dead cells which appear light pink. Further contrast enhancement was achieved by preserving tissue samples in Neutral Buffered Formalin (22-046-361, Thermo-Fisher Scientific, Waltham, MA), however, the results of this process were variable. Ablation zones, indicated by a change in tissue color and texture, were measured using digital calipers. For the three-applicator array, three measurements for each ablation zone were obtained by identifying a straight line connecting the punctures of adjacent applicator pairs then measuring the ablation margin along that line. For the single applicator and grounding pad protocol, the maximal length along the applicator insertion path and maximal width perpendicular to the applicator insertion path were recorded for each ablation zone. The length and width values for ablations within treatment groups were averaged to determine the mean ablation size and data is presented as mean±standard deviation.

Energy Delivery

Figure 24A:
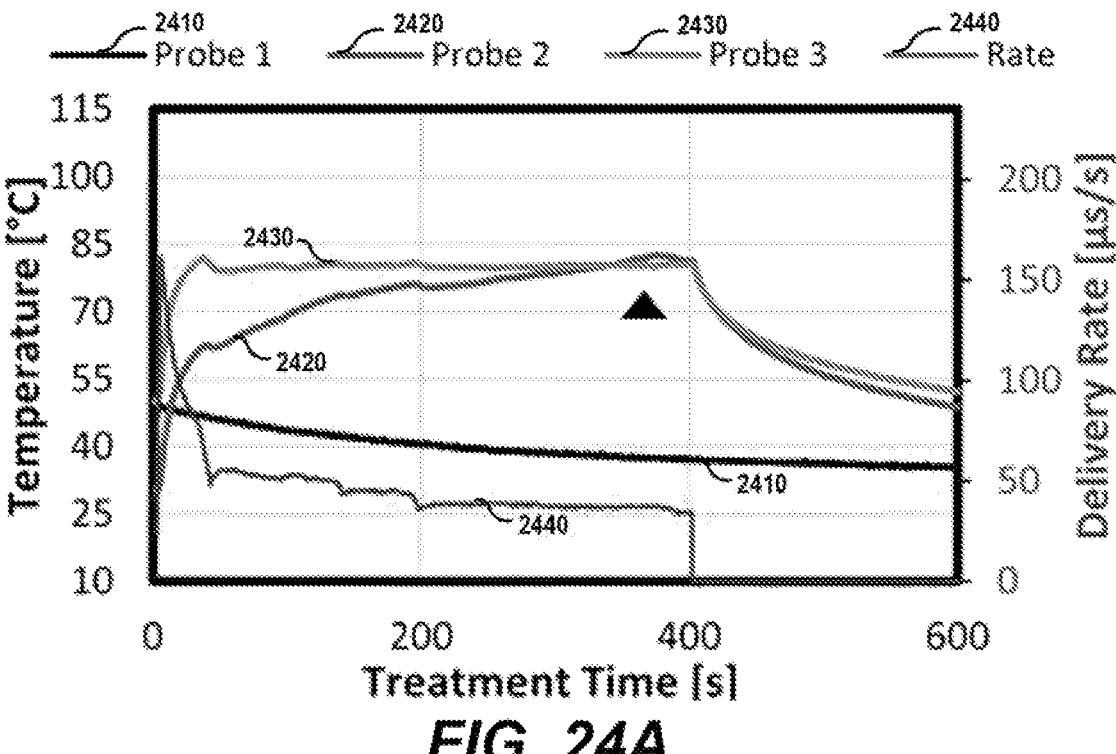
FIGS. 24A to 24C are waveforms illustrating treatment observations, according to some embodiments of the present disclosure.
Figure 24B:
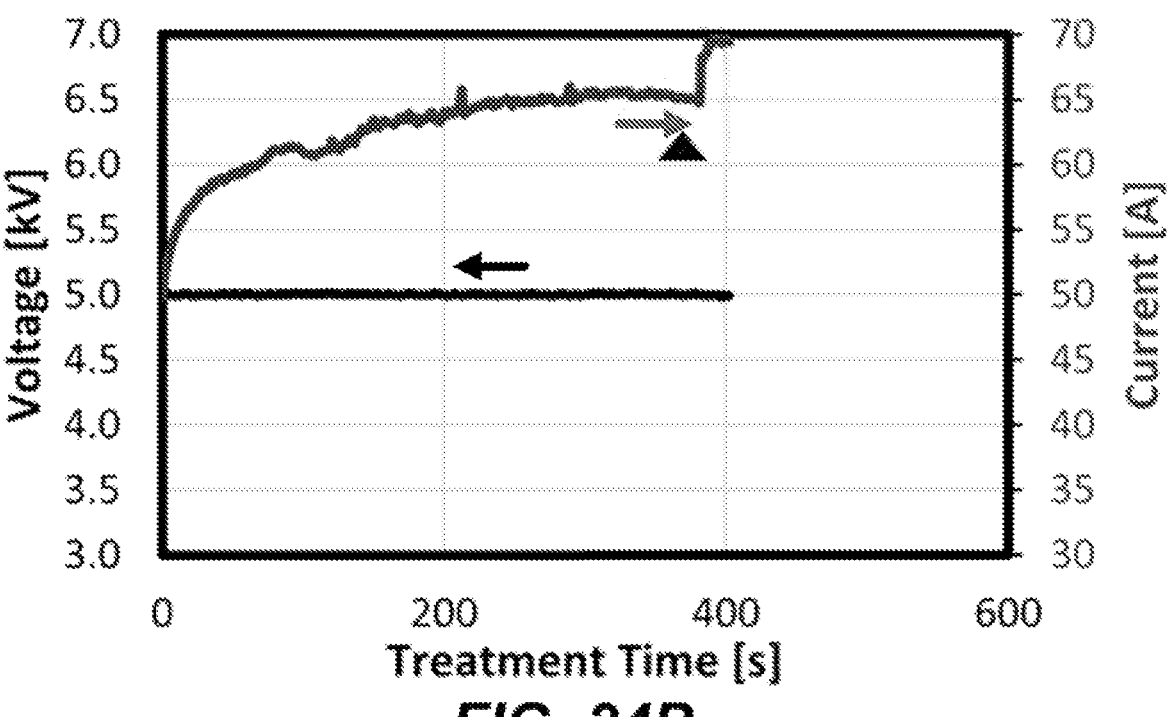

ACE waveforms (FIG. 24a) were delivered to the liver tissue via 1 mm diameter applicators (Monopolar Probe, AngioDynamics Inc., Latham, NY) which contain an adjustable insulator used to set the length of the exposed electrode (FIG. 24b). Ablations were created using two distinct applicator configurations: (1) A three applicator array (3 AA, FIG. 24c) consisting of three applicators in a triangular pattern with 3 cm center-to-center spacing and 3 cm electrode exposures. (2) An applicator and grounding pad configuration (A+GP) utilizing a single applicator with 1 cm of electrode exposure and a 4×5 cm aluminum grounding pad placed under the organ. These configurations were selected to (1) demonstrate the feasibility of creating clinically relevant ablations and (2) enable the determination of lethal electric field thresholds through the use of a simplified geometry, respectively.

All experiments were conducted using a continuous pulse delivery protocol (see FIG. 14A). A bipolar waveform consisting of a positive polarity 2 µs pulse, a 5 µs delay, and a 2 µs negative polarity pulse (2-5-2 waveform) was repeated to deliver a specified electrical dose with an integrated energized time (IET) calculated as:

$$IET = \sum_0^N \tau_p + \tau_n[s] \tag{31}$$

where N is the total number of waveforms delivered and $\tau_p$ and $\tau_n$ are the positive and negative pulse durations (2 µs), respectively. The delay (δ) between sequential 2-5-2 waveforms was either held constant or dynamically adjusted using a temperature control algorithm to achieve a specified energy delivery rate (R) calculated as:

$$R = \frac{\tau_p + \tau_n}{\delta}[\mu s/s] \tag{32}$$

Temperature Control Algorithm

Figure 20C:
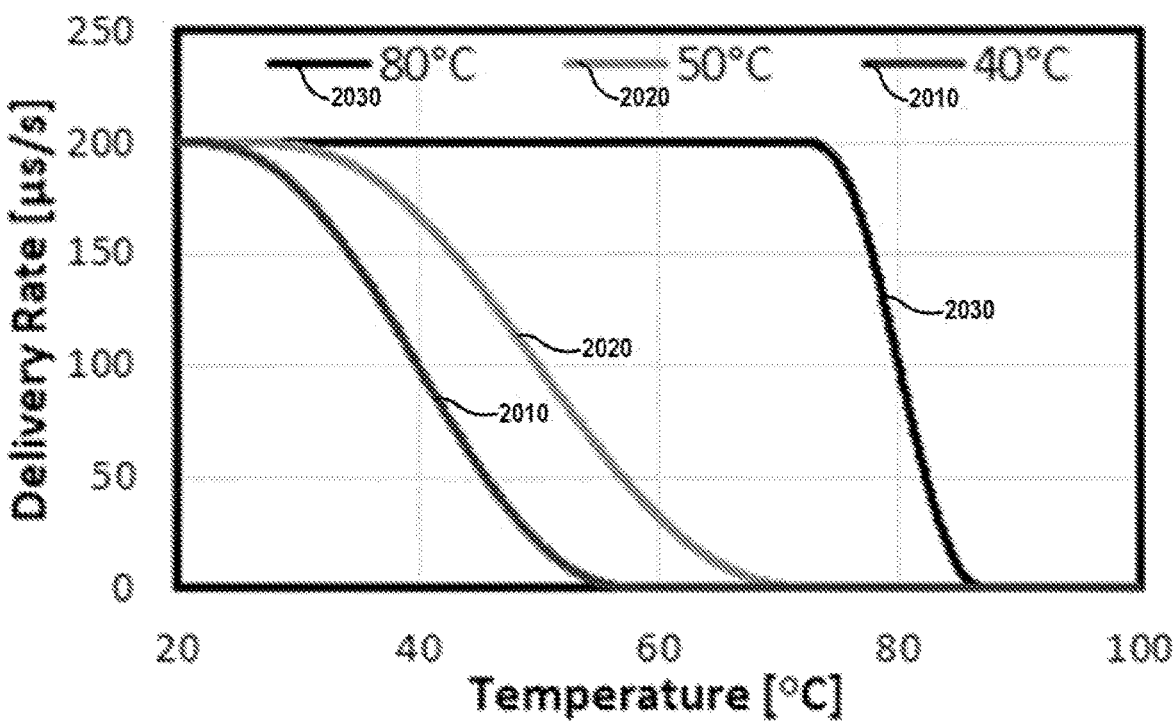
FIG. 20C is a graph illustrating a dynamic delivery rate based on temperature, according to some embodiments of the present disclosure.
Figure 20B:
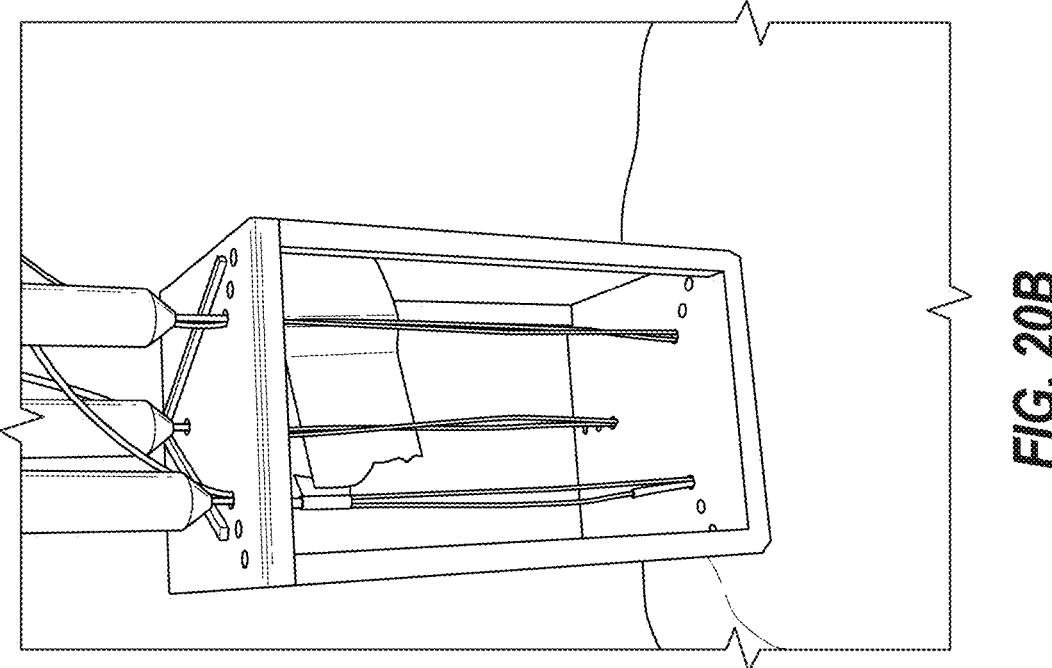
FIGS. 20A and 20B illustrate examples of an electrode applicator and an applicator array, according to some embodiments of the present disclosure.
Figure 20A:
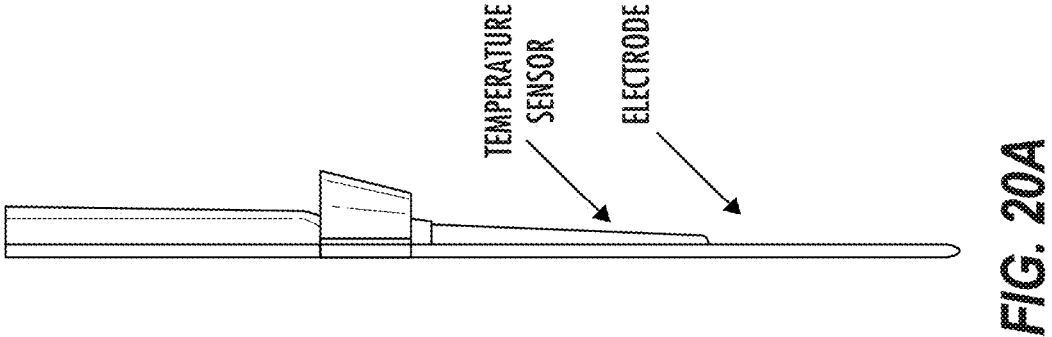

ACE utilizes a dynamic energy delivery scheme to adjust treatment parameters in real time to respond to changing tissue conditions. The waveforms used in ACE may include a variable delay between waveforms having a positive and negative component, as illustrated in FIG. 14A. FIGS. 20A and 20B illustrate examples of an electrode applicator and an applicator array, according to some embodiments of the present disclosure. The delay between successive ACE waveforms is modulated based on measurements from a temperature sensor attached to the electrode applicator (see FIG. 20A). Treatments are through a single applicator and grounding pad or through probe pairs in multi-applicator arrays (see FIG. 20B). FIG. 20C is a graph illustrating a dynamic delivery rate based on temperature, according to some embodiments of the present disclosure. FIG. 20C illustrates values for target temperatures of 40° C. (line 2010), 50° C. (line 2020), and 80° C. (line 2030). Referring to FIG. 20C, the dynamic energy delivery rate is dependent on a number of factors including the maximum prescribed rate and the target temperature. In all experiments, a fiberoptic temperature sensor (TS5, Micronor Inc., Camarillo, CA) was affixed to each applicator (see FIGS. 20A and 20B). Temperatures were acquired by a signal conditioner (Fotemp, Micronor Inc., Camarillo, CA), transmitted over a Serial connection, and recorded at 3 Hz using a custom Python application. This temperature value was used to determine the rate (R, see FIG. 20C) at which energy was delivered:

$$R(T) = R_{max} \cdot \rho(T) [\mu s/s] \tag{33}$$

$$\rho(T) = 0.5 - 0.9375 \cdot \Gamma(T) + 0.625 \cdot \Gamma(T)^3 - 0.1875 \cdot \Gamma(T)^5 \tag{34}$$

$$\Gamma(T) = \frac{T - T_t}{\beta} \tag{35}$$

$$\beta = T_t * \omega \tag{36}$$

where $R_{max}$ is the maximum energy delivery rate [μs/s] prescribed, T is the instantaneous temperature [° C.], $T_t$ is the target temperature [° C.], and ω is a coefficient affecting the slope between maximum and minimum energy delivery rates which was held constant at 0.5 for all experiments presented here. It should be noted that the temperature control algorithm, as implemented in this study, only utilized temperature data from a single user selected probe and the dominant probe was changed manually if an alternate probe exceeded the target temperature by more than 3° C.

Electrical pulses were delivered using a custom pulse generator based on an H-Bridge topology which included a 100 MSPS data acquisition system to record voltage and current waveforms in real time. For safety, the system was designed to automatically abort treatments if the software measured average currents above 75 A, the hardware detected instantaneous currents above 90 A, or the average power reached 100 Watts. These events were rare and only two software mediated over current (75 A) events occurred for the experiments presented here.

For each applicator configuration a single ramp-up experiment was conducted in which the voltage was sequentially increased from 250V to 5000V to ensure proper behavior of the pulse generator. For each additional applicator placement, the applied voltage was immediately set to 5000V.

Three Applicator Array (3 AA) Treatments

Each applicator in the 3 AA was manually placed in the tissue through a custom electrode holder (see FIG. 20B) such that the entire exposed electrode (e.g., 3 cm) and 0.5 cm of insulation were below the surface of the tissue. To facilitate sectioning, the applicators were placed perpendicular to the tissue surface. To accommodate the two outputs on the pulse generator, energy was sequentially delivered between adjacent probe pairs (1-2, 2-3, 3-1). A dose of 0.02 s IET (5000× waveforms, 10,000× pulses) was delivered between each pair resulting in a total dose of 0.06 s IET per ablation.

Non-temperature-controlled experiments were conducted with an energy delivery rate of 166.7 μs/s to match the total treatment time (6 minutes) with similar 3 applicator MWA protocols. Temperature controlled experiments were conducted with a target temperature of 80° C. and a maximum energy delivery rate of 166.7 μs/s. These parameters were selected to minimize treatment time and investigate the effects of energy delivery well beyond the threshold for instantaneous thermal damage.

Single Applicator and Grounding Pad (A+GP) Treatments

A single applicator with a 1 cm electrode exposure was inserted into the tissue such that the electrode and 0.5 cm of insulation were below the tissue surface. A 4×5 cm aluminum grounding pad was placed under the tissue and occasionally moved between treatments to maintain similar distances between experimental groups which aided in delivering consistent initial current amplitudes. For each applicator placement a total dose of 0.02 s IET was delivered with a maximum energy delivery rate of 200 μs/s and target temperatures of either 45° C. or 60° C. These values were chosen to investigate if temperature is a confounding factor in ablation size and lethal threshold calculations.

Numerical Prediction of Lethal Electric Fields

Figure 21B:
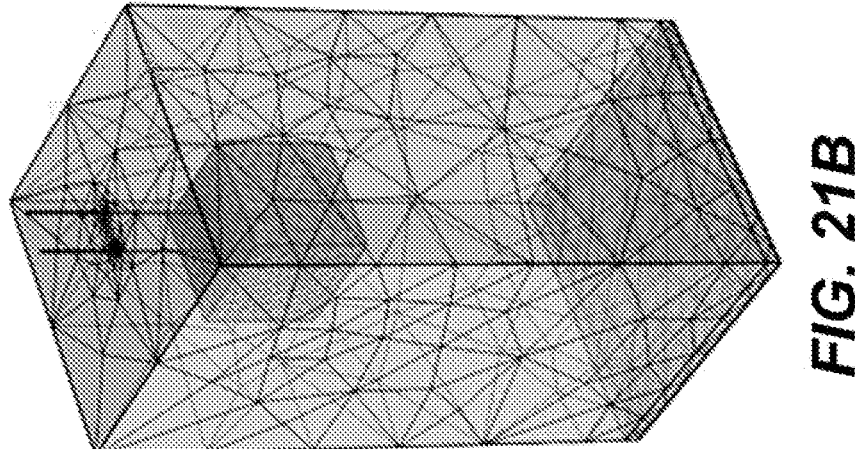
FIGS. 21A to 21D illustrate details related to the model used for portions of the analysis described herein.
Figure 21A:
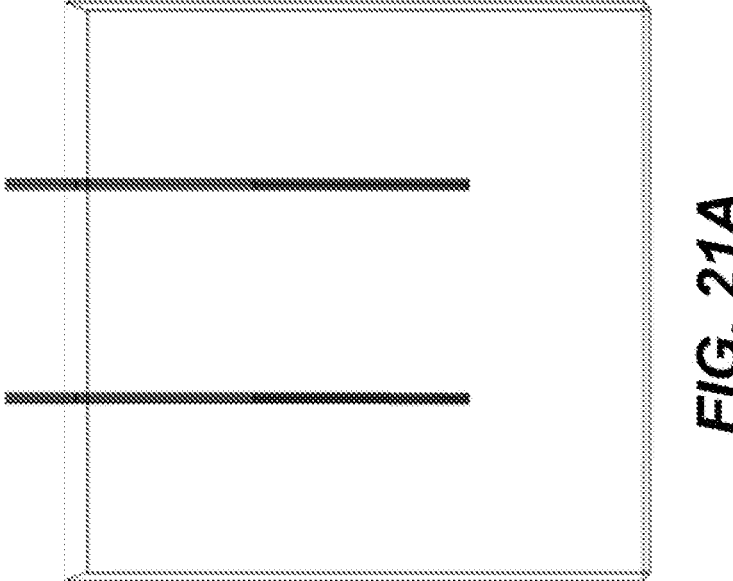
Figure 21C:
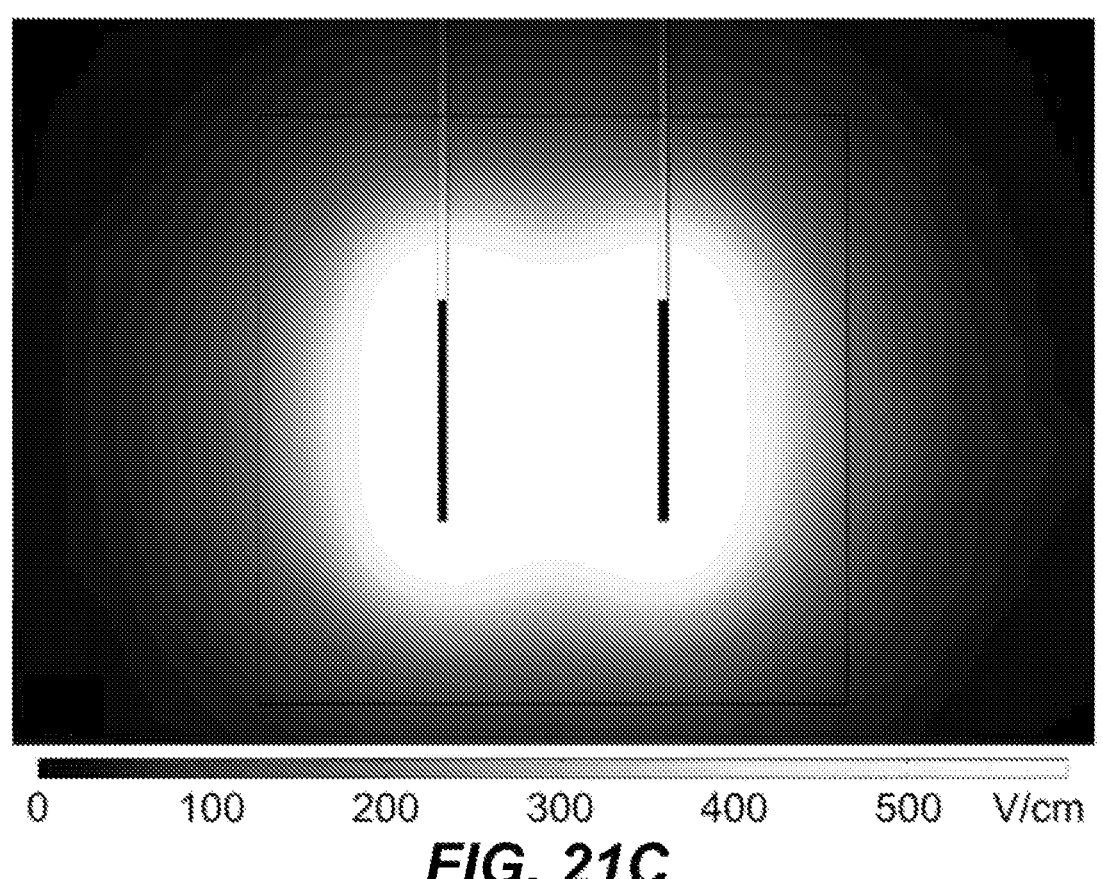
Figure 21D:
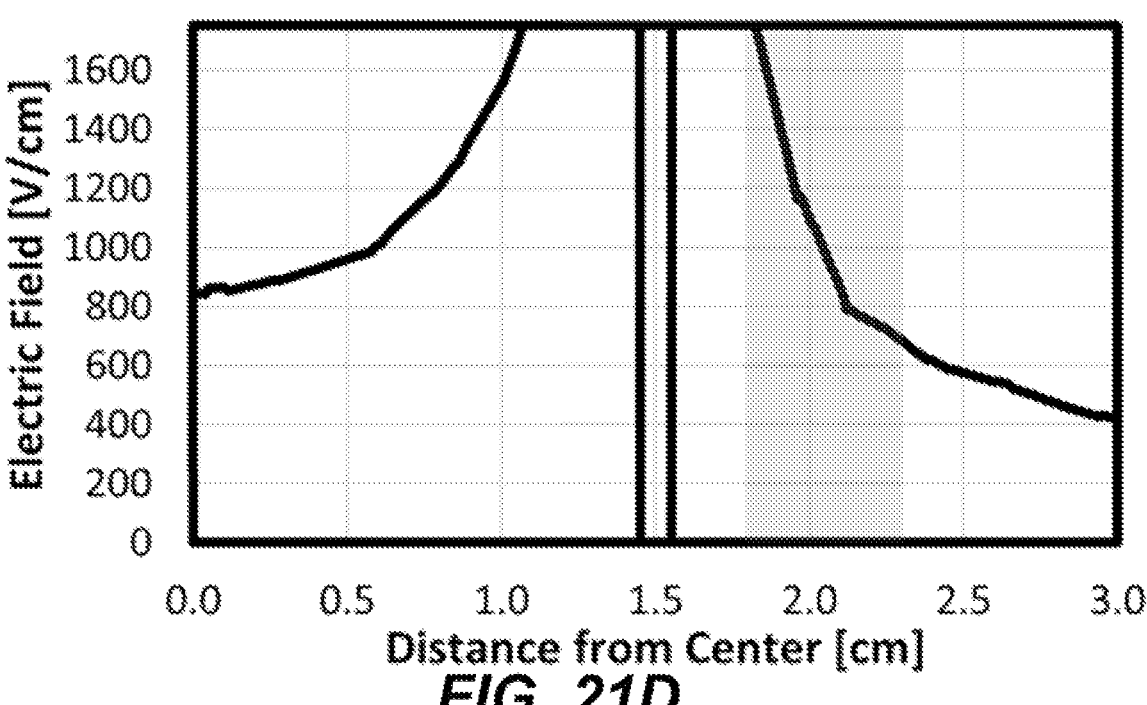

COMSOL Multiphysics was used to calculate the electric field distribution within the tissue for both experimental applicator configurations using known techniques. FIGS. 21A to 21D illustrate details related to the model used for portions of the analysis described herein. More specifically, FIGS. 21A to 21D illustrate a finite element model for the 3 AA with energy delivery between two adjacent electrodes. FIG. 21A illustrates an 8 cm refined domain that was created around the electrodes to enable adaptive mesh refinement within a smaller volume of the overall simulation domain, shown in FIG. 21B. FIG. 21C illustrates the electric field distribution around the applicators that was exported along a single line through the center of the electrodes, as illustrated in FIG. 21D to correlate ablation size to a lethal electric field strength. The grey region in FIG. 21D represents the span of ablation sizes measured in this study with the 3 AA configuration.

Briefly, 3D (3 AA) and 2D (A+GP) Electric Currents Modules were used to calculate the steady state electric field distribution around the electrodes. For the 3 AA, the electric field data along a line passing through the geometric center of two electrodes was exported to a spreadsheet. This data was then used to cross-reference the length of each ablation measurement to identify the electric field isocontour value which corresponded to the size of the ablation. For the A+GP configuration data for the electric field distributions along the lines extending parallel to and perpendicular to the center of the electrode were exported and correlated to the length and width, respectively, of the ablation zones. Lethal threshold values for each measurement within treatment groups were then averaged and data is presented as mean±standard deviation.

Numerical Prediction of Lethal Electric Fields

COMSOL Multiphysics was used to calculate the electric field distribution for the three-applicator array (3 AA) and the single applicator and grounding pad (A+GP) configurations. The steady state electric field distribution within a simulated abdomen was calculated using the 3D (3 AA) and 2D (A+GP) Electric Currents module in COMSOL Multiphysics. This solves the equations:

$$\nabla \cdot J = 0 \tag{37}$$

$$J = \sigma E \tag{38}$$

$$E = -\nabla V \tag{39}$$

where J is the local current density, E is the electric field, V is the local voltage, and σ is the electrical conductivity. This system was considered electroquasistatic as the geometry can be considered electrically small compared to the skin depth and wavelength[1]. Similarly, dielectric charging of the tissue was considered to be instantaneous due to its relatively high electrical conductivity.

The abdomen was simulated using a simplified 20×20×40 cm rectangular domain for the 3 AA and a similarly sized cylindrical geometry for the A+GP. Fat and skin were simulated by 1.0 and 0.15 cm deep domains, respectively, at the distal end of the abdomen domain. A 0.1 cm deep domain was used to simulate the distal grounding pad for the A+GP configuration which was located 30 cm from the center of the electrodes in all simulations. 1.0 mm diameter cylinders were used to represent the applicator and electrodes in each configuration.

A voltage was applied to the topmost surface of the electrode where they intersected the applicator shaft. The bottom surface of the grounding pad was set to ground:

$$V=0 \tag{40}$$

All external domain boundaries which did not contact another domain (e.g. the interface between tissue and air) were set as electrical insulation:

$$n \cdot J=0 \tag{41}$$

The rapid increase in electrical conductivity in tissue undergoing electroporation around the probe was simulated concurrently while solving for the steady state electric field distribution using a dynamic tissue conductivity function implemented as a piecewise step equation with continuous second derivative smoothing:

$$\sigma(E) \begin{cases} 0.1 & E < (1-r) \cdot E_{lethal} \\ \Gamma(E) & \text{otherwise} \\ \sigma_{final} & E > (1+r) \cdot E_{lethal} \end{cases} \tag{42}$$

$$\Gamma(E) = 0.5 + 0.9375 \cdot \gamma(E) - 0.625 \cdot \gamma(E)^3 + 0.187 \cdot \gamma(E)^5 \tag{43}$$

$$\gamma(E) = (E - E_{lethal})/(E_{lethal} * r) \tag{44}$$

where r is the size of the relative transition zone (0.499), E is the local electric field, and Elam is the lethal threshold found experimentally for the 2-5-2 waveforms used in this study (592 V/cm) [25 µs/s 0.02 sIT]. Changes in tissue conductivity were simulated with a relative increase in conductivity of 1.81× from a baseline conductivity of 0.195 S/m.

To improve the computational solution times a two-step simulation was constructed where a stationary 'pre-pulse' was applied using a voltage of 50 V. This voltage does not result in electric fields sufficiently high enough to change the tissue conductivity and allows the simulation to determine a baseline electric field distribution. The solution to this step was used as the initial value of a second sequential stationary solver with higher voltages applied to the energized electrode tines. An Algebraic Multigrid preconditioner was used with 2 iterations over 500 levels where the coarsest level had 500 degrees of freedom. The Conjugated Gradients iterative solver was used with Error Estimation Checking disabled. This was then controlled by the "Automatic Highly Non-linear Newton Method" with initial and minimum damping factors of IE-8 and IE-16, respectively. The maximum number of iterations for this solver was increased from 25 to 25000

Adaptive meshing was implemented by creating 8× adaptive meshing steps within the Mesh segment in the model builder. Then the Type of Expression was changed to "Error Indicator" and the Error Expression was defined as the equation:

$$-root.comp1.integral1(comp1.tissueField) \tag{45}$$

where comp1.tissueField was defined as the electric field norm (ec.normE) within an 8 cm cubic domain surrounding the electrode. This was defined within the Component Definitions as a variable and an integral function. The maximum element growth rate was set to 1.1 and 4 rounds of adaptive meshing were implemented. Finally, the non-linear method for this step was changed to "Double Dog Leg" which uses a combination of gradient descent and Newton's method to converge on a solution. The use of adaptive meshing dramatically reduced the simulation time in these 3D geometries as it is not necessary to begin the simulation with a highly refined global mesh or very small $(1 \times 10^{-15})$ relative tolerances as reported earlier[6,7]. Typical final meshes included approximately 1,443,000 elements after the eighth round of adaptive meshing and each parameter required approximately 2 hours and 20 minutes to solve on a 10 core Intel i7 processor with 64 GB RAM.

Results

Treatment Observations

Figure 22A:
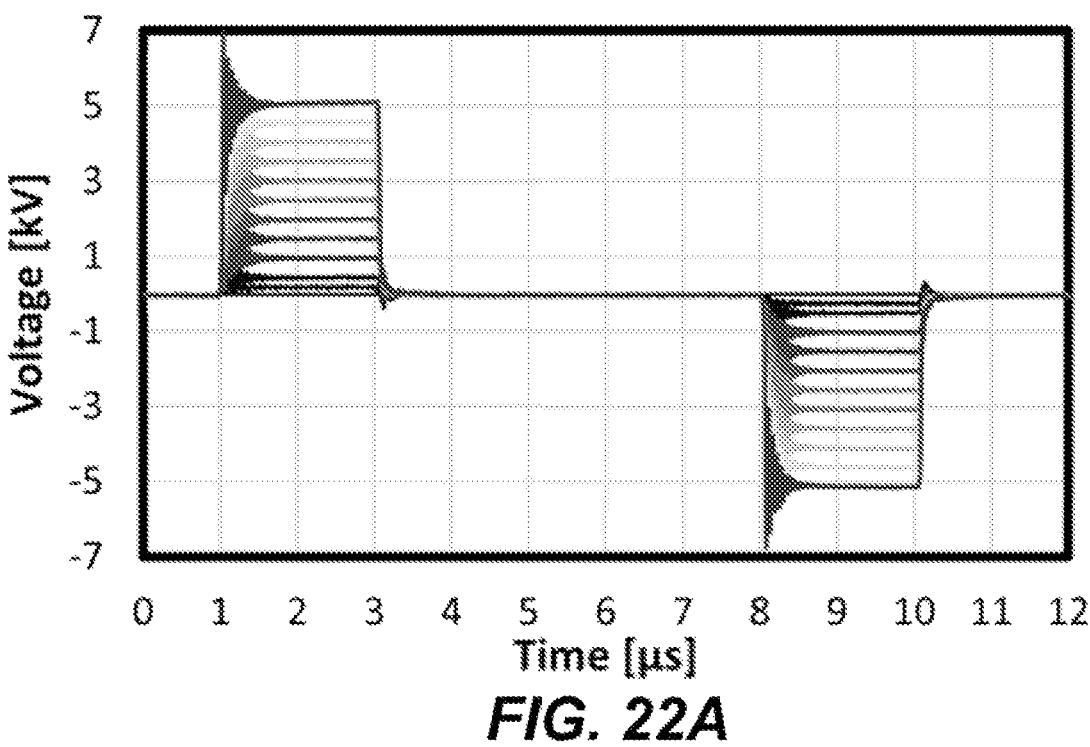
FIGS. 22A to 22C are waveforms illustrating treatment observations, according to some embodiments of the present disclosure.
Figure 22B:
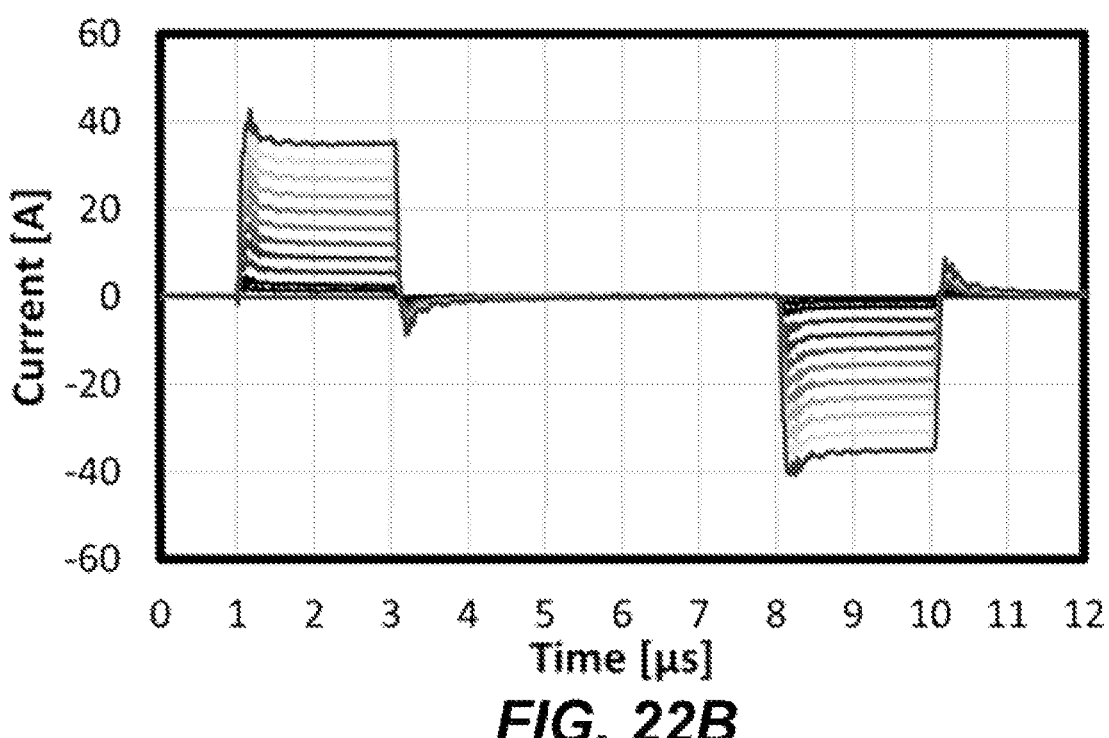
Figure 22C:
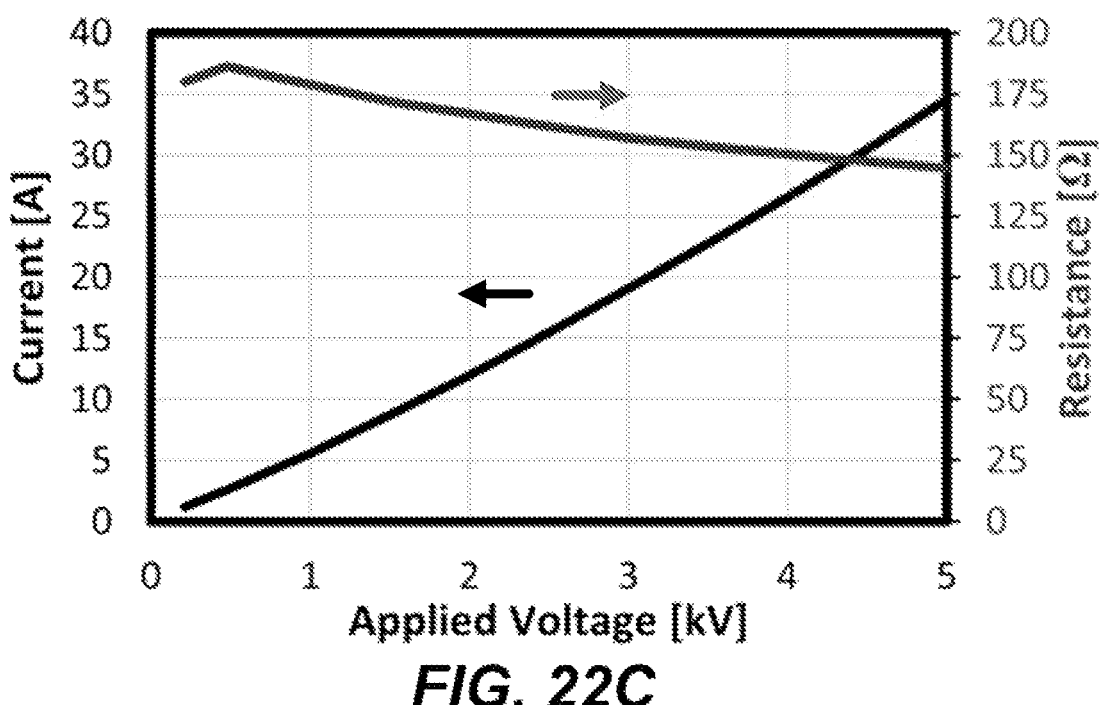

FIGS. 22A to 22C are waveforms illustrating treatment observations, according to some embodiments of the present disclosure. Voltage, (see FIG. 22A), current (see FIG. 22B), and impedance data (see FIG. 22C) found during the ramp-up procedure for the 2-5-2 waveform and 3 AA configuration with energy delivered between two adjacent applicators. This gradual ramp up was conducted for the first applicator placement to ensure that output currents were within the safe operating range of the pulse generator. Plot lines of the same color in FIGS. 22A and 22B indicate corresponding measurements.

Voltage (see FIG. 22A) and Current (see FIG. 22B) measurements taken during the ramp up protocol indicate that the impedance of untreated tissue exhibited a slight voltage dependence (see FIG. 22C) which decreased from 180 to 144Ω for pulses with amplitudes between 250 and 5000V. Voltage and current waveforms for each pulse amplitude exhibited a moderate degree of ringing during the rising and falling edges which subsided within approximately 500 ns.

Figure 23A:
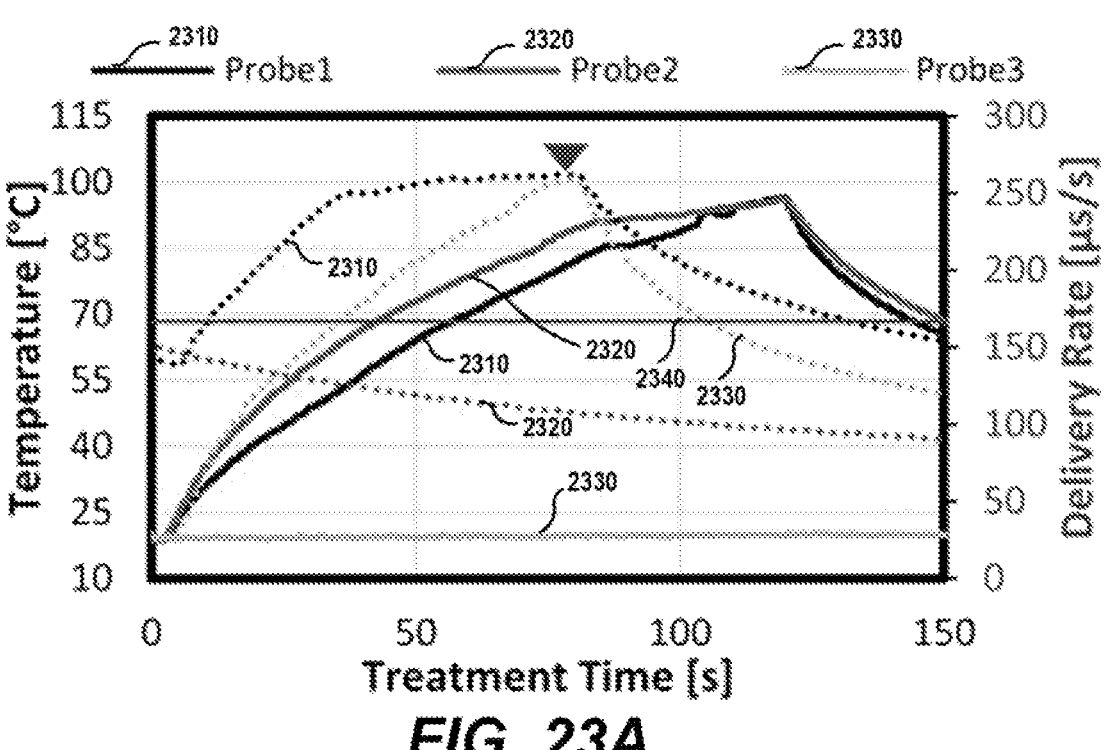
FIGS. 23A to 23C are waveforms illustrating treatment observations, according to some embodiments of the present disclosure.
Figure 23B:
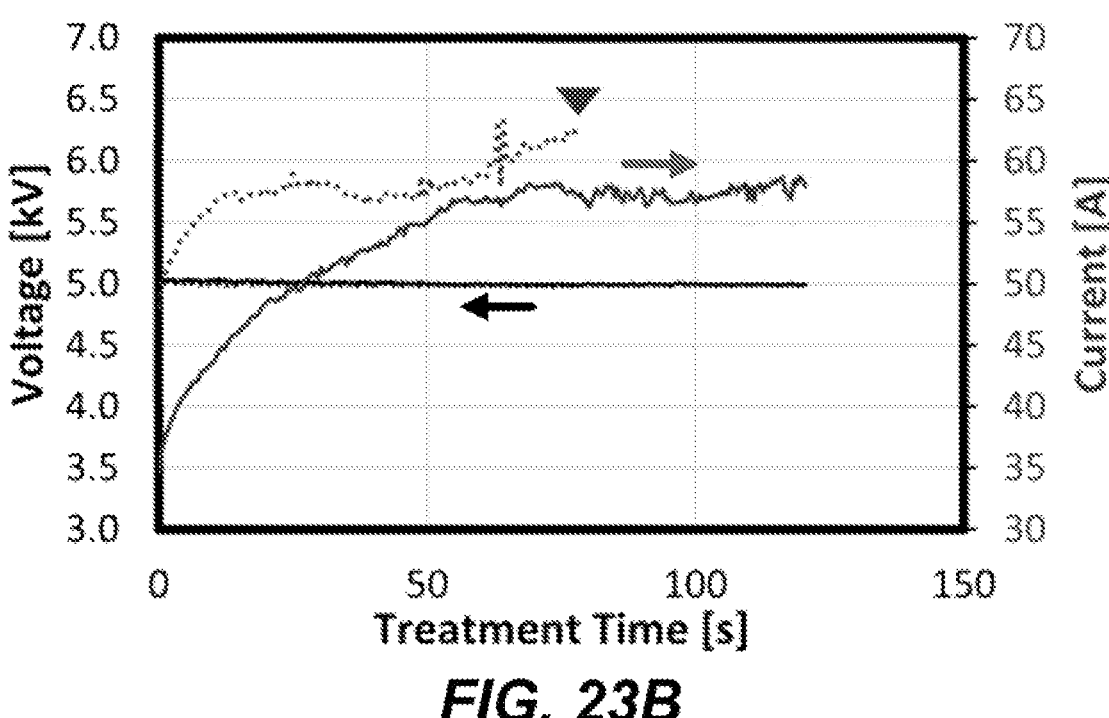
Figure 23C:
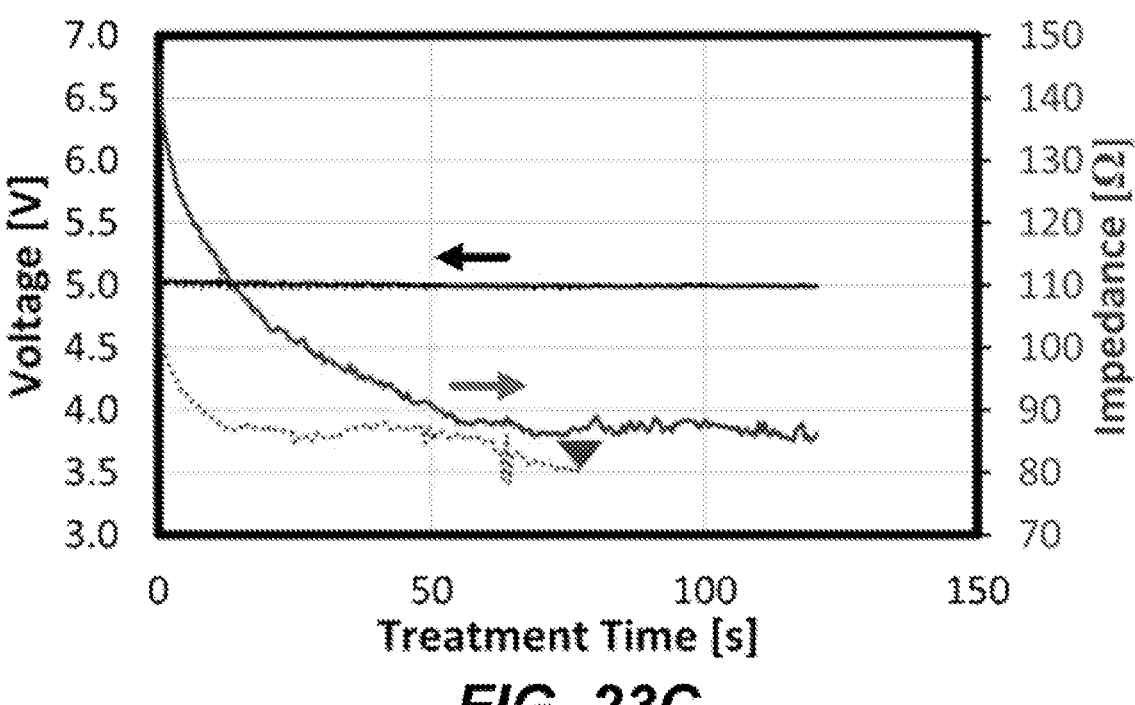

FIGS. 23A to 23C are waveforms illustrating treatment observations, according to some embodiments of the present disclosure. FIGS. 23A to 23C illustrate that treatments without thermal control enabled resulted in temperatures of 100° C. FIG. 23A illustrates plots showing the temperature profiles when an initial 0.02 s IET dose was delivered between probes 1 and 2 (solid lines) and then a second 0.02 s IET does was delivered between probes 1 and 3 (dotted lines). The initial temperature at probe 1 for the second dose was 60° C. which rapidly increased to 100° C. resulting in charring and arcing at the tissue-electrode interface at which point the treatment was aborted (arrows). The middle line (line 2340) in FIG. 23A indicates a constant energy delivery rate of 167 µs/s for these treatments. FIG. 23B illustrates voltage-current and FIG. 23C illustrate voltage—impedance plots associated with the first (solid lines) and second (dashed lines) doses showing a rapid increase in current and decrease in impedance associated with energy delivery.

Initial treatment between the first probe pairs (probes 1 and 2) without thermal control resulted in gradual increases in temperature from baseline (20° C., room temperature) to 96° C. (see FIG. 23A solid lines) over the 0.02 s IET treatment. No increase in temperature was observed for the third probe (probe 3) which was left floating. An initial current measurement of 34.7 A gradually increased to 58.5 A (see FIG. 23B) and impedance between the energized probe pair decreased from 145Ω to 85Ω over the course of this treatment. The measured voltage remained consistent (range: 5.05-4.98 kV) throughout.

Energy delivery between the next sequential probe pair (probes 1 and 3) resulted in a rapid increase in temperature to 100° C. (see FIG. 23A dots). Soon after, visible emission of steam from the applicator insertion site was observed followed by charring and arcing at the tissue surface (results not shown) at which time the treatment was aborted (see FIG. 23A, arrow heads) to prevent damage to the pulse generator by stochastic arcing and no further uncontrolled experiments were conducted. Inflection points in the current (see FIG. 23B) and tissue impedance (see FIG. 23C) plots approximately corresponded with timing of visual appearance of steam.

Figure 24C:
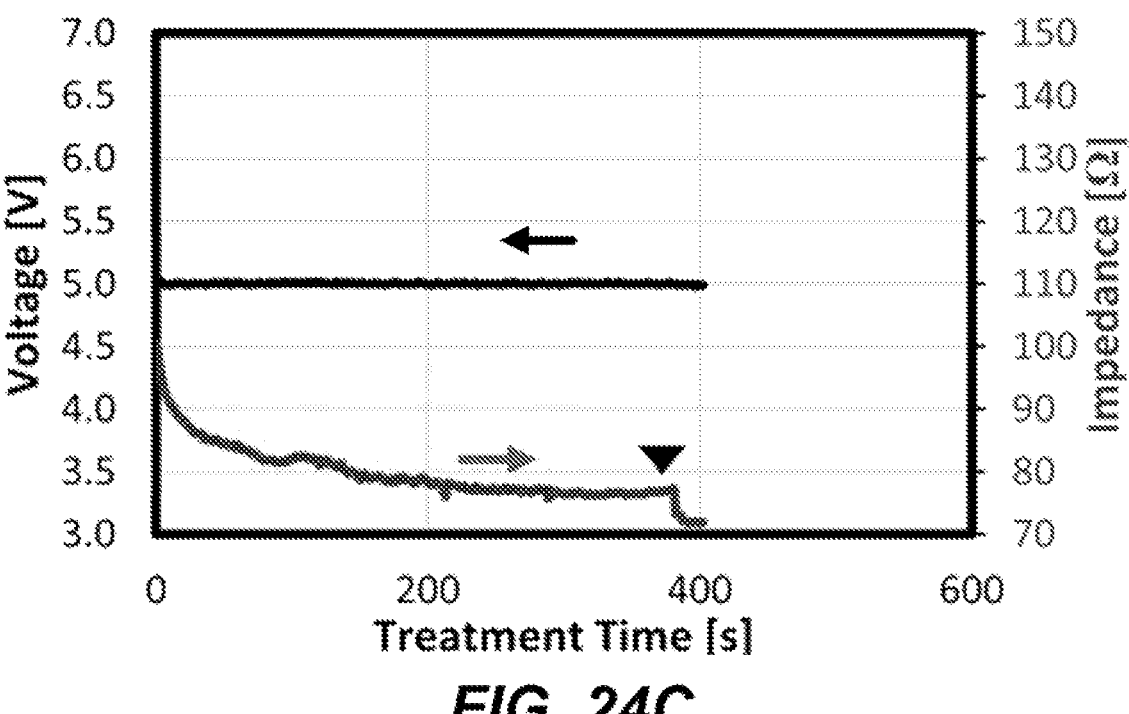

Utilization of the temperature control algorithm resulted in an increase in tissue temperatures to the target temperature with only minor overshoot before settling. FIGS. 24A to 24C are waveforms illustrating treatment observations, according to some embodiments of the present disclosure. FIGS. 24A to 24C illustrate characteristic data from 3 AA treatments with thermal control using an 80° C. temperature set point. FIG. 24A illustrates temperature plots (line 2430) showing a rapid increase to the target temperature on the controlled channel (Probe 3) with minimal overshoot. The energy deliver rate (line 2440) decreased from a baseline of 167 μs/s to a minimum of 35 μs/s to maintain the target temperature. The temperature on an uncontrolled channel (Probe 2, line 2420) briefly breached the target temperature (black arrows) resulting in a measurable change in (see FIG. 24B) current and (see FIG. 24C) impedance indicating a strong correlation of these parameters with tissue temperature.

Temperature profiles and energy delivery rates varied between treatments due to dynamic conditions in the perfused liver tissue and characteristic plots are shown in FIG. 24A. Treatment currents (see FIG. 24B) and tissue impedance (see FIG. 24C) appeared to be temperature sensitive with a dramatic change in both observed when the temperature of one probe breached the target set point (FIGS. 24A to 24C, black arrows). The temperature controlled 3 AA treatments required 26.9±8.8 minutes to complete compared to an estimated treatment time of 6.0 minutes if matched non-temperature-controlled experiments were feasible.

Figure 25A:
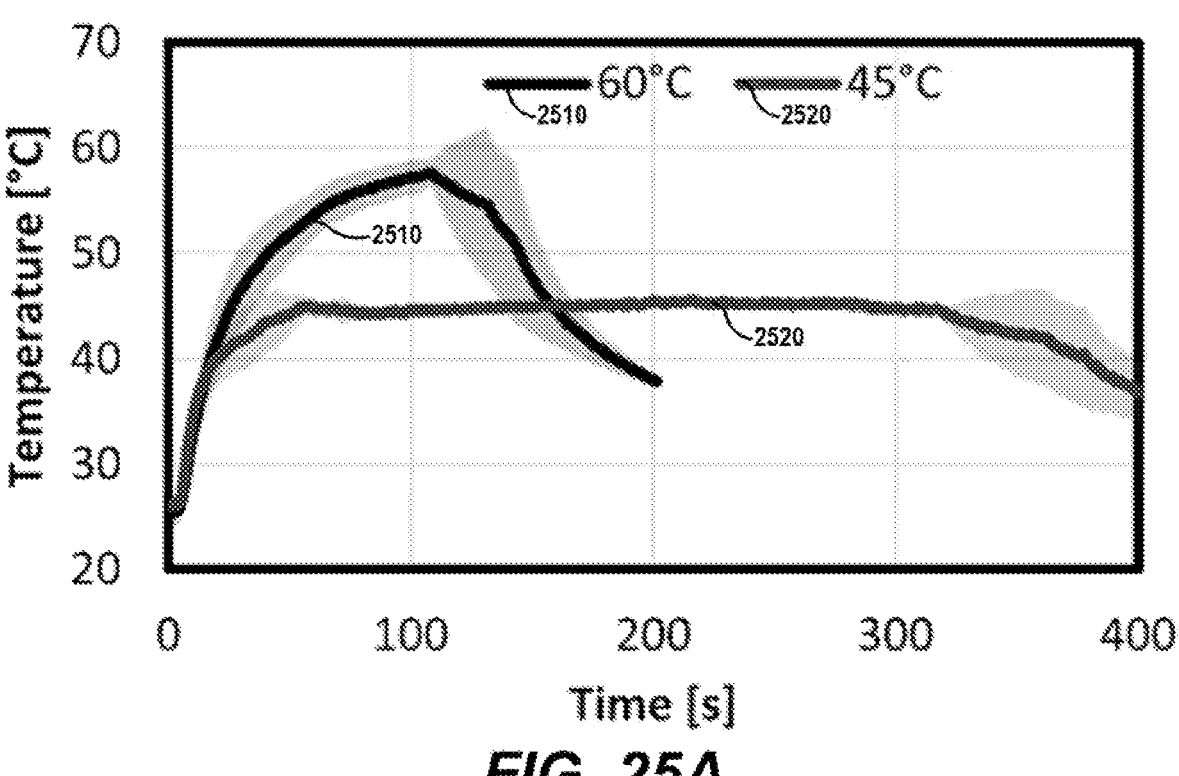
FIGS. 25A to 25C are waveforms illustrating treatment observations, according to some embodiments of the present disclosure.
Figure 25B:
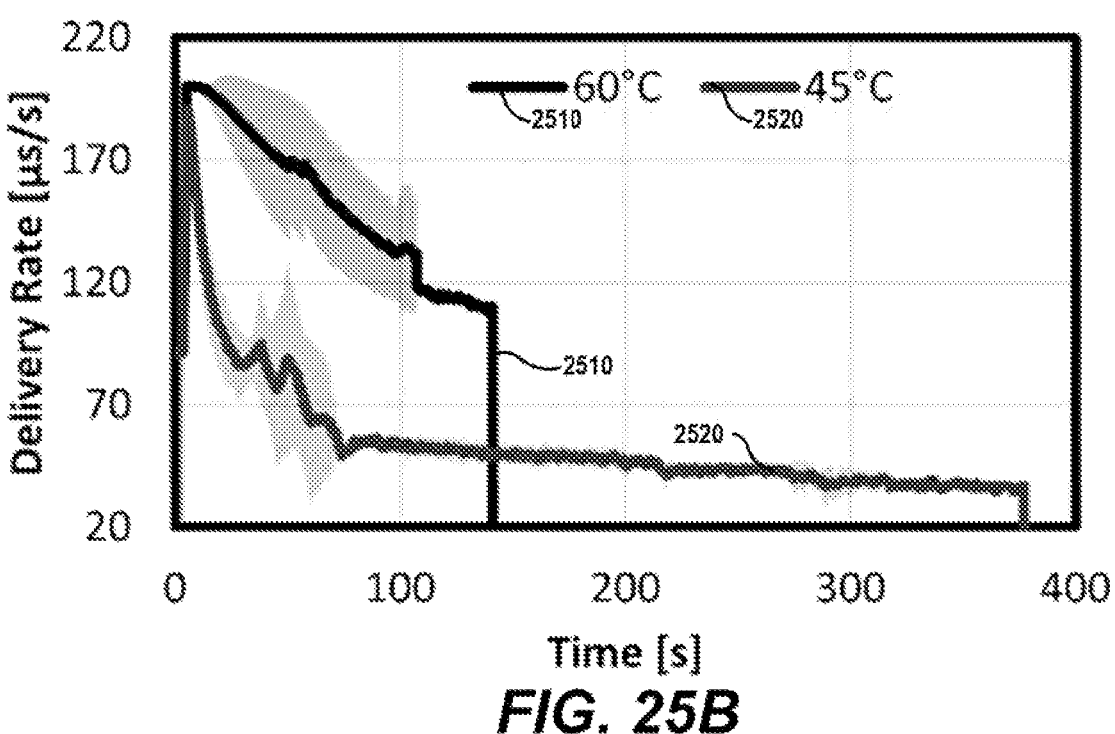
Figure 25C:
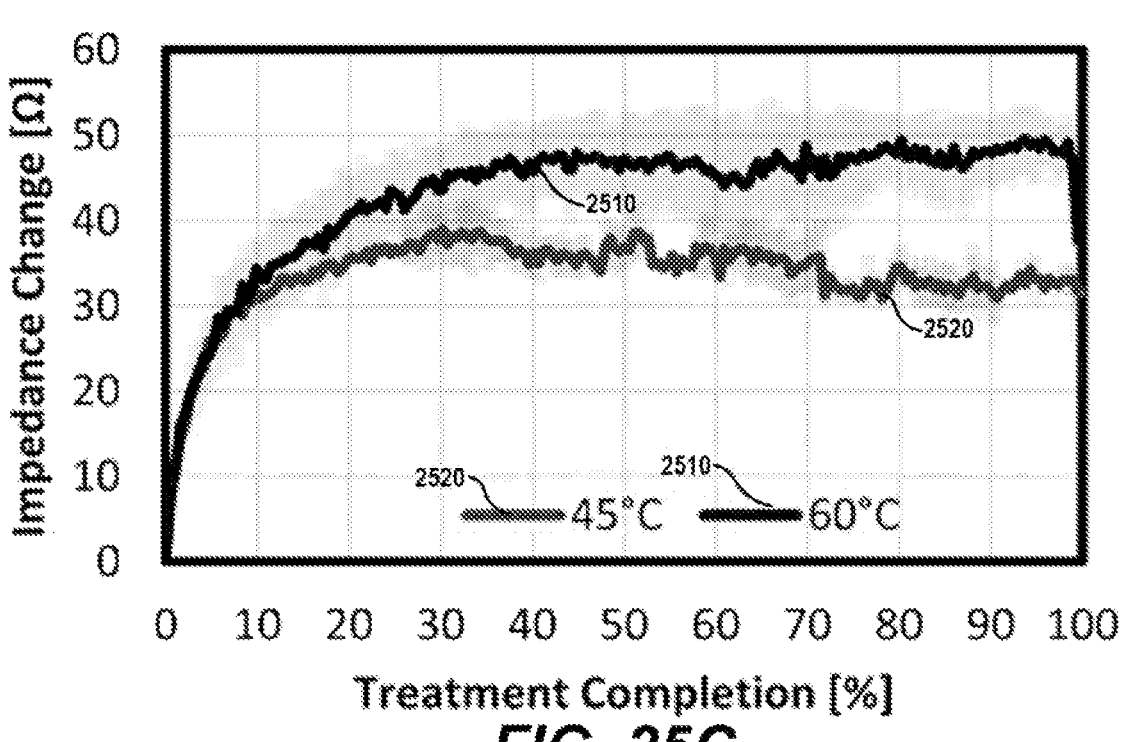

FIGS. 25A to 25C are waveforms illustrating treatment observations, according to some embodiments of the present disclosure. FIG. 25A illustrates mean treatment temperature profiles, FIG. 25B illustrates energy delivery rates, and FIG. 25C illustrates impedance changes observed for A+GP treatments with 45° C. (line 2520) and 60° C. (line 2530) temperature set points. Temperature profiles and energy delivery rates for treatments with the A+GP configuration were consistent between treatment groups. Distinct impedance changes were observed for the 45° C. and 60° C. set points (see FIG. 25C) with maximum decreases of 39.9±1.6Ω and 50.4±4.7Ω, respectively. These treatments required 5.8±0.5 and 2.4±0.19 minutes to complete.

Tissue Ablations

Figure 26A:
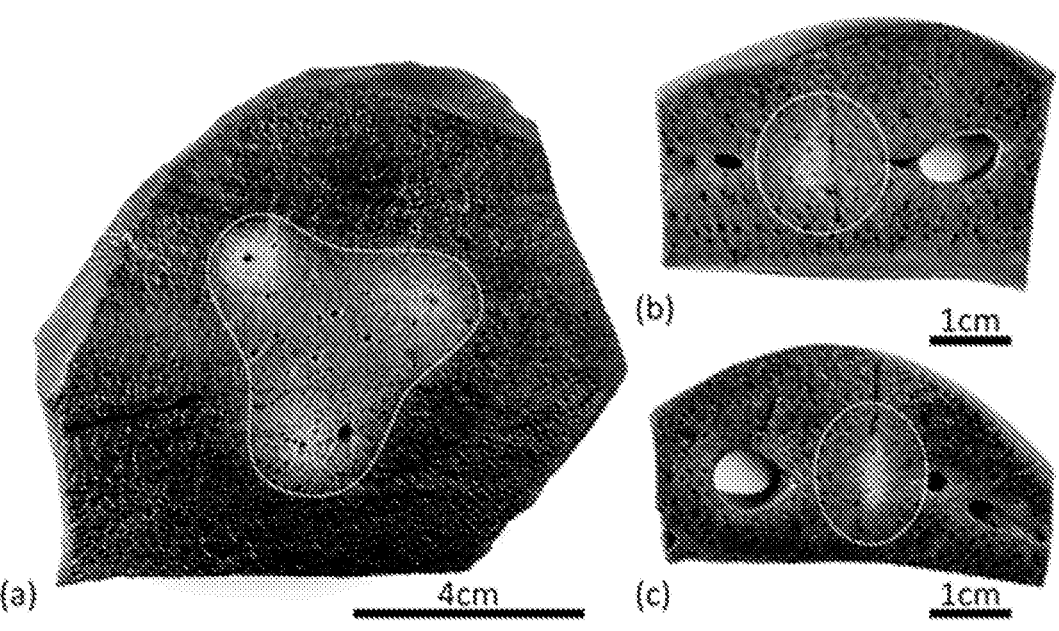
FIG. 26A includes images of ETT ablations, according to some embodiments of the present disclosure.
Figure 26B:
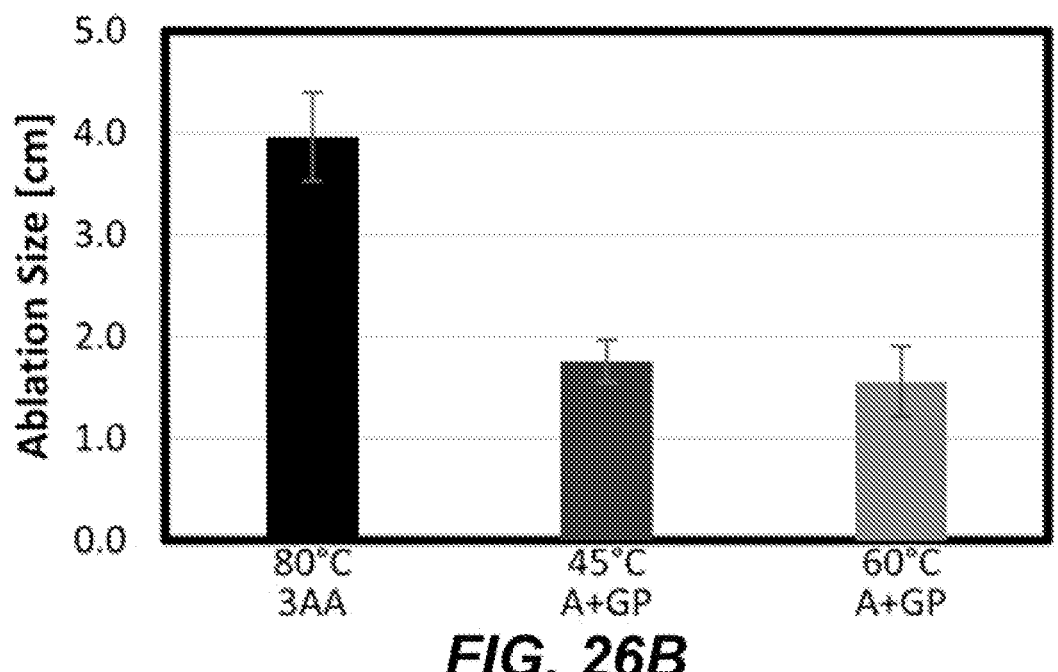
FIG. 26B is a graph of ablation sizes.
Figure 26C:
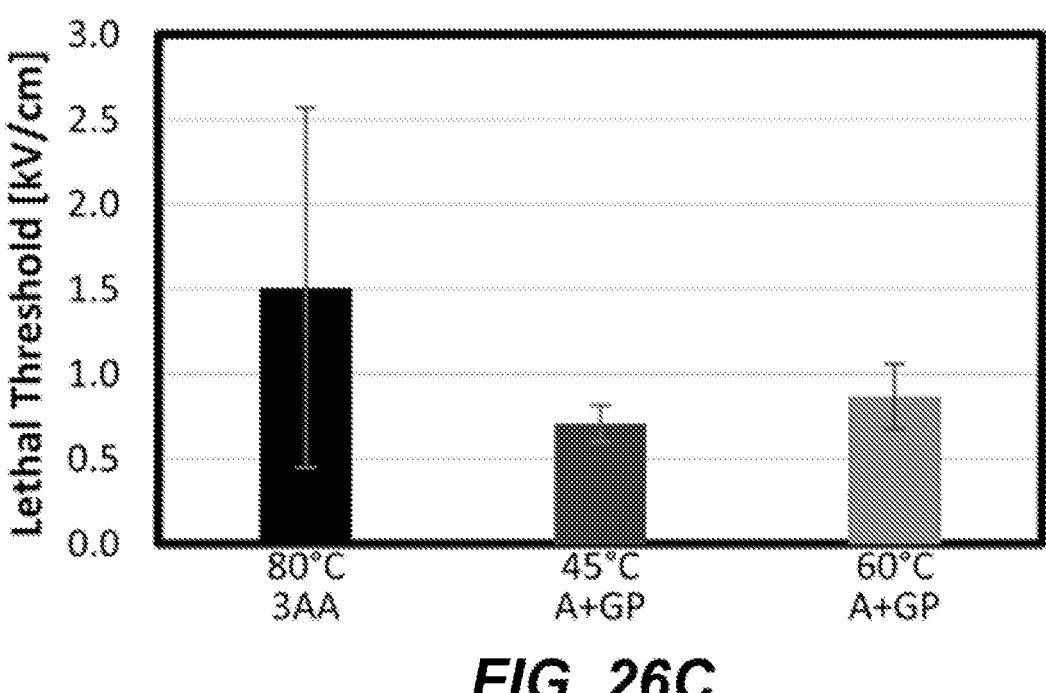
FIG. 26C is a graph of calculated lethal threshold.
Figure 26D:
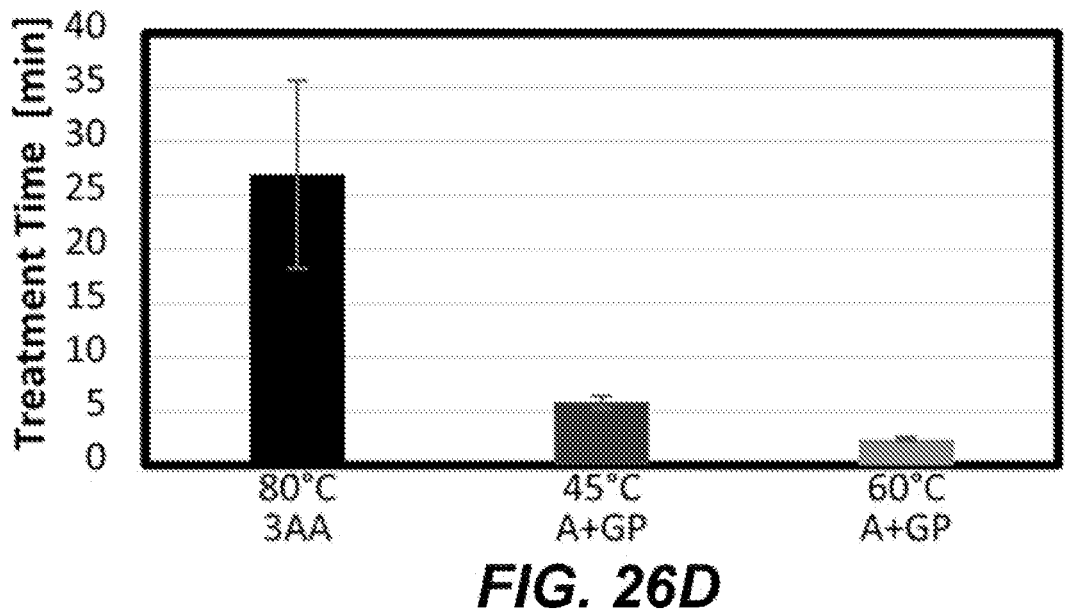
FIG. 26D is a graph of treatment times, according to some embodiments of the present invention.
Figure 27:
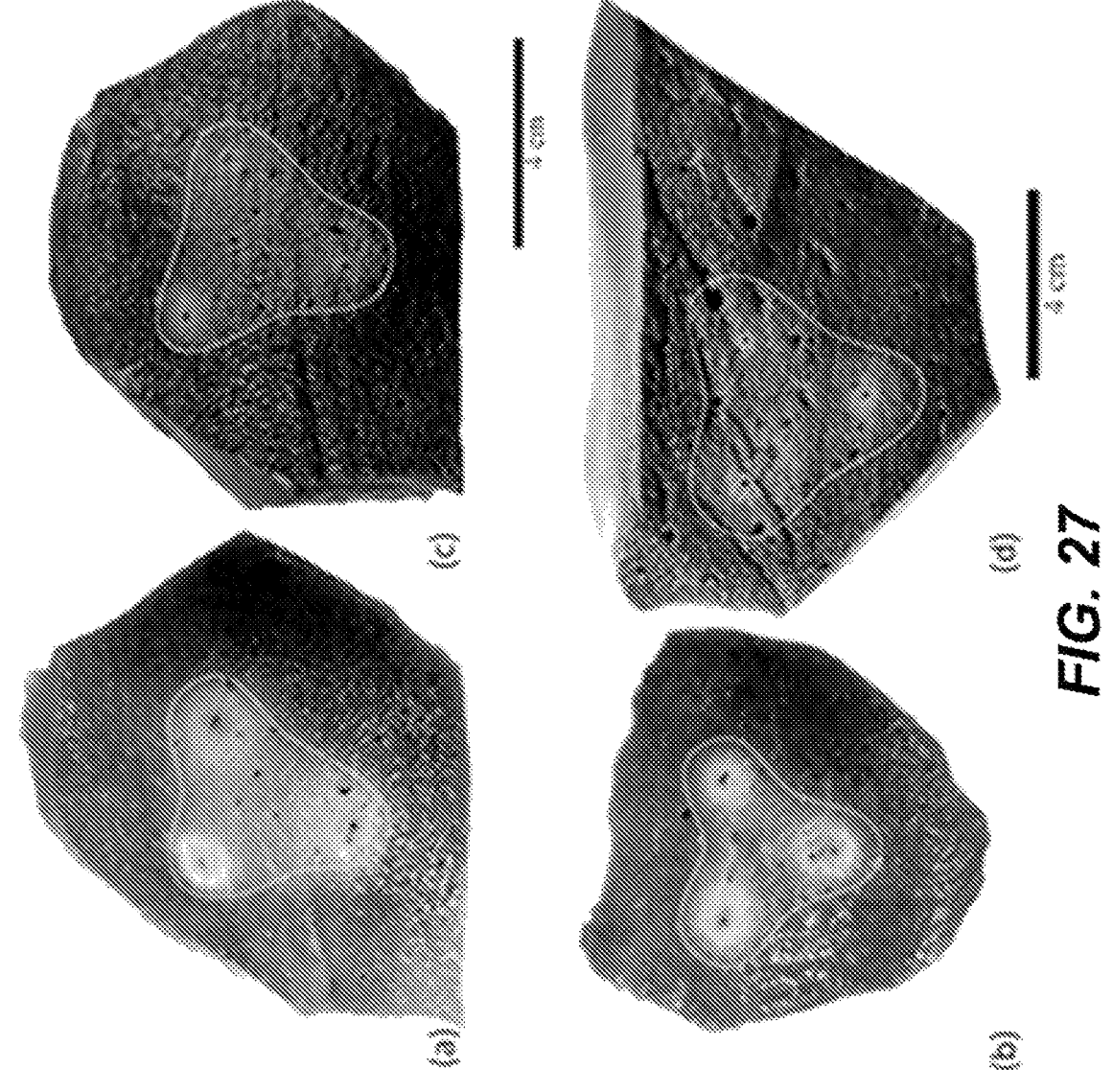
FIG. 27 includes images of representative 3 AA ablations, according to some embodiments of the present disclosure.

FIG. 26A includes images of ETT ablations created using the (a) 3 AA and (b-c) A+GP configurations. FIG. 26B is a graph of ablation sizes, FIG. 26C is a graph of calculated lethal threshold, and FIG. 26D is a graph of treatment times, according to embodiments of the present invention. As illustrated in FIGS. 26B to 26D, ablation sizes, calculated lethal threshold, and treatment times were dependent on the applicator configuration and treatment protocol. FIG. 27 includes images of representative 3 AA ablations before (a-b) and after (c-d) staining with TTC. White dotted lines indicate the approximate ablation boundary measured.

Ablation zones for the 3 AA (see FIG. 26A, image (a)) and A+GP (see FIG. 26A, images (b) and (c)) appeared lighter in color and different in texture than the surrounding unaffected tissue. An additional region of white tissue with a spongy texture indicative of thermal injury was observed adjacent to the electrode in all 3 AA (see FIG. 27) and 60° C. A+GP treatments. This was less prevalent in the 45° C. A+GP treatments. Ablations created with the 3 AA had a distinct tri-lobe shape with indentations along the outer boundary between each applicator. The A+GP ablations were oval to circular in shape which was dependent on the sectioning location relative to the applicator insertion path. The mean ablation zones measured 3.96±0.43 cm, 1.76±0.021 cm, and 1.56±0.34 cm for the 3 AA, 45° C. A+GP, and 65° C. A+GP treatments, respectively (see FIG. 26B). These corresponded to lethal thresholds of 1508±1060 V/cm, 708±108 V/cm, and 867±192 V/cm for the same respective groups (see FIG. 26C). It should be noted that the electric field distribution changes dramatically in proximity to the electrode in the 3 AA configuration and moderate changes in ablation measurement (range: 3.01-4.99 cm) resulted in large changes in the corresponding electric field calculations (range: 581-5998 V/cm).

The 3 AA treatments required the longest treatment times 26.9±8.7 minutes due to the need to deliver energy between three different probe pairs. The A+GP treatments were completed in 5.8±0.5 and 2.4±0.2 minutes for the 45° C. and 60° C. set point treatments, respectively.

Actively Cooled ACE to Control or Mitigate Thermal Injury

ACE describes a pulsed electric field treatment in which the pulse delivery rate is dynamically changed in order to regulate local tissue temperature. ACE utilizes a controls systems approach, using temperature as process feedback to manage the intra-tumor environment. For the first time this study demonstrates the use of active cooling via an internally perfused electrode combined with ACE algorithmic for control of in situ temperature profiles for tissue ablation. This was evaluated in an ex vivo tissue model with a single internally cooled applicator and grounding pad (CA+GP). The electrode configuration was used to deliver 3000V and 5000V treatments to tissue with pulse delivery rates up to 500 μs/s. The treatments were evaluated for temperature profiles, pulse delivery rates, time to completion, and extent of thermal injury. The actively cooled ACE was then compared to non-cooled treatments.

The results of this analysis indicate that active cooling of the applicator reduced thermal injury volumes by 56-84% versus non-cooled treatments. While actively cooling the electrodes, the largest thermal injury volumes (2.6±0.4 cm3) were observed for treatments with a 60° C. temperature set point. Reduction of this set point to 50° C. and 40° C. resulted in significantly smaller thermal injury volumes of 1.5±0.3 and 0.1±0.2 cm3, respectively, without significantly increasing treatment times. A combination of active cooling and temperature control (2.0 mL/min, 40° C.) was found to reduce treatment times by 84% (from 5.4 minutes to 0.9 minutes) without significantly increasing the extent of thermal injury found for matched non-cooled ACE treatments. These results confirm the use of active electrode cooling combined with ACE is a viable strategy for reducing thermal injury in pulsed electric field therapies and sets the foundation for in vivo studies.

Methods

Electrode

Figure 28A:
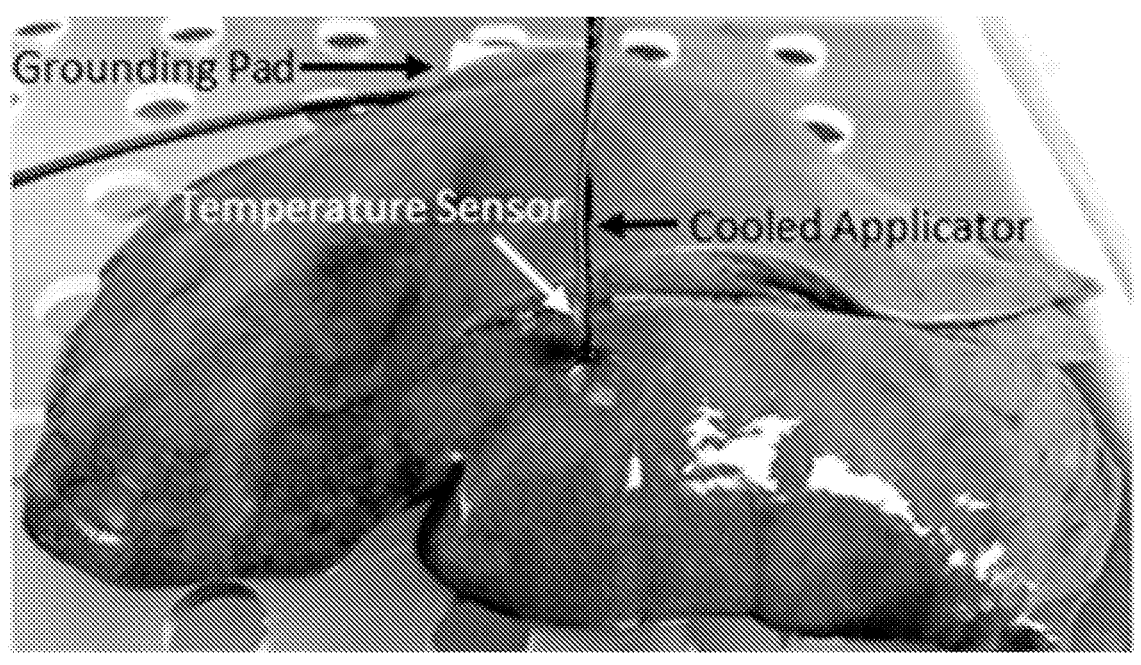
FIG. 28A is an image of a tissue treatment embodiment, according to some embodiments of the present disclosure.
Figure 28B:
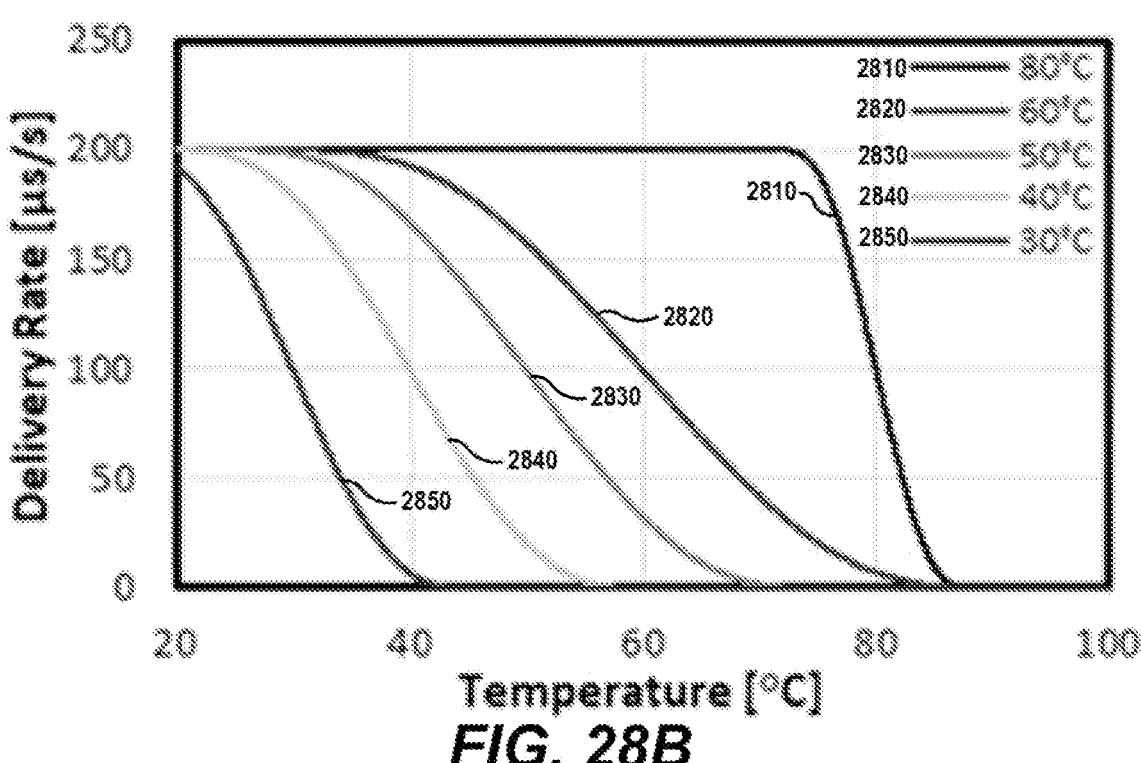
FIG. 28B is a graph illustrating delivery waveforms, according to some embodiments of the present disclosure.

FIG. 28A is an image of a tissue treatment embodiment, according to some embodiments of the present disclosure. FIG. 28B is a graph illustrating delivery waveforms, according to some embodiments of the present disclosure. FIGS. 28A and 28B illustrate an overview of an ETT treatment protocol according to some embodiments of the present disclosure. As illustrated in FIG. 28A, a fiber optic temperature sensor was attached to an internally cooled applicator with a 2 cm exposed electrode. The assembly was inserted into ex vivo tissue such that the entire applicator and 5 mm of insulation were below the tissue surface and energy was delivered via the electrode and a distal grounding pad (A+GP). Referring to FIG. 14A. a 2-5-2 (P=2, D=5, N=2) waveform was repeated continuously with a variable delay determined by the temperature dependent control algorithm illustrated in FIG. 28B to achieve a desired energy delivery rate. Treatment continued until a specified integrated energized time (dose) was achieved.

A modified 1.44 mm diameter internally cooled applicator (Cool-Tip RF, Medtronic Inc. City State) with a 2 cm electrode exposure was used to administer the treatments. To equip the electrode for high voltage experiments, the applicator handle was removed and the electrical leads from the internal temperature sensor were clipped to prevent a short circuit through the component. The original low voltage electrical lead was replaced with 10 kV rated silicone coated wire (6733-2, Pomona Electronics Inc., Everett, WA) and exposed metal at the proximal end was wrapped in polyimide and shrink wrap tubing. A fiber optic temperature sensor (TS5, Micronor Inc., Camarillo, CA) was affixed to each applicator such that the temperature sensing element was approximately halfway in the exposed area or 1 cm from the distal tip of the electrode (see FIG. 20A). In all experiments, the applicator was placed vertically into the tissue such that the entire electrode and an additional 5 mm of insulator were beneath the tissue surface (see FIG. 28A). A 4×5 cm aluminum foil grounding pad was placed underneath the tissue served as the return path to the pulse generator.

Treatment Algorithm

Electrical pulses with amplitudes of 3000 V and 5000 V were delivered using a custom pulse generator based on an H-Bridge topology which included a 100 MSPS data acquisition system to record voltage and current waveforms in real time. Temperatures were acquired by a signal conditioner (Fotemp, Micronor Inc., Camarillo, CA) and transmitted over USB where they were recorded at 3 Hz by a custom Python application which controlled the pulse generation system.

All experiments were conducted using a waveform consisting of a 2 us positive polarity pulse, a 5 μs delay, and a 2 μs negative polarity pulse (2-5-2 waveform, see, FIG. 14A). This waveform was repeated to deliver a specified electrical dose with an integrated energized time (IET) calculated as:

$$IET = \sum_{0}^{N} \tau_p + \tau_n [s] \tag{46}$$

where N is the total number of waveforms delivered and $\tau_p$ and $\tau_n$ are the positive and negative pulse durations (2 μs), respectively. The total time required to deliver the target IET (0.01 s or 0.02 s) was automatically recorded and values are reported here as mean±standard deviation.

The delay (δ) between sequential 2-5-2 waveforms was either held constant or dynamically adjusted using a temperature control algorithm to achieve a specified pulse delivery rate (R) calculated as:

$$R = \frac{\tau_p + \tau_n}{\delta} [\mu s/s] \tag{47}$$

When enabled, the temperature control algorithm determined the rate (R) at which waveforms were delivered:

$$R(T) = R_{max} \cdot \rho(T) [\mu s/s] \tag{48}$$

$$\rho(T) = 0.5 - 0.9375 \cdot \Gamma(T) + 0.625 \cdot \Gamma(T)^3 - 0.1875 \cdot \Gamma(T)^5 \tag{49}$$

$$\Gamma(T) = \frac{T - T_t}{\beta} \tag{50}$$

$$\beta = T_t * \omega \tag{51}$$

where $R_{max}$ is the maximum pulse delivery rate [μs/s] prescribed, T is the current instantaneous temperature [° C.], $T_t$ is the target temperature [° C.], and ω is a coefficient affecting the slope between maximum and minimum energy delivery rates. This was held constant at 0.5 for all experiments except those with an 80° C. set point which required a more aggressive treatment energy delivery rate (ω=0.1) to reach the target temperature (see FIG. 28B). This metric of pulse delivery rate with units of μs/s was used to enable comparison to protocols which utilize longer (e.g. 50-100 μs) and shorter (e.g. 0.5-2.0 μs) pulses with approximately equivalent average power, but different pulse repetition rates. The treatment temperature profiles are presented as the mean±standard deviation when R was held constant. For temperature-controlled treatments the median length treatment is presented due to variation in treatment lengths producing non-representative mean temperature profiles.

Active cooling of the applicator was accomplished via perfusion with ice water which was circulated using a peristaltic pump (EW-77921-65, Cole-Palmer, Vernon Hills, IL) attached to the applicator's fluid input tubing. In all actively cooled experiments, fluid flow (1-8 mL/min) was started prior to placement of the applicator and treatments were initiated as soon as safely possible after insertion of the applicator into the tissue to avoid substantially pre-cooling the treatment site.

Validation of ETT Protocol and Active Cooling

The ETT temperature control algorithm was validated by administering 3000 V, 0.01 s IET treatments with an $R_{max}$ of 200-400 μs/s and a temperature set point of 30° C. which represents an approximate 10° C. increase from baseline. The effect of active cooling on temperature profiles was separately investigated by delivering matching 3000 V, 0.01 s IET treatments with fixed pulse delivery rates of 200 μs/s. The applicator was either non-cooled (0.0 mL/min) or actively cooled via perfusion at a rate of 2 mL/min. The combinatorial effect of ETT temperature control and active cooling was then evaluated with perfusion at rates of 2 and 4 mL/min. This preliminary validation was conducted in ex vivo bovine muscle tissue which provided a consistent load impedance independent of probe placement. All tissue was obtained from a local grocer and allowed to equilibrate to room temperature prior to experiments.

Effect of Coolant Flow Rate on Thermal Injury

It was of interest to determine how treatment parameters affected thermal injury at the electrode-tissue interface. Ex vivo liver tissue was used to assess the induction of thermal injury in a clinically relevant organ. To maximize the potential of inducing thermal injury, 0.02 s IET 5 kV treatments were administered with an $R_{max}$ of 500 μs/s. This IET (0.02 s) is approximately the dose prescribed for clinical NK-IRE treatments (e.g. 90×–220×, 70 μs-100 μs pulses, 0.006-0.022 s IET) and is typical for high frequency IRE treatments.

Fluid flow rates of 0.0 (no cooling), 1.0, 2.0, 4.0, and 8.0 mL/min were investigated. To prevent extreme temperatures which can result in tissue desiccation, arcing, and damage to the pulse generator, these experiments were conducted with a temperature set point of 80° C. To mitigate the impact of treatment current as a confounding factor, the grounding pad was moved to obtain consistent mean currents, measured throughout the treatment (range: 18.3-21.1 A) for these protocols. To achieve this, a single test waveform was delivered, and the grounding pad was moved accordingly to adjust the initial current to approximately 18 A.

Effect of Temperature Set Point on Thermal Injury

To investigate the effect of ETT temperature set point on thermal injury 0.02 s IET 5000V treatments were administered with an $R_{max}$ of 500 µs/s and a perfusion flow rate of 2.0 mL/min with temperature set points of 40, 50, and 60° C. In some actively cooled temperature-controlled treatments the measured temperature failed to reach the 40, 50, or 60° C. target set points. This may have been due to deflection of the temperature sensor away from the electrode-tissue interface or elevated tissue impedance. These treatments were excluded from analysis and additional data points were acquired.

Treatments comparing the ETT waveforms to those used by the clinical NK-IRE protocols were attempted, however, intense electrical arcing was observed for 100 µs monopolar waveforms in preliminary experiments at 4000V and these treatments were aborted to avoid damaging the pulse generator. Intense electrical arc was observed during the first 4 kV 100 µs electrical pulse delivered in these treatments. Stochastic filamentous corona was observed at the tip of the electrode observed in some 5 kV ETT treatments. All other protocols were repeated a minimum of three times (N=3), with the exception of the non-cooled 40° C. ETT protocol which was repeated once due to order of magnitude greater treatment times. A full accounting of the experimental parameters investigated in this study is presented in Table 3, which is a summary of experimental conditions investigated. In Table 3, dash symbols (-) indicate non-cooled experiments.

TABLE 3

| Voltage [V] | Cooling Rate [mL/min] | Temperature Set Point [° C.] | Replicates (N) |
|---|---|---|---|
| 3000 | — | None | 3 |
| | 2 | None | 3 |
| | — | 30 | 3 |
| | 2 | 30 | 6 |
| | 4 | 30 | 5 |
| 5000 | — | 80 | 4 |
| | 1 | 80 | 3 |
| | 2 | 80 | 3 |
| | 4 | 80 | 3 |
| | 8 | 80 | 3 |
| 5000 | — | 40 | 1 |
| | — | 50 | 8 |
| | 2 | 40 | 5 |
| | 2 | 50 | 3 |
| | 2 | 60 | 3 |

Following treatment, the liver tissue was sectioned along the applicator insertion path. Some treatment locations contained a distinctly lighter region of tissue with a porous texture consistent with thermal injury. The treatment sites were photographed and measurements of the maximal width (w, perpendicular to the applicator) and maximal length (l, parallel to the applicator) of the thermal injury zone was measured for each side of the tissue section. The volume of thermal injury was then calculated as:

$$V = \frac{\pi}{6} l \cdot w^2 \left[ cm^3 \right] \tag{52}$$

Treatment sites where the needle path could not be identified due to improper sectioning were excluded from evaluation avoid to underestimating the extent of thermal injury present. Values for each treatment parameter were then averaged and are presented here as mean±standard deviation. Statistical analysis was completed via a one-sided Student's T-Test assuming unequal variances and an alpha level of 0.05 using JMP Pro 14 (SAS Institute Inc., Cary, NC).

Results

Validation of ETT Protocol and Active Cooling

Figure 29A:
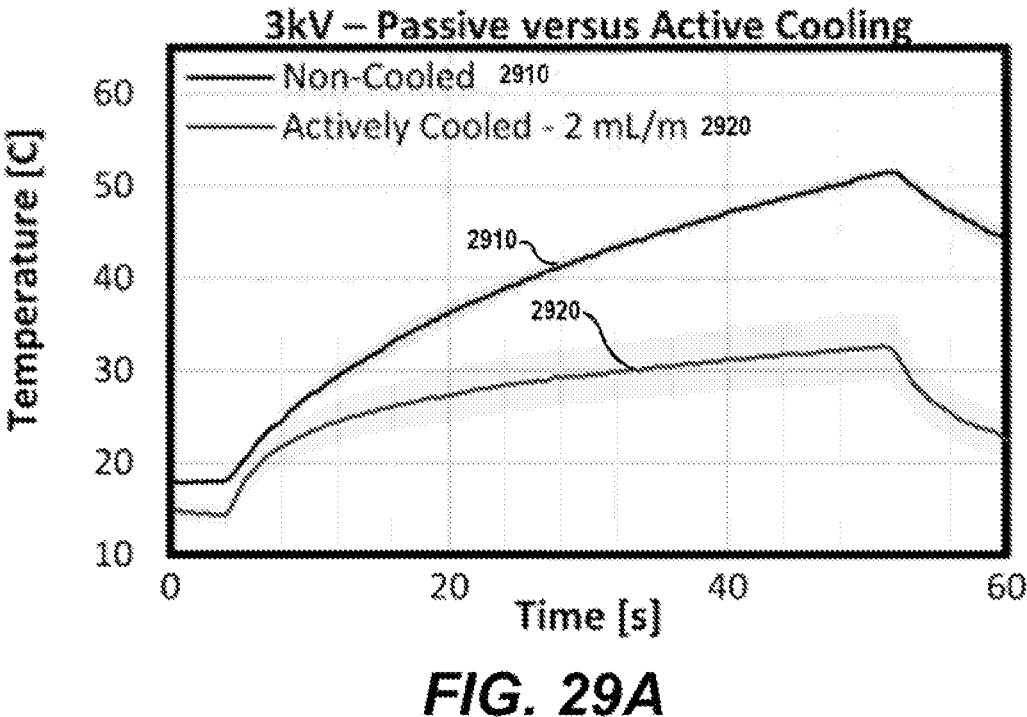
FIGS. 29A to 29D are graphs illustrating treatment observations, according to some embodiments of the present disclosure.
Figure 29B:
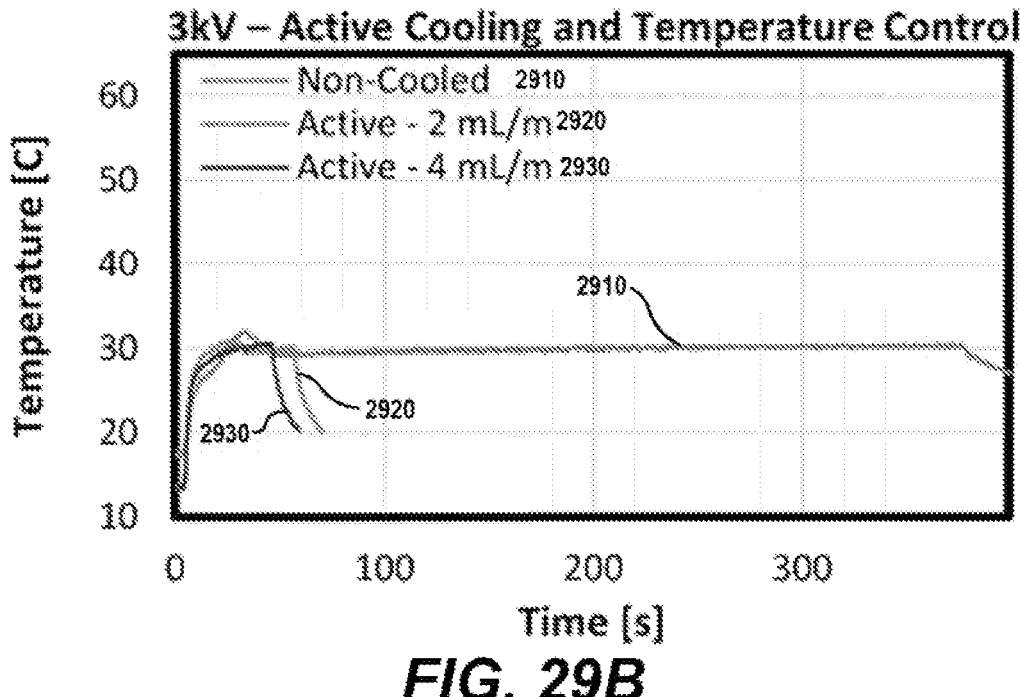
Figure 29C:
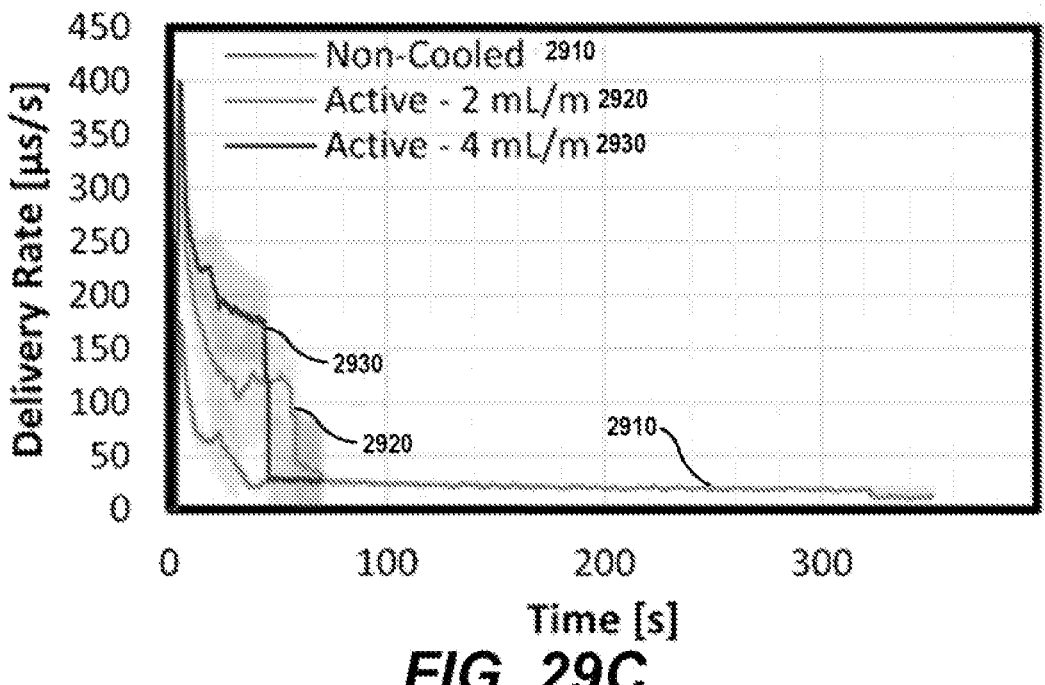
Figure 29D:
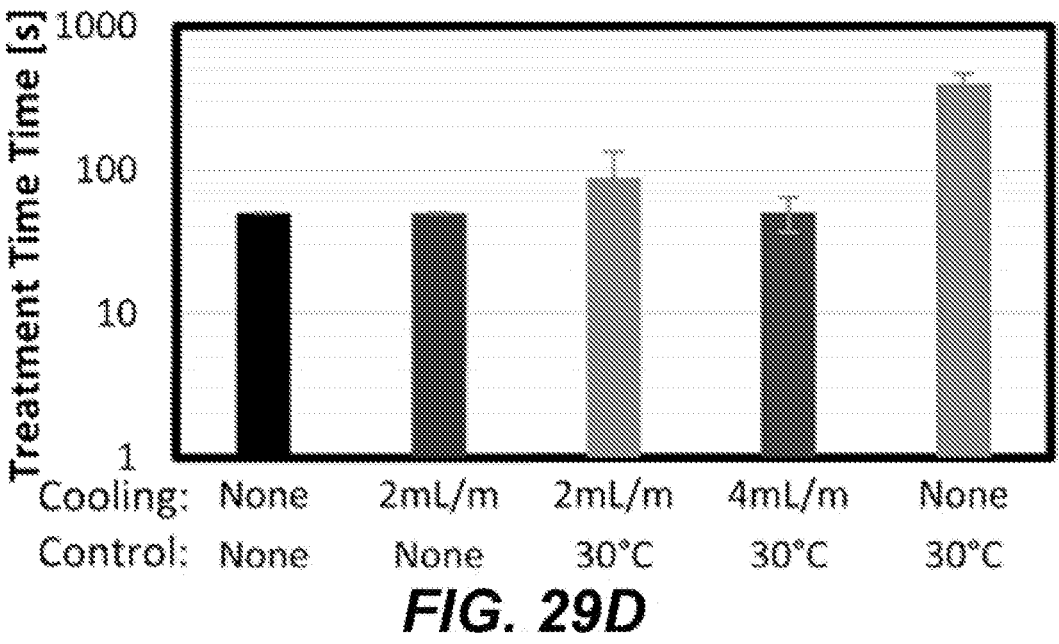

FIGS. 29A to 29D are waveforms that illustrate an effect of active cooling and temperature control algorithm, according to some embodiments of the present disclosure. FIG. 29A illustrates temperature profiles for 3 kV 0.01 s IET treatments with (line 2920) and without (line 2910) active cooling when energy was delivered at a constant rate of 200 µs/s. FIG. 29B illustrates temperature profiles 3 kV 0.01 s IET treatments with a 30° C. temperature set point with 2 mL/m (line 2920), 4 mL/m cooling (line 2930), or 0 mL/m (non-cooled) (line 2910). FIG. 29C illustrates the mean treatment durations for the protocols presented in FIGS. 29A and 29B. Shaded regions represent one standard deviation from the mean.

Non-cooled 3000V treatments delivered at a constant rate of 200 µs/s resulted in a mean temperature change of 33.6±0.6° C. (see FIG. 29A) calculated as the difference between the initial and maximum temperature for each treatment. Initiation of active cooling at a perfusion rate of 2.0 mL/min resulted in a mean temperature change of 17.8±2.7° C. for the same 0.01 s IET treatment protocol. These constant energy delivery rate protocols were completed in 50.03±0.003 s and 50.03±0.005 s, respectively.

Initiation of temperature control with a 30° C. target resulted in treatment temperature profiles which increased to 30° C. followed by minor overshoot before settling back to the target temperature (see FIG. 29B). Without cooling, the delivery rate fell from an initial peak of 200 µs/s to a steady state rate of 21.6±3.8 µs/s approximately 50 s after treatment was initiated (see FIG. 29C). Active cooling with perfusion rates of 2 and 4 mL/min enabled the use of $R_{max}$ of 400 µs/s. These treatments reached steady state temperatures after 19.2±11.7 s and 27.1±11.2 s, respectively. In general, the pulse delivery rates did not settle to steady state values prior to the completion of treatment for these actively cooled protocols. Without cooling, the 3000V, 0.01 s IET treatments had mean durations of 397.5±67.7 s. Actively cooling the applicator at perfusion rates of 2.0 mL/min and 4.0 mL/min reduced total treatment times to 87.0±47.1 s and 50.3±13.7 s, respectively (see FIG. 29D).

Effect of Coolant Flow Rate on Thermal Injury

Figure 30A:
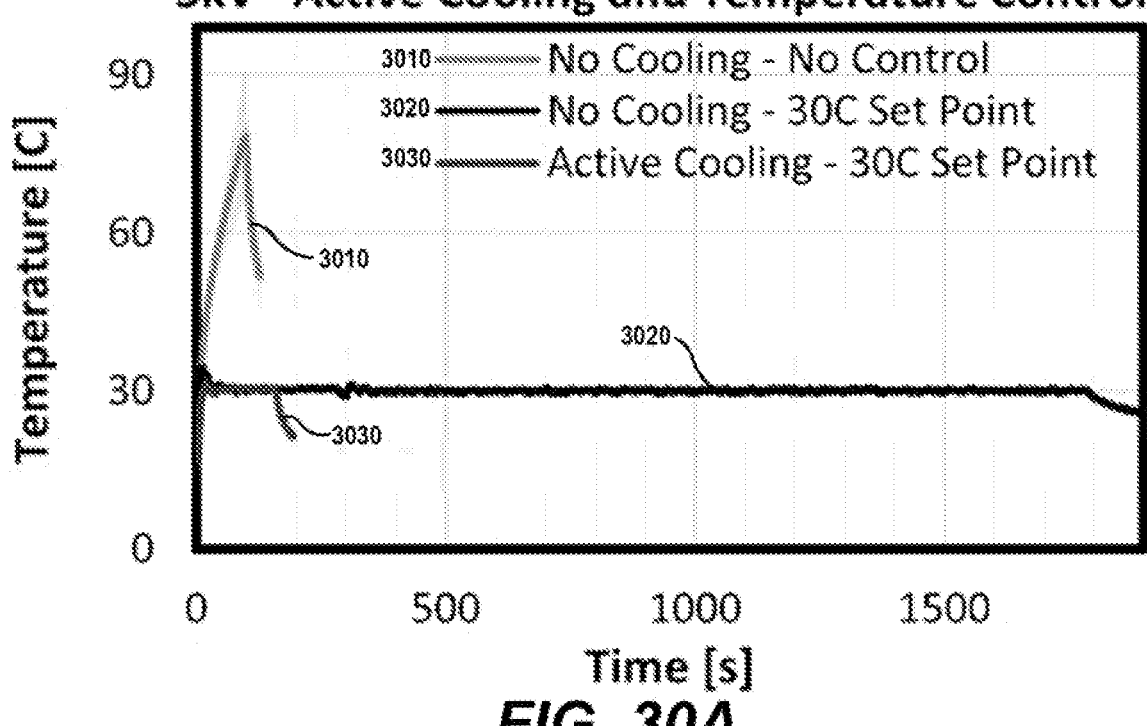
FIGS. 30A and 30B are graphs illustrating treatment observations, according to some embodiments of the present disclosure.
Figure 30B:
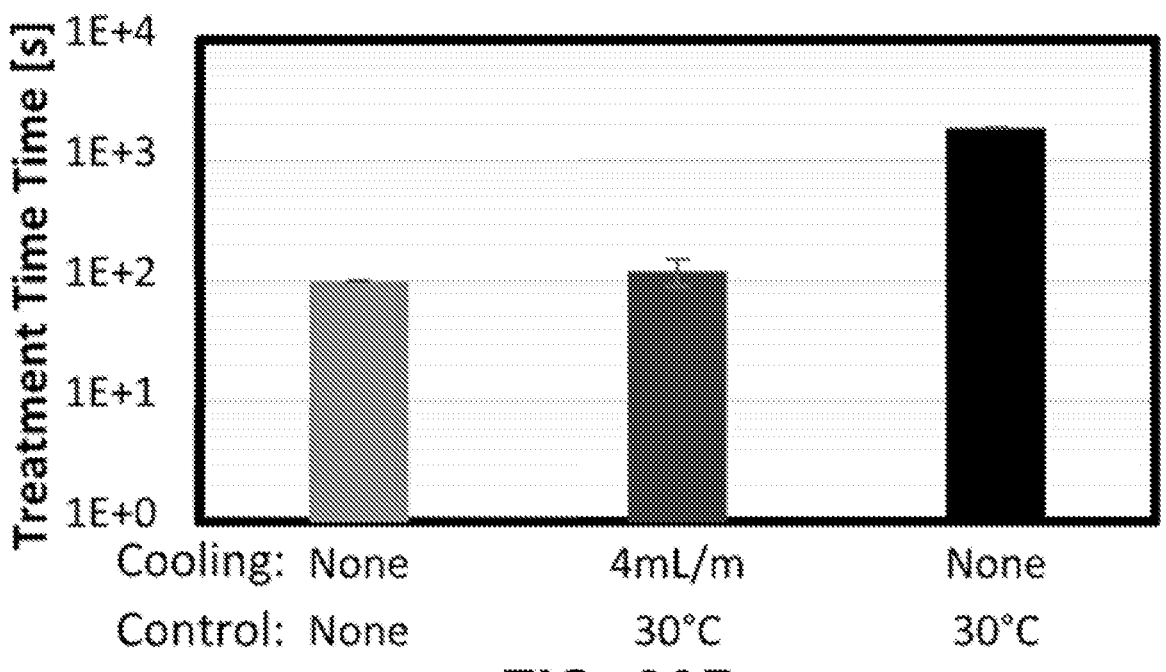

FIGS. 30A and 3B are waveforms illustrating preliminary validation of ETT protocol for 5000V treatments, according to some embodiments of the present disclosure. FIG. 30A illustrates temperature profiles for 0.01 s IET treatments with passive cooling and no temperature control (line 3010), passive cooling and 30° C. temperature control (line 3020), and active cooling (4 mL/min) and 30° C. temperature control (line 3030). FIG. 30B illustrates mean treatment durations as a function of cooling and temperature control protocol. Temperature control treatments were conducted with an initial rate of 200 μs/s while uncontrolled treatments were conducted with a constant delivery rate of 100 μs/s. Preliminary 5000V 0.01 s IET treatments utilizing a fixed pulse delivery rate of 100 μs/s without cooling resulted in a mean temperature increase of 57.0±10.9° C. during the 100.0±0.002 s duration treatments. These treatments reached peak temperatures of 78.8±12.3° C. without approaching a steady state equilibrium. Dynamic energy delivery with temperature control was therefore implemented for all subsequent 5 kV treatments to prevent the tissue from reaching temperatures associated with tissue desiccation (approximately 100° C.) in the longer 0.02 s IET treatments evaluated.

Figure 31A:
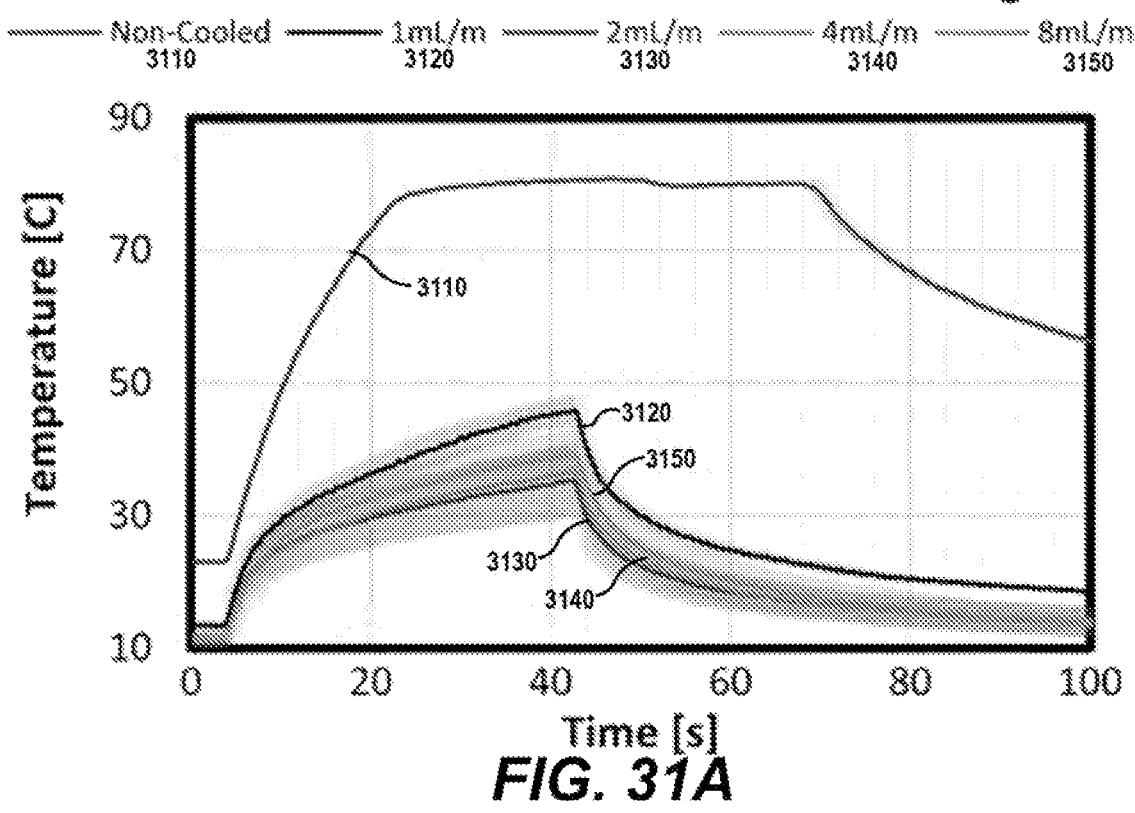
FIGS. 31A to 31C are graphs illustrating treatment observations, according to some embodiments of the present disclosure.
Figure 31B:
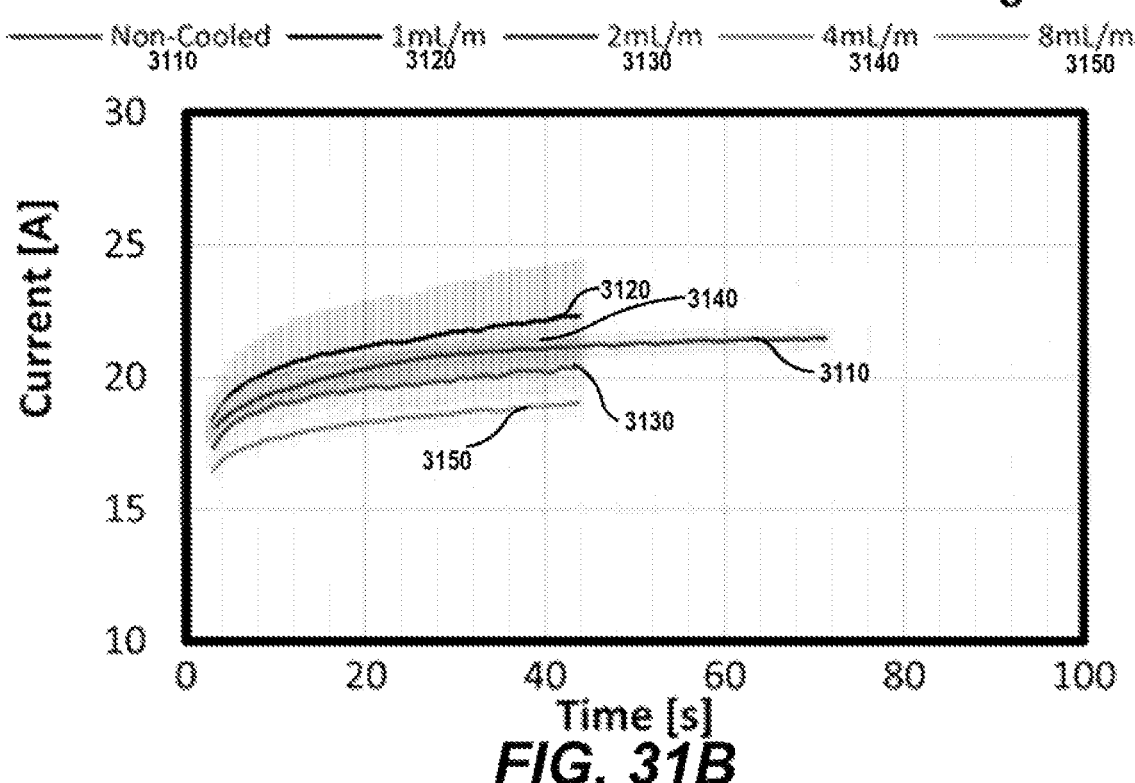
Figure 31C:
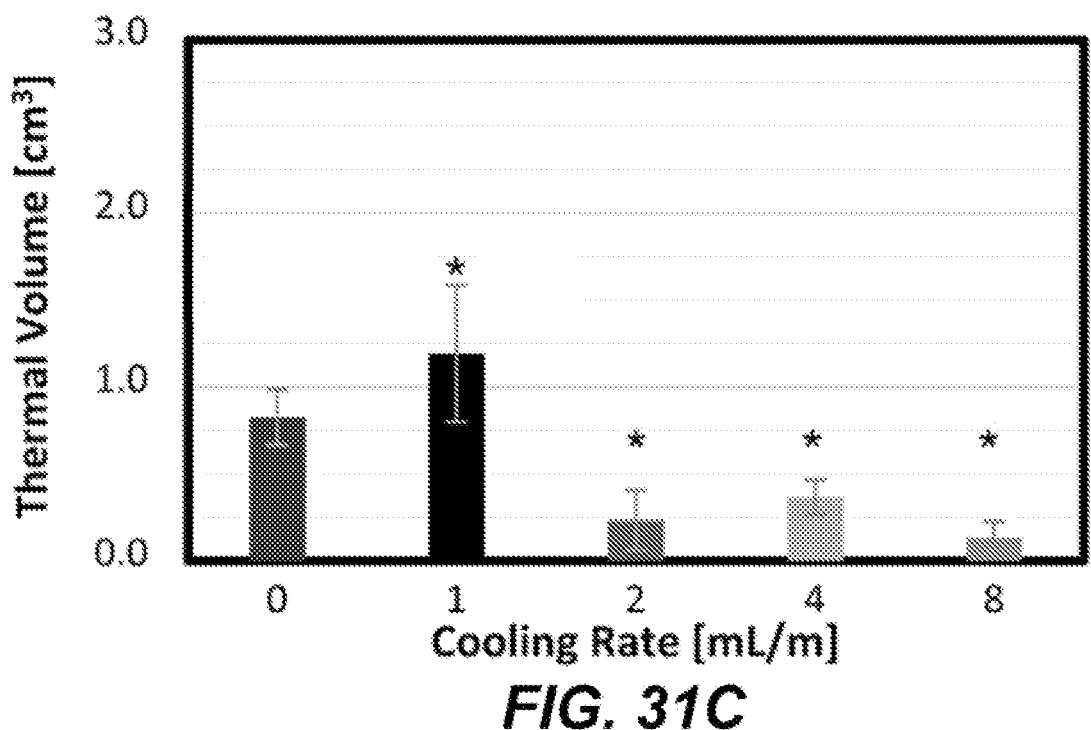

FIGS. 31A to 31C are waveforms illustrating thermal damage as a function of coolant perfusion rate. FIG. 31A illustrates temperature profiles and FIG. 31B illustrates current profiles for treatments with passive cooling (0 mL/min) (line 3110), and active cooling with perfusion rates of 1 (line 3120), 2 (line 3130), 4 (line 3140), and 8 (line 3150) mL/min. FIG. 31C illustrates calculated thermal damage volumes and representative gross sections from treatments with 0, 1.0, 2.0, 4.0, and 8 mL/min cooling rates. In FIG. 31C, a '*' indicates statistically significantly different than the non-cooled (0 mL/m) treatment group.

Without cooling (0 mL/min), 5000V ETT treatments with an $R^{max}$ of 500 μs/s reached the 80° C. temperature set point in 33.0±0.7 s (see FIG. 31A) and maintained a temperature of 80.2±0.4° C. for the duration of the treatment. These treatments had mean initial currents of 18.1±0.4 A which increased to 21.5±0.5 A (see FIG. 31B). Following treatment, distinct zones of lighter tissue with a spongy texture, indicative of thermal injury (see FIG. 31C), were observed adjacent to the electrode insertion path. For the non-cooled treatments, these regions measured 0.83±0.16 cm³. Active cooling with perfusion rates of 1, 2, 4, and 8 mL/min resulted in temperature profiles which failed to reach the 80° C. set point or a steady state before the 0.02 s IET treatment was completed. These treatments reached peak temperatures of 46.1±2.2, 35.3±4.4, 36.9±4.6, and 39.6±3.1° C., respectively (see FIG. 31A). The 1 mL/min treatments resulted in the highest final currents of 22.3±2.1, while the 8 mL/min treatments resulted in the lowest final currents of 19.1±0.7 A with the 2 and 4 mL/min currents falling non-sequentially between these values (see FIG. 31B). The largest thermal injury zones were found for the 1 mL/min treatment groups measuring 1.19±0.40 cm³ (see FIG. 31C). These were found to be statistically significantly larger than the non-cooled (p=0.004) and the remaining actively cooled treatments (p<0.001) which measured 0.24±0.17, 0.37±0.10, and 0.13±0.09 mm³ for the 2, 4, and 8 mL/min treatment groups, respectively. As the cooling rate increased, the thermal injury zone was observed to narrow along the electrode insertion path resulting in a teardrop shaped zone with the widest point occurring at the locations approximately corresponding to the electrode tip. While the 8 mL/min treatment group resulted in the smallest thermal injury zones, this group was not found to be statistically significantly different than the 2 mL/min (p=0.41) or 4 mL/min (p=0.081) treatment groups.

Effect of Temperature Set Point on Thermal Injury

Figure 32A:
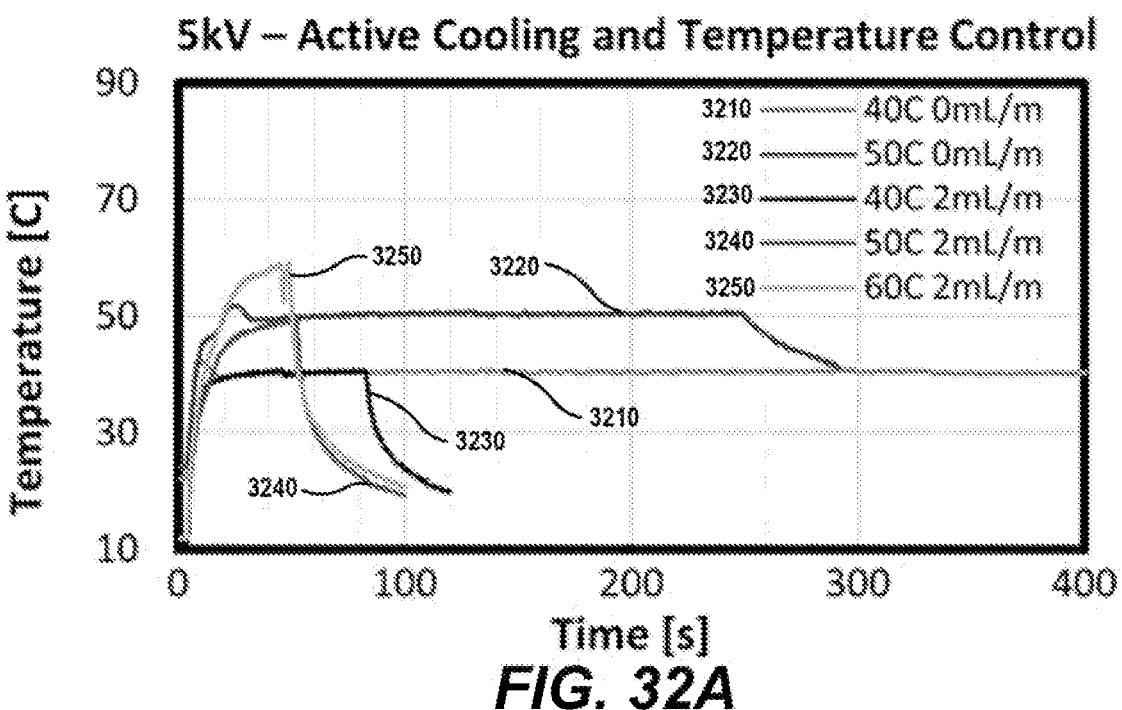
FIGS. 32A to 32D are graphs illustrating treatment observations, according to some embodiments of the present disclosure.
Figure 32B:
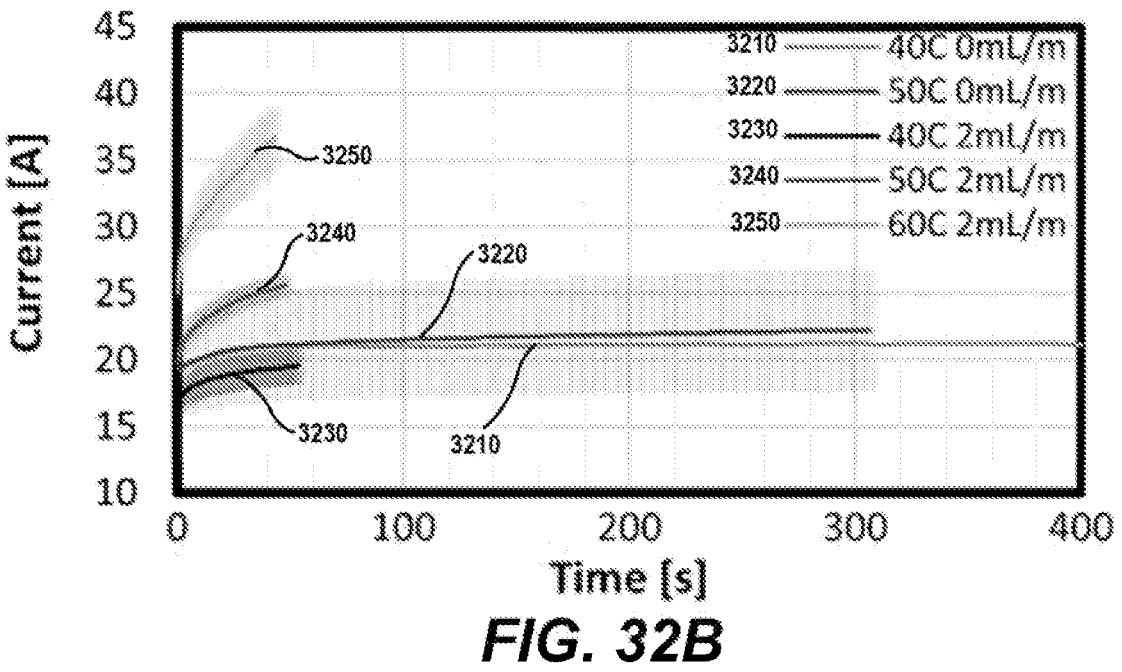
Figure 32C:
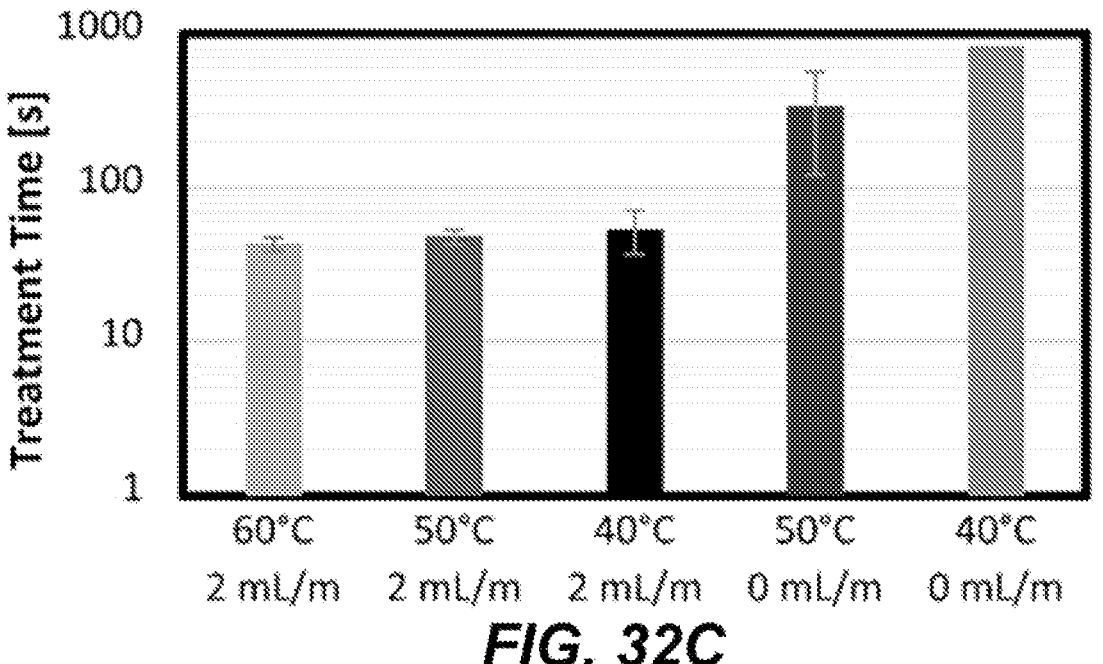
Figure 32D:
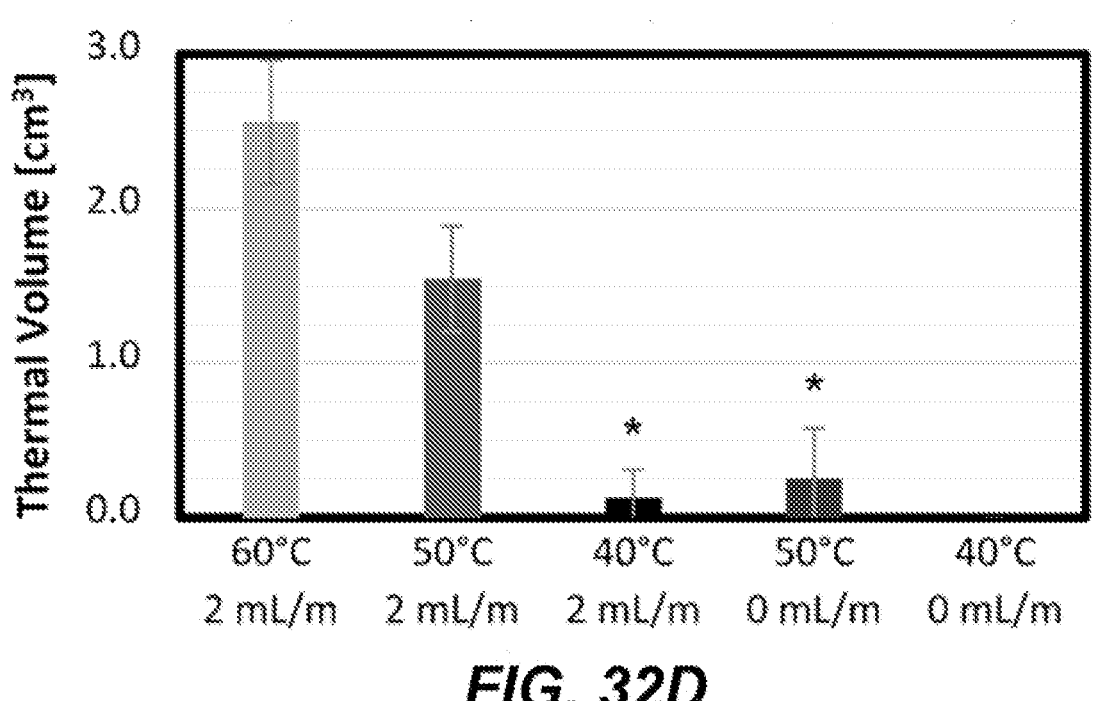

FIGS. 32A to 32D are waveforms illustrating an effect of the temperature set point on thermal injury, according to some embodiments of the present disclosure. For example, FIGS. 32A to 32D illustrate thermal injury as a function of temperature set point with a fixed coolant perfusion rate of 2 mL/min. FIG. 32A illustrates representative temperature plots for the median duration treatments for protocols with temperature set points of 40 (line 3230), 50 (line 3240), and 60° C. (line 3250). Treatments with passive cooling (0 mL/min) are additionally presented for 40° C. (line 3210) and 50° C. (line 3220) temperature set points. FIG. 32B illustrates mean current as a function of time from t=0 to the duration of the shortest treatment in each group. Shaded regions represent one standard deviation from the mean. FIG. 32D illustrates thermal injury volumes and FIG. 32C illustrates mean treatment times for each treatment group. It should be noted that the 40° C. passive cooling group was repeated N=1 time due to the extended treatment time, but is presented for comparison. In FIG. 32D, an '*' indicates a statistically significant difference from the 50 Cm 2 mL/m treatment (p<0.012).

To achieve temperature set points of 40 (line 3210), 50 (line 3220), and 60° C. (line 3230) (see FIG. 32A) with active cooling, it was necessary to modify the distance between the electrode and grounding pad to achieve higher initial treatment currents (see FIG. 32B) of 16.8±1.1, 19.9±0.8, and 25.0±0.9 A, respectively. These treatments reached maximum currents of 19.8±1.5, 25.8±1.0, and 37.2±3.1 A. The initial and maximum currents for non-cooled treatments with a set point of 50° C. measured 19.3±3.5 and 22.4±4.7 A, respectively. Actively cooled treatments with set points of 40, 50, and 60° C. required 53.7±16.7, 48.3±5.3, and 43.1±4.0 seconds to complete, respectively (see FIG. 32C). Non-cooled treatments with a temperature set point of 50° C. took significantly (p<0.011) longer to complete (342.9±220.5 s). For comparison, a single (N=1) 40° C. non-cooled treatment was conducted which required 831.4 s.

The largest thermal injury zones were observed for the actively cooled 60° C. temperature set point measuring 2.6±0.4 cm³. Significantly (p<0.0001) smaller thermal injury zones were observed for actively cooled treatments with 50° C. (1.5±0.3 cm³) and 40° C. (0.1±0.2 cm³) set points as well as the non-cooled 50° C. treatments which measured 0.3±0.3 cm³. There was not a significant difference between size of the thermal injury zones for the actively cooled 40° C. and non-cooled 50° C. treatments (p=0.35). No thermal injury zone was observed for the non-cooled 40° C. treatment (N=1).

The temperature at the electrode-tissue interface in actively cooled experiments was observed to decrease rapidly in the first few seconds after insertion. Most actively cooled experiments were conducted with an initial temperature between 10-15° C. which was 5-10° C. below baseline. While not ideal, the delay in initiating treatments was required to ensure that personnel were at a safe distance from the experimental setup. Accounting for the decreased baseline temperature active cooling resulted in a 44% reduction in temperature change versus non-cooled 3 kV treatments (14 to 33° C. versus 18 to 52° C.). The use of low temperature coolants may enable pre-cooling of the tissue yielding additional protection against thermal injury. Future optimization will be necessary to determine optimal cooling times, coolant temperatures, and clinically acceptable minimum tissue temperatures.

Figure 33A:
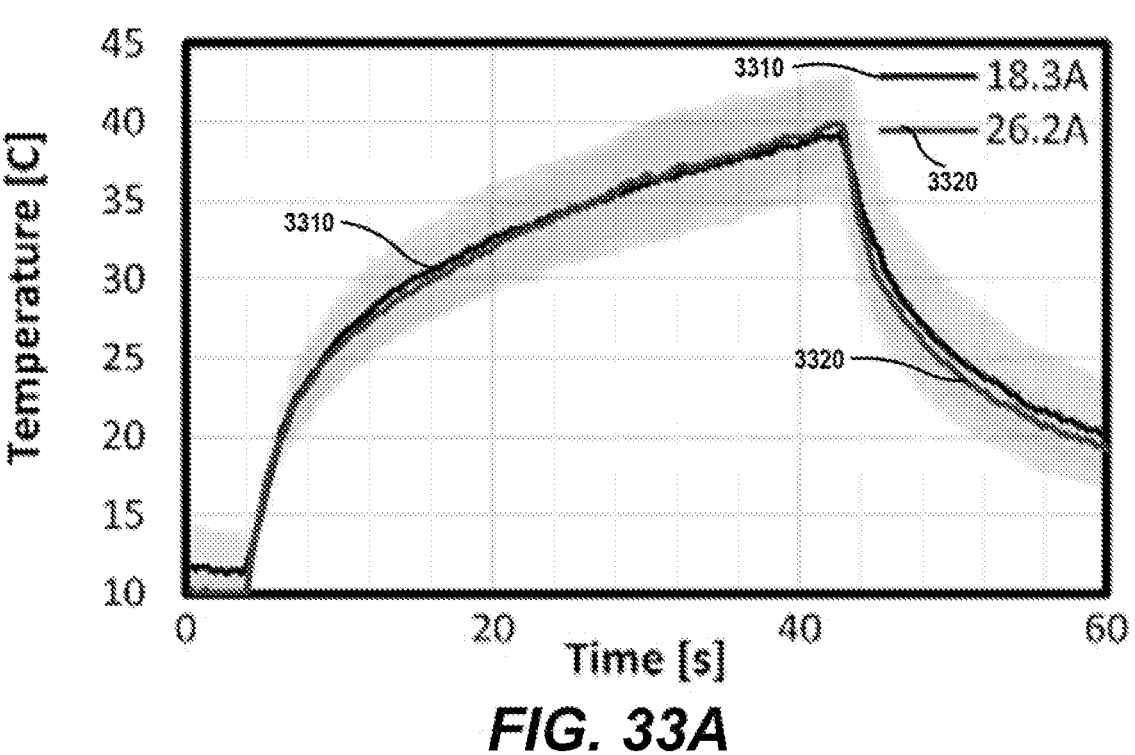
FIGS. 33A to 33C are graphs illustrating treatment observations, according to some embodiments of the present disclosure.
Figure 33B:
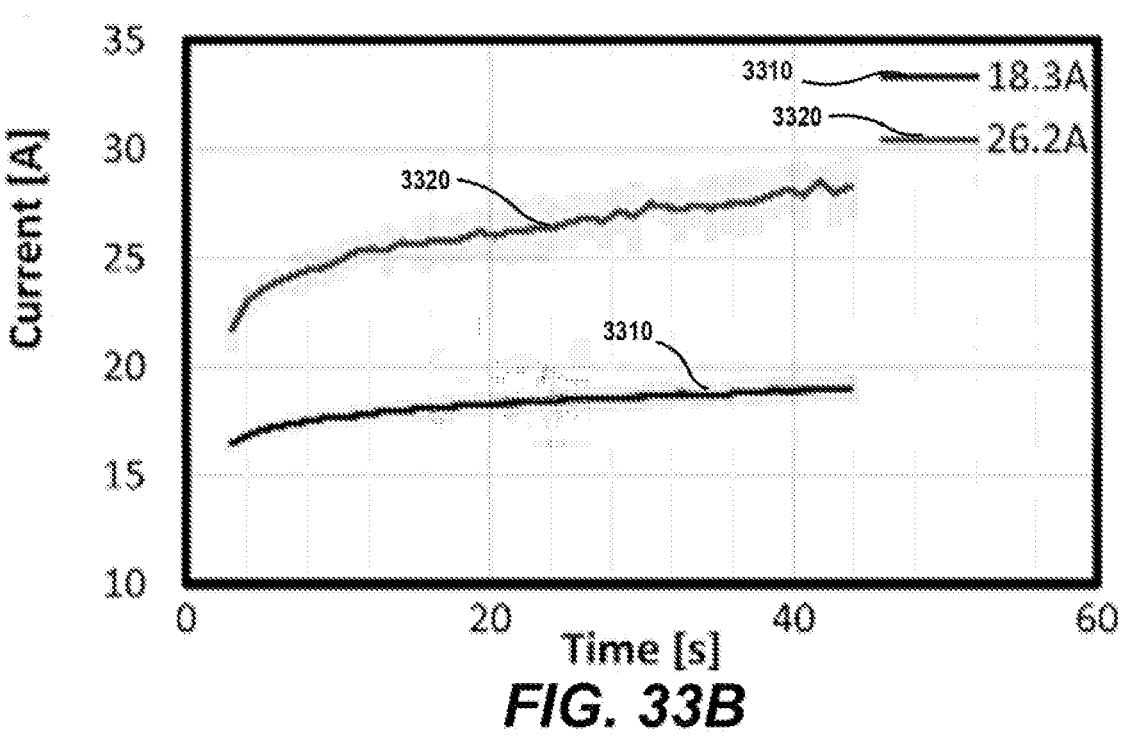
Figure 33C:
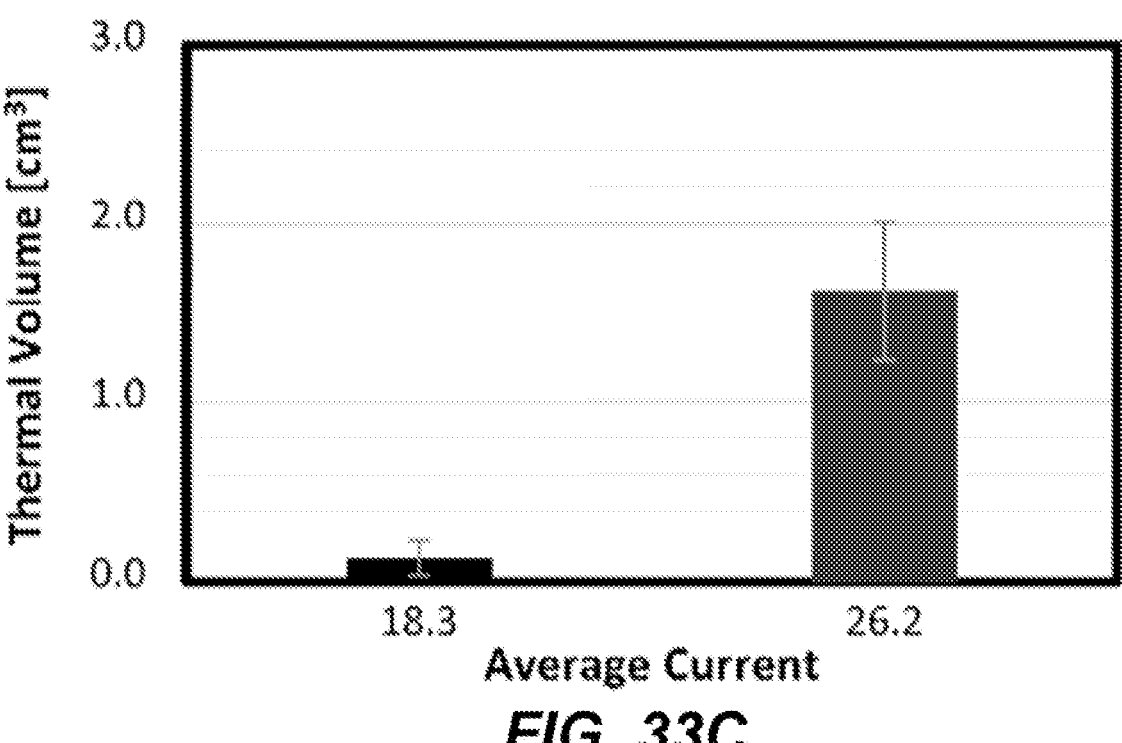

FIGS. 33A to 33C are waveforms illustrating outcomes based on delivered current, according to some embodiments of the present disclosure. FIGS. 3A to 33C illustrate an embodiment in which the thermal ablation measurements were dependent on the mean current delivered to the tissue. FIG. 33A illustrates temperature profiles, FIG. 33B illustrates current profiles, and FIG. 33C illustrates thermal injury volumes for treatment groups with mean currents of 18.3 A (line 3310) and 26.2 A (line 3310).

It was found that the induction of thermal injury is not exclusively a function of temperature at the electrode-tissue interface. Preliminary experiments indicated that when treatments had identical temperature profiles (see FIG. 33A) and coolant perfusion rates (8 mL/min) the extent of thermal injury was instead dependent on the delivered electrical current (see FIG. 33B). An increase in mean treatment current of 7.9 A (1.4×) resulted in a 12× increase in the thermal injury volume. This indicates that active cooling may be effective at reducing the temperature at the electrode-tissue interface, but may be insufficient to fully address the effect of Joule heating further from the electrode surface. As Joule heating ($Q_{JH}$) is a function of both current density (J) and electric field strength (E):

$$Q_{JH} = J \cdot E \left[ \frac{W}{m^3} \right] \tag{53}$$

increases in current will result in a greater heating per unit volume. However, the rate of heat transfer from the tissue to the coolant was likely independent of this experimental input. Therefore, treatments with greater average power delivery (e.g. approximately 65 W) resulted in substantially larger regions of thermal injury surrounding the electrode than more conservative treatments (approximately 46 W). When initial treatment currents were constrained perfusion at rates of 2, 4, and 8 mL/min were sufficient to mitigate the induction of thermal damage which became increasingly localized to the tip of the electrode. Taken in summation, these results indicate that active cooling of electrodes may not be sufficient for generically preventing the induction of thermal injury as treatment currents in vivo are dynamic and depend on tissue characteristics, applicator arrangement, applicator placement, and local temperatures.

The use of active temperature feedback by ACE from one, or multiple, locations is a potential solution to this challenge. In this study, it was demonstrated that dynamically adjusting the rate at which pulses are delivered is an effective method for achieving and maintaining a target temperature at the electrode-tissue interface. Without active cooling, the ACE algorithm was capable of maintaining temperatures of 30° C. (see FIG. 31A), 40° C., 50° C., 60° C. (see FIG. 32A) and 80° C. (see FIG. 31A), with the lower temperatures significantly reducing the extent of thermal injury at the expense of increased treatment times.

Interestingly, 50° C. treatments with active cooling resulted in larger thermal ablation zones than 50° C. treatments without cooling. The mean current values measured were not statistically different (p=0.3989) in these treatments, however, the delivery rate (413 vs 87 μs/s) and thus average power delivered was much greater for the actively cooled treatments. It is likely that in this scenario, active perfusion was unable to remove enough energy to prevent thermal injury. It is possible that the temperature sensors were measuring an average temperature of both the cooled electrode surface and the warmer adjacent tissue resulting in a mischaracterization of the tissue temperature leading the algorithm to deliver energy at a higher rate than intended. To address this challenge, it may be necessary for future algorithms to implement a maximum power limit or use average power as a means for controlling the delivery rate. Alternatively, it may be necessary to record temperatures in locations where the thermal gradient is lower or at multiple locations. However, decreasing the temperature set point to 40° C. in conjunction with active cooling resulted in negligible thermal injury with substantially reduced treatment times compared to the 50° C. non-cooled treatments (54 versus 343 s) indicating that selection of appropriate temperature set points may be sufficient for preventing thermal damage.

The $R_{max}$ used in this study (500 μs/s) represented an extreme case which is approximately 5× the rate typically used clinically. This $R_{max}$ value was selected to examine the extent to which treatment times could be reduced to overcome the highly efficient removal of heat at the electrode-tissue interface and to test the limitations of the temperature control algorithm. While it may be feasible to use rates greater than 100 μs in vivo, caution should be exercised due to the potential to induce unintended thermal injury if temperature sensing is limited to the electrode-tissue interface. The results presented in FIGS. 31A to 31C clearly demonstrate that thermal injury adjacent to the electrode is possible even if temperatures measured at the electrode are below 60° C. In these scenarios there is likely an imbalance in the rate of Joule heating in the tissue surrounding the electrode and the rate of cooling due to electrode perfusion. As tissue is a relatively poor thermal conductor there is a natural limitation to the rate at which energy can be transferred through the tissue to the cooled electrode. This limitation is likely responsible for the observation (see FIGS. 32A to 32D) that 5000V non-cooled treatments at 50° C. resulted in similar thermal injury volumes to more rapid treatments with active cooling and a 40° C. set point. Future work may be used to determine the ideal rate of pulse delivery and control schemes which utilize true energy or power delivery calculations rather than energized-timing calculations may be necessary.

The localization of thermal injury towards the electrode tip may have been due to the internal geometry of the applicator which likely has a greater distance between the coolant and distal tip than the sidewalls of the electrode. Turbulent flow within the electrode at this location may have also impeded efficient thermal transfer. Alternatively, electrical corona may have formed at the sharp tip of the electrode resulting in an additional source of localized heating not present along the main body of the electrode. Corona were not observable through the opaque liver tissue, however, they appeared stochastically in preliminary experiments conducted with the applicator placed 1-2 mm from a visible surface in muscle tissue.

Techniques for killing target cells and simultaneously reducing or eliminating thermal injury, tissue burning, tissue charring, nerve and/or blood vessel damage by adjusting the energy delivery profile in response to a measurement or a user-controlled input.

The field strength required to induce a lethal electric field mediated response is relatively high, in the range of 300-2000 V/cm. To produce relatively large ablation zones (1-6 cm) with a single applicator requires the use of high voltage (500-20,000V) electrical pulses which induce a temperature increase through Joule (resistive) heating. In some scenarios, exposure to hypothermic temperatures is acceptable, or even favorable, however even in these scenario temperatures above 90-100° C. can induce charring and arcing at the tissue-electrode interface which can impact treatment outcomes. In other scenarios, for example tumors which involve major blood vessels or critical nerves, thermal injury to critical structures is unwanted. One strategy for overcoming this is to select an energy delivery rate which is assumed to avoid excessive Joule heating. However, this generally requires some a priori knowledge of the tissue electrical properties and does not account for dynamic changes in electrical or physical properties of the tissue under treatment. Alternatively, sensing of the temperature or a proxy via a measurement technique (temperature sensor, tissue stiffness, ultrasound, MRI, imaging) can be used to dynamically adjust the rate at which energy is delivered in real time to reduce or eliminate thermal injury at the treatment site.

Measuring the temperature of pulsed electric field treatments in situ is particularly challenging due to the high electric field emitted by the applicator electrode during treatment. The near field around the electrode can induce a current in any conductive element which in turn could harm the electronics or produce inaccurate measurements. To resolve this problem of electromagnetic interference, temperature can be measured using electro-optic means. For example, wide bandgap semiconductors at the end of a fiber optic cable can be used to make temperature measurements in a high electric field environment. Additionally, an infrared detector, MM, or ultrasound imaging can be used to make non-contact measurements.

Figure 34:
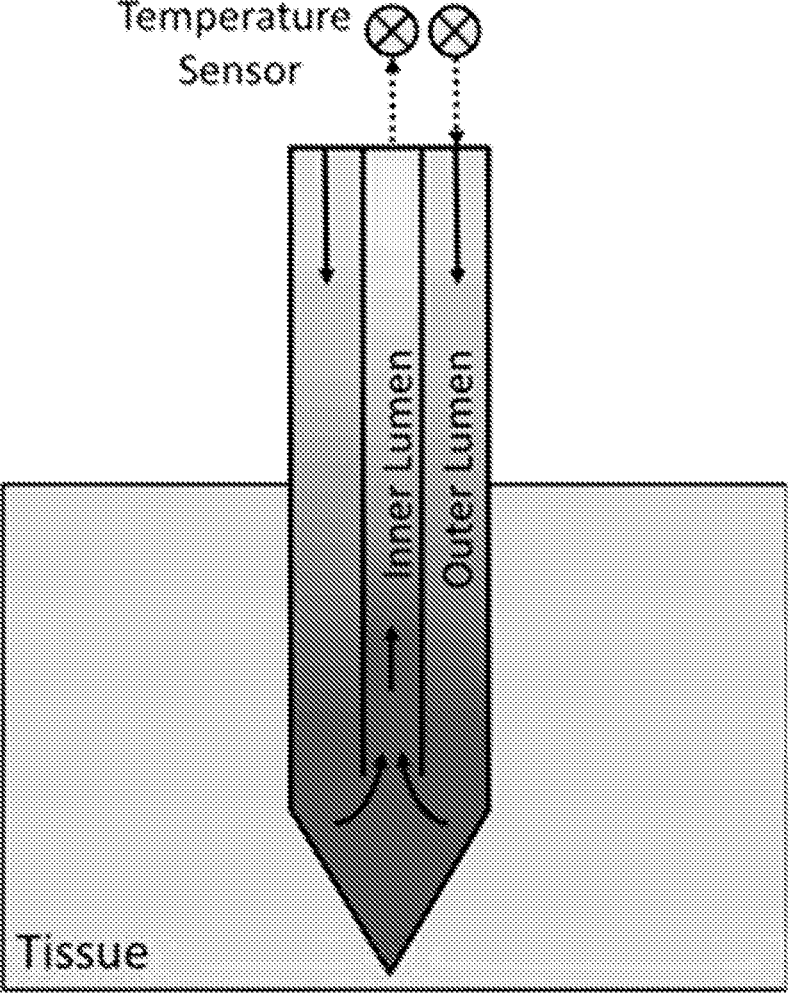
FIG. 34 is a cross sectional view of an exemplary dual lumen electrode and tissue, according to some embodiments of the present disclosure.

In some embodiments, a dual lumen electrode for proxy measurements of in situ tissue temperature can be used. FIG. 34 is a cross sectional view of an exemplary dual lumen electrode and tissue, according to some embodiments of the present disclosure. First, the temperature of the fluid is recorded prior to entering the electrode. Coolant fluid is then pumped though the outer lumen of the electrode. The coolant absorbs the heat at the electrode—tissue interface. The coolant's return path is through the inner lumen. At a point distal to the terminus of the inner lumen a sensor records the coolant's temperature.

Methods

Simulation Methods

The feasibility of using remote temperature measurements acquired via fluid perfused through an active electrode was assessed in COMSOL Multiphysics using the Heat Transfer in Fluids, Laminar Flow, Electric Currents, Nonisothermal Flow, and Electromagnetic Heating modules. Using an axisymmetric geometry, the electrode was defined as a 1.44 mm diameter (14 AWG) tube with an internal lumen measuring 0.51 mm in diameter (24 AWG). Each geometry was modeled with a 5 cm length. Domain point probes at the fluid inlet and fluid outlet boundaries were used as proxy values for a temperature sensing. While a multitude of inlet flow rates could be used experimentally (0.001-100 mL/min), a value matching experimental data (8 mL/min) was used in this simulation as the inlet boundary condition defined as a mass flow rate with a 5° C. inlet temperature. The outlet boundary condition was set to a zero pressure boundary.

Figure 35:
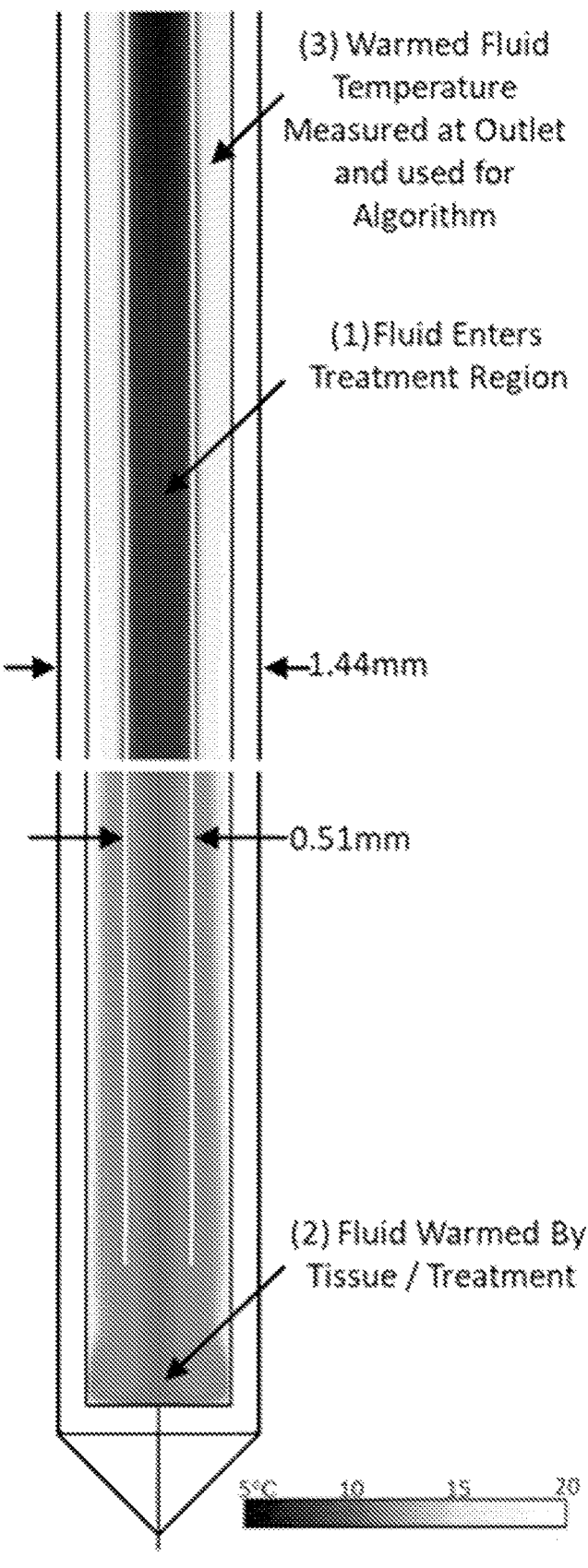
FIG. 35 illustrates schematic and thermo-fluid dynamics simulation results, according to some embodiments of the present disclosure.

An electrically insulating sheath was simulated as a 0.2032 mm diameter tube surrounding the electrode with the exception of a 2 cm region at the distal tip which was exposed and remained in contact with the simulated tissue volume. FIG. 35 illustrates schematic and thermo-fluid dynamics simulation results, according to some embodiments of the present disclosure. FIG. 35 illustrates a 5000V 0.02 s IET ACE treatment with active temperature feedback to regulate the fluid outlet temperature to 15° C. Temperature profiles were acquired at the end of each treatment (73 s, 15° C.)

Figure 36A:
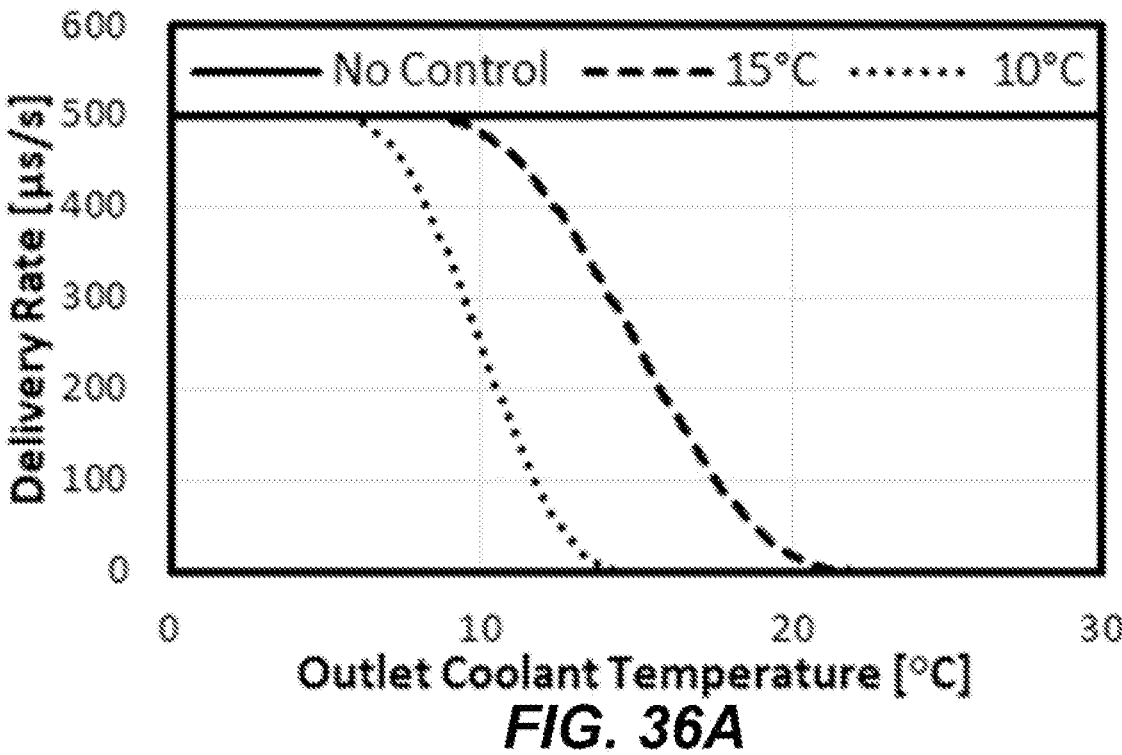
FIGS. 36A and 36B are graphs illustrating simulation observations, according to some embodiments of the present disclosure.
Figure 36B:
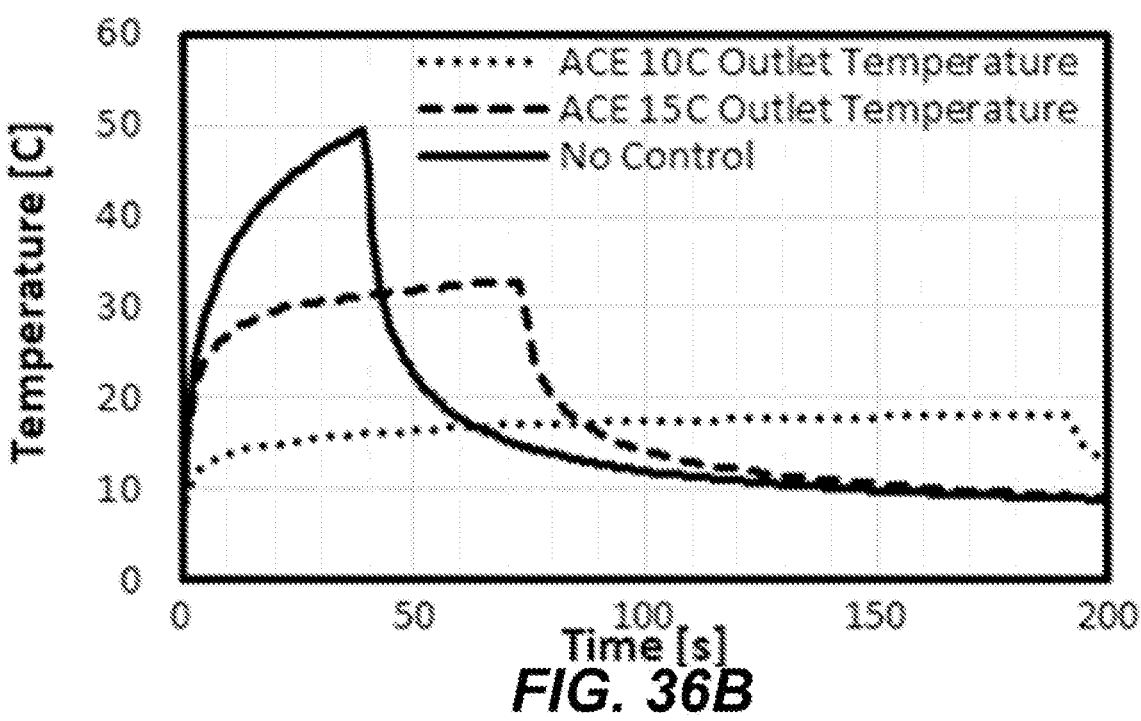

FIGS. 36A and 36B are graphs illustrating treatment observations, according to some embodiments of the present disclosure. FIG. 36A illustrates a temperature-based control profile and FIG. 36B illustrates a simulated temperature response profile measured at the tissue-electrode interface for 5000V 0.02 s IET ACE treatments when the fluid outlet temperature was used to control the energy delivery rate with target temperatures of 10 and 15° C. The electrode was energized with a 5000V electrical potential which was electrically connected to a distal 5 cm diameter grounding pad which was 11 cm from the tip of the electrode. Electrical energy was simulated with an energy delivery rate (duty cycle) of 500 μs/s to represent the non-controlled case and at a dynamic rate determined by the ACE algorithm (see FIG. 46A) with outlet fluid control temperatures of 10° C. and 15° C.

ACE ablation margins were assessed as a dynamic function of the integrated energized time (IET) which decreased from 800 V/cm for IET of 0.01 s to 587 V/cm for IET of 0.04 s. The simulations presented here were programmed to reach an IET of 0.02 s prior to the cessation of energy delivery resulting in an ACE lethal threshold corresponding to 690 V/cm. Thermal damage due to extended exposure to hyperthermic temperatures was assessed using an Arrhenius equation with a threshold of 0.53.

Results

Simulation Results

The delivery of electrical energy to the simulated tissue domain via the internally cooled electrode and grounding pad resulted in a rapid heating of the tissue in proximity to the electrode as the result of Joule Heating. Coolant flowing through the electrode rapidly absorbed and transported thermal energy from the electrode tip and out of the system. The net result was a warming of the coolant as it was transported through the electrode, to the active tip and back out of the electrode (see FIG. 35). Without active control, this resulted in a net increase in coolant temperature from 5° C. at the beginning of the treatment to 19.3° C. at the end of the 0.02 s IET treatment (40 s). This corresponded to a peak temperature at the electrode-tissue interface of 50° C. (see FIG. 36B).

Figure 37A:
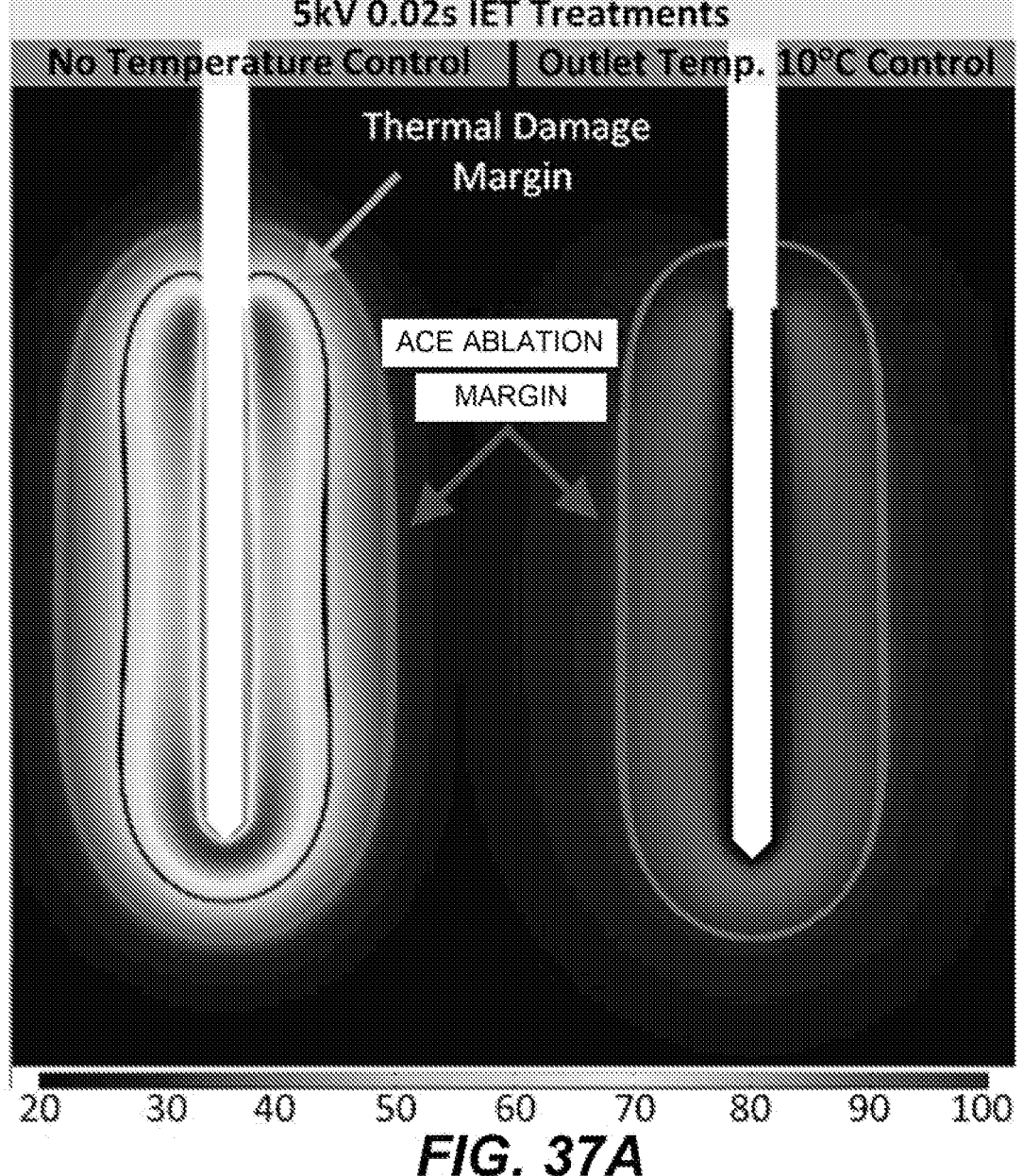
FIG. 37A is a schematic view of a simulated temperature distribution and FIGS. 37B and 37C are graphs illustrating simulation observations, according to some embodiments of the present disclosure.
Figure 37B:
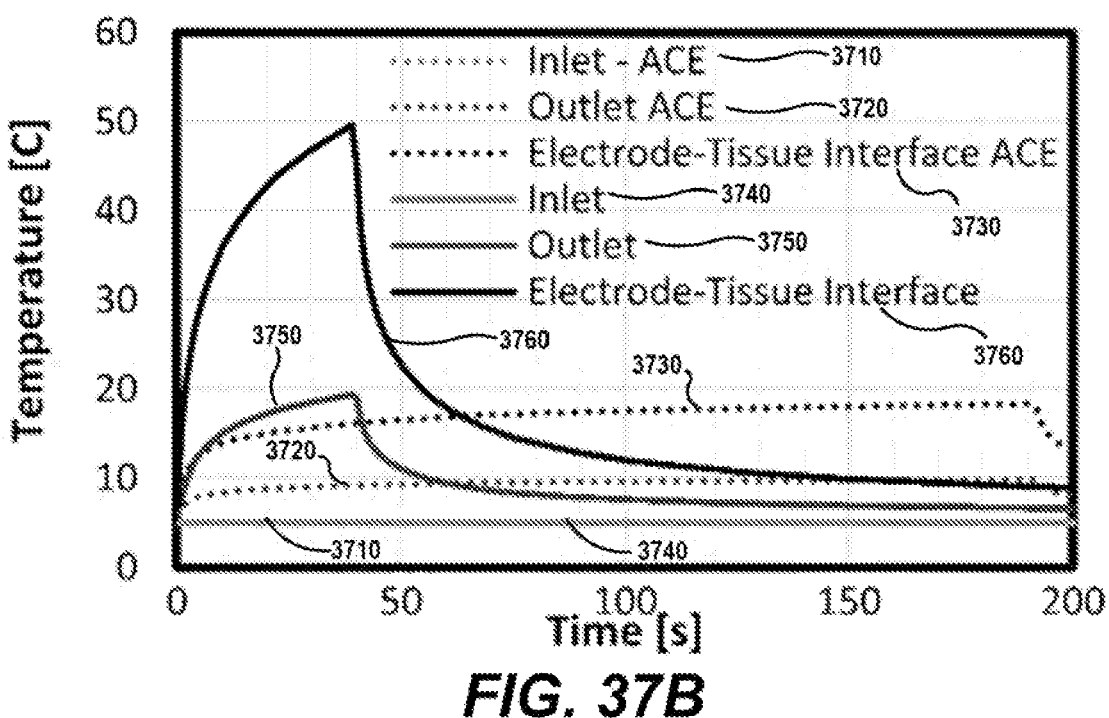
Figure 37C:
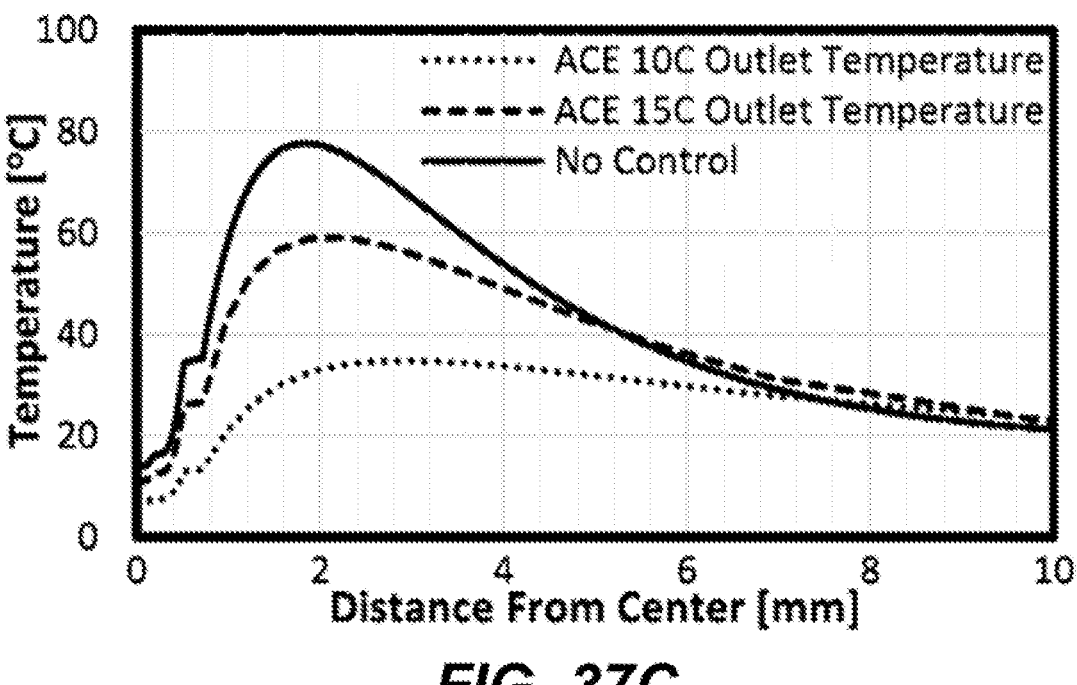

FIG. 37A is a schematic view of a simulated temperature distribution and FIGS. 37B and 37C are graphs illustrating simulation observations, according to some embodiments of the present disclosure. For example, FIG. 37A illustrates a simulated temperature distribution including a thermal damage margin (solid black line), and ACE ablation margin (solid red line) for 5000V 0.02 s IET ACE treatments without active temperature control (left side of image). FIG. 37A illustrates that no thermal injury was predicted when the fluid outlet temperature was used to control the energy delivery rate with a temperature set point of 10° C. (right side of image). FIG. 37B illustrates simulated temperatures at the tissue-electrode interface, fluid inlet, and fluid outlet ports with 10° C. temperature control (dotted lines) and without temperature control (solid lines). FIG. 37C illustrates temperature distribution measured radially outward from the center of the electrode at the time of treatment completion without temperature control (solid line, t=405), with 15° C. temperature control (dashed line, t=73 s), and with 10° C. temperature control (dotted line, t=1935). Thermal injury was assessed for Arrhenius values greater than 0.53 and ACE thresholds were assessed at 693 V/cm based on ex vivo experiments for the 0.02 s dose.

Referring to FIGS. 37A to 37C, in the absence of ACE control, with these simulated parameters, the active perfusion with 5° C. coolant was not sufficient enough to prevent thermal injury to the tissue as the tissue temperature in regions adjacent to, but not in contact with the electrode exceeded 60° C. Use of the ACE control algorithm using the fluid outlet temperature as the algorithm input with set points of 15° C. and 10° C. reduced the peak temperatures experienced by the tissue. Implementing ACE control based on a fluid outlet temperature control was effective at constraining tissue temperatures at the electrode-tissue interface to 33° C. (see FIG. 36B) while a control temperature of 10° C. reduced the temperature at the tissue-electrode interface to 18° C. ACE control at 10° C. resulted in a treatment duration of approximately 190 s with no thermal injury predicted and an ACE ablation volume of approximately 12.5 cm³ (see FIG. 37A).

These results indicate that temperature measurements from coolant perfused through an active electrode can be utilized to control the temperature of tissue surrounding the active electrode by implementing a dynamic energy delivery algorithm. These simulations predict that it is feasible to induce cell death in a large volume of tissue surrounding the electrode without thermally damaging the underlying extracellular matrix. In addition, the control algorithm can be adjusted to induce varying degrees of thermal damage in conjunction with an electrically induced ablation by modulating the target temperature of the coolant flowing through the application. These simulations indicate that it is possible to dynamically control ACE algorithms by acquiring measurements of a physical property of the tissue from a remote location. It is feasible that ultrasound, CT, MM, impedance, or mechanical measurements of the tissue could be used instead of temperature measurements of the coolant outlet temperature or the temperature at a specific location within or adjacent to the treatment zone. For example, MRI thermometry could be used to obtain a temperature measurement from the tissue adjacent to the applicator or a volumetric temperature measurement of the treatment zone. This data could be used by the algorithm to dynamically adjust the energy delivery rate such that thermal injury to the tissue is controlled, mitigated, minimized, or prevented. Alternatively, data could be obtained by a temperature sensor within a critical blood vessel or by remote temperature measurements of a proximal critical structure and this data could be used to control the algorithm to mitigate, minimize, or prevent damage to those structures.

In Vivo Validation of ACE to Control Tissue Temperatures and Muscle Contractions and Induce a Systemic Immune Response Pulsed electric field therapies are known to cause muscle stimulation clinically. Typically, this is medically managed through the use of general anesthesia in combination with neuromuscular paralytics. Unfortunately, there are clinical and physiological limitations to the doses and effectiveness of these paralytics and muscle stimulation is still possible at the maximum acceptable dosages. ACE mitigates or eliminates these muscle contractions through the use of multiple modifications to the energy delivery profile. First, the duration of each individual pulse is decreased sufficiently that the electric field required to induce muscle stimulation exceeds the electric field to which local and distant muscles are exposed.

Figure 38A:
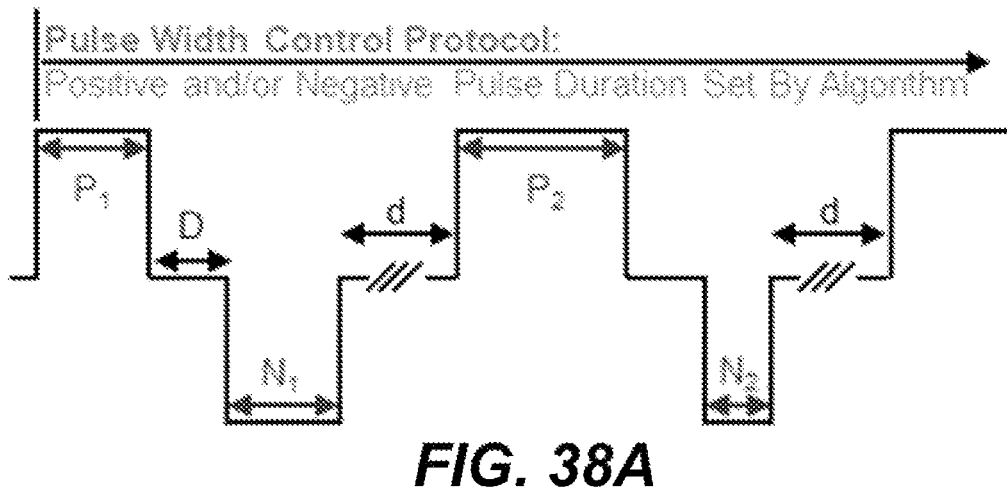
FIGS. 38A to 38C are schematic waveforms illustrating techniques for algorithmically controlling physiological, biological, or systemic outcomes in ACE treatments, according to some embodiments of the present disclosure.
Figure 38B:
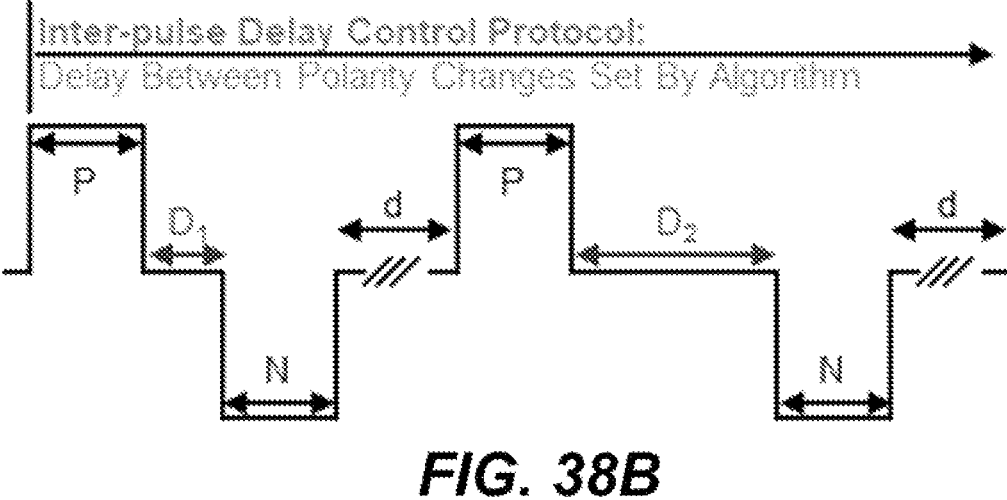
Figure 38C:
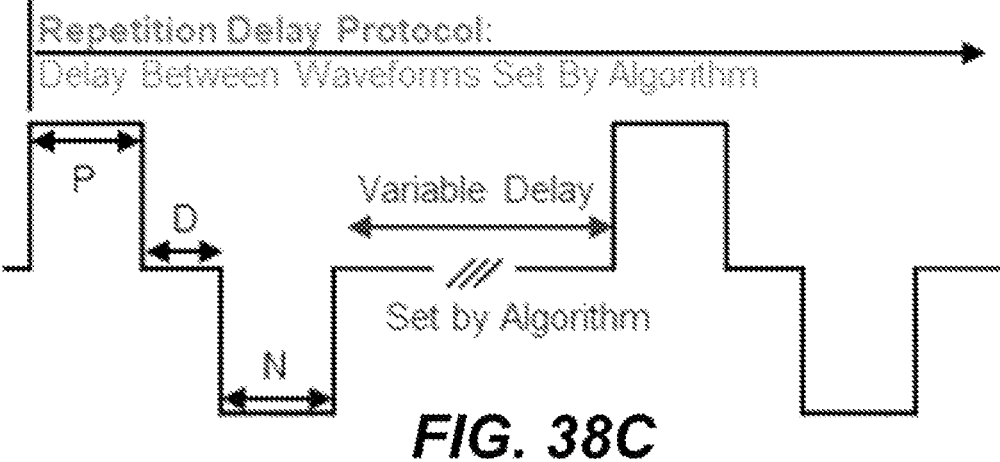

FIGS. 38A to 38C are schematic waveforms illustrating techniques for algorithmically controlling physiological, biological, or systemic outcomes in ACE treatments, according to some embodiments of the present disclosure. FIG. 38A illustrates a technique according to some embodiments of the present disclosure that includes increasing or decreasing the width of the positive (P1, P2) or negative pulses (N1, N2). FIG. 38B illustrates a technique according to some embodiments of the present disclosure that includes increasing or decreasing the delay (D1, D2) between polarity changes. FIG. 38C illustrates a technique according to some embodiments of the present disclosure that includes increasing or decreasing the delay (d) between successive waveforms. The algorithm according to some embodiment of the present disclosure may use a combination of physiological or imaging measurements and user inputs to determine the appropriate parameters. In some embodiments, combinations of two or more of the techniques of FIGS. 38A to 38C may be combined together.

In some embodiments, the width of these pulses may be dynamically adjusted by the algorithm to reduce, mitigate, or eliminate muscle contractions based on a measurement or by a user input, as illustrated in FIG. 38A. A first individual pulse may be followed in rapid succession (0.001 to 100 µs) with a second pulse of alternate polarity to inhibit action potentials and mitigate the polarization of local muscle tissue. The delay between these pulses may also be dynamically adjusted by the algorithm to reduce, mitigate, or eliminate muscle contractions based on a measurement or user input, as illustrated in FIG. 38B. Also, the delay between successive waveforms (one or more positive pulse and one or more negative pulse) may be dynamically adjusted by the algorithm or by a user input, as illustrated in FIG. 38C. It has been observed that for a given waveform (e.g. 2-5-2) decreasing the delay between successive waveforms (e.g. increasing the energy delivery rate) reduces the number of and intensity of muscle contractions. At moderate repetition rates (e.g. greater than 10 Hz) no muscle contractions or a single sustained muscle contraction is observed due to the induction of a tetanized state in the local muscles. Inversely, increasing the delay between successive waveforms (e.g. decreasing the energy delivery rate) occasionally results in the induction of individual visible muscle contractions.

Algorithmically, a number of strategies could be employed to reduce or eliminate muscle contractions. One such example is as follows:

Prior to treatment, an initial combination of pulse width, repetition rate, voltage, and target dose are selected. The target dose refers the integrated energized time associated with the energy delivered by the electrical pulses. The target dose is selected based on the target treatment volume, the voltage, and the pulse width. The treatment is initiated and upon measurement (or observation) of muscle contractions, the duration of each individual pulse is reduced by a proportional percentage (e.g. 10%). As treatment outcomes may be affected by the pulse width, a new target dose may be selected. To maintain an alternative physical outcome, biological outcome or systemic outcome (e.g., a tetanized state or a specified tissue temperature), the delay between successive waveforms may be adjusted to achieve a new specified energy delivery rate. These new treatment parameters are administered and measurements of (or observations of) muscle contractions are made and the treatment parameters are again adjusted. This process would be repeated until the target dose is administered.

In some embodiments, a pre-treatment ramp-up algorithm may be employed. In this case, prior to treatment an initial combination of pulse widths (waveforms), repetition rates, voltage, and target dose are selected. Starting from a small voltage (e.g. 25V) the specified waveform is delivered once (or a small number of times) and the physiological response is observed. If muscle contractions are not measured (or observed), the voltage is algorithmically increased until a target treatment voltage is achieved. If muscle contractions are measured (or observed), voltage escalation is delayed and the pulse widths or delay between alternating polarity pulses is decreased until the intensity of muscle contractions is reduced to an acceptable level. Then, voltage escalation is resumed, modifying the pulse parameters as necessary, until the target treatment voltage is reached. A new target dose and repetition rate are calculated based on the treatment voltage and waveform parameters and the treatment is administered. This ramp up algorithm may be accompanied by an additional treatment algorithm for dynamically adjusting the treatment parameters based on additional measurements or observations. In order to demonstrate the control of localized tissue heating and muscle contraction mitigation, ACE has been demonstrated in two animal models, mice (murine) and horse (equine). The murine model has additionally been used to demonstrate a therapeutic tumor size reduction when ACE treatments are combined with antigen capturing nanoparticles.

Methods

Equine Methods

Figure 39A:
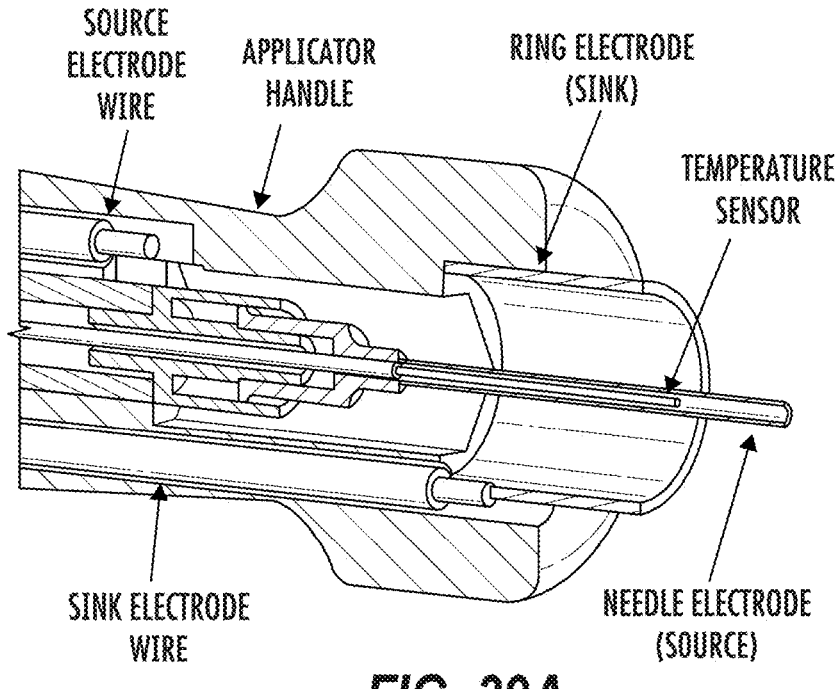
FIGS. 39A to 39D are photos of an applicator used to validate ACE treatment in in vivo equine melanoma tumors, according to some embodiments of the present disclosure.
Figure 39B:
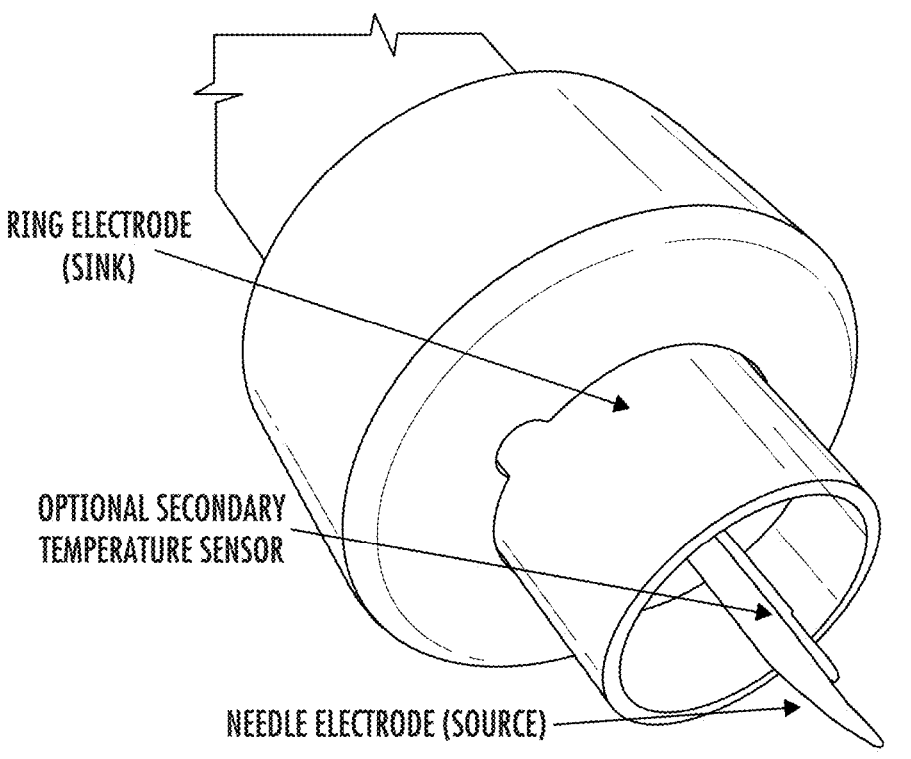
Figure 39C:
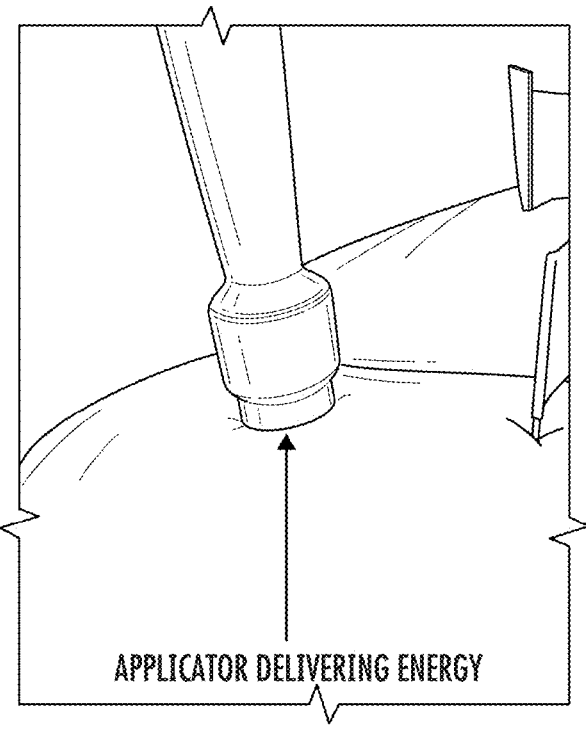
Figure 39D:
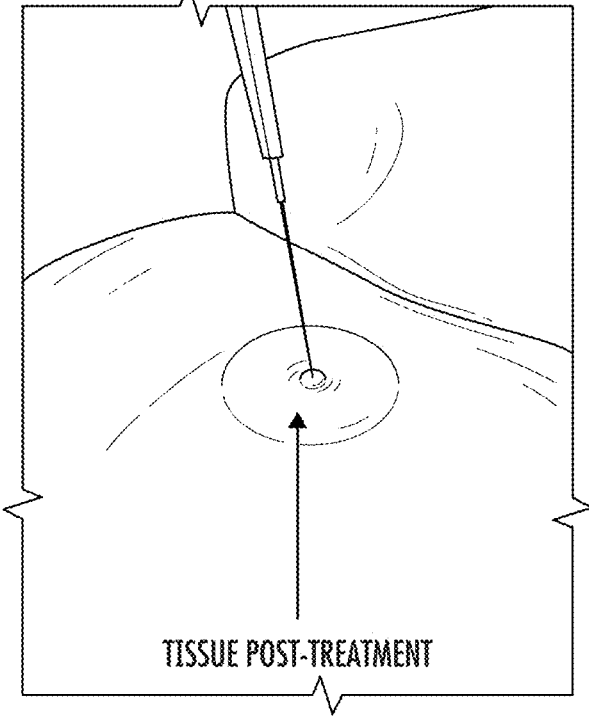

FIGS. 39A to 39D are photos of an applicator used to validate ACE treatment in in vivo equine melanoma tumors, according to some embodiments of the present disclosure. Referring to FIG. 39A, the applicator handle contains pathways for temperature sensors which can be placed internally or adjacent to the applicator electrodes and electrical wiring which connects to the source and sink electrodes. Referring to FIG. 39B, the electrode configuration consists of central needle electrode which is inserted into the tissue and an external ring electrode which makes contact with the tissue surface. Temperature sensors can be located internally to or adjacent to the needle electrode. Referring to FIG. 39C, the applicator is placed into the target tissue and energy is delivered based on the ACE algorithm. Referring to FIG. 39D, pressure from the applicator and/or energy delivered leave a visible marking on the surface which can be used to guide subsequent placements if a larger treatment volume is desired.

Bi-polar electrical pulses with amplitudes between 250V and 5000V were applied to solid equine tumors. The electrode geometry consisted of a surface applicator with a circular electrode ring and center electrode needle which was inserted into the tissue. The length of the exposed needle electrode was adjusted between 1 and 20 mm to accommodate tumors of different sizes.

Prior to ACE, the equine patients were mildly sedated, but remained standing. Local anesthetic was administered as necessary, but was not required in all cases. Treatment and control tumors were measured and photographed before and after administering the ACE therapy. Tumors measuring less than 17 mm in diameter received a single treatment while larger tumors received 5 treatments: one central to the tumor and four treatments at the top, bottom, left, and right boundaries of the tumors with the center pin being placed in a location which corresponded to the placement of the ring in the central treatment.

The standard treatment consisted of a 2-5-2 waveform with a target voltage of 2000V an initial energy delivery rate of 100 μs/s, and a target dose of 0.02 s. ACE protocols were used to control the electrical energy delivery rate to achieve a target temperature of 60° C. measured at the tumor-electrode interface. As a precautionary measure, in the cases where a 60° C. temperature was not achieved, the energy delivery rate was not increased beyond 100 μs/s. However, future algorithms may enable an increase beyond the initial energy delivery rate.

Following treatment, the animals were allowed to recover from anesthesia and typically discharged on the same day. Photographs were obtained by owners daily for 7 days and once a week for 1 month following treatment. Patients returned twice at approximately one-month intervals for evaluation, re-treatment, or treatment of additional tumors.

Murine Methods

Figure 40A:
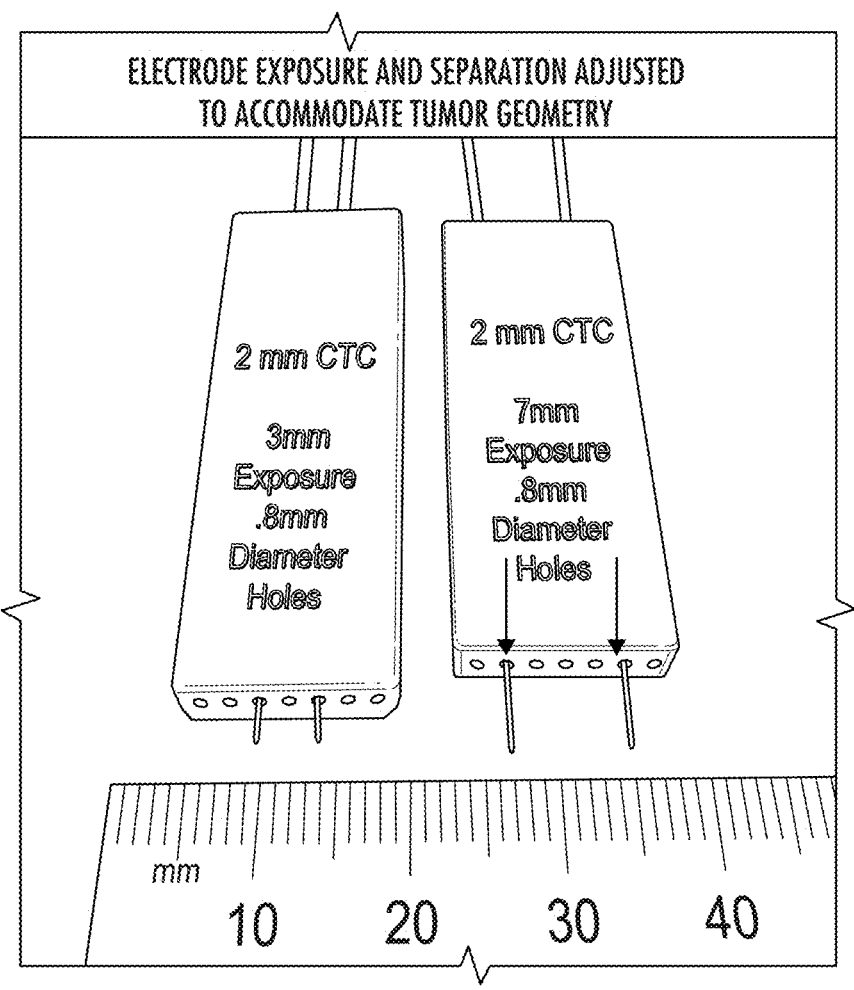
FIGS. 40A and 40B are photos illustrating an applicator used to validate ACE treatment in in vivo murine melanoma tumors, according to some embodiments of the present disclosure.
Figure 40B:
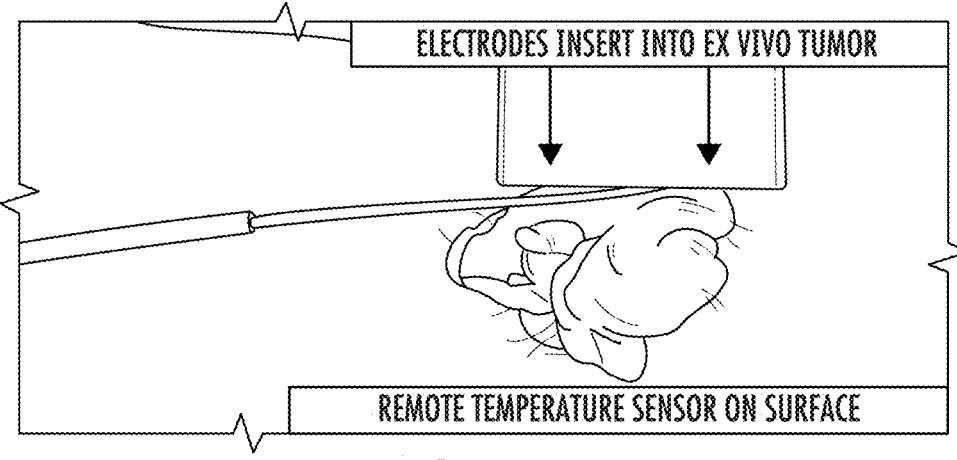
Figure 41A:
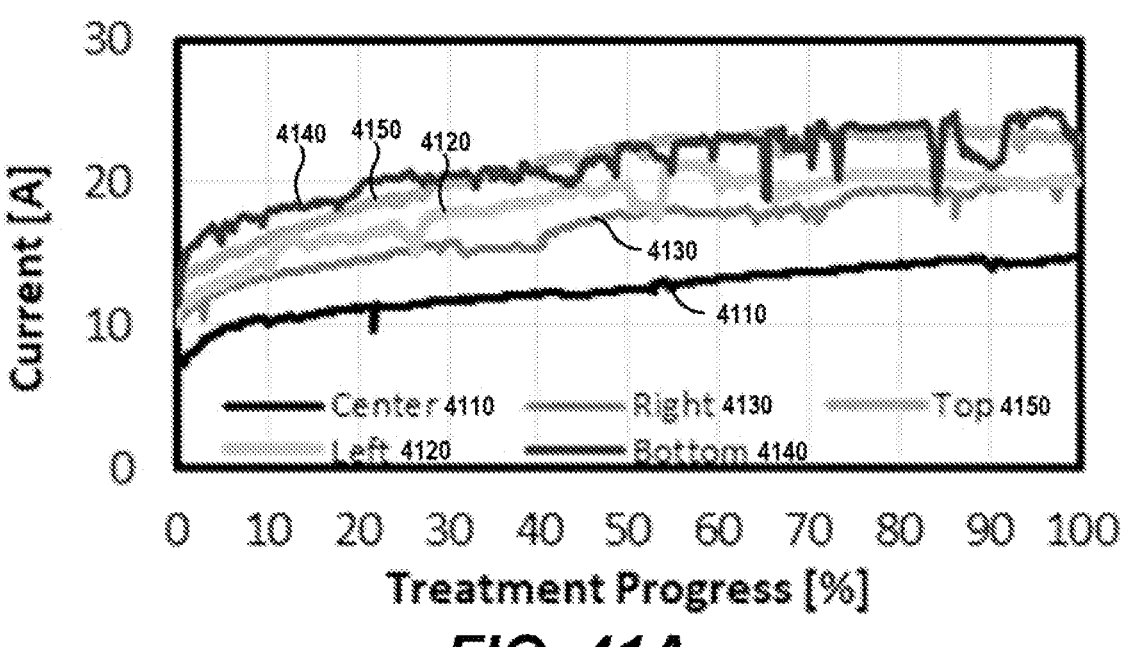
FIGS. 41A to 41D are graphs of representative data recorded from the ACE treatment of a single tumor, according to some embodiments of the present disclosure.
Figure 41B:
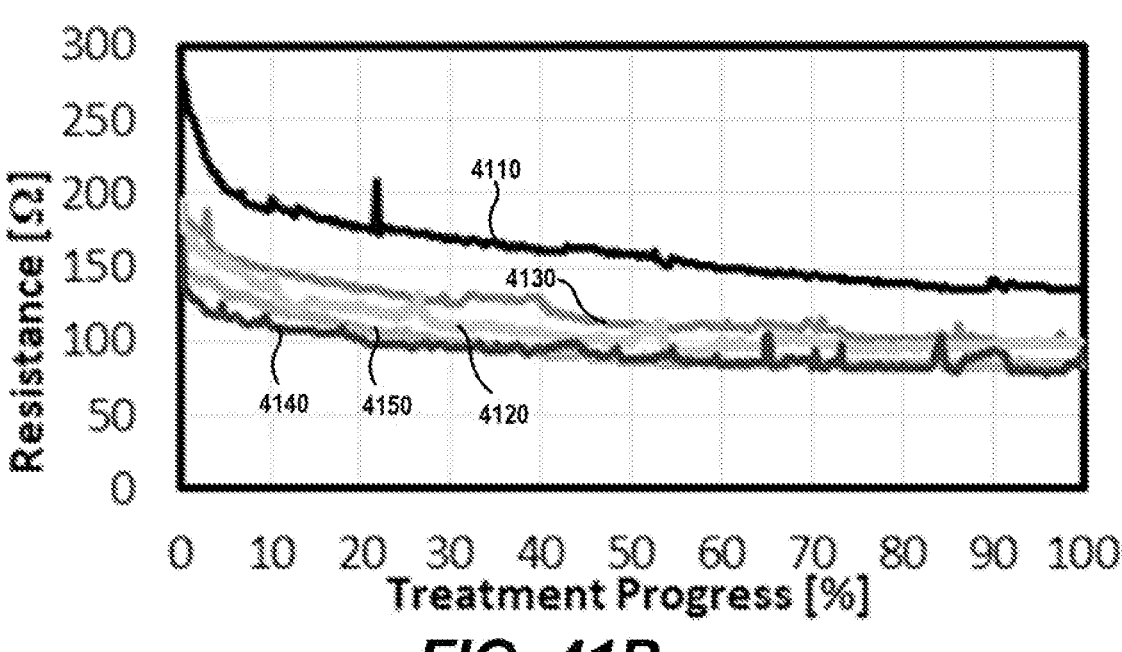
Figure 41C:
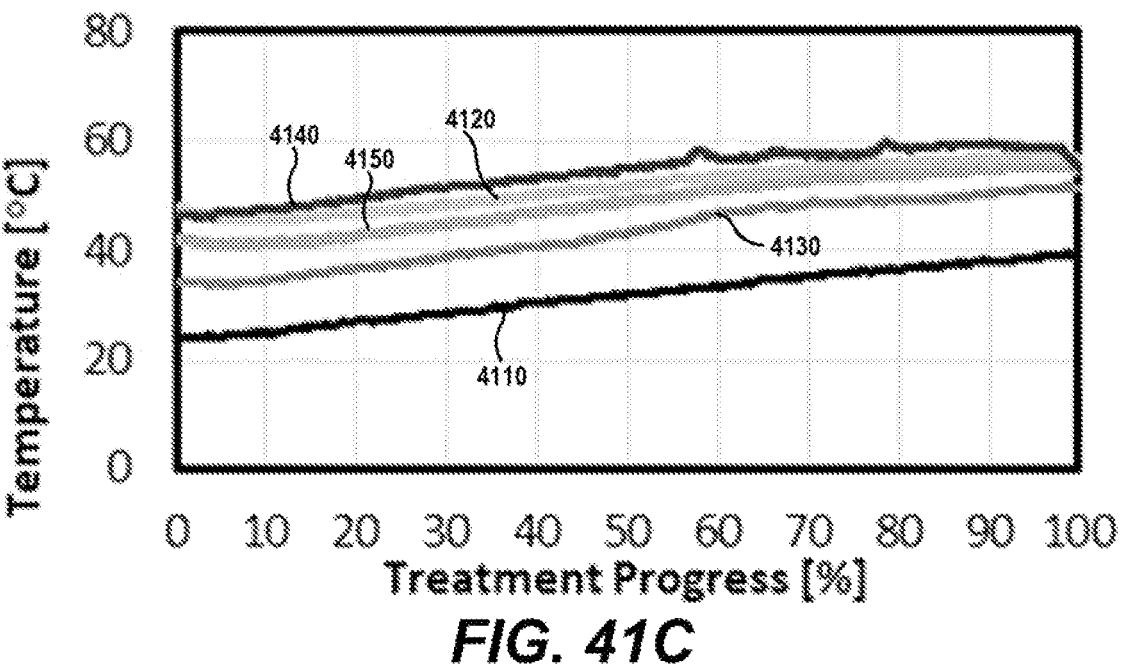
Figure 41D:
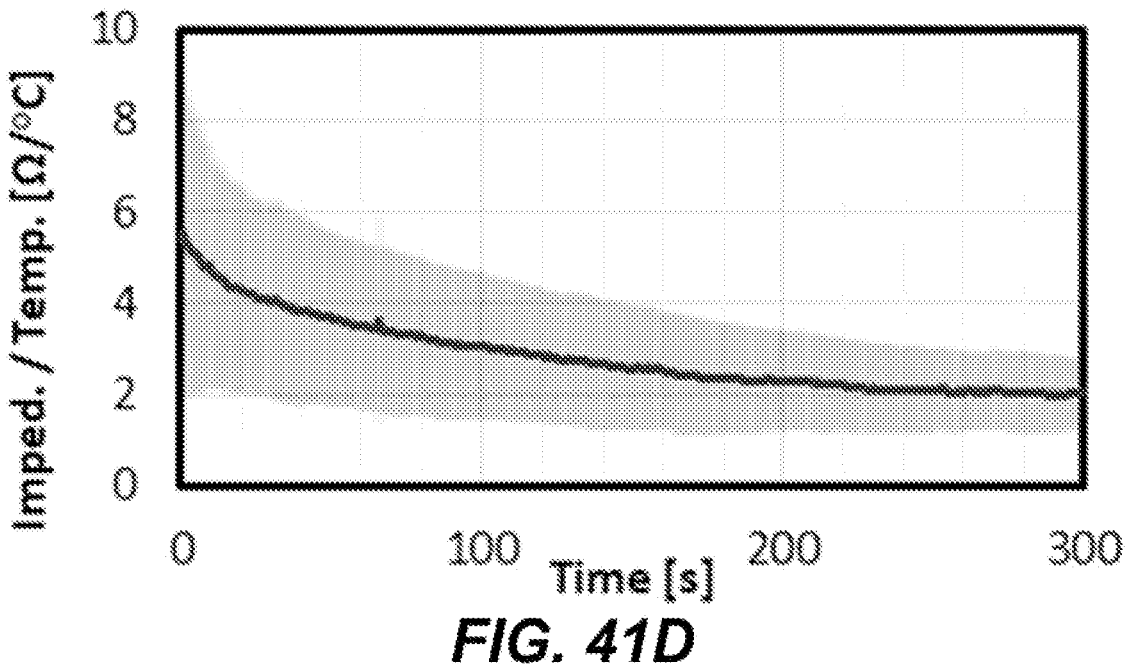

FIGS. 40A and 40B are photos illustrating an applicator used to validate ACE treatment in in vivo murine melanoma tumors, according to some embodiments of the present disclosure. Referring to FIG. 40A, a 3D printed applicator handle was used to enable rapid adjustment of the electrode separations and exposures based on tumor measurements. Referring to FIG. 40B, this applicator was designed to accommodate a remote temperature sensor placed at a distal location (here treating an ex vivo tumor) or through a center channel to enable direct contact with the skin (not shown).

BL6 mice were inoculated with $5 \times 10^4$ Bl6F10 melanoma cells injected subcutaneously. Approximately 7-9 days later, tumors were measured around 4-8 mm in size and treated with ACE. For these tumors, a two needle electrode configuration was used (see FIGS. 40A and 40B) and the voltage to distance ratio [V/cm] of the applied electrical pulses was maintained at 2500 V/cm based on the electrode separation. In most treatments, the center to center distance of the electrical needles was adjusted to either 4 mm or 6 mm, depending on tumor size. The needle exposure was typically 6 mm, was adjusted for smaller or larger tumors. A fiber optic temperature probe was inserted between the two electrode needles such that a remote temperature measurement was acquired on the surface of the skin. This measurement was used as a proxy for inter-tumoral temperature and used as a feedback measurement for the ACE algorithm. The maximum rate of energy delivery was set to be either 100 μs/s or 200 μs/s depending on the target temperature. Prior to treatment, a baseline temperature measurement (typically 29-30° C.) was acquired. The algorithm was then programmed to achieve a target temperature which was 5° C., 10° C., or 20° C. above the baseline temperature. Upon initiation of treatment, the ACE algorithm automatically adjusted the rate of energy delivery in order to achieve and maintain the targeted temperature set points. All treatments were administered with a target dose of 0.02 s.

To evaluate the potential of inducing an adjunctive positive immune response, antigen capturing nanoparticles coated with maleimide polyethylene glycol suspended in phosphate buffered saline were injected directly into the tumors immediately after a subset of ACE treatments. Tumor size and resulting volume were then calculated at 2 to 3 day intervals following treatments.

Results

Equine Results

No adverse events were observed intraoperatively on any patients. Slight twitching or muscle contractions were observed during the ramp-up procedure in which only a single waveform was delivered. This typically subsided during the full treatment as a tetanic state was induced. Individual muscle twitches were occasionally observed as the treatment temperature approached the target set point (60° C.) and the energy delivery rate was algorithmically reduced to maintain the target temperature. In some treatments, muscle contractions were mitigated by increasing the target temperature thereby increasing the steady state energy delivery rate (pulse repetition rate) or by decreasing the pulse width which had the effect of increasing the pulse repetition rate to maintain the algorithmically determined energy delivery rate.

Immediately following treatment, slight dermal abrasion corresponding to the location of the ring electrode and black discharge from the insertion sites were occasionally observed. Photographic follow up indicates that in the days following treatment the tumor volume decreased followed by the formation of a dermal scab and generation of depigmented skin at the treatment site. At treatment follow up (typically 3-6 weeks) gentle scrubbing of scab at the treatment site was sufficient to remove the scab and expose a vascularized region of healing dermal tissue. FIGS. 41A to 41D are graphs of representative data recorded from the ACE treatment of a single tumor, according to some embodiments of the present disclosure. FIGS. 41A to 41D illustrate measurements of current (FIG. 41A), resistance (FIG. 41B), and temperature (FIG. 41C) during treatment indicate a temperature and dose dependent change (FIG. 41D) in the impedance-to-temperature ratio which may be beneficial in determining a treatment end point. Treatment current (see FIG. 41A) increased in a logarithmic trend during the treatment. The measured resistance (see FIG. 41B) followed an inverse decreasing logarithmic trend. These values appeared to plateau towards a stead state which corresponded to the treatment achieving the target 60° C. temperature. This behavior was corroborated via the calculation of the Impedance to Temperature ratio which decreased from an initial value of approximately 6 to a final steady state value of approximately 2. While not explicitly explored in this study, this parameter may be useful as an indication of treatment completion with a steady state impedance-to-temperature ratio indicating that the desired ablative outcome has been achieved.

Murine Results

Figure 42A:
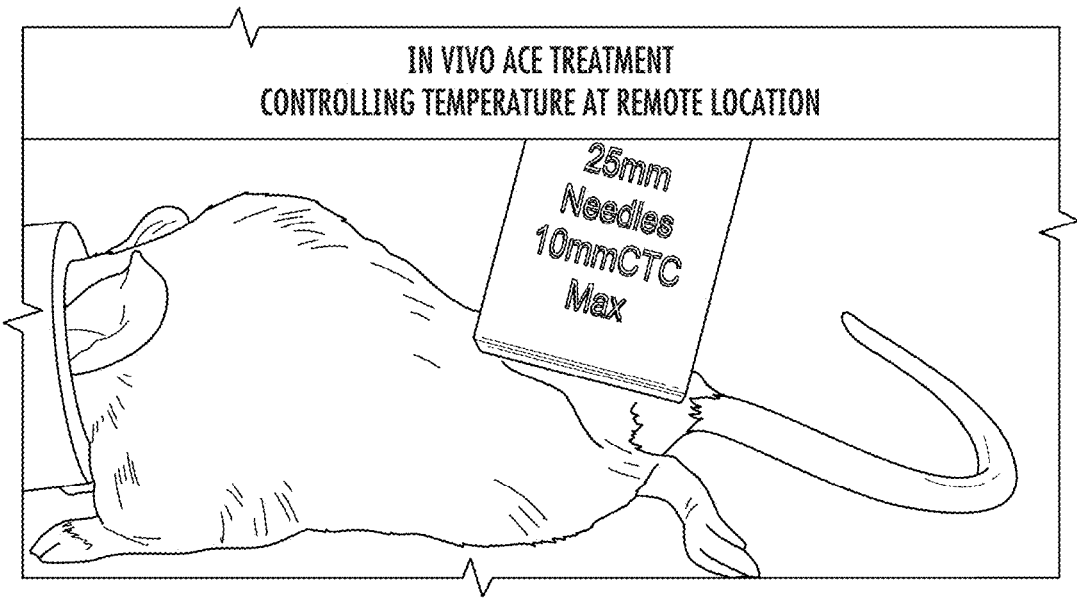
FIGS. 42A and 42B are photos illustrated murine treatment, according to some embodiments of the present disclosure.
Figure 42B:
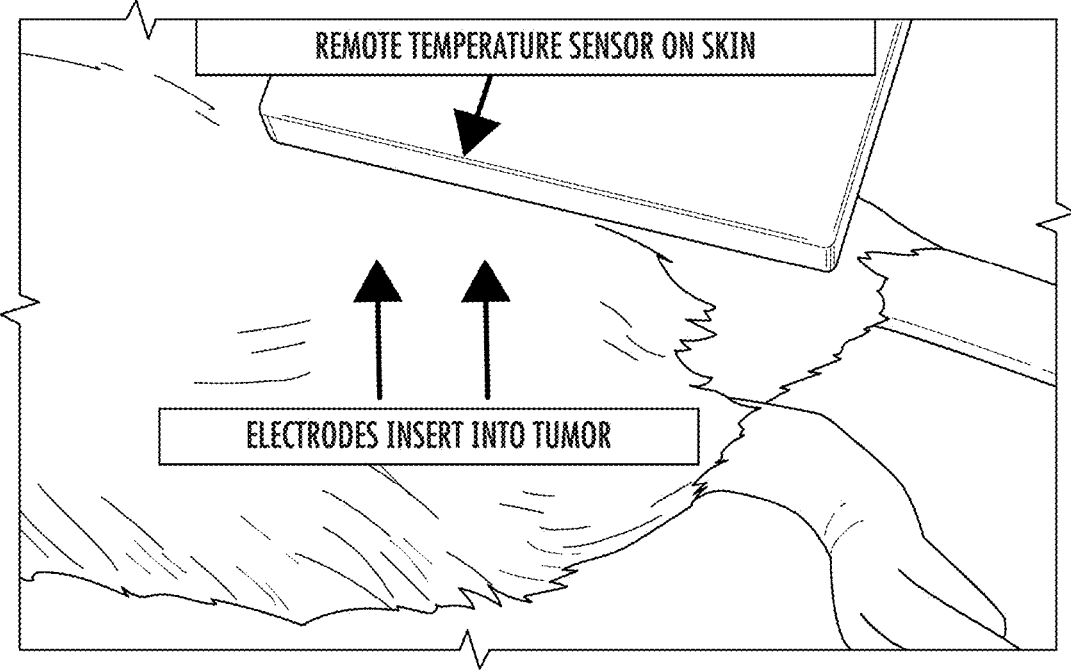
Figure 42C:
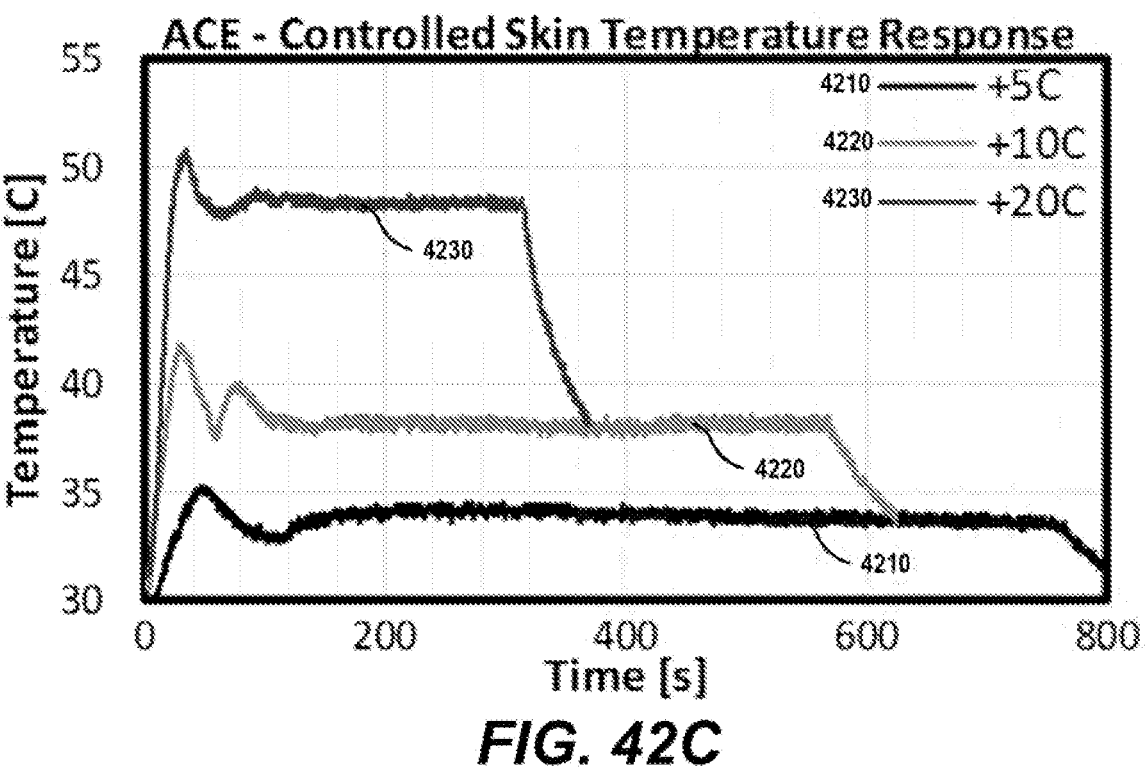
FIGS. 42C to 42D are graphs of representative data recorded from the ACE murine treatment, according to some embodiments of the present disclosure.
Figure 42D:
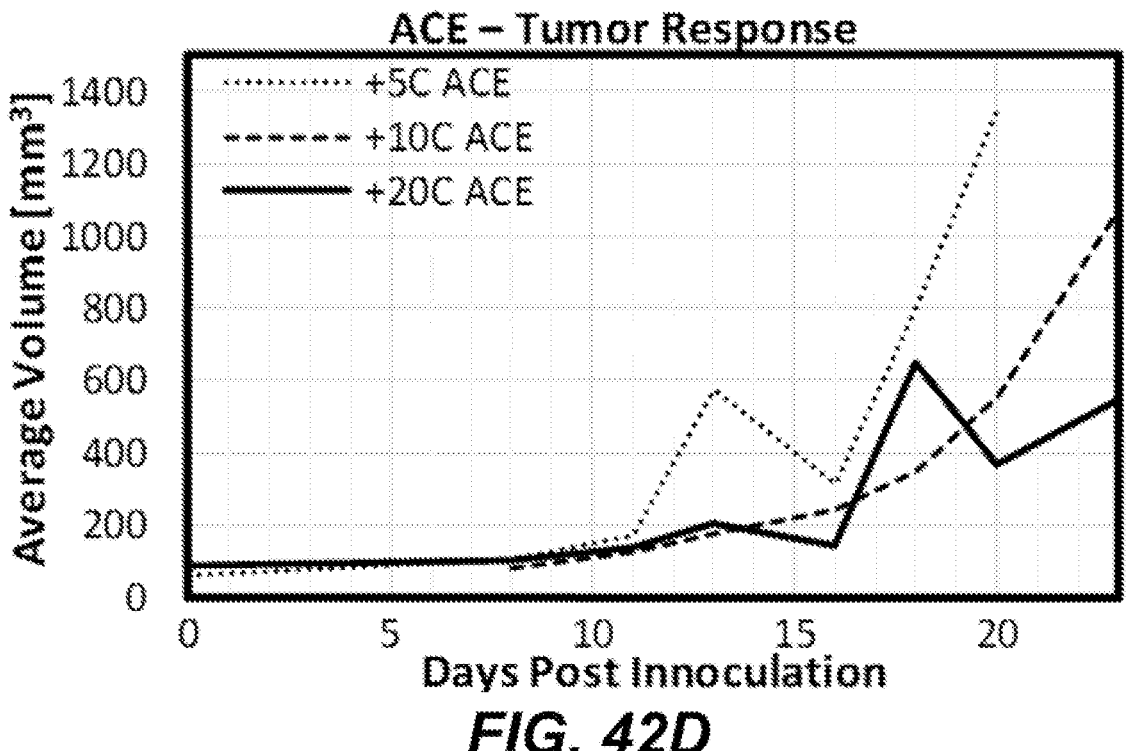

FIGS. 42A and 42B are photos illustrated murine treatment, according to some embodiments of the present disclosure. FIGS. 42C to 42D are graphs of representative data recorded from the ACE murine treatment, according to some embodiments of the present disclosure.

FIG. 42A illustrates a demonstration of in vivo ACE treatments using a remote temperature sensor to control temperatures in proximity to a critical structure (skin) in proximity to the tumor under treatment. Referring to FIG. 42B, two electrodes were inserted directly into the tumor under treatment and a fiber optic temperature sensor was placed externally in contact with the skin. Referring to FIG. 42C, energy was delivered algorithmically to achieve a desired temperature increase (5, 10, 20C) at the surface of the skin. FIG. 42C illustrates tumor growth curves following ACE treatments.

The ACE algorithm was able to successfully control the temperature of a critical structure (skin) at a location that was not directly adjacent to the electrode applicators (see FIGS. 42A, 42B). The algorithm was capable of achieving stable temperatures which were 5, 10, and 20° C. above the baseline pre-treatment temperature (see FIG. 42C). The algorithm successfully delivered energy until a target dose (integrated energized time of 0.02 s) was administered at which time, energy delivery was halted. Following treatment, the animals were recovered from anesthesia, returned to their cages, and the tumors were measured every 2-3 days until euthanasia criteria were met. Preliminary observations indicate that target temperature affected the growth rate of the tumors and treatments achieving a 20° C. temperature rise resulted in the most substantial inhibition of tumor growth.

Figure 43A:
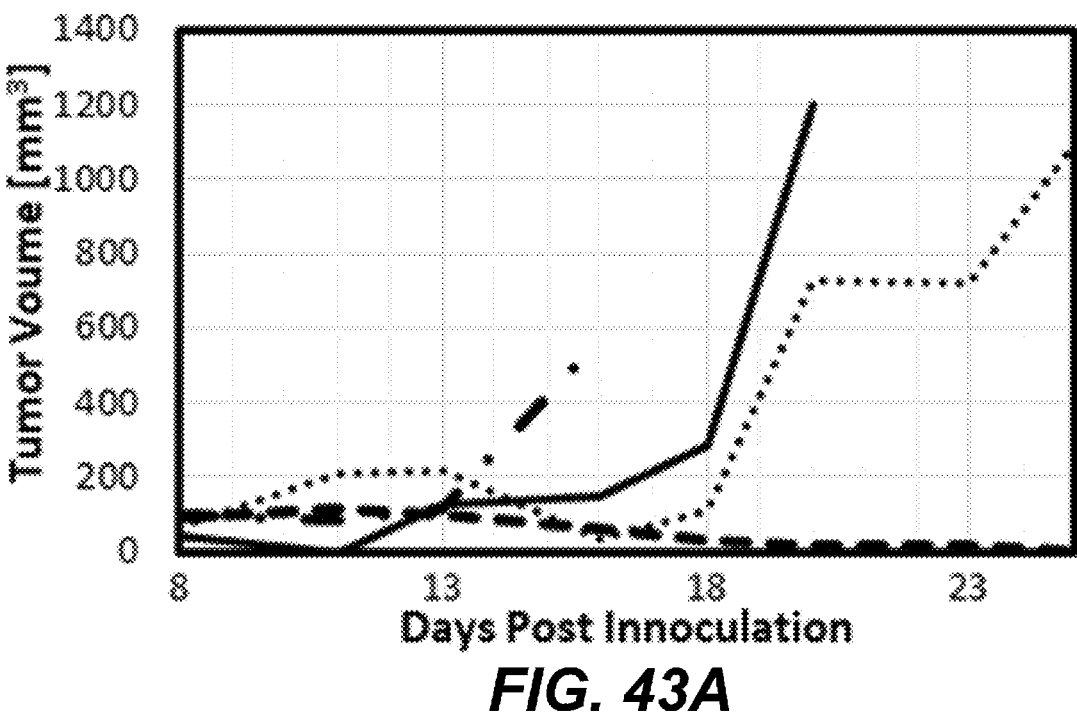
FIGS. 43A to 43C are graphs of results of murine treatment incorporating immunostimulatory nanoparticles, according to some embodiments of the present invention.
Figure 43B:
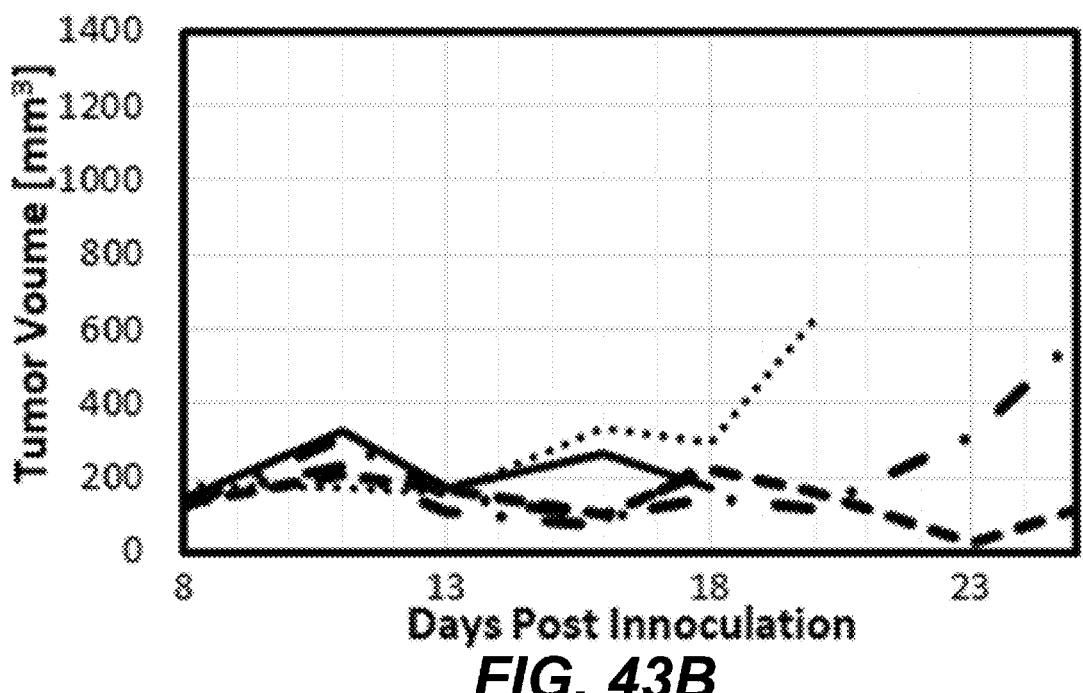
Figure 43C:
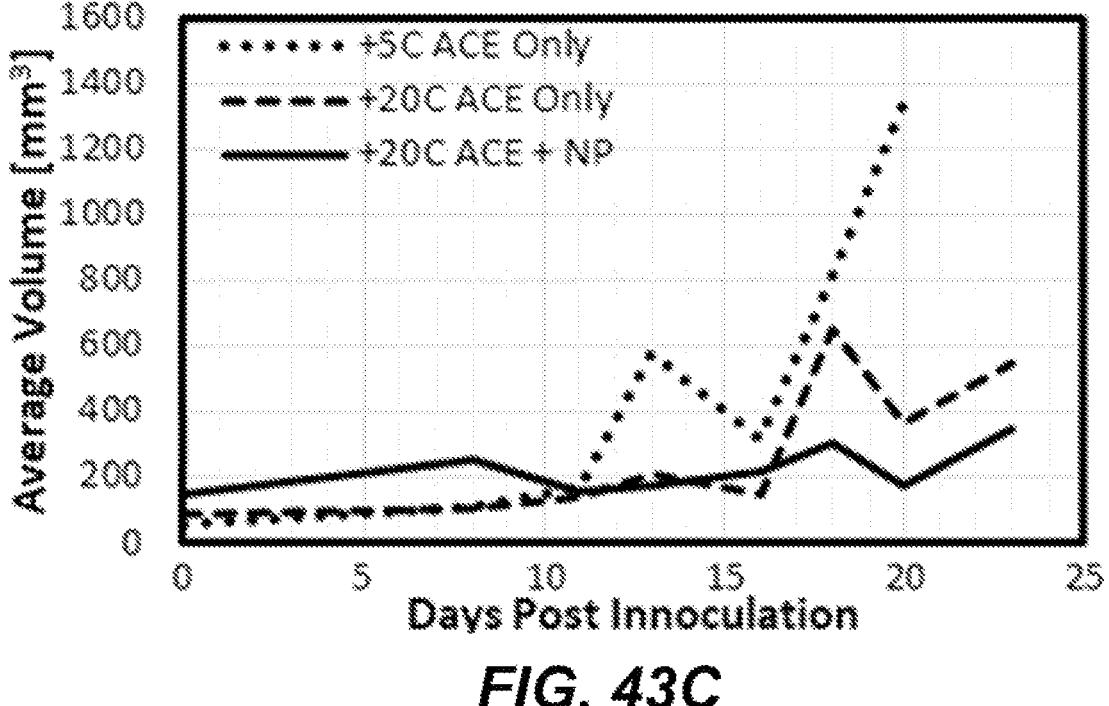

FIGS. 43A to 43C are graphs of results of murine treatment incorporating immunostimulatory nanoparticles, according to some embodiments of the present invention. As illustrated in FIGS. 43A to 43C, in some embodiments immunostimulatory nanoparticles enhance ACE treatment in vivo. FIG. 43A illustrates growth curves for Bl6F10 murine melanoma tumors treated with ACE only and FIG. 43B illustrates growth curves for Bl6F10 murine melanoma tumors treated with ACE+immune system stimulating nanoparticles injected at the time of treatment. FIG. 43C illustrates mean tumor growth curves for +5° C. only, +20° C. only, and +20° C.+nanoparticle treatments.

Interestingly, the addition of immunostimulatory nanoparticles (see FIGS. 43A to 43C) resulted in additional tumor growth inhibition indicating that ACE is capable of preserving antigens released following cell death and that adjunctive particles capable of presenting these antigens to the immune response results in a favorable outcome. Given these results, it is feasible that ACE treatments could be used to treat tumors by inducing cell death (thermal necrosis, non-thermal necrosis, apoptosis, senescence, or delayed cell death) while preventing thermal denaturing of important immune-stimulatory proteins or antigens which in turn can be used to induce a positive immune response against the primary tumor or metastatic disease.

Figure 44B:
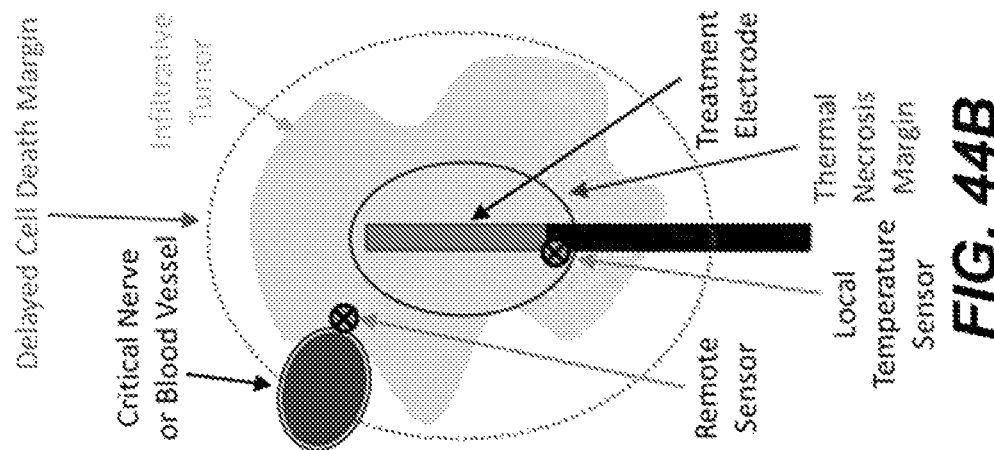
FIG. 44B is a schematic diagram of ACE therapy in which a remote sensor is used to control the algorithmic delivery of energy, according to some embodiments of the present invention.
Figure 44A:
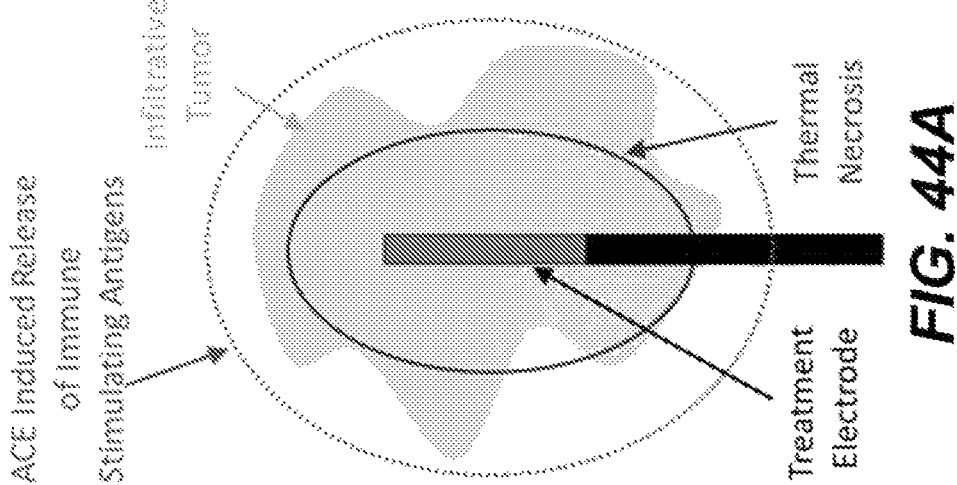
FIG. 44A is a schematic diagram of ACE induced immunotherapy in which an electrode is used to induce the release of immune stimulating antigens or recruit immune cells, according to some embodiments of the present invention.

FIG. 44A is a schematic diagram of ACE induced immunotherapy in which an electrode is used to induce the release of immune stimulating antigens or recruit immune cells, according to some embodiments of the present invention. The ACE algorithm can be implemented to induce a volume of thermal necrosis which ablates part of the tumor while preventing thermal denaturing of antigens by inducing a non-thermal form of immediate or delayed cell death in the remainder of the tumor. In some embodiments, the algorithm may be tuned to prevent any thermal necrosis.

FIG. 44B is a schematic diagram of ACE therapy in which a remote sensor is used to control the algorithmic delivery of energy, according to some embodiments of the present invention. Referring to FIG. 44B, a remote sensor may be used to detect conditions (e.g., temperature) near critical structures, such as a critical nerve or blood vessel. The algorithmic delivery of energy may thus be controlled to avoid damage to the critical structure while providing a thermal necrosis margin that ablates part of the tumor, while delayed cell death (e.g., through the use of induced immunotherapy) may destroy additional parts of the tumor.

This study also demonstrates the use of ACE algorithms to incorporate measurements from a distal location into the feedback algorithm. In this study, measurements of the skin adjacent to the tumor were used, however, it is feasible that temperature sensors or MRI thermometry could be used to acquire temperatures adjacent to critical nerves, blood vessels, or other sensitive structures which can be incorporated into the algorithm.

ACE Treatments Evaluated in a 3D Tumor Model

INTRODUCTION

Pulsed electric fields (PEFs) induce a transient increase in electrical potentials across cell and organelle membranes. The magnitude of this transient is dependent on a number of parameters including the electrical properties of the cell and its environment, the magnitude of the local electric field, and the time domain characteristics of the pulses. Similarly, the biological responses following PEF exposure are dependent on a complex combination of stochastic energy dependent phenomena. These range in severity and include the absence of a measurable response, disruption of mitotic spindle formation, temporary permeabilization of the cell membrane, induction of apoptosis, and outright membrane disruption leading to a necrotic form of cell death.

Clinical PEF treatments leading to the destruction of unwanted tissue (ablation) are generally referred to as irreversible electroporation (IRE) due to the presumed induction of permanent defects in the cell membrane caused by the electrical pulses. These IRE treatments are rapidly gaining traction as a clinical treatment for inoperable tumors, especially in cases where surgical, radiological, and thermal procedures are contraindicated. The success of the only FDA approved intervention, the NanoKnife (NK-IRE), has led to interest in improving the technique. Of note the NK-IRE may be limited in the size of tumors which can feasibly be treated due to the induction of intense muscle contractions by the 50-100 μs electrical pulses delivered, electrical arcing between probe pairs, and by the potential to induce unintended thermal injury due to a lack of active feedback during energy delivery.

These limitations have led to investigations of microsecond duration alternating polarity pulses as an alternative strategy. These high frequency irreversible electroporation (H-FIRE) protocols mitigate muscle contractions, reduce the potential for electrical arcing, and enable the use of significantly higher treatment voltages[9]. However, these treatments generally require greater electric field strength, possibly due to a proposed cancelation effect, to induce lethal effects and result in smaller treatment zones than NK-IRE when treatment voltages and doses are held constant.

This leads to some question as to whether or not microsecond or nanosecond pulses can achieve the same degree of clinical utility as the 50-100 μs pulses used in NK-IRE. Here, a potential alternative strategy is investigated, integrated time nanosecond pulse irreversible electroporation, substantially similar to the ACE treatments described herein, in which the stochastic nature of PEF responses is exploited by delivering significantly larger electrical doses (integrated times) than common with NK-IRE. The results show that while NK-IRE ablation sizes appear to reach a steady state, ACE ablations increase sequentially with integrated times of 0.001, 0.01, and 0.1 s. Computational models were used to investigate the charging/discharging behavior of cell membranes during exposure to ACE treatments and to determine the treatment voltages and overall treatment durations that would be necessary for ACE to achieve equivalent ablation sizes as NK-IRE clinically. For experiments conducted at physiological temperatures, 0.01 s IET ACE treatments with 350 ns, 500 ns, and 750 ns pulses require electric field intensities of 1109V/cm, 954 V/cm, and 698V/cm, respectively, to induce cell death. To achieve similar ablation volumes as NK-IRE these protocols would require the use of 6.7 kV, 5.8 kV, and 4.2 kV pulses, respectively. To inhibit significant thermal injury adjacent to the electrode, 44° C. temperature-controlled treatments were simulated and required 1190 s, 870 s, and 450 s, respectively, to achieve identical ablation volumes to standard 100 s 3 kV NK-IRE protocols.

Methods

Cell Culture and 3D Tumor Model

Due to interest in utilizing PEFs for the treatment of brain tumors where thermal transients can be especially deleterious, U118 human glioblastoma cells were utilized in this study. The cells were cultured in DMEM supplemented with penicillin/streptomycin and 10% fetal bovine serum. Upon reaching approximately 80% confluence the cells were harvested from 2D culture via trypsinization. After deactivating the trypsin with fresh media, the cells were centrifuged, and resuspended in media at a concentration of $1 \times 10^6$ cells/mL. 3D tumor constructs were created by mixing the cell suspension in a one-to-one ratio with PureCol Ez on ice to achieve a 2.5 mg/mL concentration of collagen and a final cell concentration of $0.5 \times 10^6$ cells/mL. This mixture was then rapidly aliquoted into 12-well plates with 0.5 mL/well.

A carful swirling motion was used with a 500 μL pipette to achieve complete coverage of the well surface. The well plate was then incubated overnight at 37° C. in a 5% $CO_2$ atmosphere to allow the matrix to solidify. 500 μL of fresh media was then added to each well to provide hydration and nutrients prior to experiments.

Pulse Delivery

Figure 45:
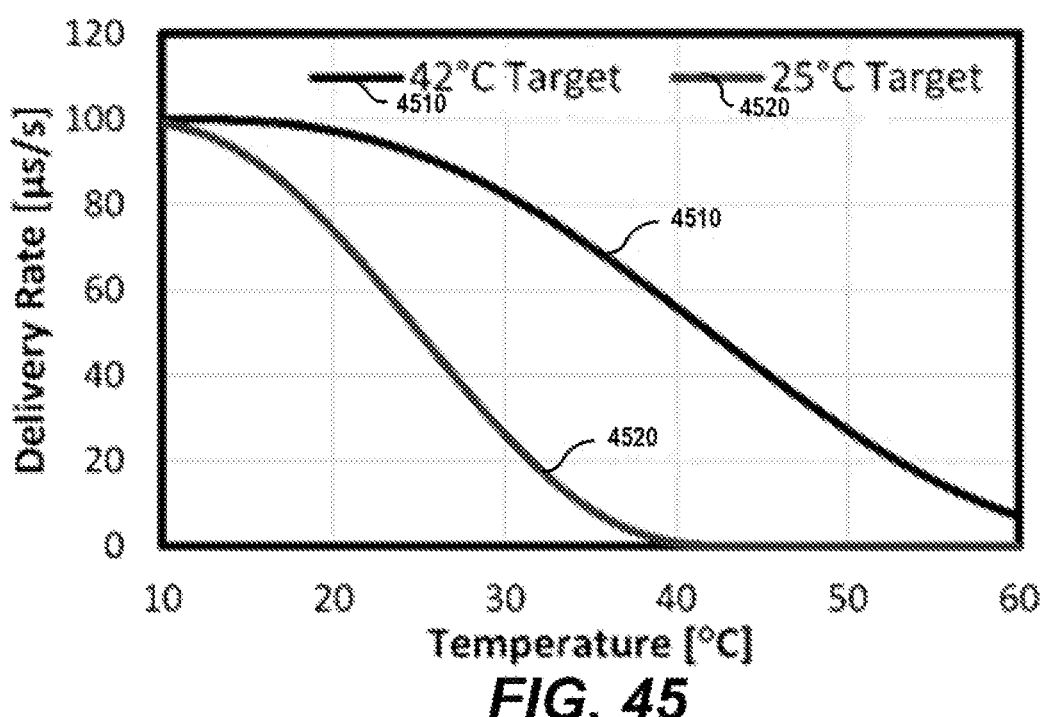
FIG. 45 is a graph of a target energy delivery rate, according to some embodiments of the present invention.

ACE treatments waveforms consisted of a positive pulse (P), a brief delay (D) e.g., equal to 1 μs, and a negative pulse (N) (see FIG. 14A). In some embodiments, the positive and negative pulses may be on the order of microseconds. This alternating polarity waveform is designed to mitigate muscle contractions in vivo. In the experiments, the waveform was symmetric meaning that the positive and negative pulses had the same duration of either 350, 500, 750, 1000, or 2000 ns, though the embodiments of the present disclosure are not limited to this configuration. The minimum pulse width corresponded to the minimum pulse with achievable with the custom H-Bridge pulse generator utilized in this study. The delay between successive waveforms was algorithmically controlled such that transient temperature increases of 5° C. were achieved and maintained. The delay between successive waveforms was controlled algorithmically based on temperature readings. Because pulse widths vary between treatment groups the algorithm calculates a target energy delivery rate (see FIG. 45) based on the instantaneous temperature which is measured at the center of the ring and pin electrode (see FIG. 3A) via a temperature sensor placed within the center pin electrode (see FIG. 3B). As treatments had different pulse widths, the algorithm calculated a target mean energy delivery rate (μs/s, see 45A) which was then converted into a waveform delay based on the experimental pulse width being evaluated. Voltage and current waveforms were recorded in real time via a custom 100 MSPS data acquisition system. To enable comparison between treatments with different pulse widths, treatment doses were defined as a specified integrated energized time (IET) calculated as:

$$IET = \sum_{n}^{N}(t_p + t_n) \quad (54)$$

where N is the total number of pulses delivered, and $t_p$ and $t_n$ are the durations of the positive and negative pulses, respectively. A baseline dose of 0.01 s was defined based on NK-IRE treatments which deliver 100× 100 μs electrical pulses. Two additional doses representing 0.1× (0.001 s) and 10× (0.1 s) as the baseline dose were investigated. All treatments had an initial energy deliver rate of 100 μs/s which decreased based on the temperature control algorithm.

All experiments were conducted by placing well plates containing the 3D tumor models on top of a custom machined aluminum block with a thin layer of ethanol between the block and well plate to aid in thermal transport. The aluminum block was placed on the heating/cooling surface of a Peltier thermoelectric heater and the samples were allowed to normalize to the treatment temperature (20° C. or 37° C.) prior to the initiation of treatments. All treatments were administered through a custom coaxial electrode consisting of a 17 mm outer ring and a 1 mm hollow center pin held in place by a laser cut acrylic holder (see FIG. 3B). A 200 μm diameter fiber optic temperature sensor was placed through the center pin into the center of the 3D tumor where thermal transients were assumed to be at an approximate maximum. Temperature data was recorded at 3 Hz and utilized by a temperature control algorithm built into the pulse delivery system to achieve and maintain a 5° C. temperature increase throughout the treatments. Transient voltage and current measurements for each treatment were acquired via a custom 100 MSPS data acquisition system integrated into the pulse generator.

Figure 46A:
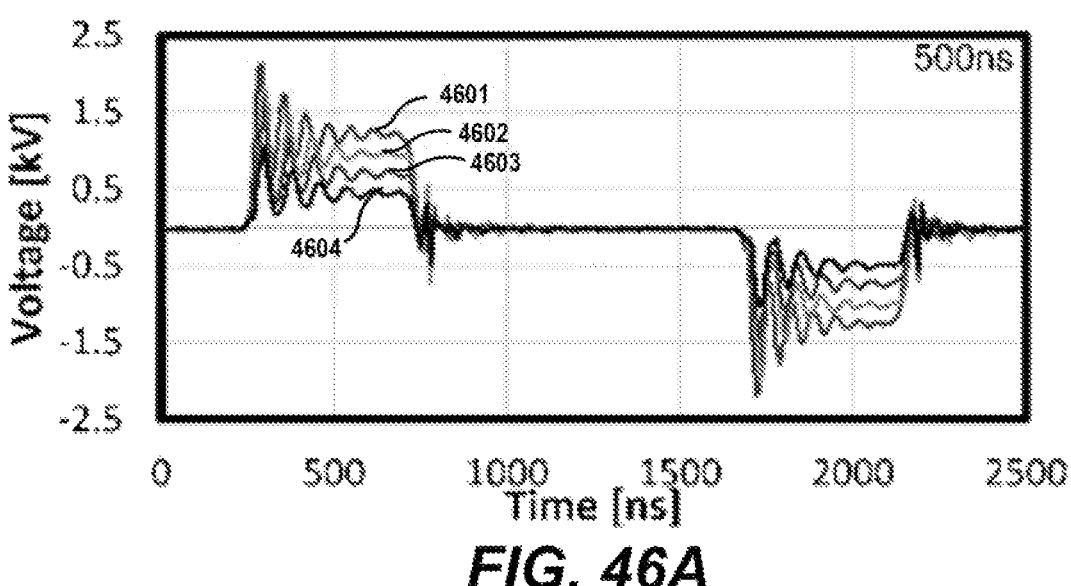
FIGS. 46A to 46E illustrate example treatment waveforms, according to some embodiments of the present disclosure.
Figure 46B:
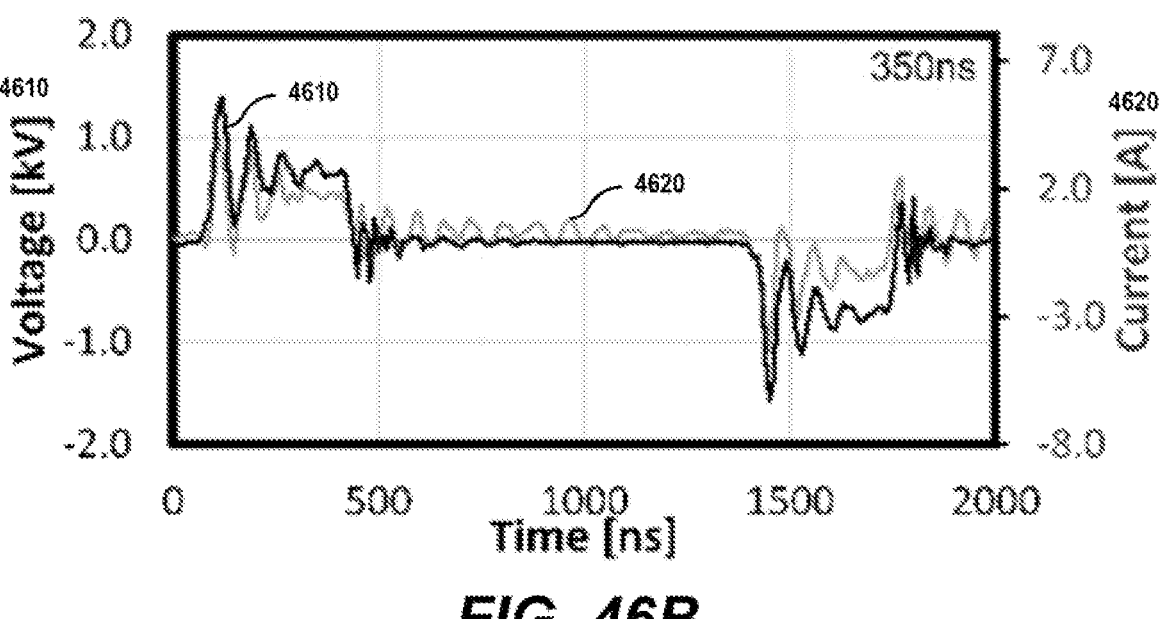
Figure 46C:
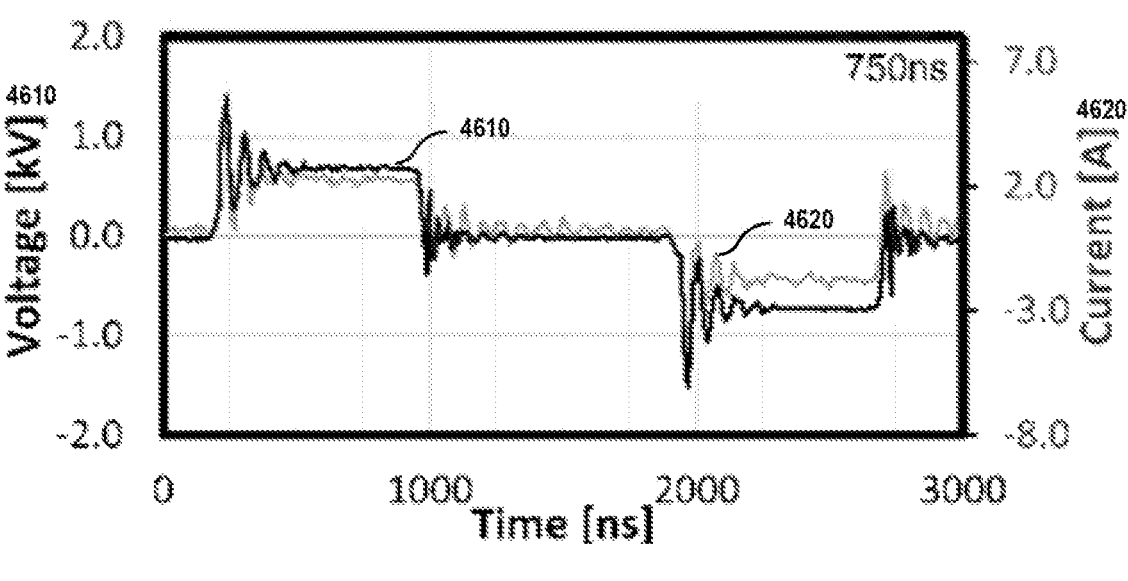
Figure 46D:
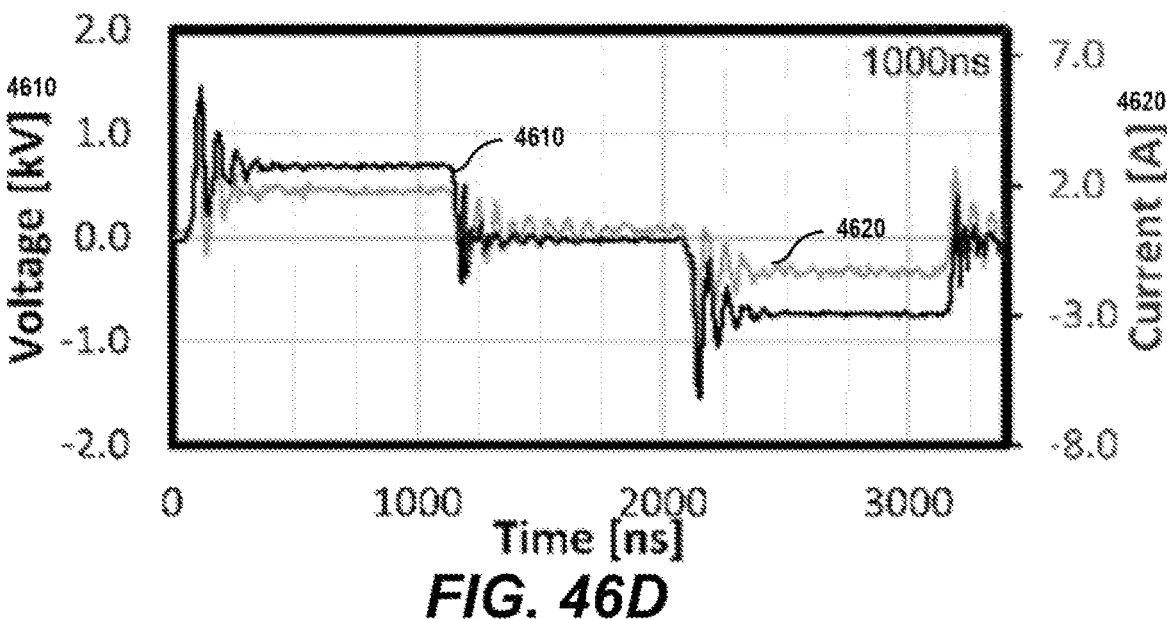
Figure 46E:
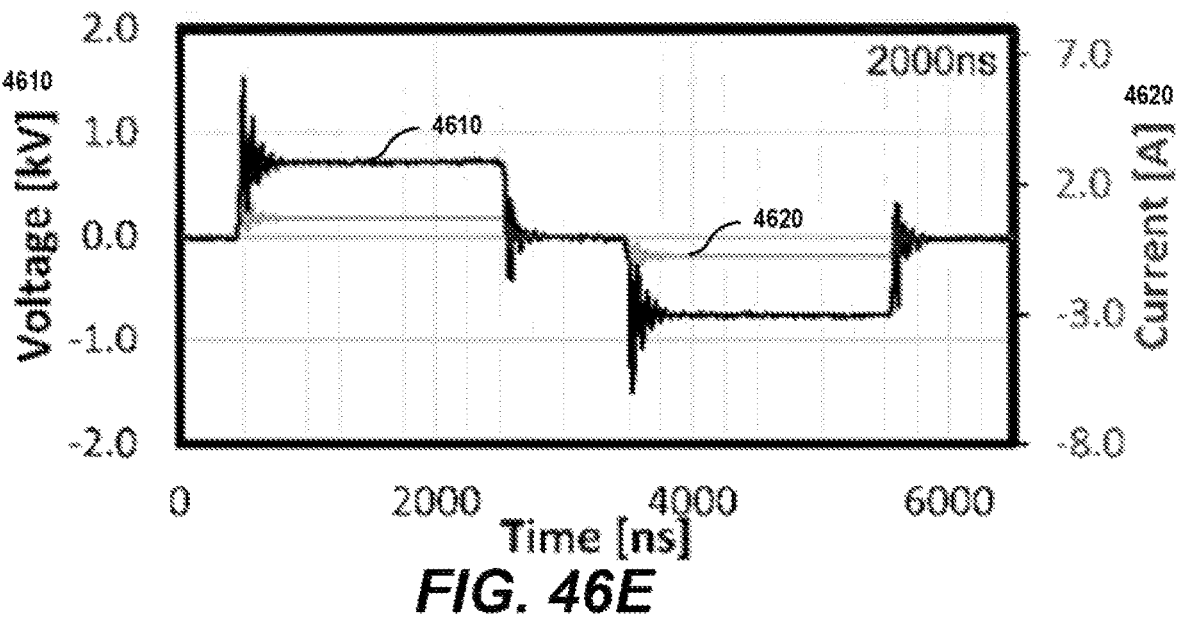

FIGS. 46A to 46E illustrate example treatment waveforms, according to some embodiments of the present disclosure. FIG. 46A illustrates representative waveforms for 500 ns ACE treatments with pulse voltages of 500V (line 4604), 750V (line 4603), 1000V (line 4602), and 1250V (line 4601). FIGS. 46B to 46E illustrate representative voltage (line 4610) and current (line 4620) waveforms for 750V ACE treatments with pulse durations of 350 ns (see FIG. 46B), 750 ns (see FIG. 46C), 1000 ns (see FIG. 46D), and 2000 ns (see FIG. 46E). To determine appropriate voltage settings to produce visible treatment zones across a wide pulse-duration space an initial voltage escalation study was conducted using 500 ns pulses, a dose of 0.01 s, and voltages of 500, 750, 1000, and 1250V. A voltage of 750V was found to provide the greatest dynamic range for these pulse widths (350-2000 ns) and utilized in all remaining experiments.

To characterize the pulse duration space, a series of experiments were conducted at 750V with a dose of 0.01 s and pulse widths of 350, 500, 750, 1000, and 2000 ns at room temperature. A subset of these were repeated with a baseline temperature 37° C. (350, 500, and 750 ns) and target temperature of 42° C. to evaluate if the lethal effects of these pulses was dependent on temperature. Finally, to determine the effect of integrated time on treatment outcomes, a subset of treatments was repeated for IET of 0.001, 0.01, and 0.1 s (500 and 2000 ns pulses).

All treatment parameters were evaluated in a minimum of three (N=3) times. In some cases, individual parameters needed to be investigated on different experimental days, in these cases a minimum of two replicates was conducted per day resulting in some parameters with more than three replicates. Statistical analysis was conducted via a one-sided Student's T-test with a significance level of 0.05 ($\alpha$=0.05) using JMP (14.1.0 Pro, SAS Institute Inc. Cary, NC).

Computational Modeling

To elucidate potential mechanisms for the observed experimental results, finite element computational models were constructed to evaluate (a) what electric field iso-contours corresponded with the diameter of each treatment administered (the lethal threshold), (b) to evaluate the relative transmembrane potential increase induced in cells at the margin of each treatment zone, and (c) to determine approximate voltages necessary for ACE protocols to achieve similar ablation volumes as NK-IRE in a clinical setting. Briefly, the electric field distribution within the 3D tumor models, around a single cell, and surrounding a clinical applicator were calculated using separate 2D axisymmetric finite element models in COMSOL Multiphysics (V5.5, COMSOL Inc., Los Altos, CA) via established techniques. The Electric Currents, Heat Transfer in Solids, and Electromagnetic Heating modules were used to calculate the electric field distributions taking the temperature dependent electrical conductivity of tissues and cell culture media into account. These figures utilized adaptive meshing techniques (see, e.g., FIGS. 8A and 8B) to ensure convergence of solutions in regions where high electric field gradients were observed.

Results

Computational Determination of Lethal Thresholds

Separate finite element simulations were conducted for each experimental case using a temperature dependent electrical conductivity function to account for thermal effects on the electric field distribution. It was found that treatment voltage substantially impacted the electric field distribution within the simulated 3D tumor surrounding the coaxial ring and pin electrode. However, the baseline temperature (20° C. vs 37° C.) and the total dose delivered (0.001 s vs 0.01 s vs 0.1 s) did not change the electric field distribution found at times corresponding to the end of each parameter simulated. Independent of this finding, the simulated electric field distribution corresponding to respective experimental treatments was used in calculating lethal electric field thresholds.

Voltage Escalation: 500 ns 0.01 s IET Treatments

Figure 47A:
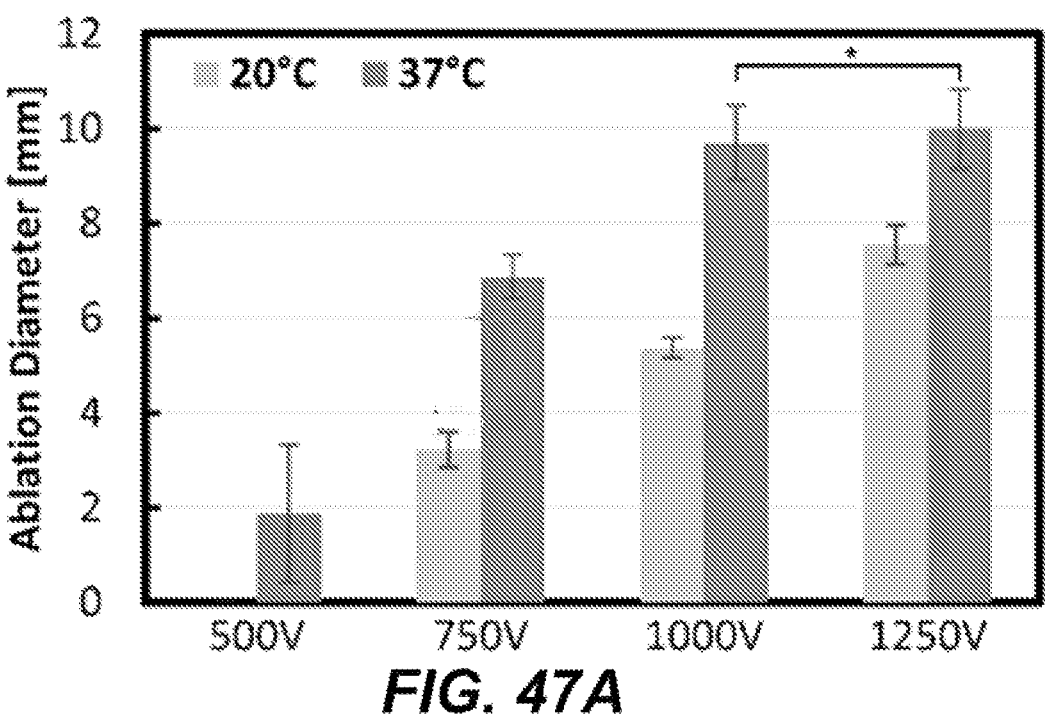
FIGS. 47A to 47C are graphs illustrating treatment observations, according to some embodiments of the present disclosure.
Figure 47B:
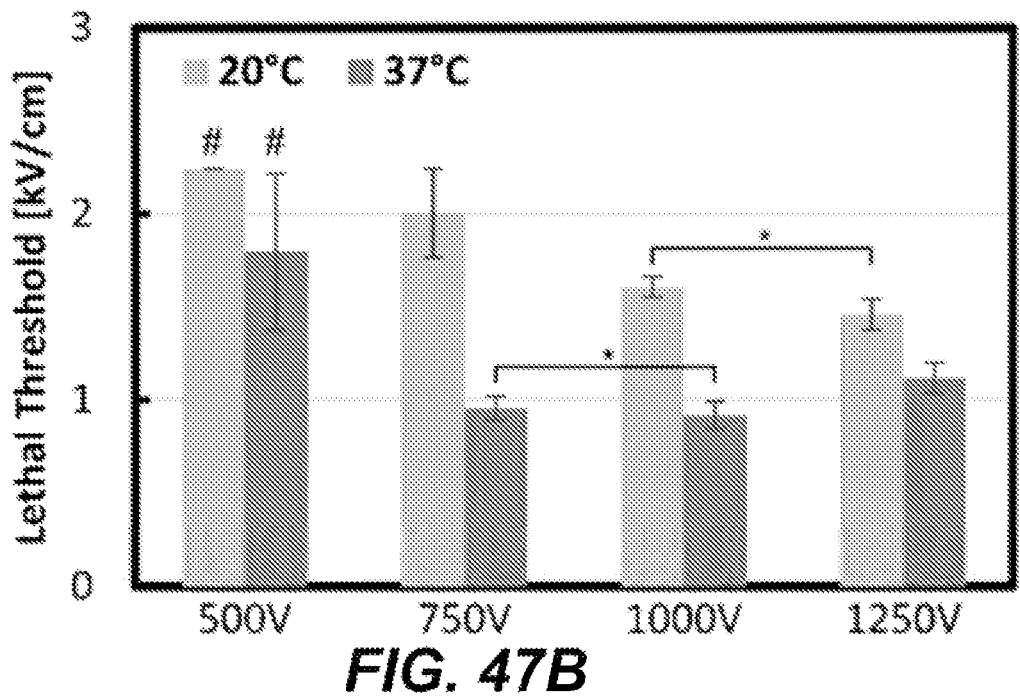
Figure 47C:
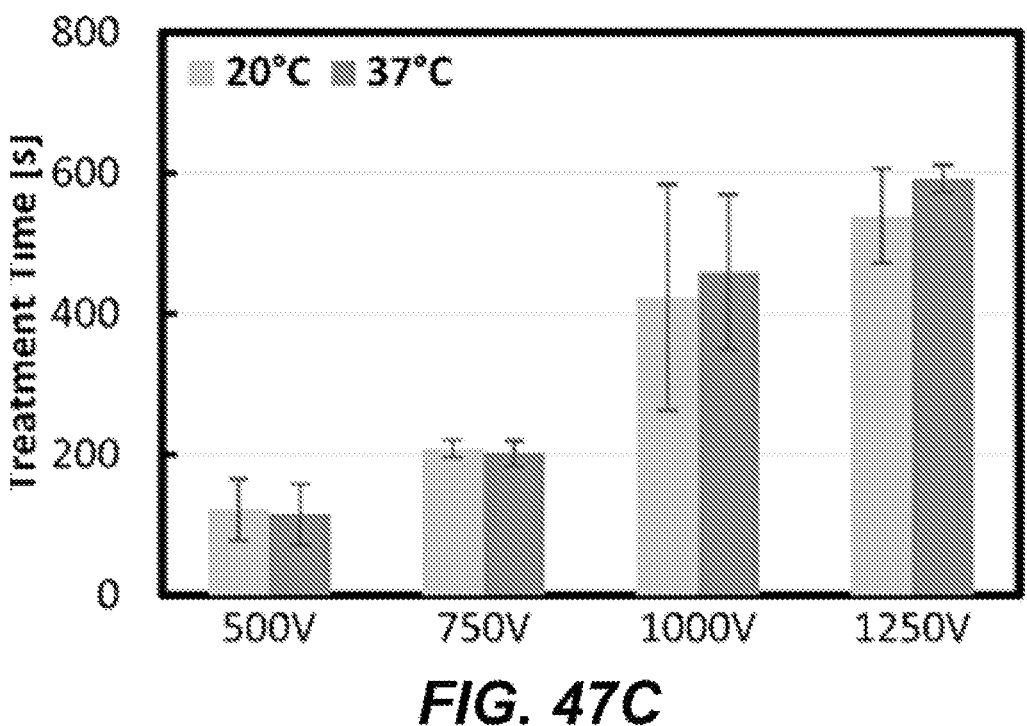

FIGS. 47A and 47C are graphs illustrating treatment observations, according to some embodiments of the present disclosure. FIGS. 47A to 47C illustrate ablation diameters (see FIG. 47A), lethal thresholds (see FIG. 47B), and treatment times (see FIG. 47C) for 0.01 s IET 500 ns treatments with 500V, 750V, 1000V, and 1250V with initial temperatures of 20° C. and 37° C. In FIGS. 47A to 47C, a '#' symbol indicates treatments with non-measurable ablation diameters with electric field thresholds presumed to be 2.24 kV/cm and a '*' symbol indicates groups which were not statistically significantly different (p>0.05).

Referring to FIGS. 47A to 47C, a voltage escalation study was conducted to determine optimal treatment parameters for evaluating treatment outcomes over a wide range of experimental pulse widths. For 500 ns 0.01 s treatments administered at 37° C. resulted in the smallest measurable ablations (1.87±1.46 mm). In this group, 2 of 6 (33%) resulted in non-existent ablations. Increasing the applied voltage to 750V, 1000V, and 1250V resulted in sequentially larger mean ablation diameters (see FIG. 47A). However, the 1000V and 1250V treatments were not found to be statistically significantly different (p=0.4574). When these treatments (500 ns, 0.01 s) were replicated at 20° C. the 500V treatment group did not produce measurable ablation zones. However, the 750V, 1000V, and 1250V treatments resulted in sequentially larger (see FIG. 47A) ablation diameters which were all significantly different (p<0.0001). For voltage-matched treatments all of the 37° C. ablations were found to be statistically significantly larger than the corresponding 20° C. treatment (p<0.0001). Of interest, no difference was found between the 37° C. 750V treatment and the 20° C. 1250V treatment (p=0.0138).

Statistically significant differences (p<0.02) were found between the lethal electric field thresholds (see FIG. 47B) for all treatments except the 20° C. treatments administered at 1000V and 1250V (p=0.07) and the 37° C. treatments administered at 750V and 1000V (p=0.62). Both 500V treatment groups resulted in immeasurable ablation zones (20° C.: 100%, 37° C.: 33%). For these treatments the electric field value found at the electrode interface (2.24 kV/cm) was substituted to avoid skewing results towards lower predictions by omitting data.

Due to higher voltages inducing greater rates of Joule heating, the treatments sequentially required longer durations to complete despite the delivery of a constant 0.01 s dose (see FIG. 47C). As a compromise between the minimum/maximum ablation sizes observable and the total treatment time all remaining treatments were administered with 750V pulse amplitudes.

Effect of Pulse Width: 750V 0.01 s IET Treatments

Figure 48A:
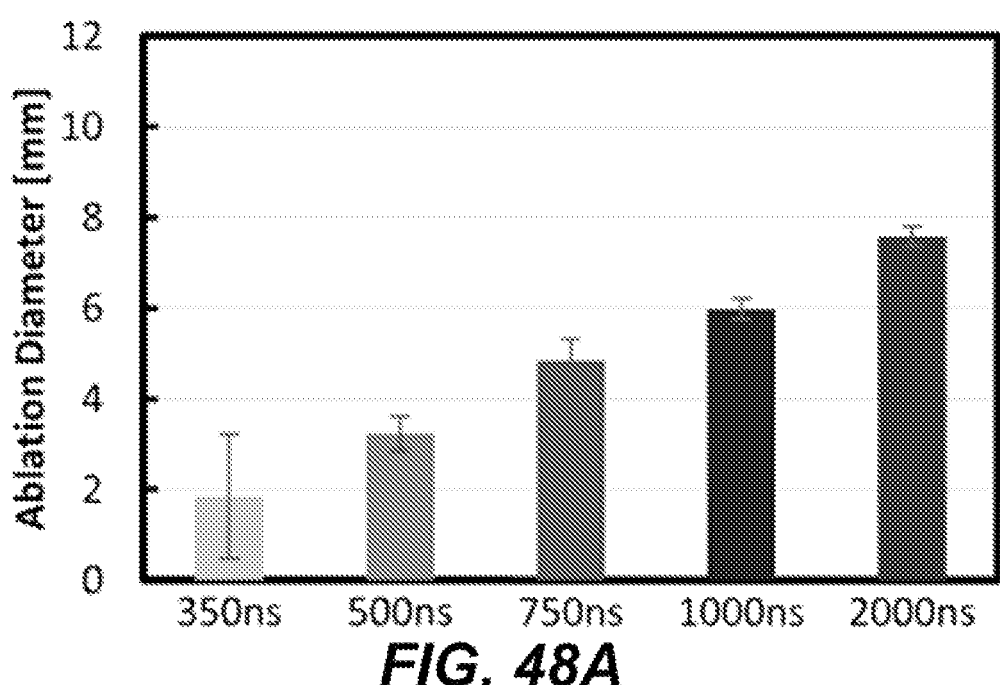
FIGS. 48A and 48B are graphs illustrating treatment observations, according to some embodiments of the present disclosure.
Figure 48B:
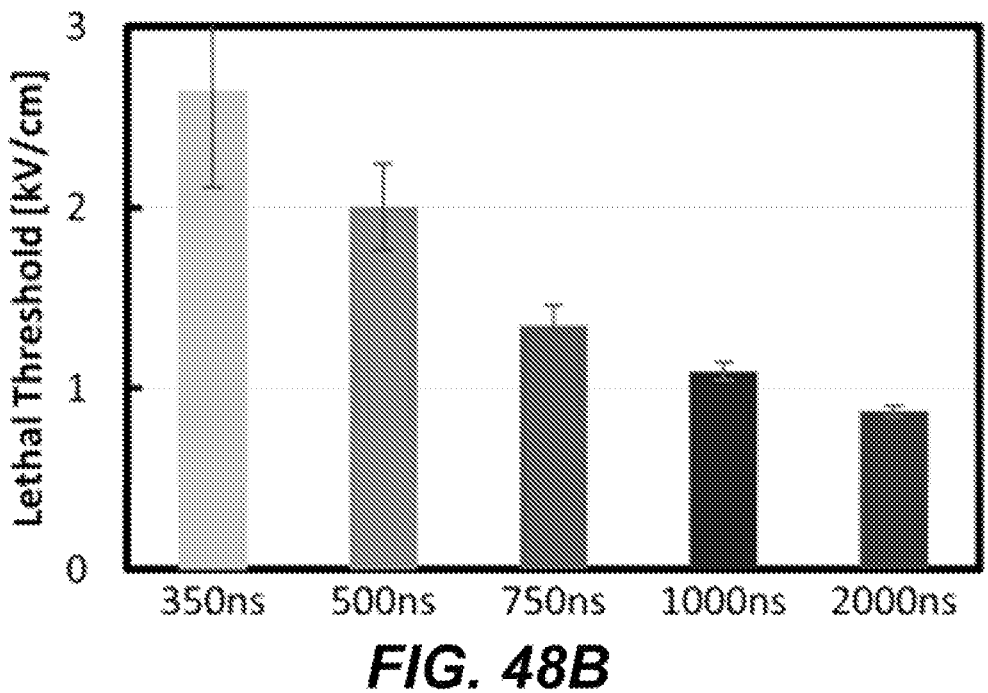

FIGS. 48A and 48B are graphs illustrating treatment observations, according to some embodiments of the present disclosure. FIGS. 48A and 48B illustrate mean ablation diameters (see FIG. 48A) and lethal electric field thresholds (see FIG. 48B) as a function of constitutive pulse widths. Referring to FIGS. 48A and 48B, ablation diameters and lethal thresholds were all found to be statistically significantly different between (p<0.0028). It was found that ablation diameter was a function of pulse width when 0.01 s IET treatments were administered with 750V pulses at 20° C. The smallest ablations were found for treatments with 350 ns pulses with sequentially larger ablation volumes found for treatments with 500 ns, 750 ns, 1000 ns, and 2000 ns pulses. These ablation volumes were found to be statistically significantly different (p<0.0001, see FIG. 48A). Similarly, lethal electric field thresholds decreased from 2648±573 V/cm for 350 ns treatments to 827±27 V/cm for 2000 ns treatments (see FIG. 48B).

Temperature was found to impact the ablation volumes for the sub-microsecond duration pulse treatments investigated with 37° C. treatments resulting in significantly (p<0.0001) larger ablations and significantly (p<0.0001) lower lethal electric field thresholds than 20° C. treatments. When 0.01 s IET treatments were administered at 37° C. lethal thresholds of 1109±171, 954±63, 698±45 V/cm were found for 350, 500, and 750 ns pulse durations, respectively. In contrast, when treatments were administered at 20° C., lethal thresholds of 2648±537, 2002±239, 1347±114 V/cm were found for the same respective treatment parameters.

Effect of Integrated Time: 750V 500 and 2000 ns Treatments

Figure 49A:
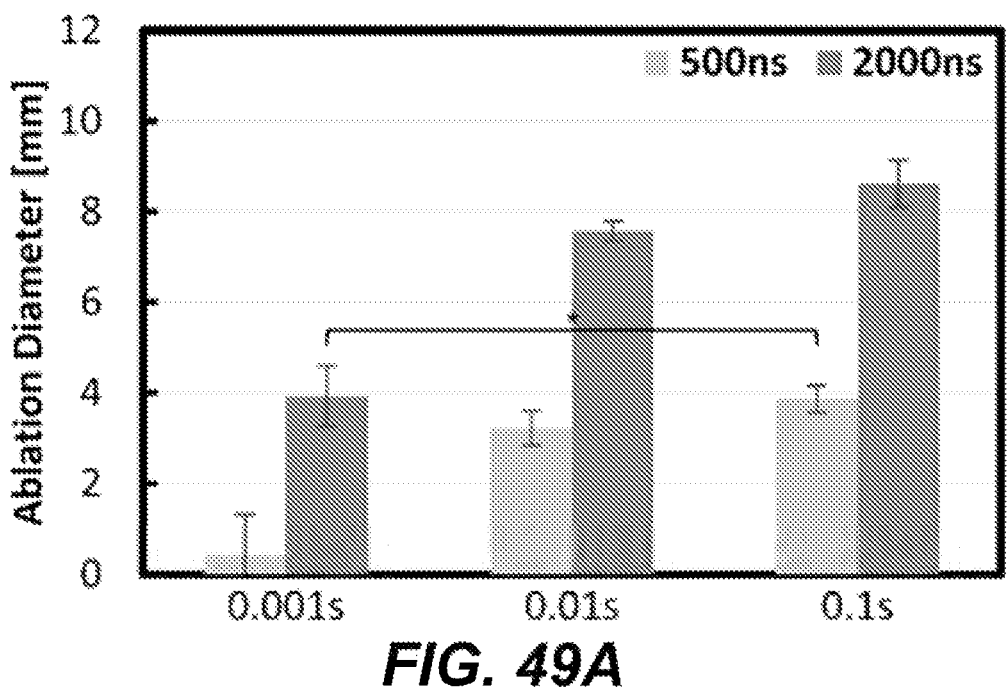
FIGS. 49A and 49B are graphs illustrating treatment observations, according to some embodiments of the present disclosure.
Figure 49B:
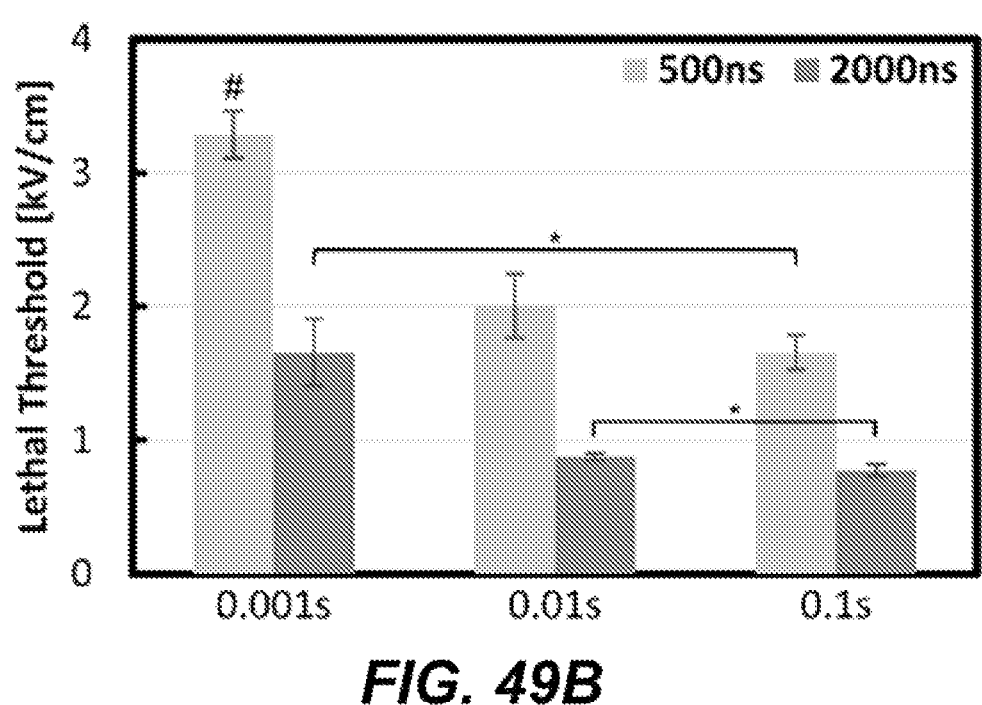

FIGS. 49A and 49B are graphs illustrating treatment observations, according to some embodiments of the present disclosure. FIGS. 49A and 49B illustrate an effect of dose on ablation size. FIG. 49A illustrates that ablation diameters sequentially increased and FIG. 49B illustrates that lethal thresholds sequentially decreased for 750V ACE treatments with pulse durations of 500 ns and 2000 ns when the dose (integrated energized time) was increased from 0.001 s to 0.1 s. Treatments were administered at 20° C. In FIGS. 49A and 49B, a '#' symbol indicates treatments with non-measurable ablation diameters with electric field thresholds presumed to be 3.37 kV/cm, and a '*' symbol Indicates groups which were not statistically significantly different (p>0.14). Referring to FIGS. 49A and 49B, increases in integrated time from 0.001 s to 0.1 s resulted in significant increases in ablation diameter (see FIG. 49A) for 750V treatments with 500 ns and 2000 ns pulses, For treatments with 500 ns pulses, doses of 0.001 s resulted in 80% of treatments (4 of 5 treatments) without a measurable ablation. For these treatments, the lethal threshold was assumed to be a minimum of 3.37 kV/cm representing the value at the electrode interface. Under these 500 ns treatments, the lethal threshold (see FIG. 49A) was found to be significantly (p<0.001) lower for each 10× increase in dose (see FIG. 49A). A significant decrease in lethal threshold was found for 2000 ns pulses between 0,001 and 0.01 s (p<0.0001), but not between 0.01 and 0.1 s (p=0.1495). Interestingly, a statistically significant difference was not found between the 0.1 s IET 500 ns and 0.001 s IET 2000 ns ablation diameters (p=0.7589) or lethal thresholds (p=0.9648).

Membrane Potentials

Figure 50A:
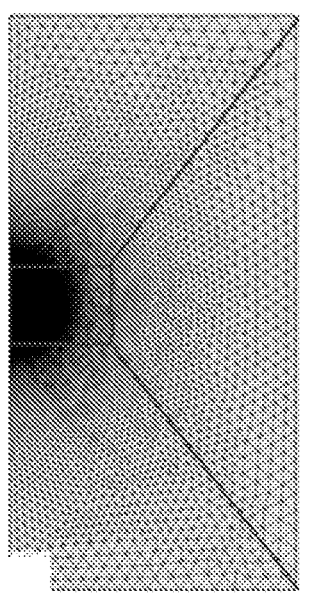
FIGS. 50A to 50C illustrate simulation data for ACE treatments, according to some embodiments of the present invention.
Figure 50B:
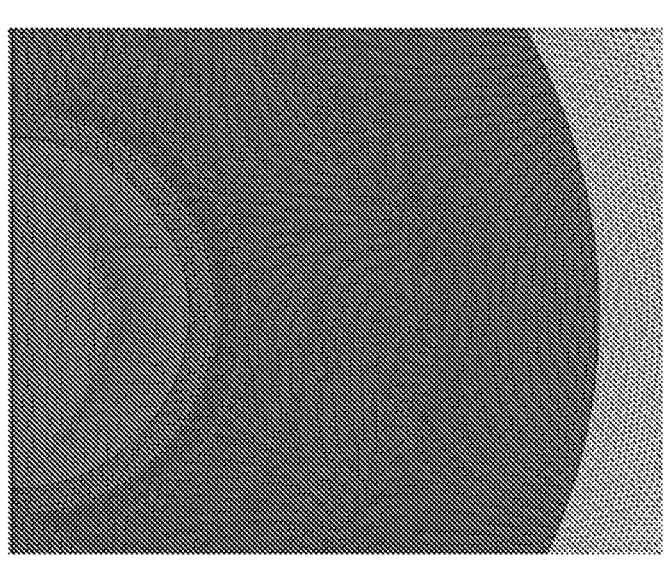
Figure 50C:
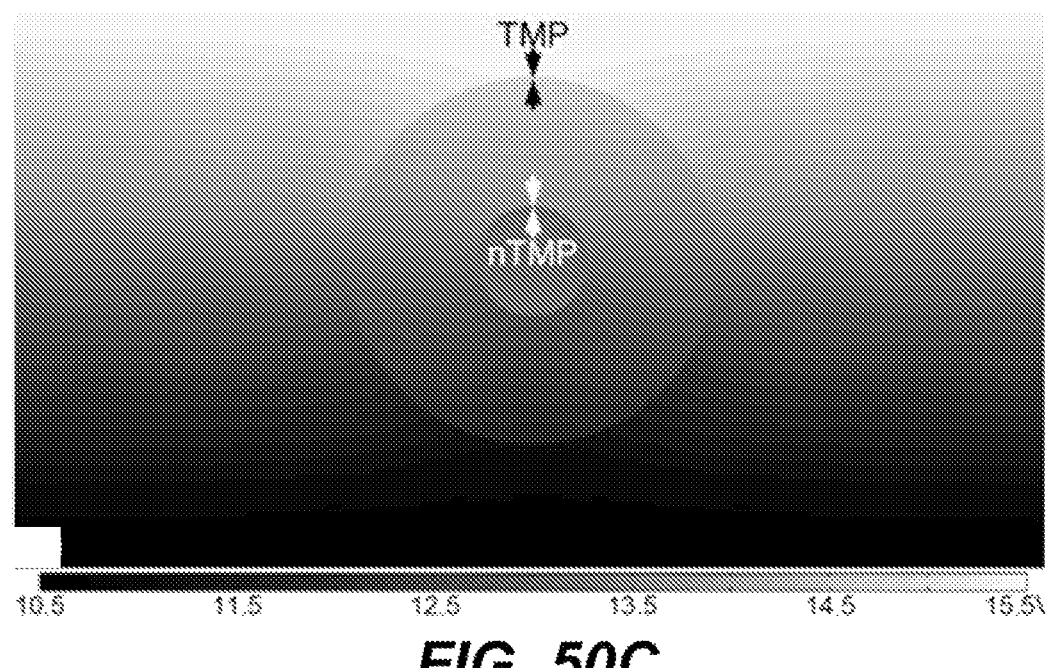
Figure 50D:
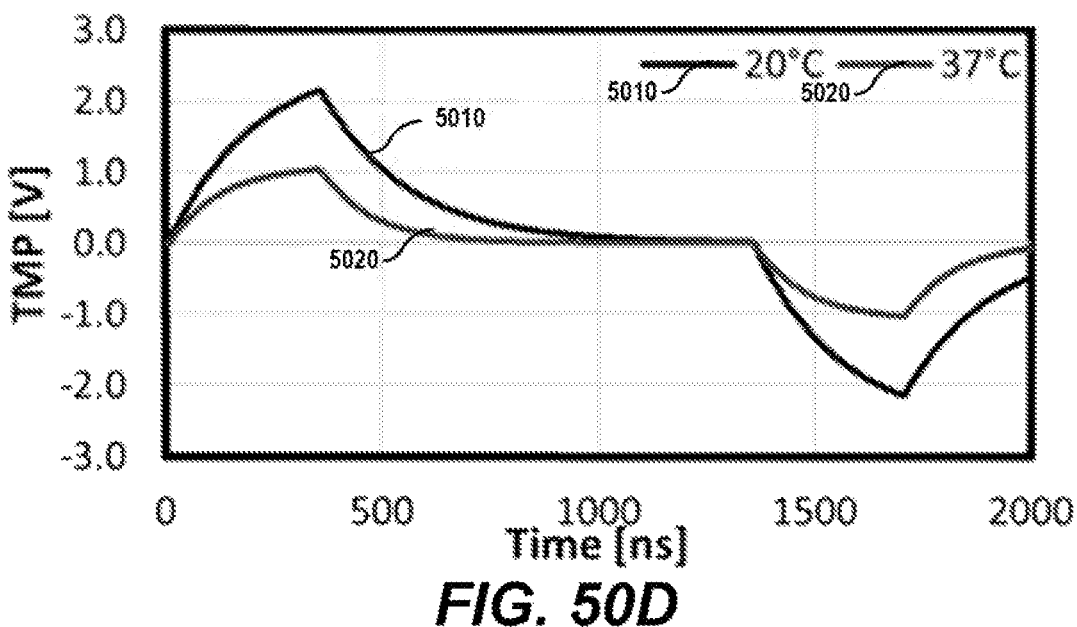
FIGS. 50D and 50E are graphs illustrating simulation observations, according to some embodiments of the present disclosure.
Figure 50E:
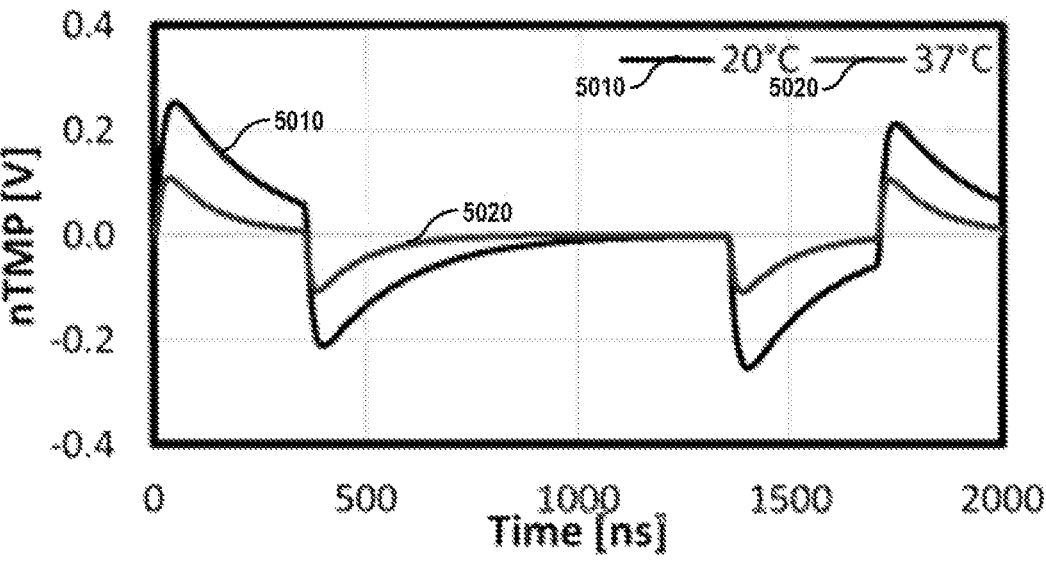

FIGS. 50A to 50C illustrate simulation data for ACE treatments, according to some embodiments of the present invention. FIGS. 50D and 50E are graphs illustrating simulation observations, according to some embodiments of the present disclosure. FIGS. 50A to 50E illustrate computational models to determine the membrane potentials across the cell membrane (TMP) and nuclear envelop (nTMP) under experimental conditions. FIGS. 50A and 50C illustrate finite element mesh showing the simulation domain (see FIG. 50A) and cell and nucleus domains (see FIG. 50A). FIG. 50C illustrates voltage distribution around the cell at t=50 ns for simulated treatments of 350 ns pulses at 20° C. with an applied electric field of 2648 V/cm. FIGS. 50D and 50E illustrate the resulting temporal TMP (see FIG. 50D) and nTMP (see FIG. 50E) profiles for 350 ns treatments administered at 20° C. (2648 V/cm) and 37° C. (1109 V/cm). A finite element simulation of a single cell (see FIGS. 50A and 50B, diameter=13.1 μm) at the ablation margin was conducted to investigate if the voltage drop (see FIG. 50C) across the cell membrane (TMP) or nuclear envelop (nTMP) were affected by the experimental parameters. These simulations were conducted at 20° C. or 37° C. with an applied voltage sufficient to induce an electric field equivalent to the lethal electric field threshold for each pulse-width investigated (350-2000 ns). For 350 ns pulses the transient TMP (see FIG. 50D) and nTMP (see FIG. 50E) were found to be smaller for simulations conducted at 37° C. than for those conducted at 20° C. Similar results were found for 500 ns and 2000 ns pulses. Similarly, transient temperature changes across the cell membranes were found to be smaller for simulations of treatments at 37° C. than those at 20° C.

Clinical Treatment Parameters and Outcomes

Figure 51A:
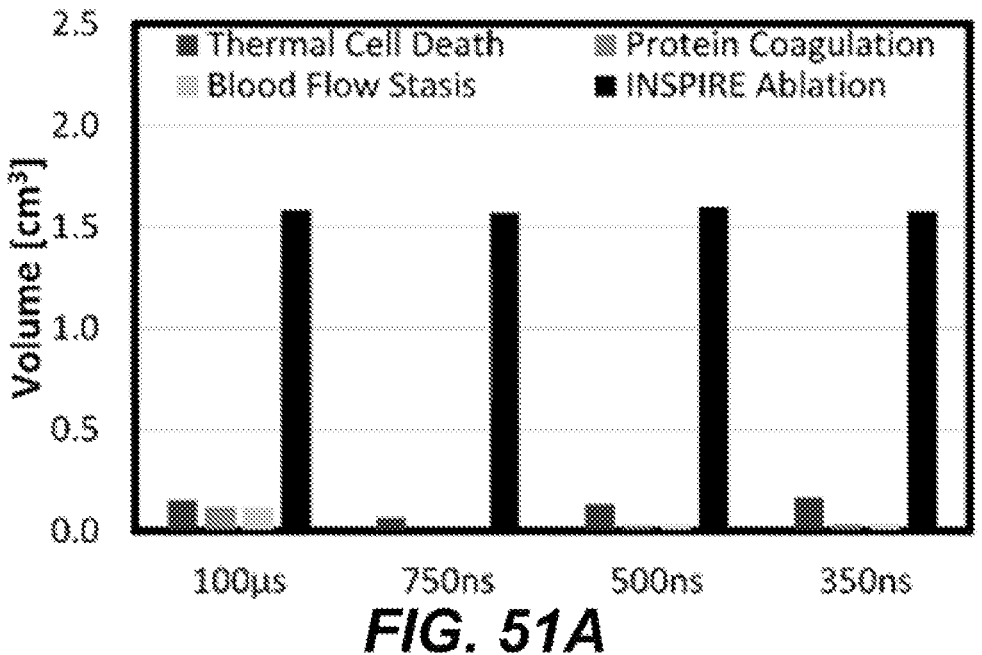
FIG. 51A is a graph illustrating simulation observations, according to some embodiments of the present disclosure.

As clinical administration of ACE treatments will require the development of new instrumentation, it is of interest to determine appropriate treatment parameters and control schemes to enable these treatments. FIG. 51A is a graph illustrating simulation observations, according to some embodiments of the present disclosure. FIGS. 51B to 51E illustrate simulation data for ACE treatments, according to some embodiments of the present invention.

Figures 51B, 51C, 51D:
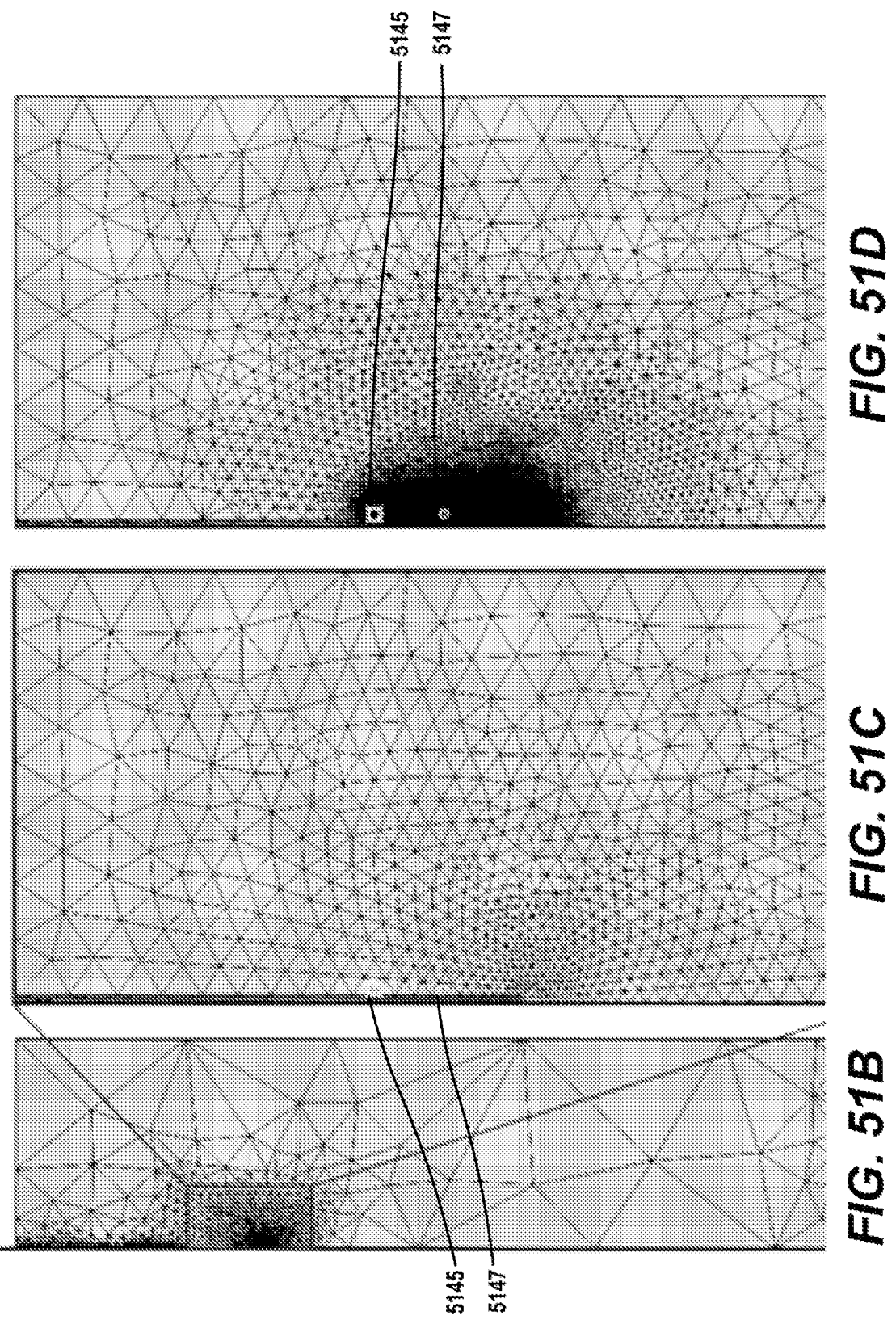
FIGS. 51B to 51E illustrate simulation data for ACE treatments, according to some embodiments of the present invention.
Figure 51E:
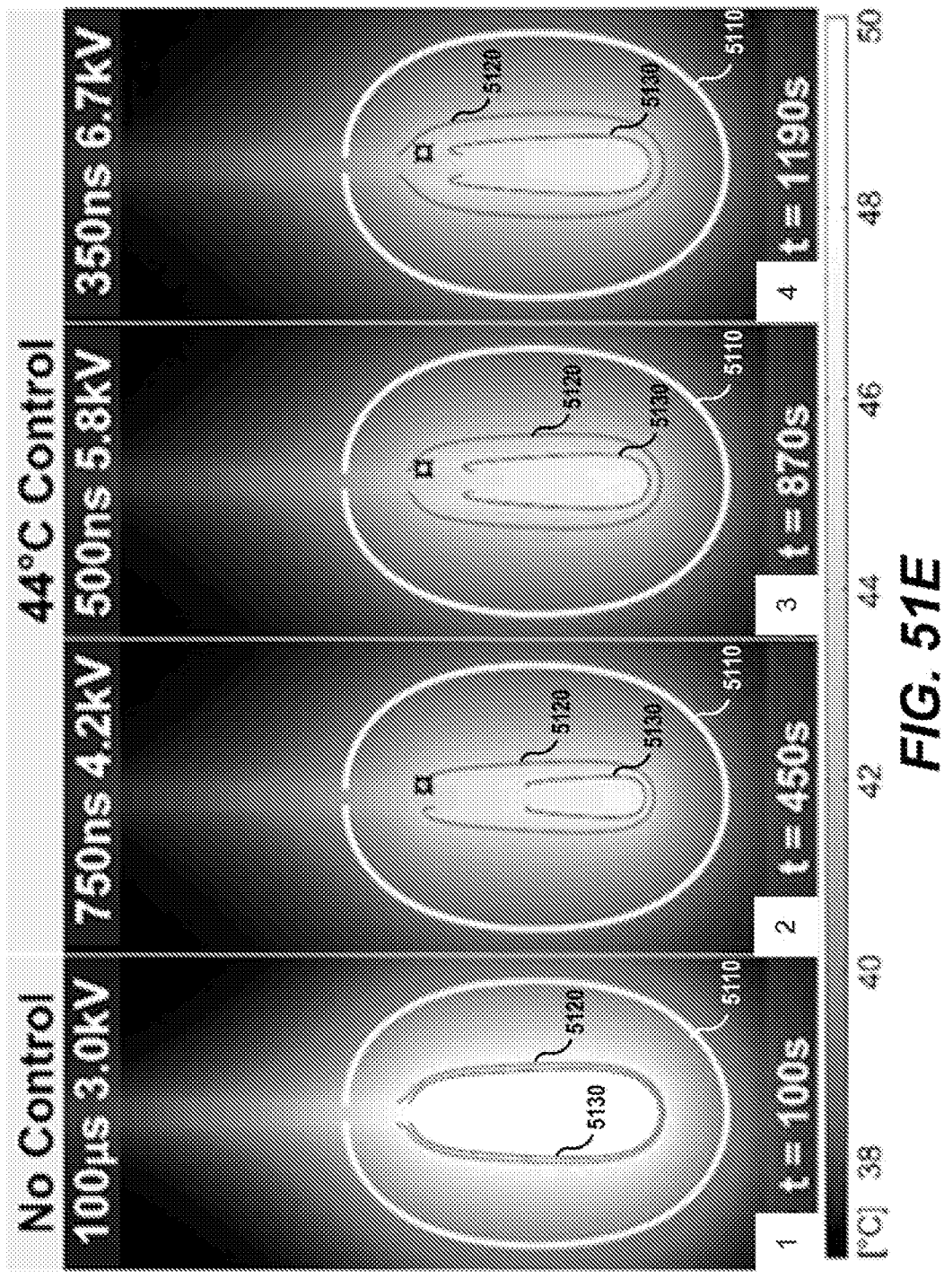

FIGS. 51A to 51E illustrate simulated applicator and grounding pad (A+GP) treatments required to induce similar ablation volumes using NK-IRE and INSPIRE protocols. FIG. 51B illustrates an initial mesh for the entire simulation domain and zoomed in region proximal to the exposed electrode before (see FIG. 51C) and after (see FIG. 51D) 5 rounds of adaptive meshing. FIG. 51E illustrates temperature distribution at the end (t=100 s) of a 3 kV 0.01 s NK-IRE treatment and the predicted ablation zone (white outline—5110) corresponding an electric field threshold of 500V/cm. FIG. 51E also illustrates temperature distributions, predicted ablation (white outline—5110), and thermal cell death (red outline—5120), and protein coagulation (dark grey—5130) zones at the end of 0.01 s ACE treatments with 750 ns 4.2 kV pulses (t=450 s, 698V/cm), 500 ns 5.8 kV pulses (t=870 s, 953V/cm), and 350 ns 6.7 kV pulses (t=1190 s, 1110V/cm) when 44° C. temperature control was implemented. FIG. 51A is a graph that illustrates predicted volumes associated with each form of cell death at the end of 0.01 s IET treatments for NK-IRE (100 μs) without temperature control and ACE (350, 500, 750 ns) treatments with 44° C. temperature control. In FIGS. 51B to 51D, point 5145 Indicates the approximate location of the temperature acquisition for controlling energy delivery while point 5147 indicates the location of temperature measurements at the center of the electrode.

Referring to FIGS. 51A to 51E, a finite element simulation of a single applicator and grounding pad (A+GP) configuration was utilized (see FIGS. 51B to 51D). As a baseline, typical NK-IRE treatments were simulated (3 kV, 100× 100 μs pulses [0.01 s LET], 1 Hz [100 μs/s]) to determine the volume of tissue which would undergo irreversible electroporation (500V/cm), thermal cell death, protein coagulation, and blood flow stasis. Under these nominal conditions the NK-IRE treatment induced 1.58 cm$^3$ IRE, 0.16 cm$^3$ thermal death, 0.12 cm$^3$ protein coagulation, and 0.12 cm$^3$ blood flow stasis volumes (see FIG. 51E, image 1).

To create an equivalent IRE volume (1.58 cm$^3$) with 0.01 s IET INSPIRE treatments the 350 ns (1109V/cm), 500 ns (953V/cm), and 750 ns (698V/cm) protocols required simulated voltages of 6.7 kV, 5.8 kV, and 4.2 kV. As NK-IRE treatments are currently administered without temperature feedback, this scenario was investigated for 350 ns ACE treatments with 6.7 kV pulses administered at a nominal rate of 100 μs/s as well as with active temperature control utilizing a simulated temperature sensor at the electrode-insulator interface similar to those presented experimentally. It was found that peak tissue temperatures above 100° C. were induced without active temperature control yielding 1.54 cm$^3$ IRE, 1.73 cm$^3$ thermal death, 1.59 cm$^3$ protein coagulation, and 1.54 cm$^3$ blood flow stasis volumes.

A parametric analysis was conducted to determine the temperature set point necessary to induce an equivalent thermal cell death volume between nominal NK-IRE (0.16 cm$^3$) and 350 ns ACE treatments. It was found that this was achieved when the temperature at the insulator-electrode interface was maintained at 44° C. The temperature controlled ACE treatments required sequentially higher voltages to maintain the IRE ablation volume (1.6 cm$^3$) as pulse width was decreased and the simulated 750 ns (see FIG. 51E, image 2), 500 ns (see FIG. 51E, image 3), and 350 ns (see FIG. 51E, image 4) pulse width treatments required 450 s, 870 s, and 1190 s to complete, respectively. These temperature-controlled ACE treatments induced similar predicted thermal cell death volumes (0.07-0.17 cm$^3$) to NK-IRE, however, smaller volumes undergoing protein coagulation and blood flow stasis were predicted (see FIG. 51A) for all ACE treatments.

Finally, it was of interest to determine if ACE treatments with 0.001 s IET doses ($\frac{1}{10}$$^{th}$ NK-IRE) could produce ablation volumes equivalent to nominal NK-IRE treatments. It was found that, for this dose, 500 ns (2475 V/cm) and 2000 ns (1464 V/cm) treatments would require the application of pulses with amplitudes of 15200V and 8900V, respectively. Without temperature control enabled, these treatments required 10 s (100 μs/s) to complete with predicted thermal cell death volumes of 0.71 cm$^3$ and 0.27 cm$^3$, respectively. With temperature control enabled at 44° C. these treatments required 578 s and 203 s and induced thermal cell death volumes of 0.10 cm$^3$ and 0.02 cm$^3$, respectively.

Figure 52A:
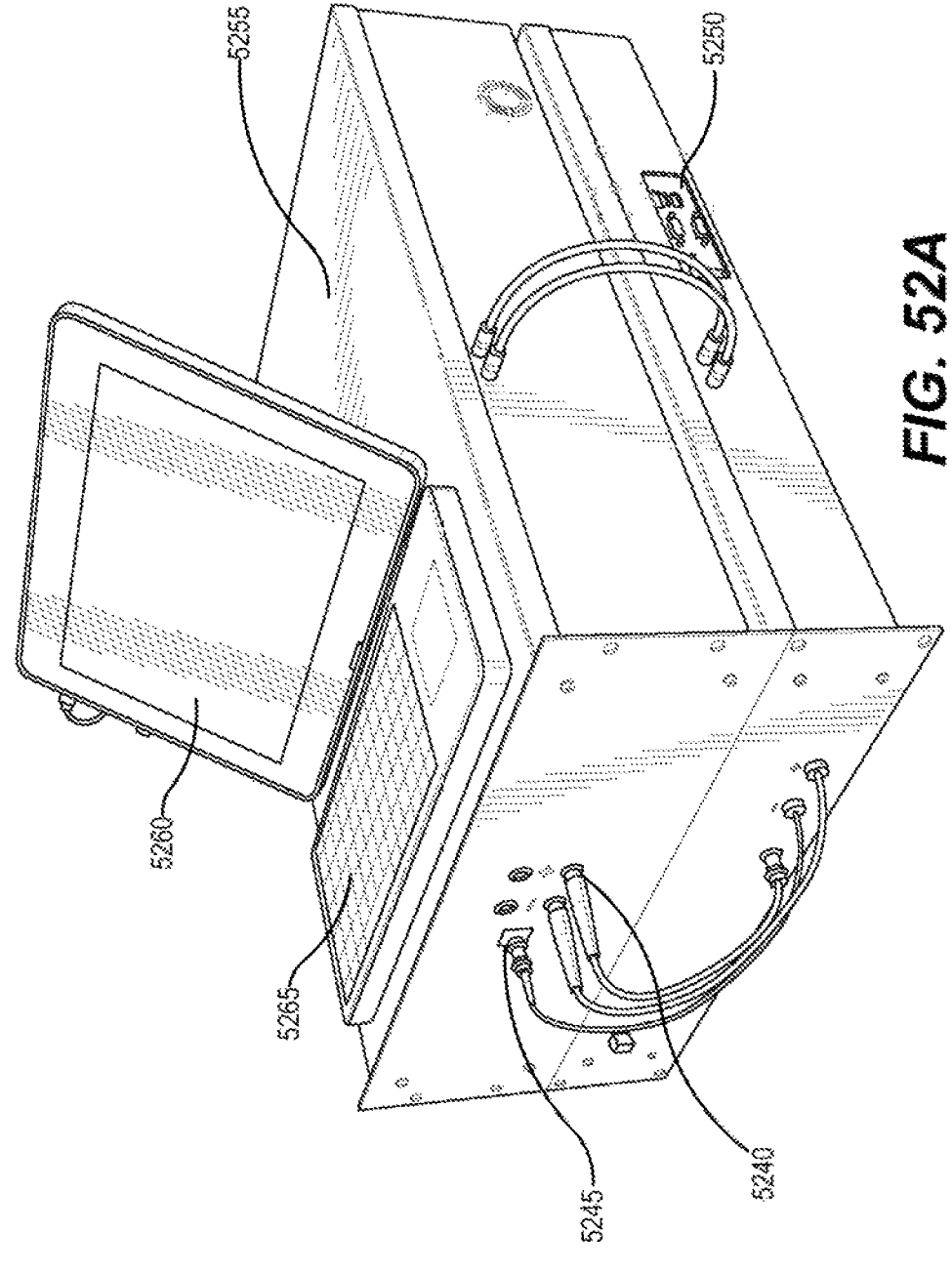
FIGS. 52A and 52B illustrate example systems configured to deliver electrotherapy treatments, according to embodiments described herein
Figure 52B:
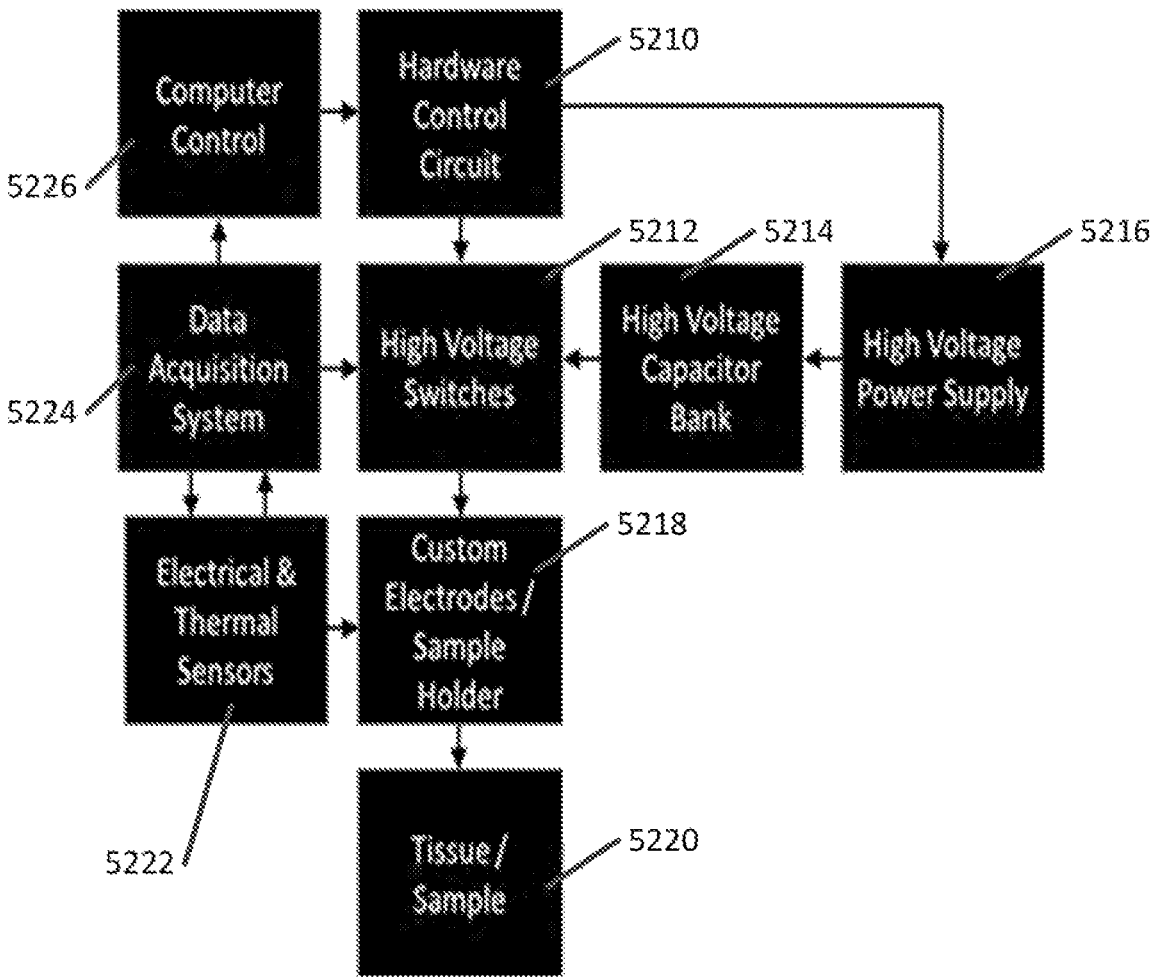

FIGS. 52A and 52B illustrate example systems configured to deliver electrotherapy treatments, according to embodiments described herein. Referring to FIG. 52A, an example electrotherapy treatment system may include electrode outputs 5245 and temperature sensor inputs 5240. The electrode outputs 5245 may be configured to deliver a series of electrical pulses to target tissue (e.g., for ablation and/or treatment). The temperature sensor inputs 5240 may measure a temperature of the target tissue and/or tissue in the vicinity of the target tissue. In some embodiments, the temperature sensors may be part of and/or collocated with the electrode, as described herein. Target tissues that may be treated by electrotherapy include, but are not limited to, tumors and/or mucous membranes (e.g., mucosal linings of, for example, the lung, stomach, and/or intestines). In some embodiments, electrotherapy treatments may be used to decellularize and allow repopulation of healthy tissue with new cells (e.g., stem cells, genetically modified cells). In some embodiments, electrotherapy treatments may be used for cosmetic applications (e.g., fat, cellulite, skin tags, moles, blemishes, and/or warts). In some embodiments, electrotherapy treatments may be used for cardiac tissue, such as for the correction of arrhythmia and atrial fibrillation. In some embodiments, electrotherapy treatments may be performed on the duodenal lining in a subject in need thereof to assist with the regulation of diabetes. In some embodiments, electrotherapy treatments may be used for pain management (e.g., peripheral nerves) in a subject in need thereof. In some embodiments, electrotherapy treatments may be used for benign prostatic hyperplasia (BPH) to treat healthy prostate tissue. In some embodiments, electrotherapy treatments may be performed on brain tissue to, for example, enhance drug delivery, treat Parkinson's/tremors, and/or treat depression/anxiety.

An example electrotherapy treatment system may also include a controller 5250, which may include, for example, control hardware and/or one or more processors. The controller 5250 may control an output delivered to the electrode outputs 5245 based on the temperature measured by the temperature sensor inputs 5240. That is to say that the controller 5250 may control a waveform that includes the series of electrical pulses based on the measured temperature.

The example electrotherapy treatment system may also include a high voltage energy storage 5255. The high voltage energy storage 5255 may provide power for the series of electrical pulses that are generated for deliver to the electrode outputs 5245. In some embodiments, the high voltage energy storage 5255 may include switch and/or capacitor configurations. However, the embodiments described herein are not limited there to. The high voltage energy storage 5255 may include any power supply configuration capable of being configured to deliver the series of electrical pulses described further herein.

The example electrotherapy treatment system may also include an input device 5265 and a display 5260. The input device 5265 may allow for configuration and adjustment of the electrotherapy treatment system. The display 5260 may allow of the confirmation of treatment options and visualization of treatment progress.

FIG. 52B illustrates a schematic representation of an example electrotherapy treatment system. As illustrated in FIG. 52B, the example electrotherapy treatment system may include a hardware control circuit 5210. The hardware control circuit 5210 may control a series of high voltage switches 5212 to deliver a series of electrical pulses. The high voltage switches 5212 may be connected to a high voltage capacitor bank 5214 that is powered by a high voltage power supply 5216. The high voltage power supply 5216 may be further controlled by the hardware control circuit 5210.

The high voltage switches 5212 may provide the electrical energy stored in the high voltage capacitor bank 5214 as a series of electrical pulses delivered via electrodes 5218 to a tissue sample 5220. The series of electrical pulses may provide the electrotherapy treatment to the tissue sample 5220.

Thermal sensors 5222 may be further coupled to the tissue sample 5220. The thermal sensors 5222 may measure a temperature of the tissue sample 5220 and/or an area in the vicinity of the tissue sample 5220. In some embodiments, the thermal sensors 5222 may be part of and/or connected to, the electrodes 5218. The thermal sensors 5222 may be coupled to a data acquisition system 5224 configured to collect data from, for example, the thermal sensors 5222. In some embodiments, electrical sensors may also be used. Electrical sensors may be used for impedance measurements to detect if the tissue has undergone a "sufficient" change to indicate treatment is successful. Other electrical sensors could be, for example, physical temperature sensors. In some embodiments, fiber optic sensors may be used. In some embodiments, negative/positive temperature coefficient thermistors may be used, as well as thermocouples or semiconductor-based temperature sensors. The data acquisition system 5224 may be provided to a computer control 5226. The computer control 5226 may control the hardware control circuit 5210 to control the delivery of the electrical pulses. In some embodiments, an energy delivered by the electrical pulses can be controlled responsive to the temperature measured by the thermal sensors. In some embodiments, the delivery of the electrical pulses may be configured to be controlled so as to maintain a temperature of the target tissue with a particular range. In the example electrotherapy treatment system of FIG. 52B, data may be obtained from electrical and/or thermal sensors 5222, which may be on the electrodes 5218 and/or in tissue 5220, and used to modulate the rate at which energy is delivered and determine treatment completion.

Figure 53:
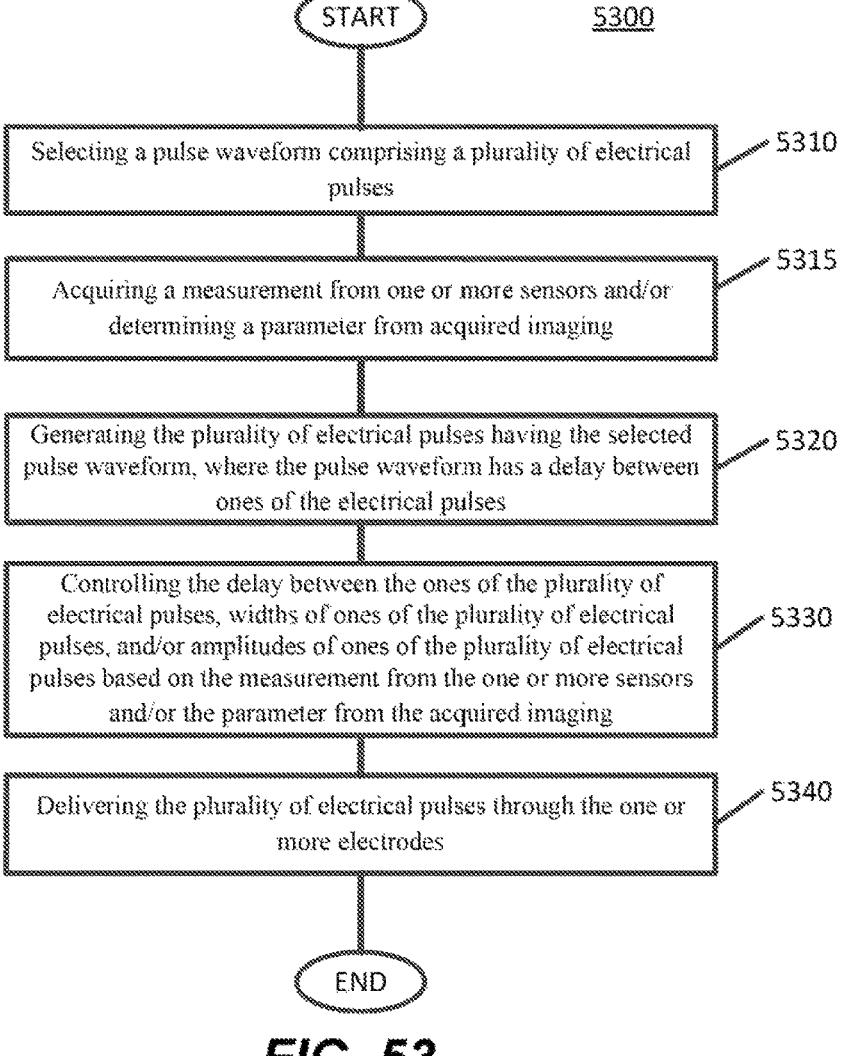
FIG. 53 illustrates operations for performing electronically controlled electrotherapy, according to embodiments described herein.

FIG. 53 illustrates operations 5300 for performing electronically controlled electrotherapy, according to embodiments described herein. The operations 5300 may begin at block 5310 in which a pulse waveform comprising a plurality of electrical pulses is selected. The waveform selected may be, for example, of the waveforms discussed with respect to FIGS. 14A and 38A to 38C, though the embodiments described herein are not limited thereto.

The operations 5300 may continue with block 5315 a measurement from one or more sensors is acquired and/or a parameter from acquired imaging is determined. In some embodiments, the measurement may include a thermal measurement, an acceleration measurement, an impedance measurement, a voltage measurement, a current measurement, an ultrasound measurement, a cardiac measurement, an electrocardiogram measurement, an electroencephalogram measurement, a blood pressure measurement, a pulse-oxygen measurement, an electrocardiogram measurement, a respiration measurement, an acoustic measurement, a photoacoustic measurement, an infrared thermometry, video, magnetic resonance imaging, x-ray imaging, and/or a computed tomography measurement.

The operations 5300 may continue with block 5320 in which the plurality of electrical pulses having the selected pulse waveform are generated. In some embodiments, the pulse waveform may have a delay between ones of the electrical pulses. The electrical pulses may be delivered from a high voltage power supply and/or capacitor bank, such as that described with respect to FIGS. 52A and 52B.

The operations 5300 may continue with block 5330 that includes controlling the delay between the ones of the plurality of electrical pulses, widths of ones of the plurality of electrical pulses, and/or amplitudes of ones of the plurality of electrical pulses based on the measurement from the one or more sensors and/or the parameter from the acquired imaging. The waveform may be controlled, for example, by a hardware and/or software controller similar to the controller illustrated in FIGS. 52A and 52B.

The operations 5300 may continue with block 5340 in which the plurality of electrical pulses is delivered through the one or more electrodes. The one or more electrodes may be similar, for example, to the electrodes discussed herein with respect to FIGS. 20A, 20B, 34, 35, 39A, 39B, 52A, and 52B, though the embodiments described herein are not limited thereto.

As illustrated in FIG. 53, methods of performing electrotherapy may include delivering a waveform including a plurality of electrical pulses to a patient and modifying or killing target cells and simultaneously reducing or eliminating thermal injury, tissue burning, tissue charring, nerve, and/or blood vessel damage by adjusting an energy delivery profile of the waveform in response to a measurement and/or a user controlled input.

Pursuant to embodiments of the present invention, a method of performing electronically controlled electrotherapy may include modifying or killing target cells and simultaneously modifying a secondary outcome by delivering electrical pulses and dynamically adjusting an energy delivery profile of the electrical pulses in response to a measurement. The secondary outcome may be a physical outcome, a biological outcome, and/or a systemic outcome.

In some embodiments, the target cells may be cancerous cells inside or outside of a tumor.

In some embodiments, the target cells may be healthy cells of or in the liver, kidney, brain, blood, lungs, spleen, gastrointestinal tract, skin, lymphatic system, or other organs.

In some embodiments, modifying the target cells may include introducing new DNA or genetic material, introducing a drug or chemotherapy, stimulating protein expression, stimulating antigen production, preventing or inhibiting mitosis, and/or preventing or inhibiting cell replication.

In some embodiments, killing target cells may include inducing necrosis, apoptosis, thermal necrosis, non-thermal necrosis, a loss of homeostasis, senescence, cell membrane rupture, membrane permeabilization, pore formation, delayed cell death, instantaneous cell death, coagulative necrosis, liquefactive necrosis, fat necrosis, fibrinoid necrosis, necroptosis, cell membrane rupture, activation-induced cell death, autophagy, anoikis, ferroptosis, an accumulation of lipid peroxides leading to cell death, ischemic cell death, mitotic catastrophe, immunogenic cell death, pyroptosis, or caspase-independent programmed cell-death.

In some embodiments, the physical outcome may include a change in temperature, impedance, pH, mechanical properties, light absorbance, light reflectance, ultrasound reflectance, ultrasound absorbance, and/or medical imaging contrast (e.g., ultrasound MRI or CT).

In some embodiments, the measurement may include a measurement of the secondary outcome or a measurement of an independent change in temperature, impedance, pH, density, water content, stiffness, strength, viscoelasticity, other mechanical properties, light absorbance, light reflectance, ultrasound reflectance, ultrasound absorbance, medical imaging contrast (e.g., ultrasound MRI or CT), acceleration due to muscle contractions, and/or a user controlled input device.

In some embodiments, the biological outcome may include muscle contractions, nerve stimulation, cardiac rhythm, protein expression, insulin production, hormone production, edema, and/or swelling.

In some embodiments, the systemic outcome may include the induction of an immune response, induction of an abscopal response, induction of a vaccine-like response, and/or reduction of pain.

In some embodiments, delivering electrical pulses may include delivering a plurality of electrical pulse waveforms that comprise only positive polarity pulses, only negative polarity pulses, or a combination of positive and negative polarity pulses.

In some embodiments, adjusting the energy delivery profile may include modulating a delay between successive waveforms of the electrical pulses, increasing or decreasing a width of a positive and/or negative pulses of the electrical pulses that are delivered, and/or modifying a delay between polarity changes of the electrical pulses.

In some embodiments, adjusting the energy delivery profile may include changing a volume of coolant flowing through electrodes used to deliver the electrical pulses.

Pursuant to embodiments of the present invention, a method of performing electronically controlled electro-therapy may include delivering a waveform comprising a plurality of electrical pulses to a patient; and modifying or killing target cells and simultaneously reducing or eliminating muscle contractions by adjusting an energy delivery profile of the waveform in response to a measurement of an accelerometer, imaging, or a user controlled input.

In some embodiments, a width of at least one of the electrical pulses may be decreased to reduce muscle stimulation.

In some embodiments, a symmetry of the waveform may be modulated to reduce muscle stimulation.

In some embodiments, a rate of energy delivery of the electrical pulses may be increased to reduce muscle stimulation.

In some embodiments, a width of the electrical pulses may be decreased, and a rate of energy delivery of the electrical pulses is increased, to maintain a constant energy delivery rate between 1 and 10,000 microseconds per second, preferably between 10 and 500 microseconds per second.

In some embodiments, a width of the electrical pulses may be modified, and a target treatment dose may be modified, to achieve a target dose associated with the modified electrical pulse width.

In some embodiments, a width of the electrical pulses may be increased, and the target treatment dose may be decreased, to achieve a target dose associated with the modified electrical pulse width.

In some embodiments, a width of the electrical pulses may be decreased, and the target treatment dose may be increased, to achieve a target dose associated with the modified electrical pulse width.

Pursuant to embodiments of the present invention, a method of performing electronically controlled electro-therapy may include: delivering a waveform comprising a plurality of electrical pulses to a patient; and modifying or killing target cells and simultaneously reducing or eliminating thermal injury, tissue burning, tissue charring, nerve, and/or blood vessel damage by adjusting an energy delivery profile of the waveform in response to a measurement and/or a user controlled input.

In some embodiments, the method may further include selecting a target ablation size and maximum temperature; automatically selecting a treatment voltage, a treatment waveform, and/or a target dose to be delivered responsive to the selection of the target ablation size and the maximum temperature.

In some embodiments, the measurement may include a signal from a temperature sensor placed inside an electrode, adjacent to the electrode, or at a location remote from the electrode.

In some embodiments, the measurement may include a temperature of coolant exiting an internally perfused electrode.

In some embodiments, the measurement may include a difference in temperature between coolant entering and exiting an internally perfused electrode.

In some embodiments, the measurement may include Mill, ultrasound, or CT imaging.

In some embodiments, the energy delivery profile may be modified by reducing the repetition rate of the electrical pulses to prevent the measured temperature from exceeding a specific value.

In some embodiments, the energy delivery profile may be modified by increasing a repetition rate of the electrical pulses to enable a measured temperature to reach a threshold.

In some embodiments, the energy delivery profile may be modified by reducing a width of the electrical pulses delivered to prevent a measured temperature from exceeding a threshold, and a target dose to be delivered is increased to a value associated with the reduced pulse width.

In some embodiments, the energy delivery profile may be modified by increasing a width of the electrical pulses delivered to enable a measured temperature to reach a threshold, and a target dose to be delivered is decreased to a value associated with the increased pulse width.

In some embodiments, the energy delivery profile may be modified by reducing a voltage of the electrical pulses delivered to prevent a measured temperature from exceeding a threshold, and a target dose to be delivered is increased to a value associated with the reduced voltage.

In some embodiments, the energy delivery profile may be modified by increasing a voltage of the electrical pulses delivered to enable a measured temperature to reach a threshold, and a target dose to be delivered is decreased to a value associated with the increased voltage.

Pursuant to embodiments of the present invention, a method of performing electronically controlled electro-therapy method may include modifying or killing target cells and simultaneously inducing a secondary immune response by delivering electrical pulses and dynamically adjusting an energy delivery profile of the electrical pulses in response to a measurement to induce cell modification or death via one or more desired pathways.

In some embodiments, the secondary immune response may include a systemic response to a local or metastatic disease.

In some embodiments, the secondary immune response may include an antigen specific response of the adaptive immune system triggered by a release of tumor antigens.

In some embodiments, the secondary immune response may include a recruitment of T-cells, B-cells, neutrophils, macrophages, dendritic cells, leukocytes, hematopoietic stem cells, Gamma delta T cells, Helper T cells, granulo-cytes (e.g., neutrophils, mast cells, basophils, or eosino-phils), innate lymphoid cells (e.g., natural killer cells, Group 1, Group 2, or Group 3 ILCs), natural helper cells, nuocytes, innate helper cells, and/or other immunological cells to the treatment site.

In some embodiments, the secondary immune response may include a stimulation of the complement system, induc-tion of a biochemical cascade, or activation of the innate immune system.

In some embodiments, the secondary immune response may be induced via a release of antigens, proteins, neo-antigens, pathogen-associated molecular patterns (PAMPs) (e.g., peptidoglycan, nucleic acid, RNA, dsRNA, CpG oligodeoxynucleotides), damage-associated molecular patterns (DAMPS) (e.g., chromatin-associated leaderless secreted proteins, DNA, RNA. calcium modulated proteins, S100 proteins, nucleotides such as ATP, nucleosides such as adenosine, monosaccharides, polysaccharides), transmembrane proteins, toll-like receptor (TLR) binding molecules, inflammasomes, inflammatory cytokines, tumor markers (e.g., Alphafetoprotein, Carcinoembryonic antigen, CA-125, MUC-1, Epithelial tumor antigen, Tyrosinase, Melanoma-associated antigen, RAS, p53, Alpha fetoprotein, CA15-3, CA27-29, CA19-19, CA-125, Calcitonin, Calretinin, CD34, CD99, CD117, Chromogranin, Cytokeratin, Glial fibrillary acidic protein, HMB-45, HER-2, MART-1, Melanin-A, prostate specific antigen), and/or other molecules that are released from a cell, cell membrane, organelles, organelle membranes, nucleus, and/or nuclear envelope to induce an immune response.

In some embodiments, antigens, proteins, and/or molecules released by treatment may be protected from thermal damage by adjusting the energy delivery profile to prevent temperatures from exceeding a value that would result in the denaturing of molecules or reduction of a utility of the molecules to the immune system.

In some embodiments, cell death may be induced via thermal necrosis, non-thermal necrosis, coagulative necrosis, liquefactive necrosis, fat necrosis, fibrinoid necrosis, necroptosis, cell membrane rupture, activation-induced cell death, apoptosis, autophagy, anoikis, ferroptosis, an accumulation of lipid peroxides, ischemic cell death, mitotic catastrophe, immunogenic cell death, pyroptosis, and/or caspase-independent programmed cell-death.

In some embodiments, the method may further include: selecting an immune-stimulatory or non-immuno-stimulatory cell death pathway; and automatically adjusting treatment parameters to favor one treatment outcome over another by controlling a target temperature, pulse waveform, dose, and/or voltage.

In some embodiments, the method may further include adjusting the energy delivery profile based on a temperature measurement as the measurement to produce a first zone of thermal necrosis surrounded by a second zone of non-thermal necrosis or apoptosis.

In some embodiments, a first zone of thermal necrosis may be surrounded by a second zone of cells that have been modified by introducing new DNA or genetic material, introducing a drug or chemotherapy or nano-particle, and/or stimulated to enhance protein or antigen expression.

In some embodiments, a first zone of cell death via non-thermal necrosis or apoptosis may be surrounded by a second zone of cells which have been modified by introducing new DNA or genetic material, introducing a drug or chemotherapy, and/or stimulated to enhance protein or antigen expression.

In some embodiments, the new DNA or genetic material may be designed to produce or release molecules which stimulate an immune response.

In some embodiments, the method may further include injecting adjunctive drugs or particles into a tumor prior to, during, or after the electrical pulses are delivered.

In some embodiments, the method may further include delivering adjunctive drugs or particles prior to, during, or after electrical energy is delivered.

In some embodiments, the adjunctive drug may be an immunostimulant, steroid, check point inhibitor, interleukin (IL-12) or immunotherapy including Anti-PD-1 (e.g., Nivolumab, Pembrolizumab, Cemiplimab), Ant-CTLA-4

(Ipilimumab), Anti-PD-L1 (e.g., Atezolizumab, Avelumab, Durvalumab), Anti-CD20 (e.g., Rituximab, Retuxan, Truxima).

In some embodiments, the adjunctive particle may be a protein, live bacteria, dead bacteria, live virus, dead virus, inactivated virus, DNA, RNA, a nanoparticle, and/or a nanotube configured to enhance an immune response or to traffic molecules and/or antigens to the lymphatic system.

In some embodiments, the energy delivery profile may include a waveform with a positive polarity pulse, followed by a delay, followed by a negative polarity pulse that is repeated until a target dose is reached.

In some embodiments, the positive and negative polarity pulses may be of a same duration between 1 nanosecond and 1 millisecond, preferably between 0.1 and 10 microseconds.

In some embodiments, the positive and negative polarity pulses may be of different durations, with each pulse preferably having a duration between 0.1 and 10 microseconds.

In some embodiments, only positive polarity pulses may be delivered or negative polarity pulses are delivered.

In some embodiments, a width of the positive and/or negative polarity pulses in the waveform may be modified response to the measurement.

In some embodiments, the delay between positive and negative polarity pulses may be between 1 nanosecond and 1 millisecond, preferably between 0.1 and 10 microseconds.

In some embodiments, the delay between positive and negative polarity pulses in the waveform may be modified in response to the measurement.

In some embodiments, a delay between successive waveforms comprising one positive polarity pulse and one negative polarity pulse may be between 1 nanosecond and 10 seconds, preferably between 1 and 10,000 microseconds.

In some embodiments, the delay between successive waveforms may be modified responsive to the measurement.

Pursuant to embodiments of the present invention, an apparatus for electronically controlled electrotherapy may include one or more electrodes for insertion into a target tissue, one or more sensors, and a computer controller configured to perform operations include: selecting a pulse waveform comprising a plurality of electrical pulses; acquiring a measurement from the one or more sensors and/or determining a parameter from acquired imaging; generating the plurality of electrical pulses having the selected pulse waveform, wherein the pulse waveform has a delay between ones of the electrical pulses; controlling the delay between the ones of the plurality of electrical pulses, widths of ones of the plurality of electrical pulses, and/or amplitudes of ones of the plurality of electrical pulses based on the measurement from the one or more sensors and/or the parameter from the acquired imaging; and delivering the plurality of electrical pulses through the one or more electrodes.

In some embodiments, the measurement may include a thermal measurement, an acceleration measurement, an impedance measurement, a voltage measurement, a current measurement, an ultrasound measurement, a cardiac measurement, an electrocardiogram measurement, an electroencephalogram measurement, a blood pressure measurement, a pulse-oxygen measurement, an electrocardiogram measurement, a respiration measurement, an acoustic measurement, a photo-acoustic measurement, an infrared thermometry, video, magnetic resonance imaging, x-ray imaging, and/or a computed tomography measurement.

In some embodiments, the computer controller may be further configured to obtain thermal, acceleration, impedance, voltage, current, ultrasound, cardiac, electrocardiogram, electroencephalogram, blood pressure, pulse-oxygen, electrocardiogram, respiration, acoustic, photo-acoustic, infrared thermometry, video, magnetic resonance imaging, x-ray imaging, and/or computed tomography measurements.

In some embodiments, the computer controller may be further configured to determine whether the measurement is above, below, or at a target value, or within a tolerance window.

In some embodiments, the computer controller may be further configured to reduce or increase a duration of the electrical pulses.

In some embodiments, the computer controller may be further configured to increase or decrease a delay between sequential electrical pulses of the plurality of electrical pulses.

In some embodiments, the computer controller may be further configured to increase or decrease the amplitude of a voltage or a current delivered by the plurality of electrical pulses.

In some embodiments, the computer controller may be further configured to increase or decrease an average energy delivery rate of the plurality of electrical pulses.

In some embodiments, the apparatus may further include a high voltage switching circuit comprising a plurality of switches to create an H-Bridge configuration that are configured to deliver the plurality of electrical pulses comprising positive and negative polarity from a high voltage power supply In some embodiments, the apparatus may further include: a plurality of switches in an H-Bridge or totem pole configuration that are configured to deliver the plurality of electrical pulses comprising positive and negative polarity from a positive and a negative power supply.

In some embodiments, the apparatus may further include: a transformer coupled to a plurality of switches in an H-Bridge or totem pole configuration to step up a lower voltage to a higher voltage.

In some embodiments, the apparatus may further include a voltage source connected to a capacitor or a plurality of capacitors.

In some embodiments, the delay between the ones of the plurality of electrical pulses may be between 0.1 and 10 microseconds.

In some embodiments, a delay between positive and negative pulses in the waveform may be modified in response to a measurement.

In some embodiments, a delay between successive waveforms comprising one positive pulse and one negative pulse may be between 1 microsecond and 10 seconds.

In some embodiments, the delay between successive waveforms may be modified response to a measurement.

In some embodiments, the width of positive or negative pulses may be modified response to a measurement.

In some embodiments, a voltage of positive or negative pulses may be modified response to a measurement.

In some embodiments, the electrodes may be actively cooled.

In some embodiments, the apparatus may be further configured to acquire temperature measurements from an inlet or an outlet of the actively cooled electrodes and the temperature measurements are used to modify an energy delivery profile of the plurality of electrical pulses.

In some embodiments, the apparatus may further include an applicator comprising a first electrode that makes contact with a surface of the target tissue and a second electrode that is inserted into the target tissue.

In some embodiments, an electric field magnitude of the first electrode may point completely or predominantly in one direction.

In some embodiments, an electric field magnitude of the second electrode points predominantly in the radial direction between the first electrode and the second electrode.

In some embodiments, the first electrode includes a ring-shaped electrode in contact with the surface of the target tissue.

In some embodiments, the apparatus may further include a pad, mesh and/or conductive material in contact with the surface of the target tissue.

In some embodiments, the second electrode includes a needle that is inserted into the target tissue, wherein the needle is partially or fully insulated.

In some embodiments, the second electrode includes an internally cooled electrode.

In some embodiments, the second electrode includes one or more inner lumens for perfusing the second electrode with coolant.

In some embodiments, the apparatus may further include a temperature sensor that is configured to measure a coolant temperature as it enters and/or exits the second electrode.

In some embodiments, the apparatus may further include a temperature sensor inside of the second electrode.

In some embodiments, the apparatus may further include a temperature sensor in contact with the tissue, within the tissue, or adjacent to the tissue.

In some embodiments, a depth of the insertion of the second electrode is configured to be adjusted.

In some embodiments, an amount of insulation or exposed electrode of the second electrode is configured to be adjusted.

In some embodiments, the first electrode may have a diameter between 0.1 mm and 8 mm.

In some embodiments, the first electrode may have a length of 0.1 to 250 mm.

In some embodiments, the first electrode may be insulated along its entire length except for a distal region measuring between 0.1 and 40 mm.

Pursuant to embodiments of the present invention, a computer program product may include a tangible non-transitory computer readable storage medium comprising computer readable program code embodied in the computer readable storage medium that when executed by at least one processor causes the at least one processor to perform operations comprising: measuring a value from a sensor or image during a pulsed electric field therapy comprising a plurality of electrical pulses; and dynamically modifying a delivery profile of the electrical pulses responsive to the value from the sensor.

As will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely in hardware, entirely in software (including firmware, resident software, micro-code, etc.) or combining software and hardware implementation that may all generally be referred to herein as a "circuit," "module," "component," or "system." Furthermore, aspects of the present disclosure may take the form of a computer program product embodied in one or more computer readable media having computer readable program code embodied thereon.

Any combination of one or more computer readable media may be utilized. The computer readable media may be a computer readable signal medium or a computer readable storage medium. A computer readable storage medium may be, for example, but not limited to, an electronic, magnetic, optical, electromagnetic, or semiconductor system, apparatus, or device, or any suitable combination of the foregoing. More specific examples (a non-exhaustive list) of the computer readable storage medium would include the following: a portable computer diskette, a hard disk, a random access memory (RAM), a read-only memory (ROM), an erasable programmable read-only memory (EPROM or Flash memory), an appropriate optical fiber with a repeater, a portable compact disc read-only memory (CD-ROM), an optical storage device, a magnetic storage device, or any suitable combination of the foregoing. In the context of this document, a computer readable storage medium may be any tangible non-transitory medium that can contain or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device. Program code embodied on a computer readable signal medium may be transmitted using any appropriate medium, including but not limited to wireless, wireline, optical fiber cable, RF, etc., or any suitable combination of the foregoing.

Aspects of the present disclosure are described herein with reference to flowchart illustrations and/or block diagrams of methods, apparatuses (systems) and computer program products according to embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable instruction execution apparatus, create a mechanism for implementing the functions/acts specified in the flowchart and/or block diagram block or blocks. As used herein, "a processor" may refer to one or more processors.

These computer program instructions may also be stored in a computer readable medium that when executed can direct a computer, other programmable data processing apparatus, or other devices to function in a particular manner, such that the instructions when stored in the computer readable medium produce an article of manufacture including instructions which when executed, cause a computer to implement the function/act specified in the flowchart and/or block diagram block or blocks. The computer program instructions may also be loaded onto a computer, other programmable instruction execution apparatus, or other devices to cause a series of operational steps to be performed on the computer, other programmable apparatuses or other devices to produce a computer implemented process such that the instructions which execute on the computer or other programmable apparatus provide processes for implementing the functions/acts specified in the flowchart and/or block diagram block or blocks.

The flowchart and block diagrams in the FIGS. illustrate the architecture, functionality, and operation of possible implementations of systems, methods, and computer program products according to various aspects of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the FIGS. For example, two blocks shown in succession may, in fact, be executed substantially concurrently, or the blocks may sometimes be executed in the reverse order, depending upon the functionality involved. Although some of the diagrams include arrows on communication paths to show a primary direction of communication, it is to be understood that communication may occur in the opposite direction to the depicted arrows. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

Computer program code for carrying out operations for aspects of the present disclosure may be written in any combination of one or more programming languages, including an object oriented programming language such as Java, Scala, Smalltalk, Eiffel, JADE, Emerald, C++, C#, VB.NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Other methods, systems, articles of manufacture, and/or computer program products will be or become apparent to one with skill in the art upon review of the embodiments described herein. It is intended that all such additional systems, methods, articles of manufacture, and/or computer program products be included within the scope of the present disclosure. Moreover, it is intended that all embodiments disclosed herein can be implemented separately or combined in any way and/or combination.

The terminology used herein is for the purpose of describing particular embodiments only and is not intended to be limiting to other embodiments. As used herein, the singular forms "a," "an," and "the" are intended to include the plural forms as well, unless the context clearly indicates otherwise. It will be further understood that the terms "comprises," "comprising," "includes," and/or "including," "have," and/or "having" (and variants thereof) when used herein, specify the presence of stated features, integers, steps, operations, elements, and/or components, but do not preclude the presence or addition of one or more other features, integers, steps, operations, elements, components, and/or groups thereof. In contrast, the term "consisting of" (and variants thereof) when used in this specification, specifies the stated features, integers, steps, operations, elements, and/or components, and precludes additional features, integers, steps, operations, elements and/or components. Elements described as being "to" perform functions, acts and/or operations may be configured to or otherwise structured to do so. As used herein, the term "and/or" includes any and all combinations of one or more of the associated listed items and may be abbreviated as "/".

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the various embodiments described herein.

Many different embodiments have been disclosed herein, in connection with the above description and the drawings. It will be understood that it would be unduly repetitious and obfuscating to literally describe and illustrate every combination and subcombination of these embodiments. Accordingly, all embodiments can be combined in any way and/or combination, and the present specification, including the drawings, shall support claims to any such combination or subcombination.

When a certain example embodiment may be implemented differently, a specific process order may be performed differently from the described order. For example, two consecutively described processes may be performed substantially at the same time or performed in an order opposite to the described order.

Like numbers refer to like elements throughout. Thus, the same or similar numbers may be described with reference to other drawings even if they are neither mentioned nor described in the corresponding drawing. Also, elements that are not denoted by reference numbers may be described with reference to other drawings.

In the drawings and specification, there have been disclosed typical embodiments and, although specific terms are employed, they are used in a generic and descriptive sense only and not for purposes of limitation, the scope of the disclosure being set forth in the following claims.

What is claimed is:

1. A method of performing electronically controlled electrotherapy comprising modifying or killing target cells of a target tissue and simultaneously modifying a secondary outcome by delivering electrical pulses to the target tissue and dynamically adjusting an energy delivery rate of the electrical pulses in response to a measurement, wherein the secondary outcome comprises at least one of a physical outcome, a biological outcome, or a systemic outcome, and wherein dynamically adjusting the energy delivery rate of the electrical pulses comprises increasing a width of at least one of the electrical pulses in response to the measurement indicating that a temperature of the target tissue is below a threshold value, to thereby increase the temperature of the target tissue.

2. The method of claim 1, wherein the physical outcome comprises a change in temperature, impedance, pH, mechanical properties, light absorbance, light reflectance, ultrasound reflectance, ultrasound absorbance, and/or medical imaging contrast.

3. The method of claim 1, wherein the biological outcome comprises muscle contractions, nerve stimulation, cardiac rhythm, protein expression, insulin production, hormone production, edema, and/or swelling.

4. The method of claim 1, wherein the systemic outcome comprises an induction of an immune response, induction of an abscopal response, induction of a vaccine-like response, and/or reduction of pain.

5. The method of claim 1, wherein dynamically adjusting the energy delivery rate of the electrical pulses further comprises changing a volume of coolant flowing through one or more electrodes used to deliver the electrical pulses to the target tissue, in response to the measurement.

6. The method of claim 1, further comprising:

inserting one or more electrodes and one or more sensors into the target tissue; and selecting a target temperature value for the target tissue, where the target temperature value corresponds to the threshold value, wherein the electrical pulses are delivered to the target tissue via the one or more electrodes, wherein the energy delivery rate of the electrical pulses is dynamically adjusted based on a difference between the measurement and the target temperature value, where the one or more sensors provide the measurement, and wherein dynamically adjusting the energy delivery rate of the electrical pulses comprises increasing the energy delivery rate in response to the measurement indicating that the temperature of the target tissue is below the target temperature value.

7. The method of claim 6, further comprising selecting a maximum energy delivery rate of the electrical pulses, wherein dynamically adjusting the energy delivery rate of the electrical pulses comprises setting the energy delivery rate to the maximum energy delivery rate in response to the measurement indicating that the temperature of the target tissue is below the target temperature value.

8. The method of claim 1, wherein, after delivering the electrical pulses to the target tissue, the target tissue comprises a first zone of thermal necrosis that is at least partially surrounded by a second zone of non-thermal necrosis or apoptosis.

9. The method of claim 1, wherein, after delivering the electrical pulses to the target tissue, the target tissue comprises a first zone of thermal necrosis that is at least partially surrounded by a second zone of cells that have been modified by introducing new DNA or genetic material, introducing a drug or chemotherapy or nano-particle, and/or stimulated to enhance protein or antigen expression.

10. The method of claim 1, wherein, after delivering the electrical pulses to the target tissue, the target tissue comprises a first zone of cell death via non-thermal necrosis or apoptosis that is at least partially surrounded by a second zone of cells which have been modified by introducing new DNA or genetic material, introducing a drug or chemotherapy, and/or stimulated to enhance protein or antigen expression.

11. The method of claim 1, wherein the electrical pulses comprise a plurality of multi-pulse groups of electrical pulses including a first multi-pulse group of electrical pulses that precedes a second multi-pulse group of electrical pulses by an intergroup delay, the first multi-pulse group of electrical pulses including at least a first pair of intragroup pulses, which have opposite polarities relative to each other and are spaced in time from each other by a first delay, and the second multi-pulse group of electrical pulses including at least a second pair of intragroup pulses, which have opposite polarities relative to each other and are spaced in time from each other by a second delay, and wherein dynamically adjusting the energy delivery rate of the electrical pulses further comprises adjusting at least one of the first delay or the second delay in response to the measurement.

12. The method of claim 11, wherein dynamically adjusting the energy delivery rate of the electrical pulses further comprises adjusting the intergroup delay in response to the measurement.

13. The method of claim 11, wherein adjusting the at least one of the first delay or the second delay in response to the measurement comprises reducing a duration of the at least one of the first delay or the second delay in response to the measurement indicating that the temperature of the target tissue is below the threshold value, to thereby increase the temperature of the target tissue.

14. A method of performing electronically controlled electrotherapy comprising:

delivering a plurality of electrical pulses to a target tissue of a patient; and modifying or killing target cells of the target tissue and simultaneously reducing or eliminating muscle contractions of the patient by adjusting an energy delivery rate of the electrical pulses in response to at least one of a user input, a measurement from one or more sensors, or a measurement from imaging, wherein adjusting the energy delivery rate of the electrical pulses comprises reducing a delay between ones of the electrical pulses in response to the at least one of the user input, the measurement from the one or more sensors, or the measurement from the imaging, to thereby reduce or eliminate muscle contractions of the patient.

15. The method of claim 14, wherein adjusting the energy delivery rate of the electrical pulses further comprises reducing a width of at least one of the electrical pulses and increasing the energy delivery rate of the electrical pulses to maintain a constant energy delivery rate between 10 and 500 microseconds per second.

16. The method of claim 14, wherein adjusting the energy delivery rate of the electrical pulses further comprises reducing a width of at least one of the electrical pulses in response to the at least one of the user input, the measurement from the one or more sensors, or the measurement from the imaging, to thereby reduce or eliminate muscle contractions of the patient.

17. The method of claim 14, wherein adjusting the energy delivery rate of the electrical pulses further comprises increasing the energy delivery rate in response to the at least one of the user input, the measurement from the one or more sensors, or the measurement from the imaging, to thereby reduce or eliminate muscle contractions of the patient.

18. The method of claim 14, wherein the delay between the ones of the electrical pulses is reduced in response to the at least one of the user input, the measurement from the one or more sensors, or the measurement from the imaging indicating that the patient has muscle contractions, and wherein the method further comprises increasing a voltage of at least one of the electrical pulses in response to the patient not having muscle contractions.

19. A method of performing electronically controlled electrotherapy comprising:

delivering a plurality of electrical pulses to a target tissue of a patient; and modifying or killing target cells of the target tissue and simultaneously adjusting an energy delivery rate of the electrical pulses in response to an impedance measurement of the target tissue received from one or more sensors, wherein adjusting the energy delivery rate of the electrical pulses comprises increasing the energy delivery rate in response to the impedance measurement of the target tissue being above a threshold value.

20. The method of claim 19, wherein the electrical pulses are delivered to the target tissue via one or more electrodes, and wherein the one or more sensors comprise a first sensor at a location that is remote from the one or more electrodes.

\* \* \* \* \*